United States Patent
Yang et al.

(10) Patent No.: US 11,198,761 B2
(45) Date of Patent: Dec. 14, 2021

(54) BIODEGRADABLE POLYIONENES

(71) Applicant: AGENCY FOR SCIENCE, TECHNOLOGY AND RESEARCH, Singapore (SG)

(72) Inventors: Yi Yan Yang, Singapore (SG); Shrinivas Venkataraman, Singapore (SG); Pang Kern Jeremy Tan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 126 days.

(21) Appl. No.: 16/481,881

(22) PCT Filed: Feb. 19, 2018

(86) PCT No.: PCT/SG2018/050077
§ 371 (c)(1),
(2) Date: Jul. 30, 2019

(87) PCT Pub. No.: WO2018/151682
PCT Pub. Date: Aug. 23, 2018

(65) Prior Publication Data
US 2020/0040136 A1    Feb. 6, 2020

(30) Foreign Application Priority Data
Feb. 16, 2017  (SG) .......................... 10201701243X

(51) Int. Cl.
| | | |
|---|---|---|
| A61K 31/785 | (2006.01) | |
| A61K 8/84 | (2006.01) | |
| A61P 31/04 | (2006.01) | |
| A61Q 17/00 | (2006.01) | |
| A61Q 19/10 | (2006.01) | |
| C08G 69/44 | (2006.01) | |
| C08G 73/02 | (2006.01) | |

(52) U.S. Cl.
CPC ............... *C08G 69/44* (2013.01); *A61K 8/84* (2013.01); *A61K 31/785* (2013.01); *A61P 31/04* (2018.01); *A61Q 17/005* (2013.01); *A61Q 19/10* (2013.01); *C08G 73/0293* (2013.01)

(58) Field of Classification Search
CPC ..... C08G 69/44; C08G 73/0293; A61P 31/04; A61K 8/84; A61K 31/785; A61Q 17/005; A61Q 19/10
See application file for complete search history.

(56) References Cited

U.S. PATENT DOCUMENTS

| | | | |
|---|---|---|---|
| 4,247,476 A |  | 1/1981 | Haase et al. |
| 4,386,013 A | * | 5/1983 | Callahan |
| 4,422,853 A |  | 12/1983 | Jacquet et al. |
| 4,923,619 A |  | 5/1990 | Legros |
| 5,552,391 A | * | 9/1996 | Coutts |
| 7,754,241 B1 | * | 7/2010 | Webb |
| 8,349,303 B1 |  | 1/2013 | Phillips et al. |

FOREIGN PATENT DOCUMENTS

| | | | |
|---|---|---|---|
| GB | 2415373 | * | 12/2005 |
| JP | 2008-248224 A |  | 10/2008 |
| WO | WO-03/094616 A1 |  | 11/2003 |
| WO | WO-2016/209175 A1 |  | 12/2016 |

OTHER PUBLICATIONS

Kim (Journal of Agricultural and Food Chemistry, published 2003, pp. 165-169). (Year: 2003).*
Seki et al. (Microporous and Mesoporous Materials, Published 2009, pp. 30-35) (Year: 2009).*
Bennett (Journal of the Chemical Society, Transactions, Published 1925, vol. 127, pp. 1277-1282). (Year: 1925).*
Sohrabi (Colloids and Surfaces B: Biointerfaces, Published 2013, pp. 29-35) (Year: 2013).*
Chen (Polymer Chemistry, Published Dec. 28, 2015, pp. 1397-1404) (Year: 2015).*
Written Opinion in SG Application No. 11201906022S dated Sep. 8, 2020, 9 pages.
Zhang et al., "Simple and Cost-Effectie Polycondensation Routes to Antimicrobial Consumer Products", Polym. Chem., vol. 7, No. 23, May 11, 2016, pp. 3923-3932.
Coneski et al., "Thermal Polycondensation of Poly(diol citrate)s With Tethered Quaternary Ammonium Biocides", RSC Adv., vol. 2, No. 33, Oct. 23, 2012, pp. 12824-12834.
International Search Report and Written Opinion in International Application No. PCT/SG2018/050077 dated May 11, 2018, 10 pages.
Office Action in CN Application No. 201880011811.8 dated Apr. 8, 2021, 14 pages.
Kim et al., "Organic Matter Effects on Phase Partition of 1,3-Dichloropropene in Soil", J. Agric. Food Chem, vol. 51, 2003, pp. 165-169.
Seki et al., "Preparation and Vapor Adsorption Properties of Quaternary Diammonium-montmorillonites", Microporous and Mesoporous Materials, vol. 124, 2009, pp. 30-35.
Sohrabi et al., "Investigation of DNA-cationic Bolaform Surfactants Interaction With Different Spacer Length", Colloids and Surfaces B: Biointerfaces, vol. 110, 2013, pp. 29-35.
Chen et al., "Controllable Supramolecular Polymerization Through Self-sorting of Aliphatic and Aromatic Motifs", Polym. Chem, vol. 7, 2016, pp. 1397-1404.

(Continued)

*Primary Examiner* — Alma Pipic
(74) *Attorney, Agent, or Firm* — Marshall, Gerstein & Borun LLP

(57) ABSTRACT

Synthesis of polyionenes with built-in degradable linkers through addition polymerization of a novel class of degradable $A_2$-type monomers (d-$A_2$), and their use as antimicrobial agents are disclosed. A library of biodegradable polyionenes and Gemini-surfactants made from d-$A_2$ monomers are also disclosed. These materials have potent and broad spectrum of antimicrobial activity with high selectivity over mammalian cells.

19 Claims, 54 Drawing Sheets

(56) References Cited

OTHER PUBLICATIONS

Office Action in CN Application No. 201880011811.8 dated Sep. 13, 2021, 27 pages.
STN-Registry, Chemical Abstract, Feb. 15, 2017, 23 pages.

* cited by examiner

[Fig. 1]
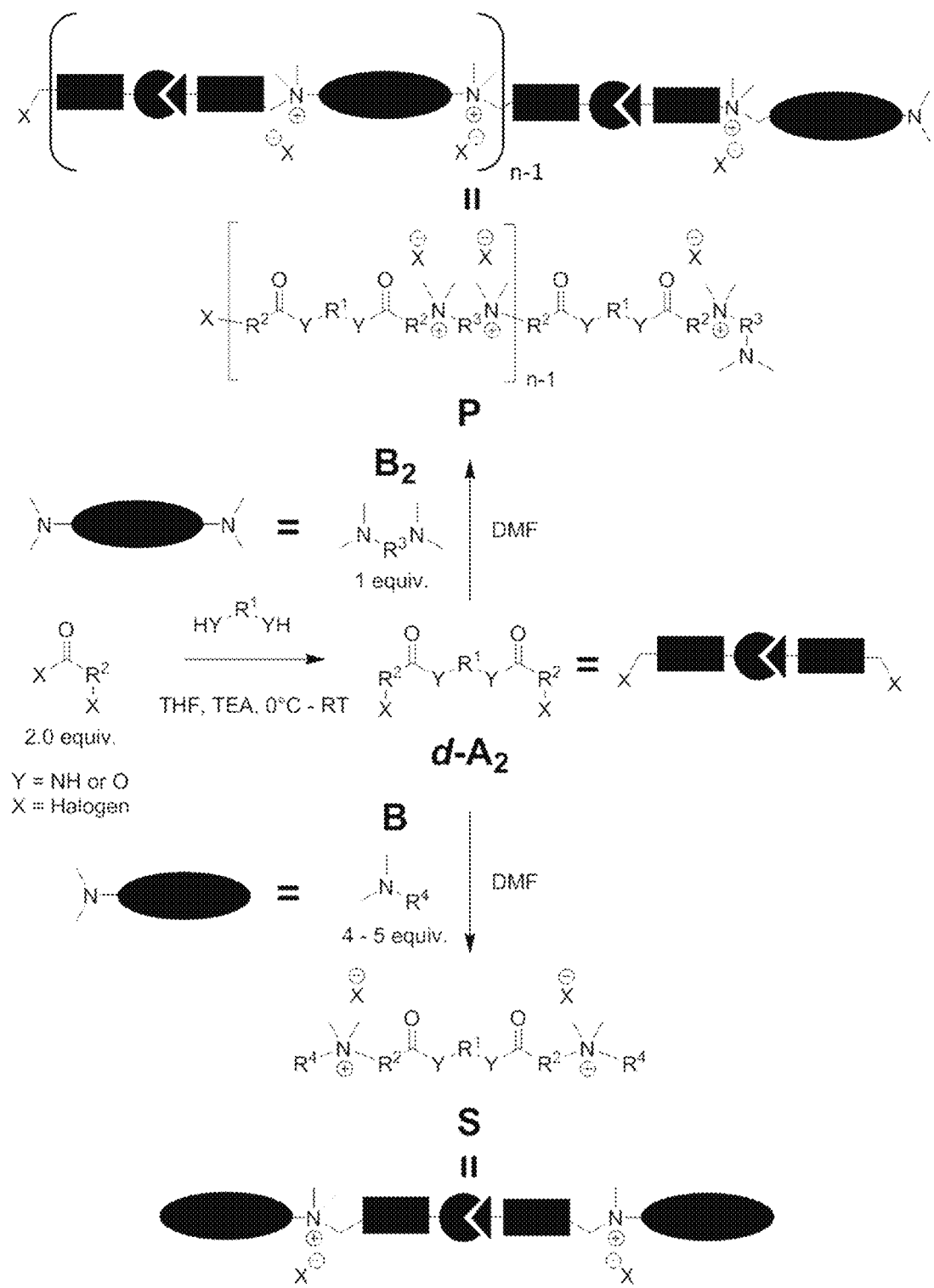

[Fig. 2]
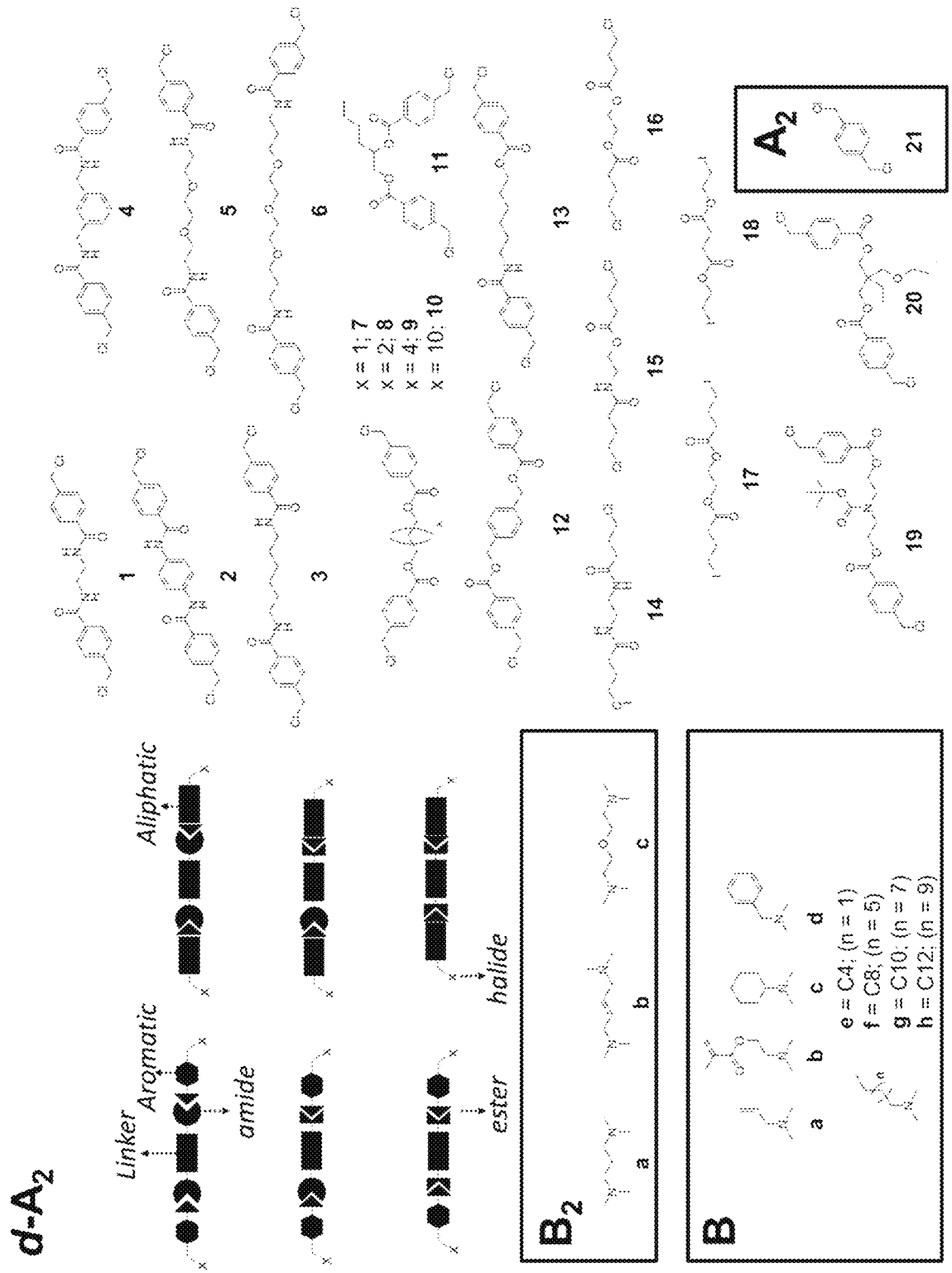

[Fig. 3]
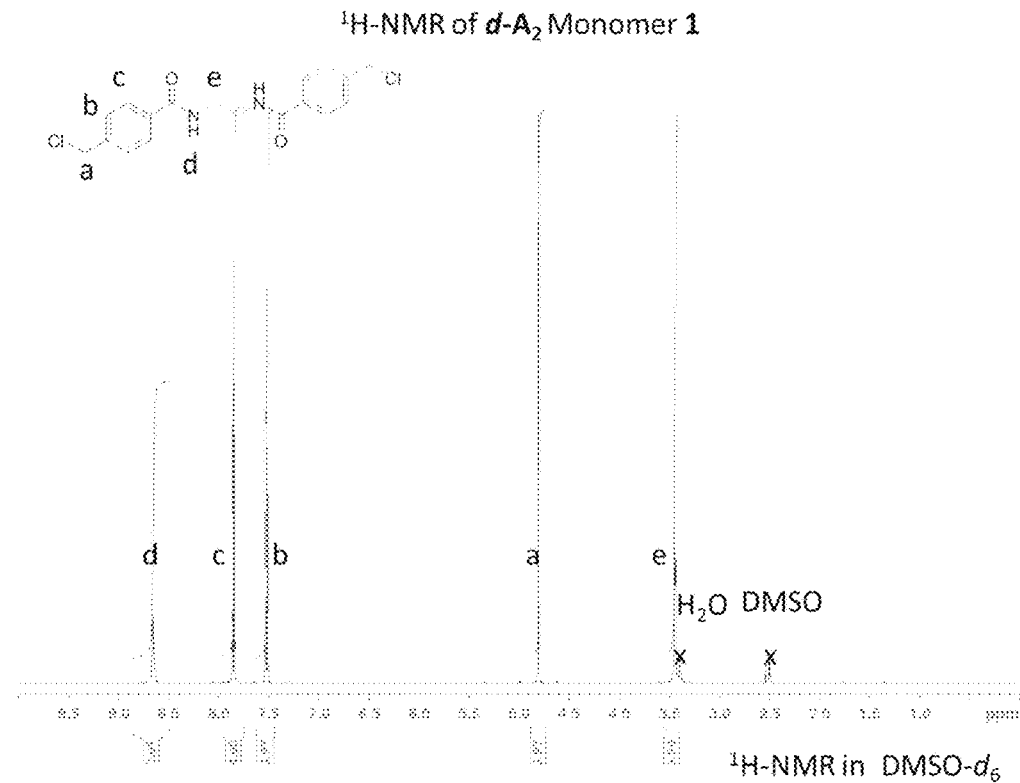
[Fig. 4]
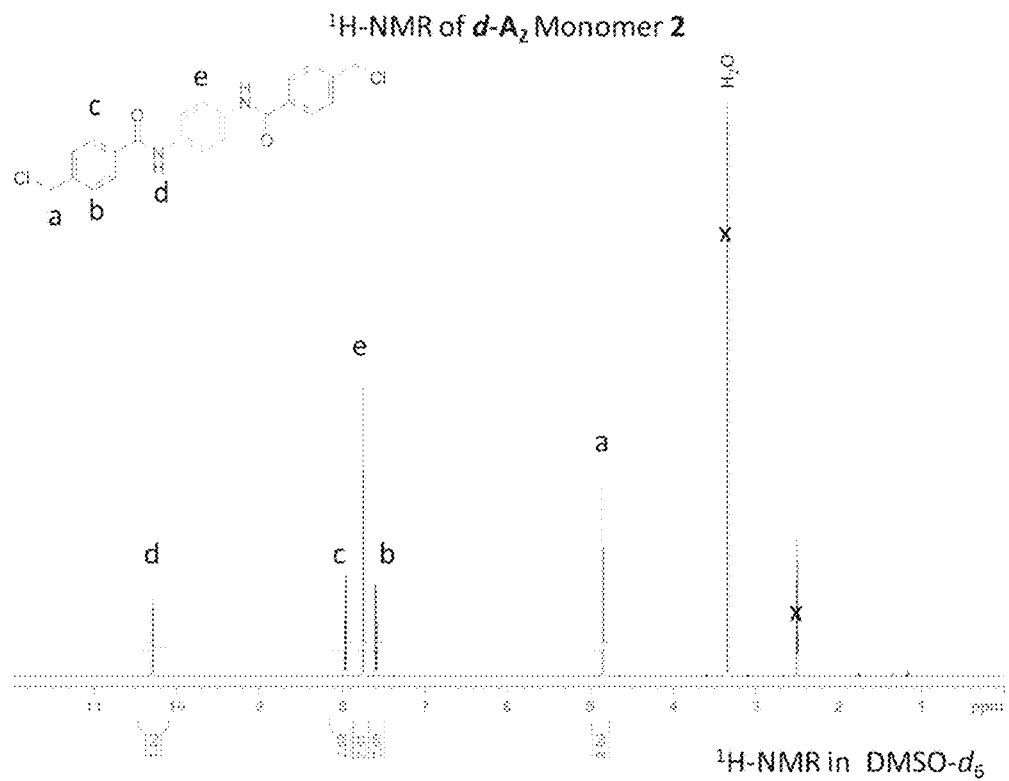

[Fig. 5]
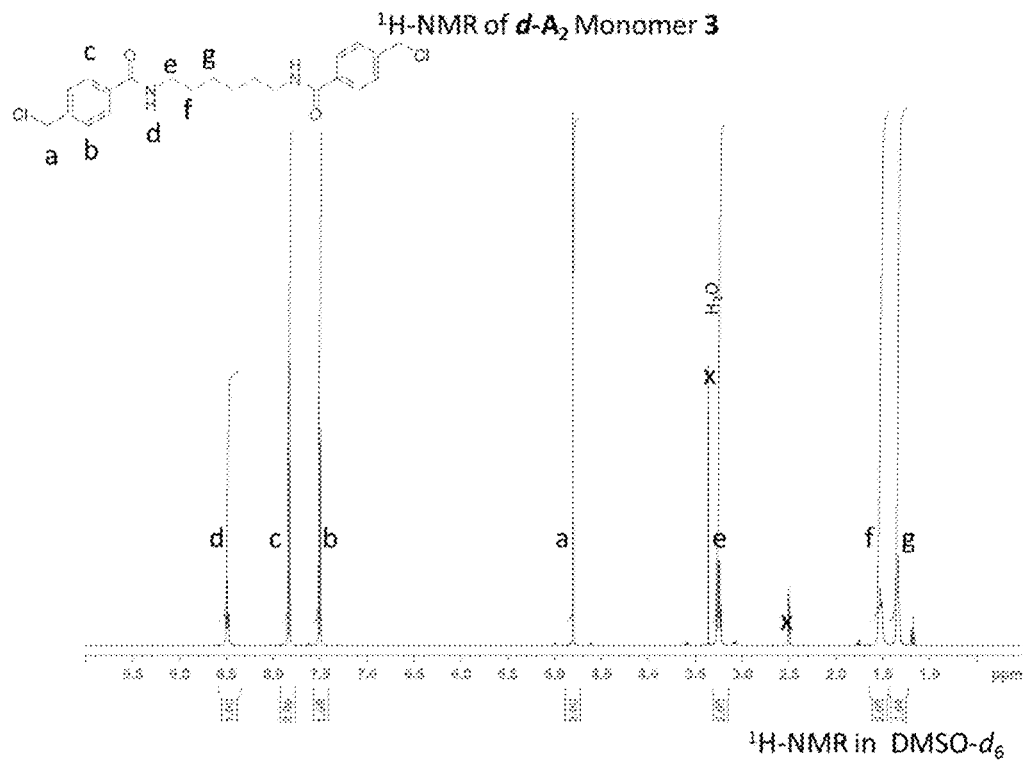
[Fig. 6]
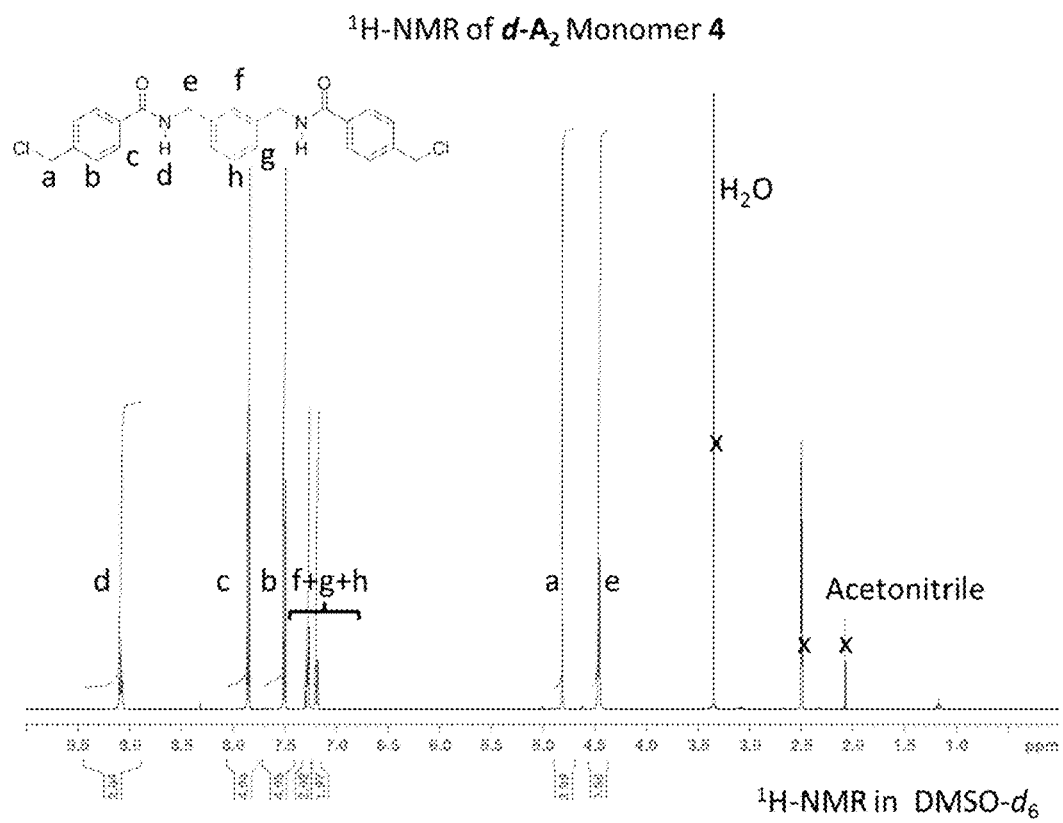

[Fig. 7]
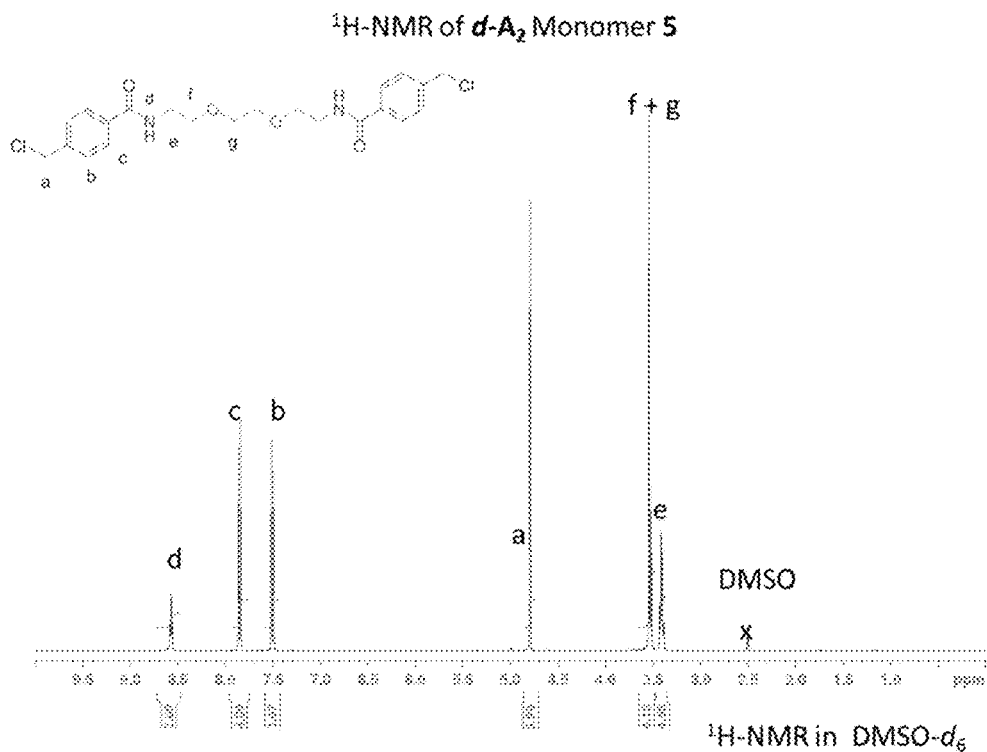
[Fig. 8]
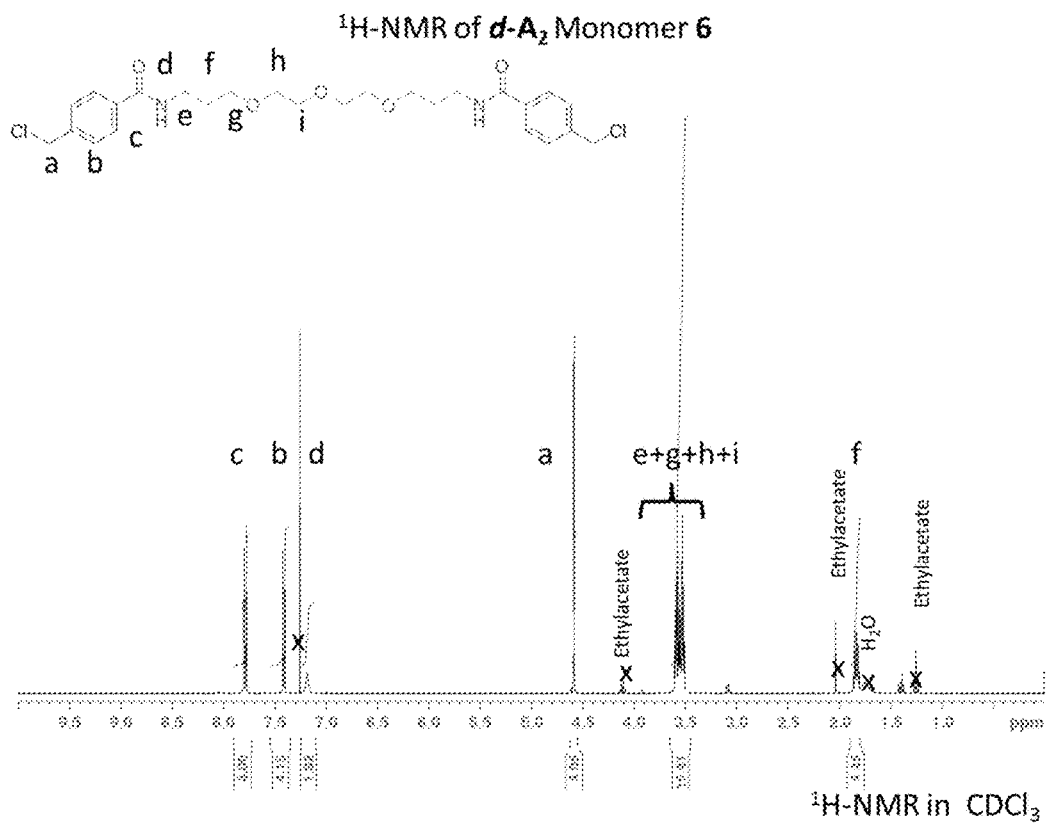

[Fig. 9]
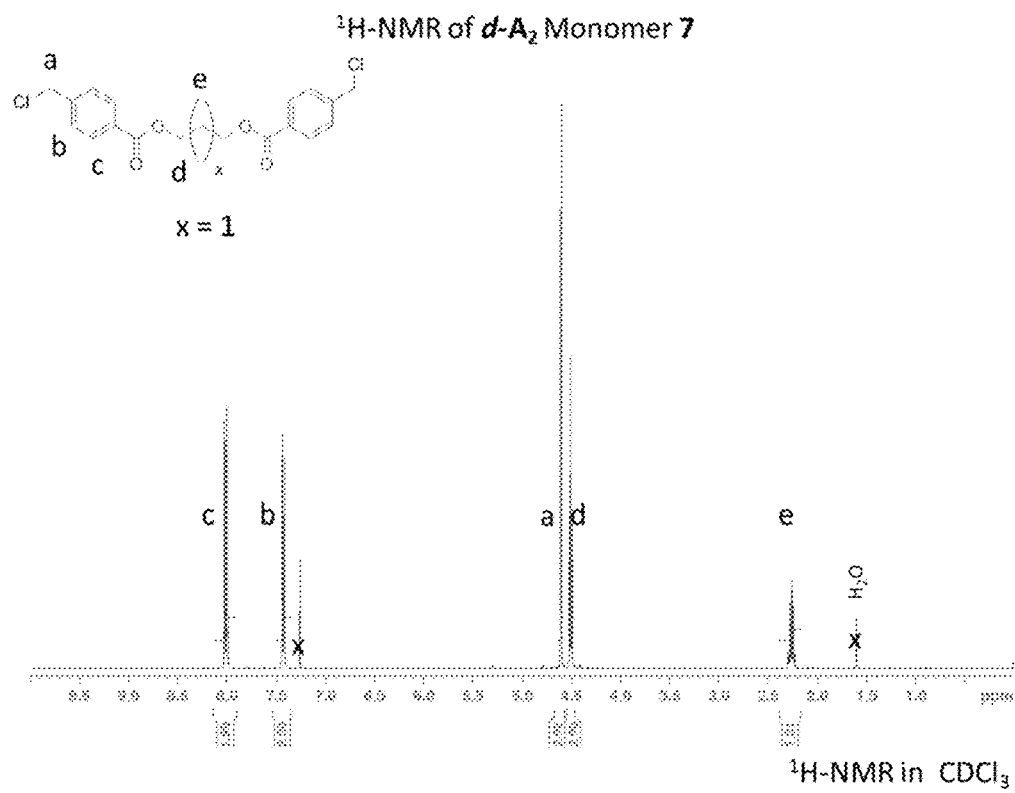
[Fig. 10]
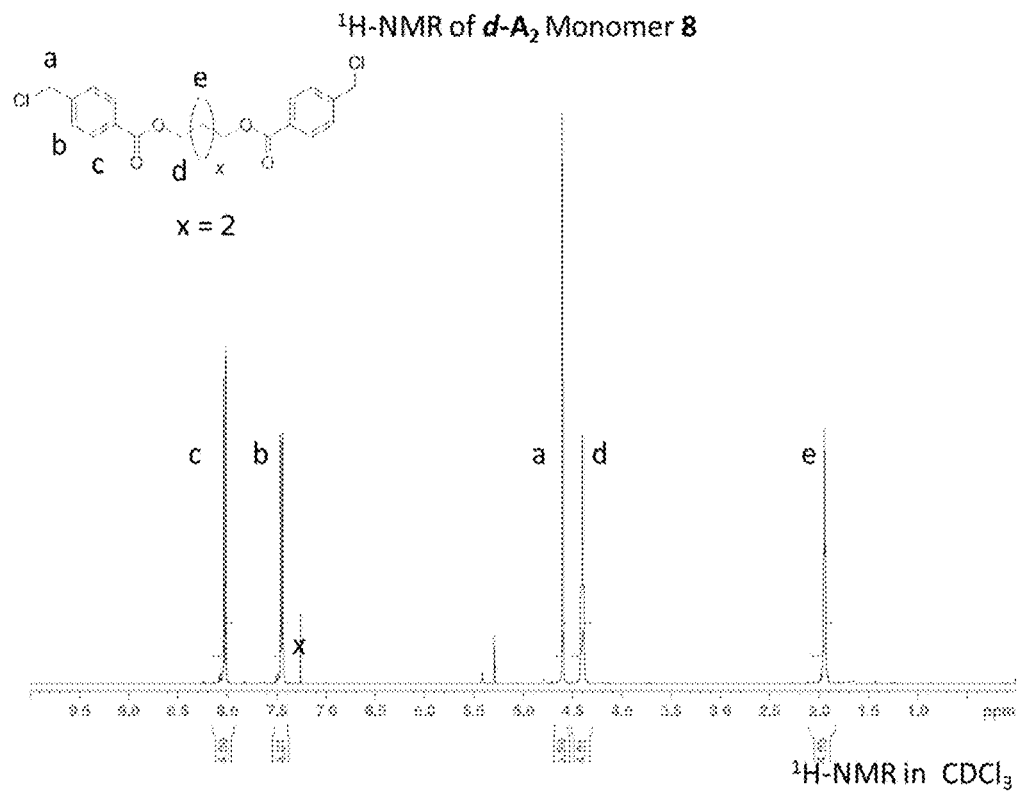

[Fig. 11]
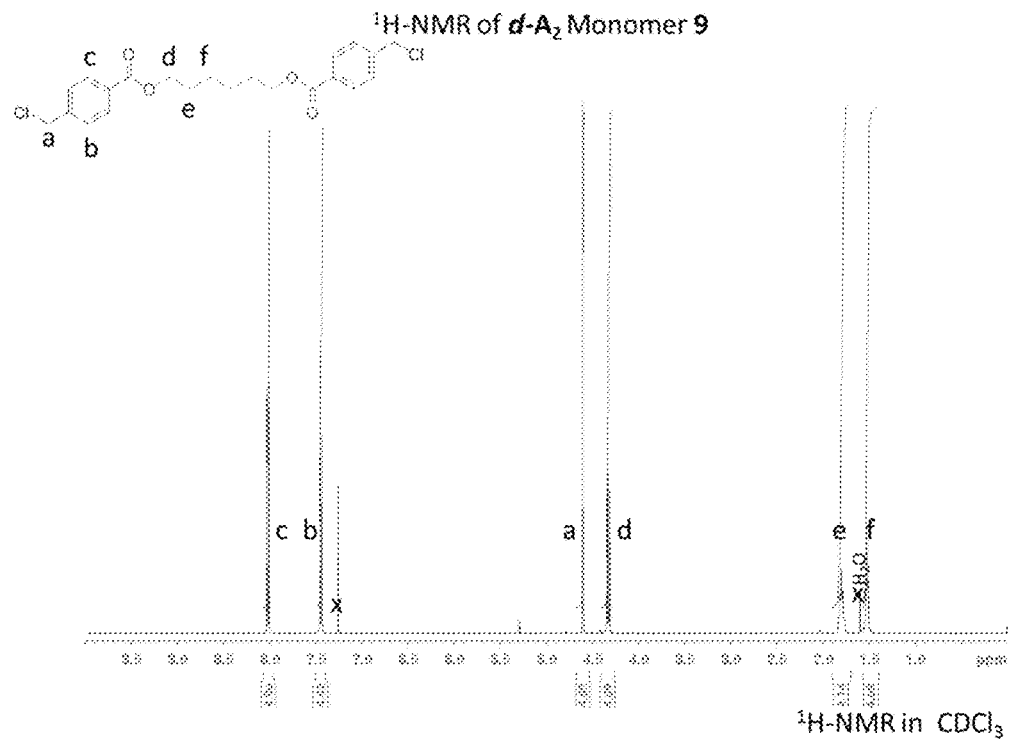
[Fig. 12]
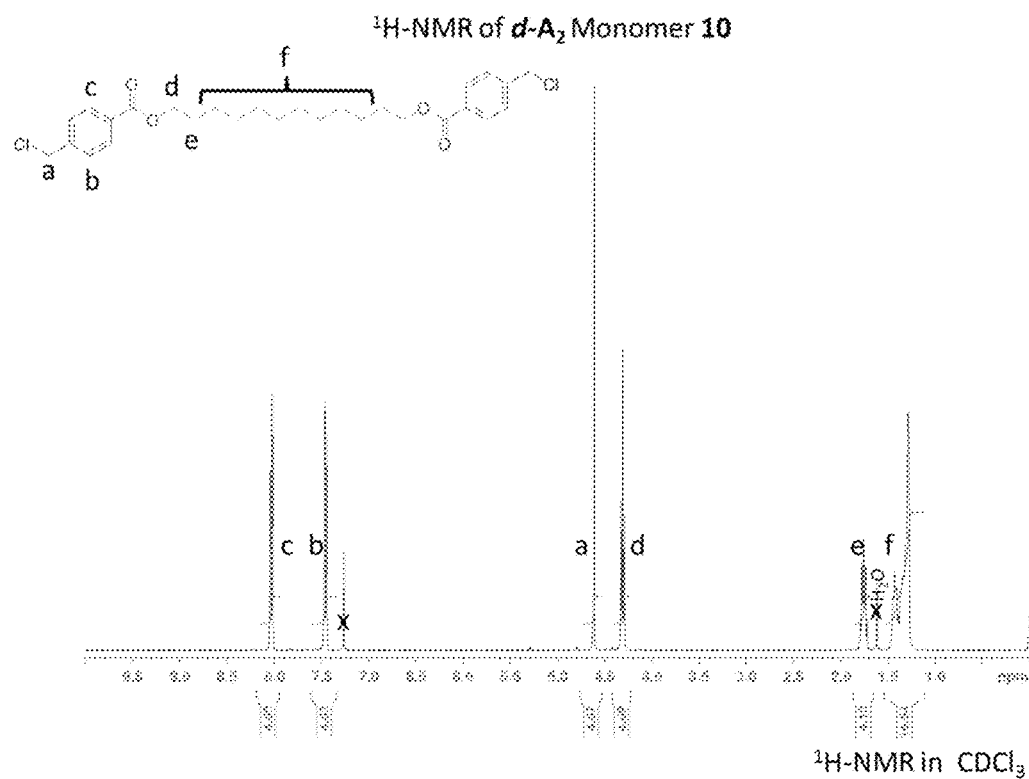

[Fig. 13]
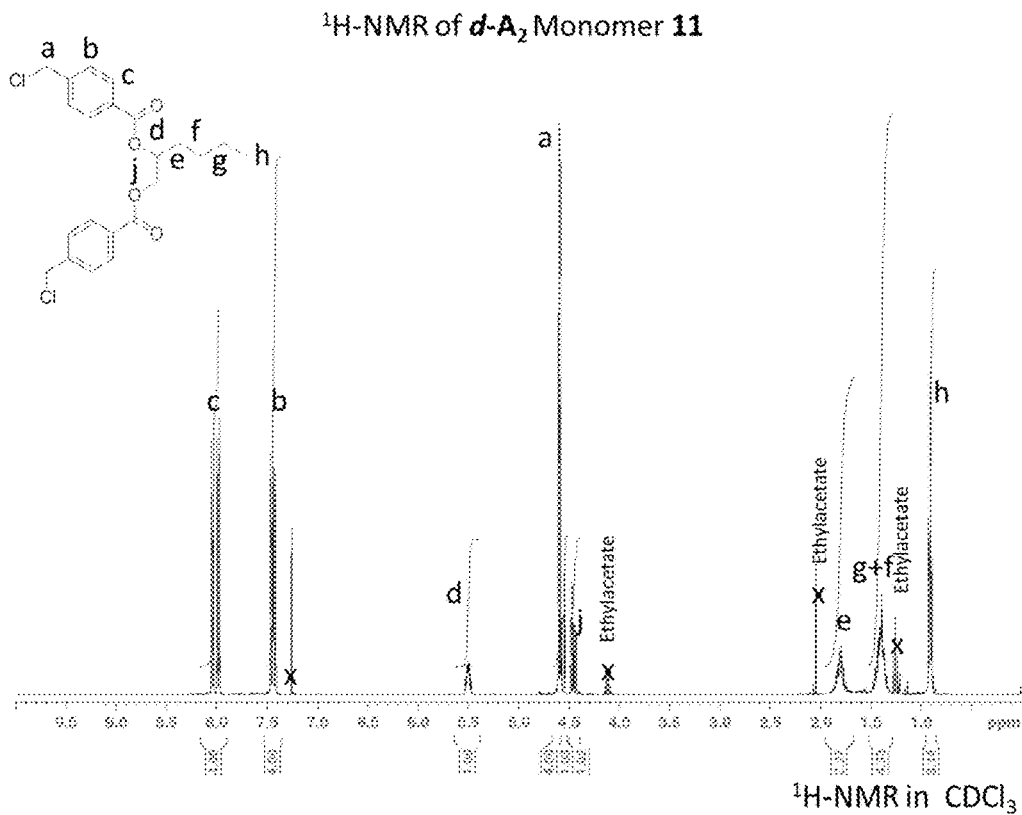
[Fig. 14]
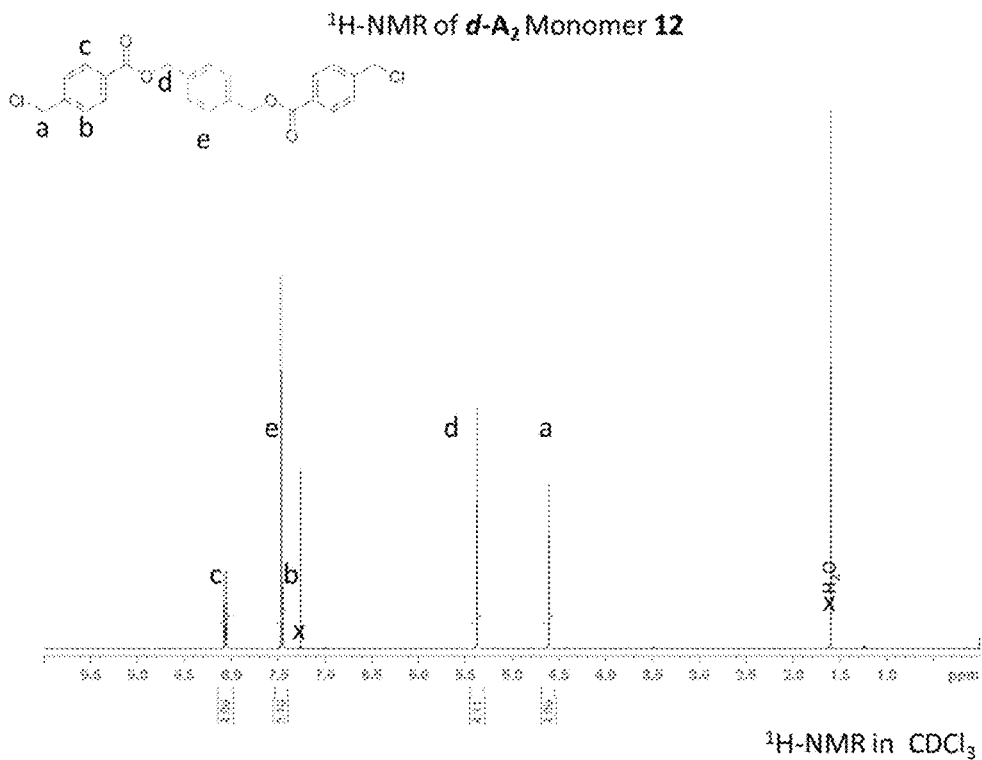

[Fig. 15]
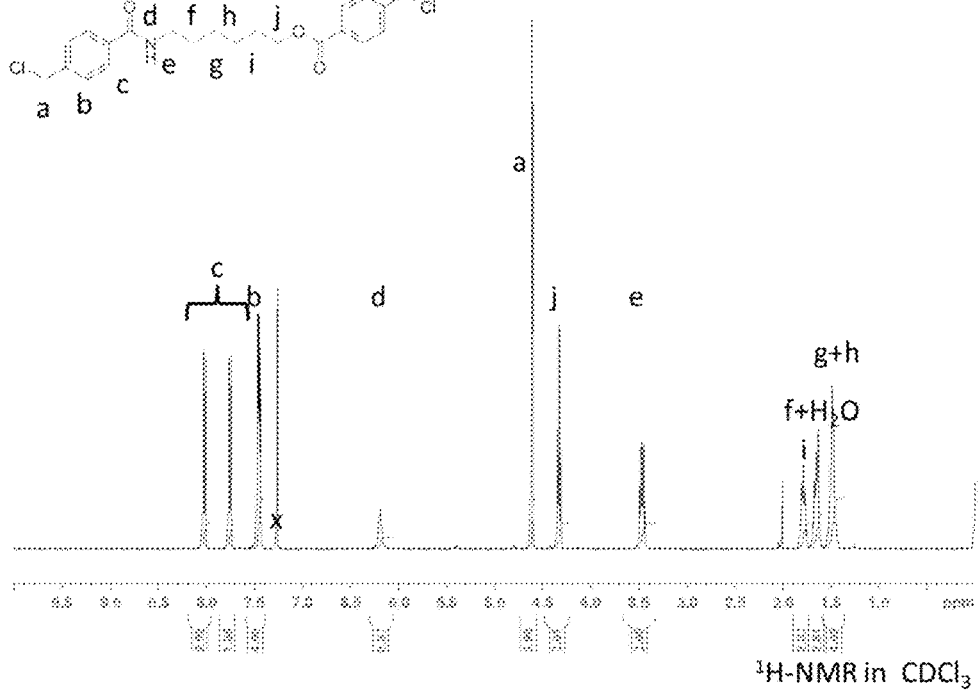
[Fig. 16]
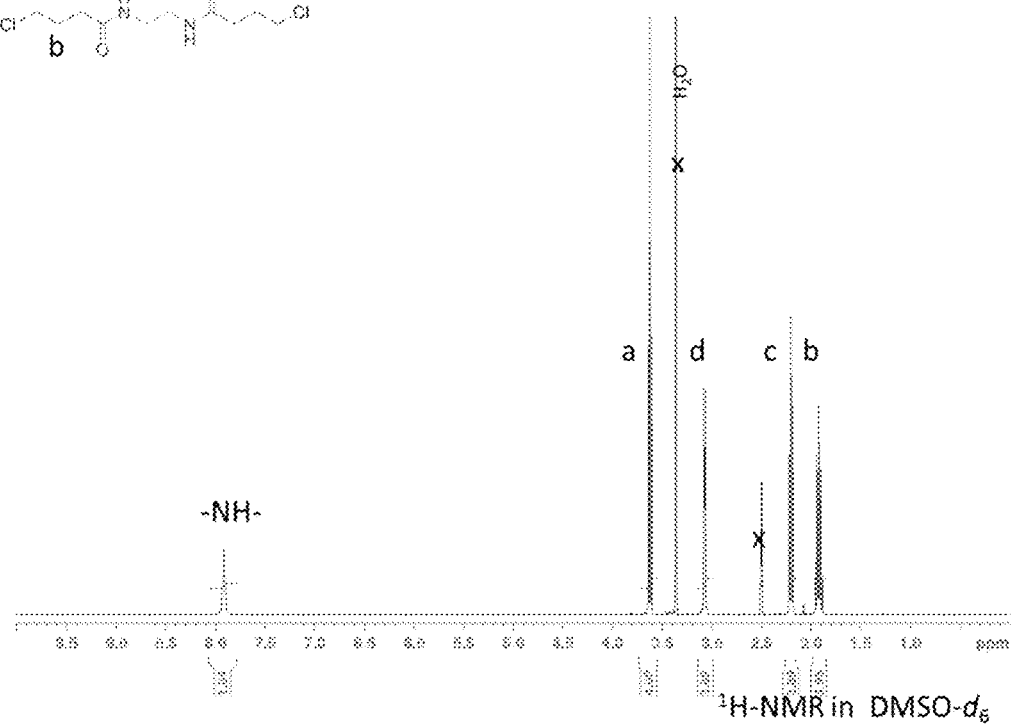

[Fig. 17]
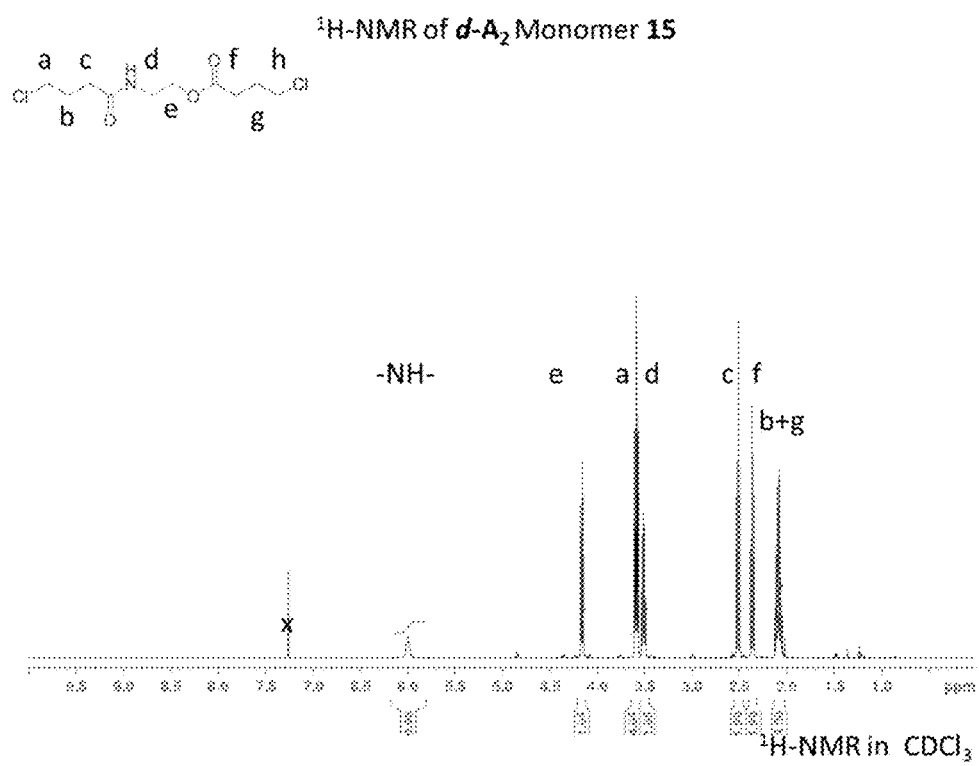
[Fig. 18]
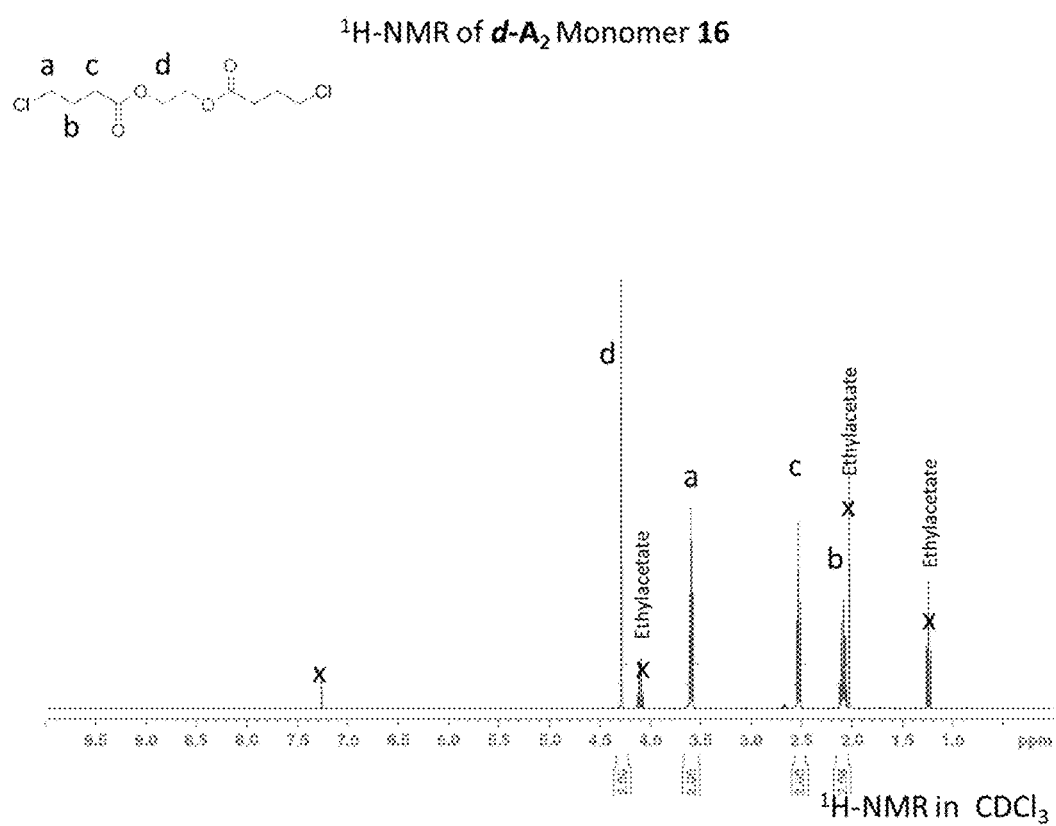

[Fig. 19]
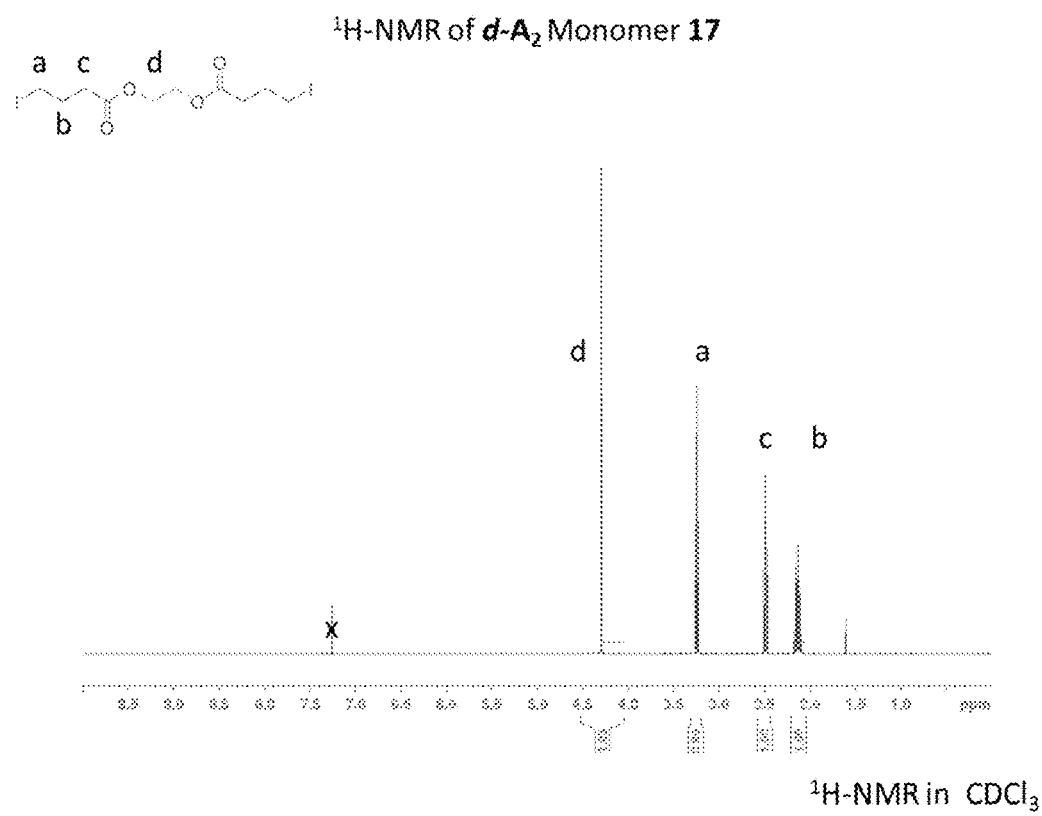
[Fig. 20]
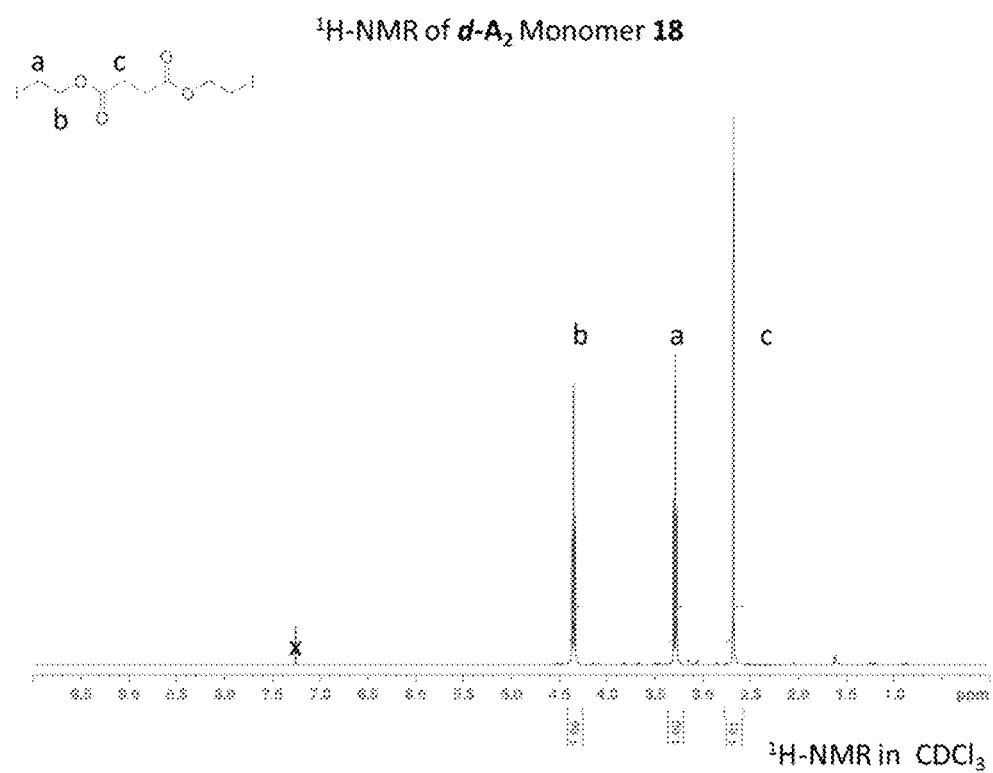

[Fig. 21]
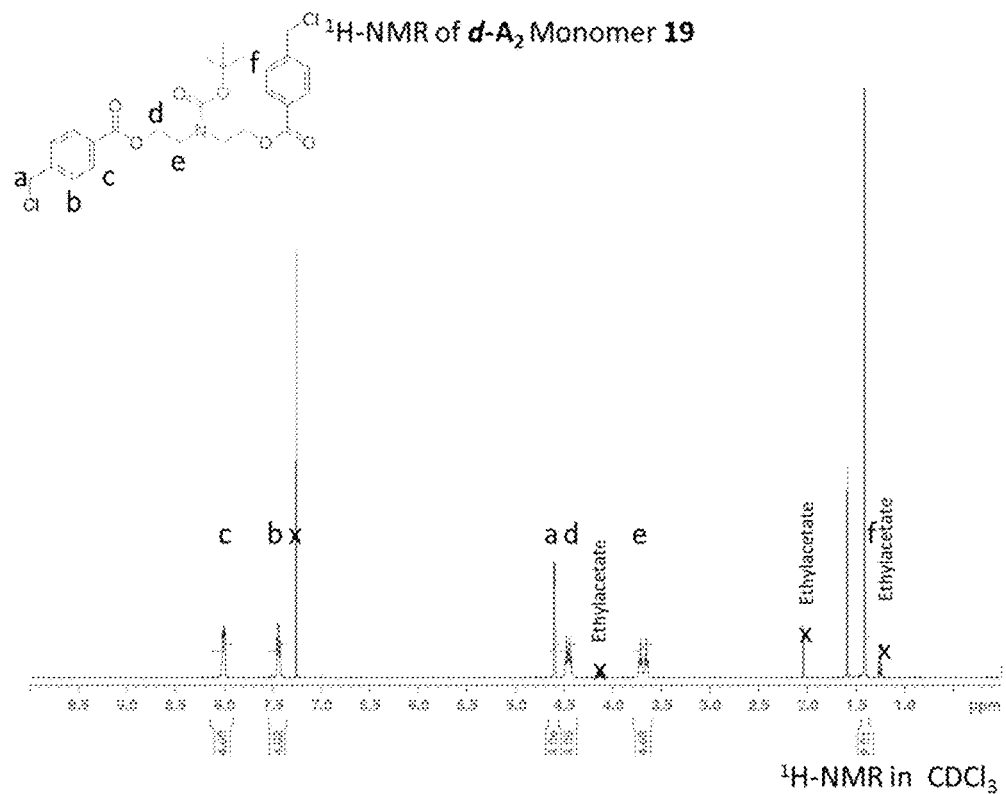
[Fig. 22]
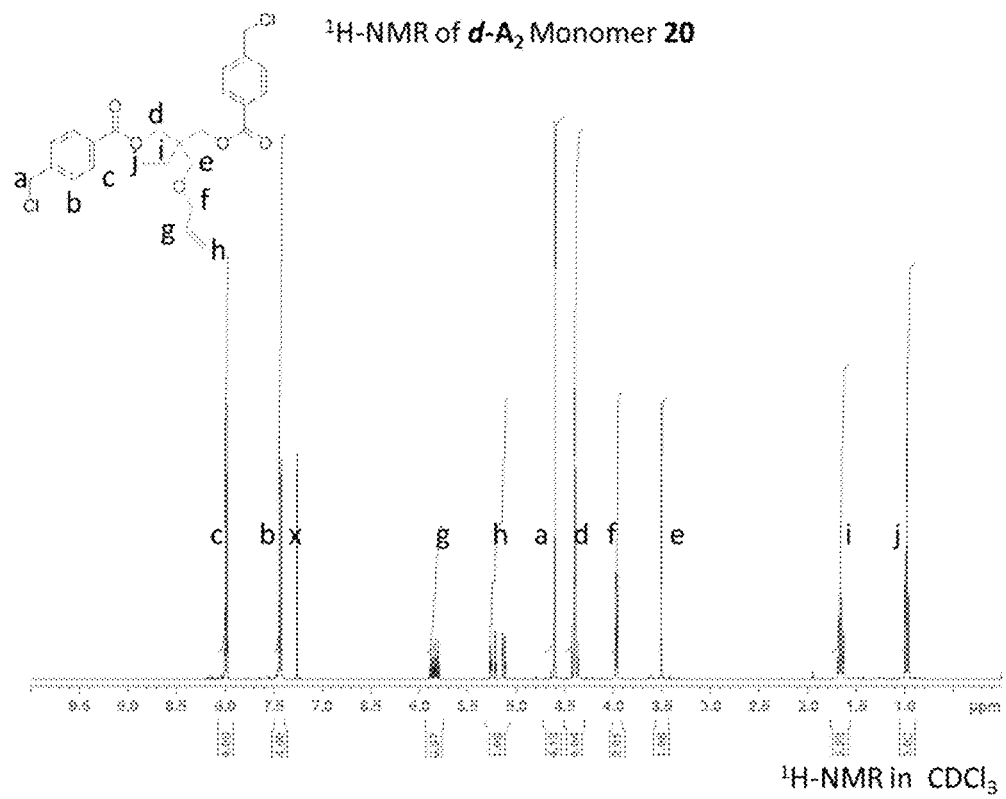

[Fig. 23]
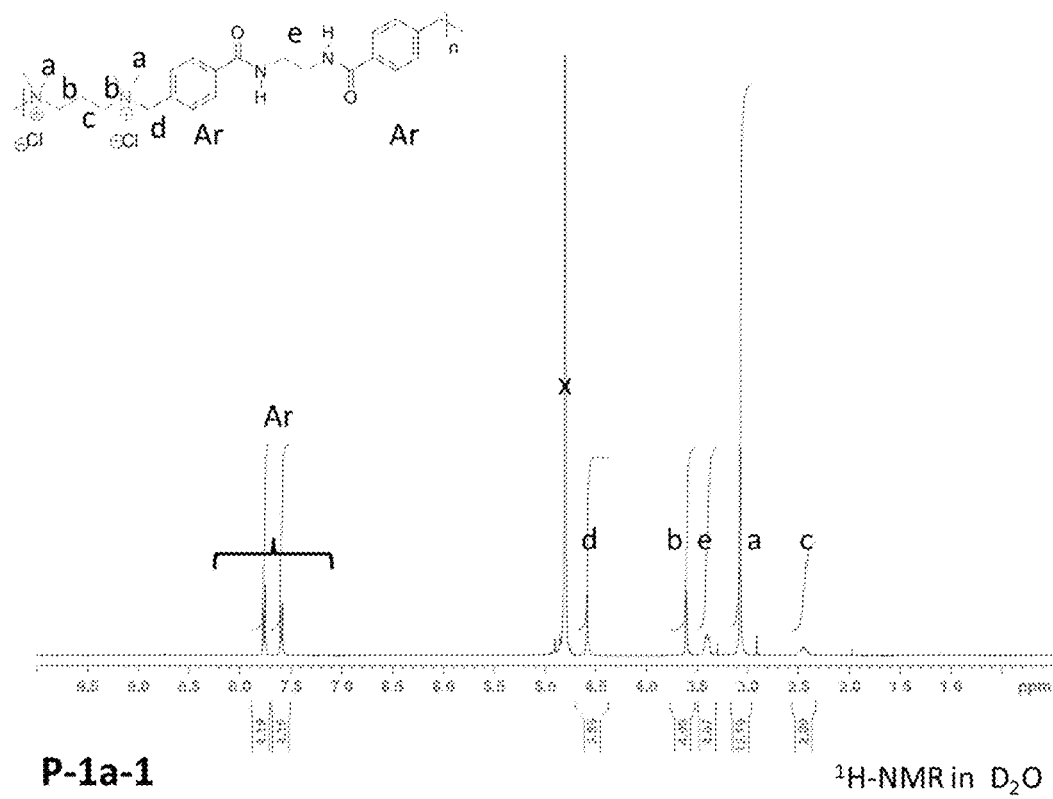
P-1a-1      $^1$H-NMR in $D_2O$
[Fig. 24]
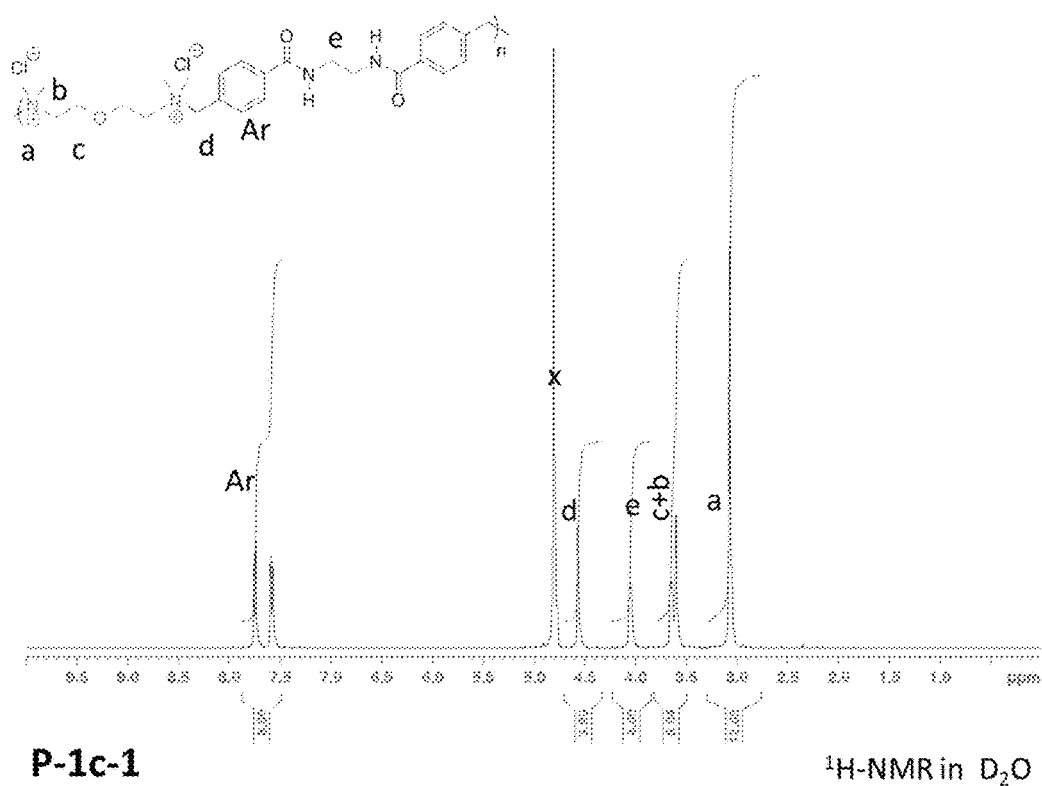
P-1c-1      $^1$H-NMR in $D_2O$

[Fig. 25]
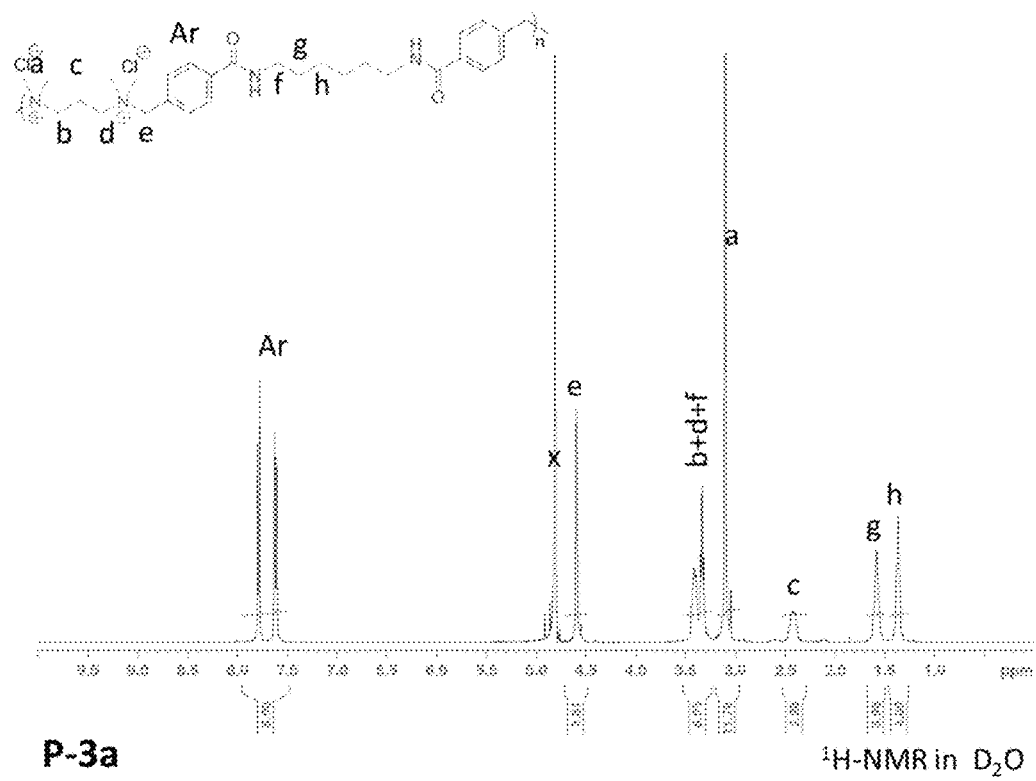
P-3a          $^1$H-NMR in $D_2O$
[Fig. 26]
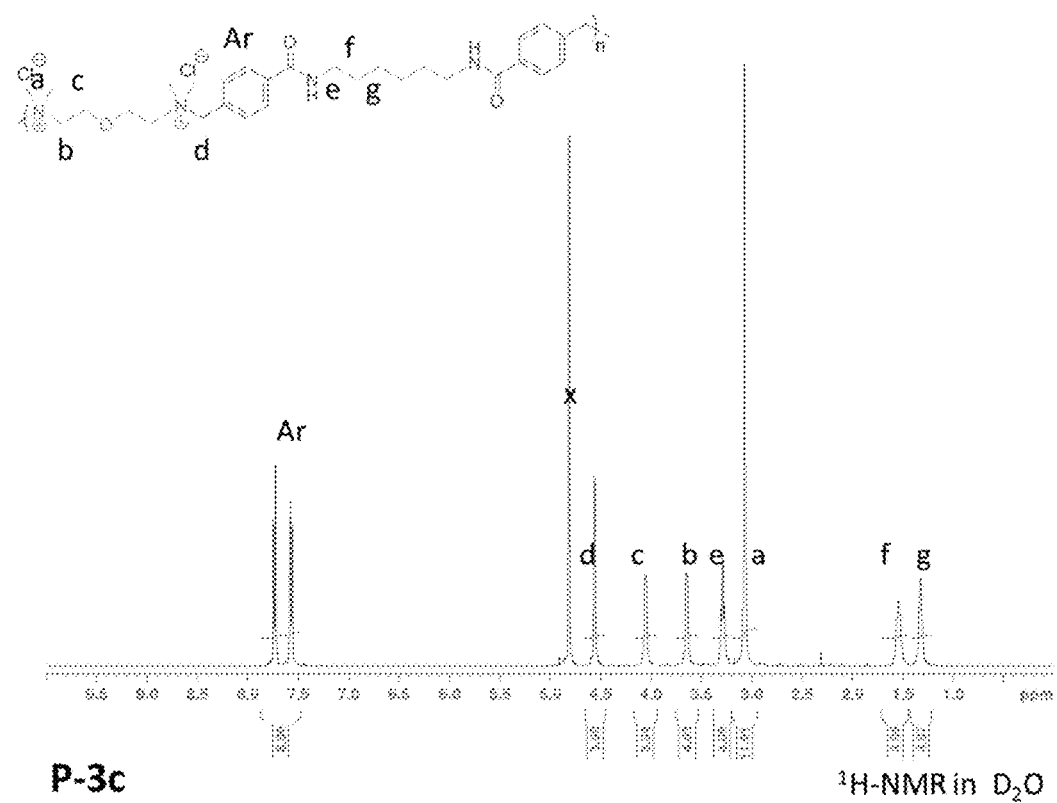
P-3c          $^1$H-NMR in $D_2O$

[Fig. 27]
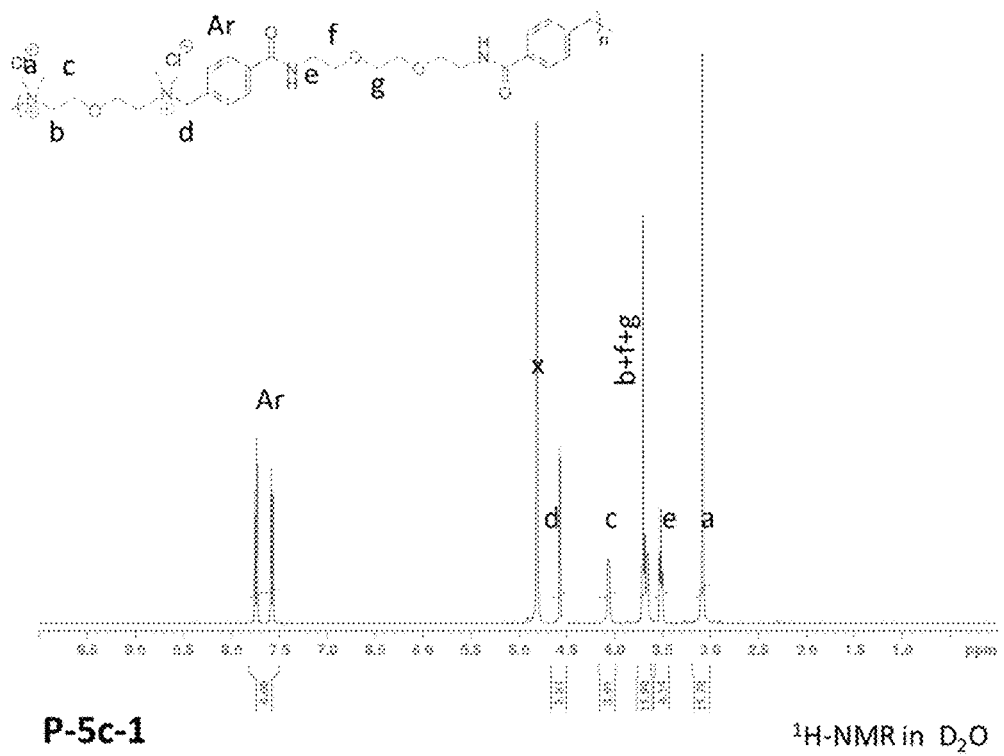
P-5c-1           $^1$H-NMR in $D_2O$
[Fig. 28]
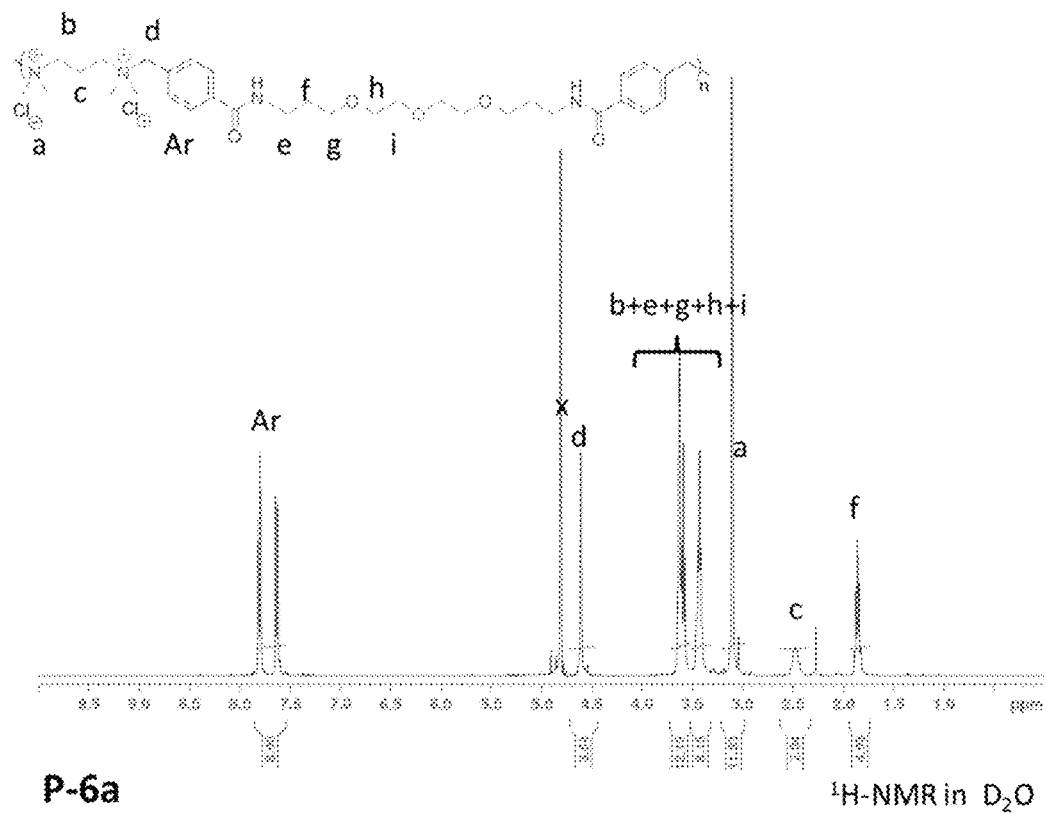
P-6a           $^1$H-NMR in $D_2O$

[Fig. 29]
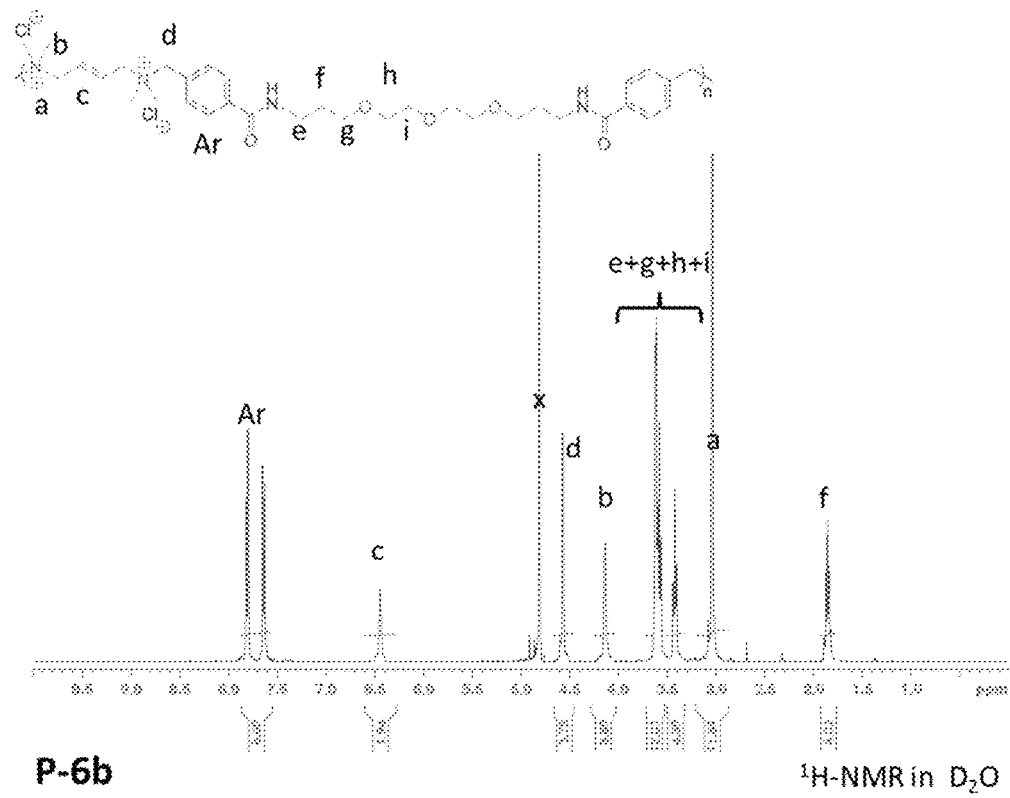
P-6b  $^1$H-NMR in D$_2$O
[Fig. 30]
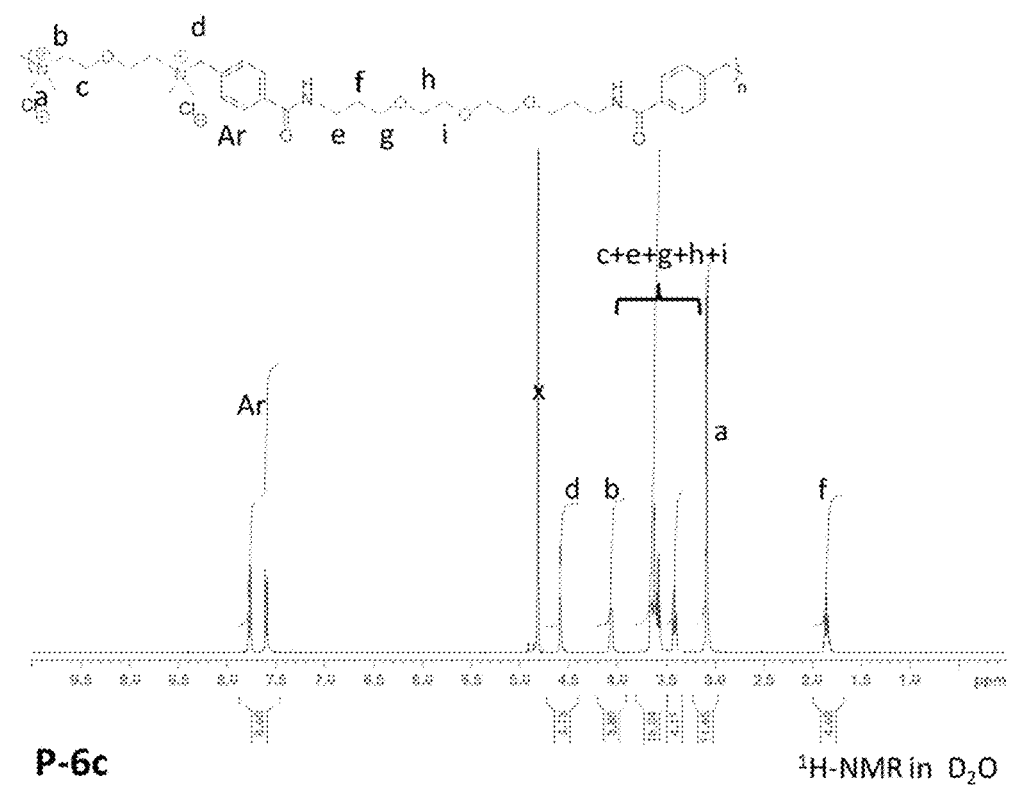
P-6c  $^1$H-NMR in D$_2$O

[Fig. 31]
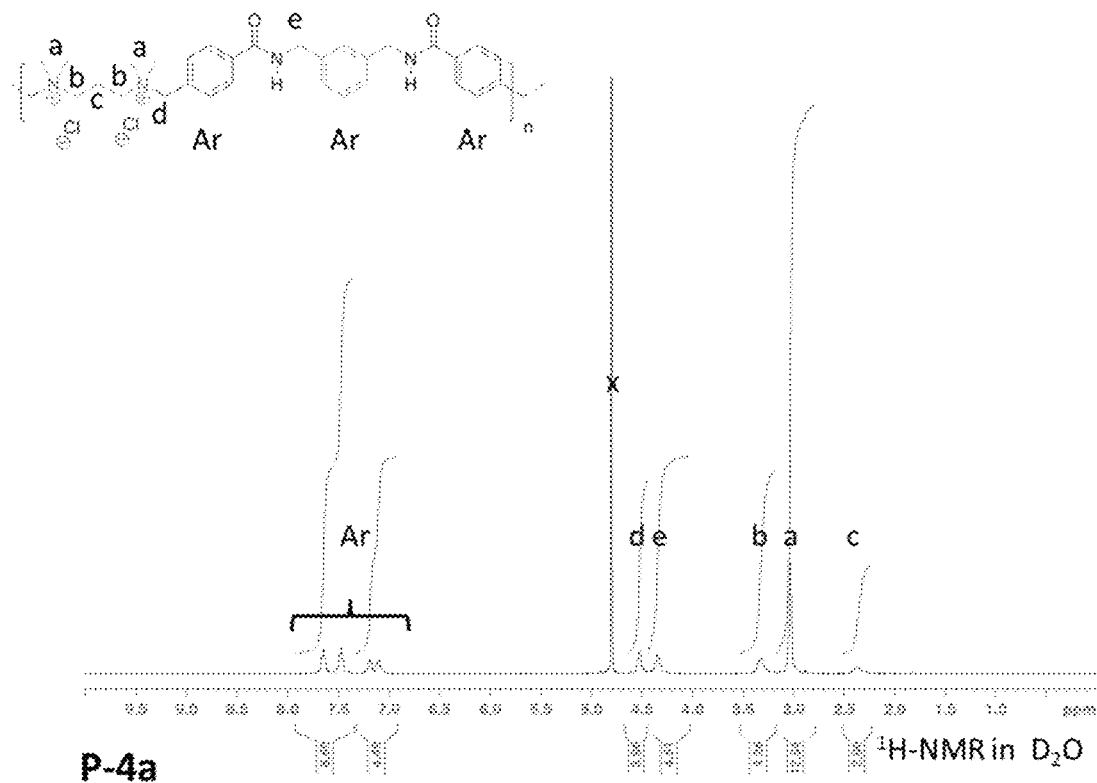
P-4a
[Fig. 32]
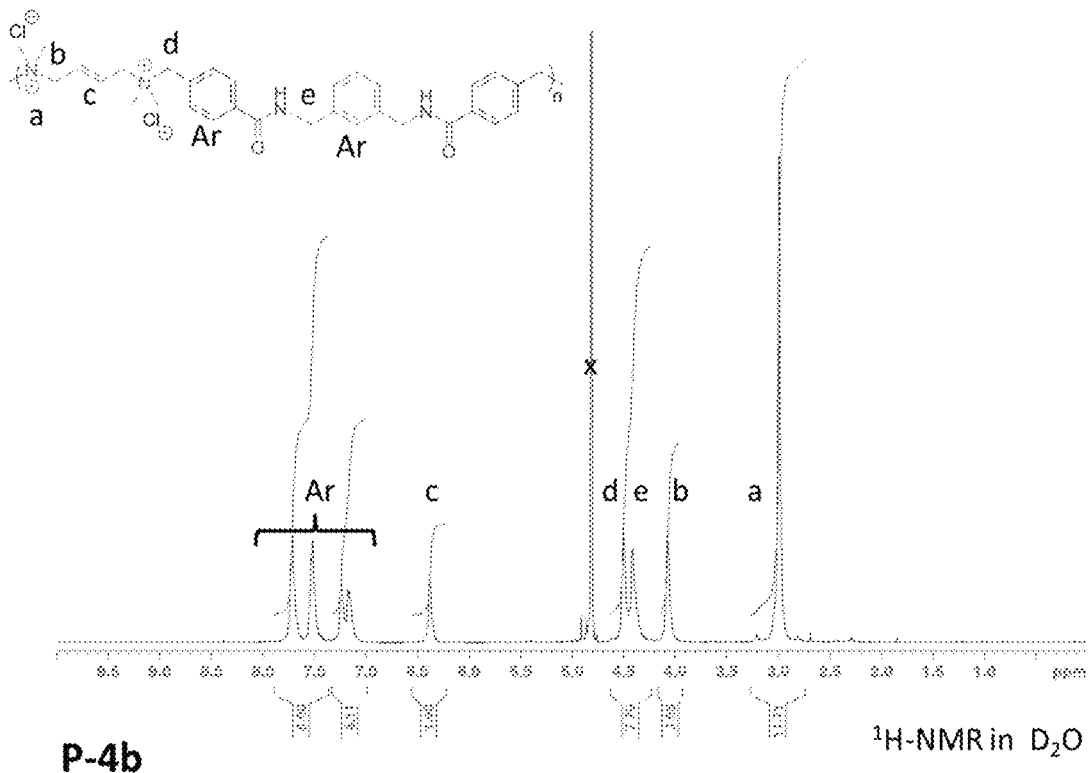
P-4b

[Fig. 33]
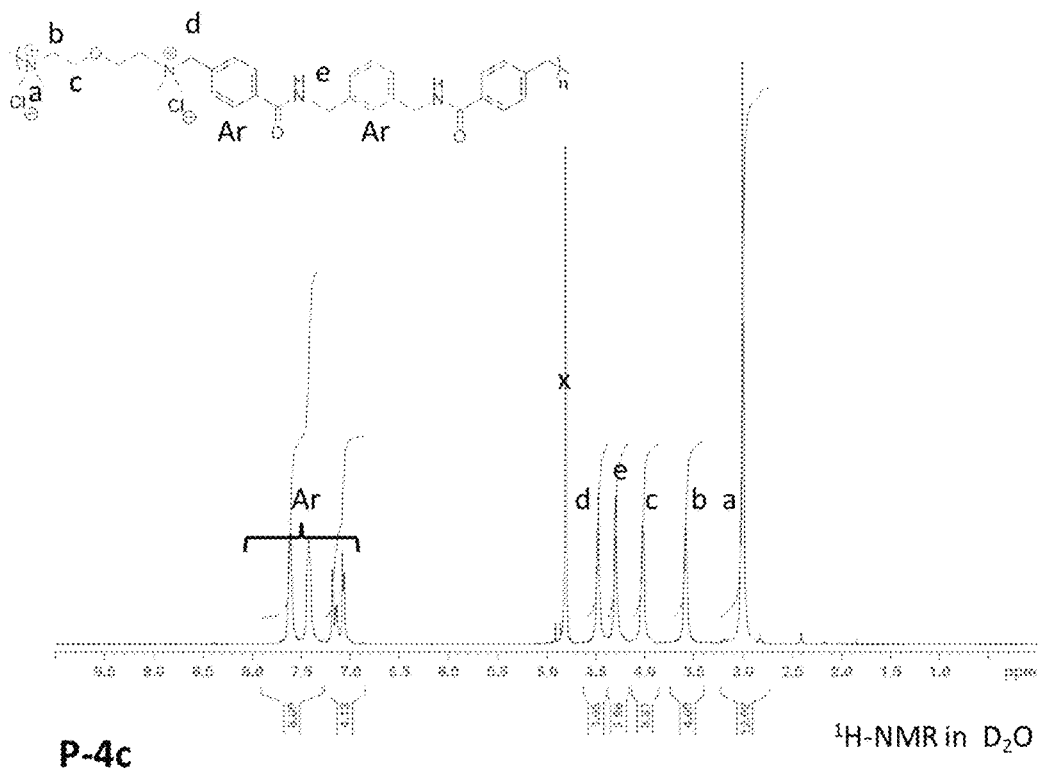
P-4c  ¹H-NMR in D₂O
[Fig. 34]
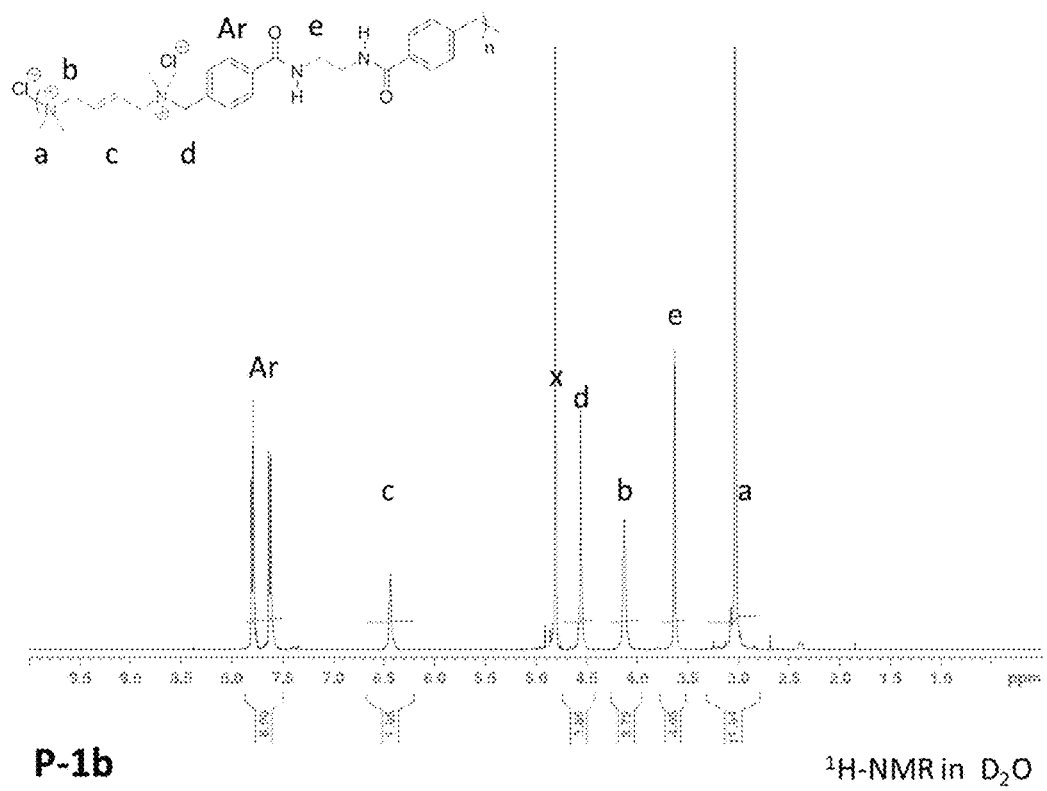
P-1b  ¹H-NMR in D₂O

[Fig. 35]
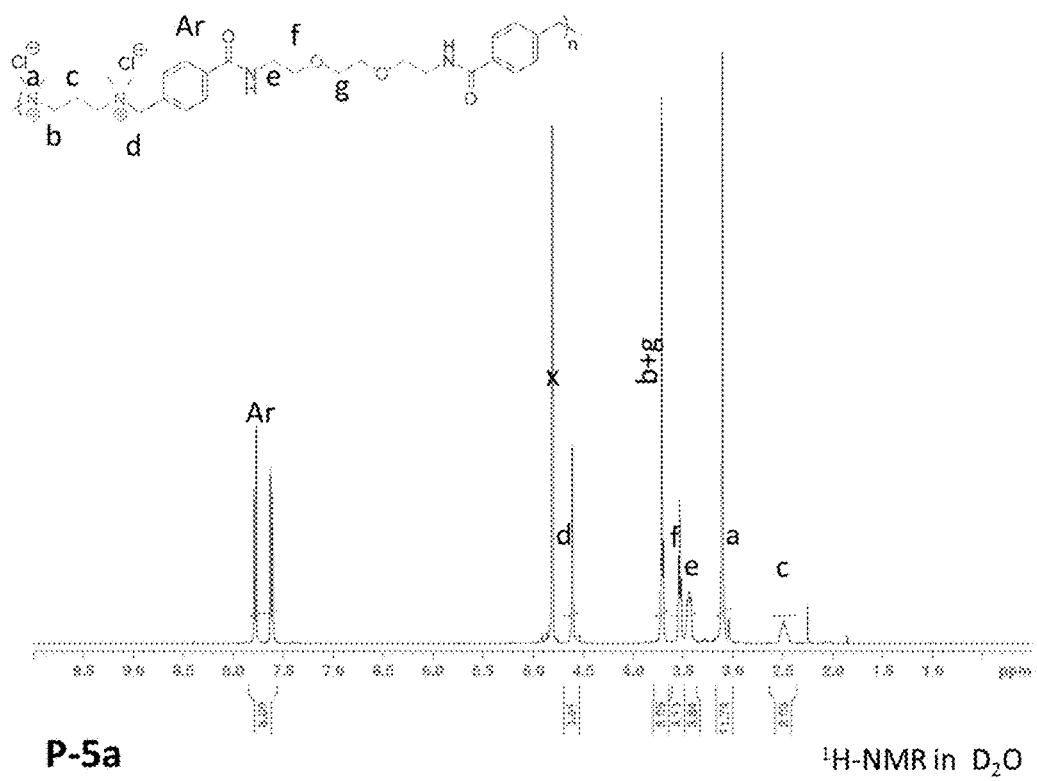
P-5a  $^1$H-NMR in $D_2O$
[Fig. 36]
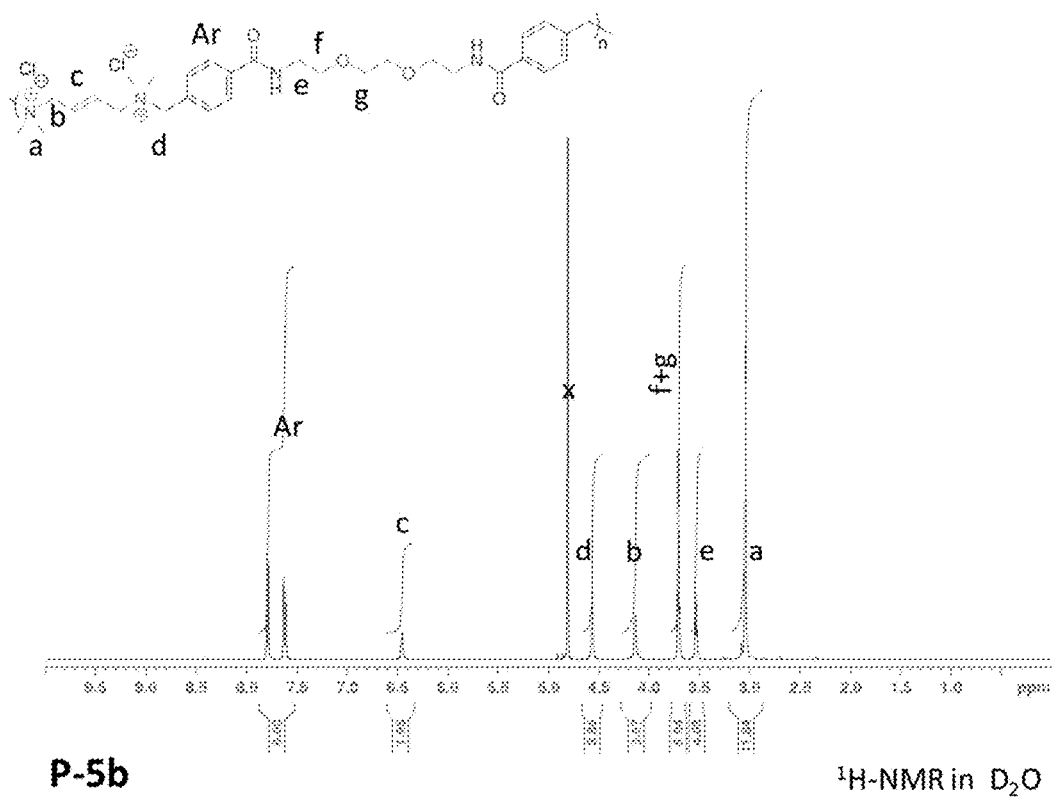
P-5b  $^1$H-NMR in $D_2O$

[Fig. 37]
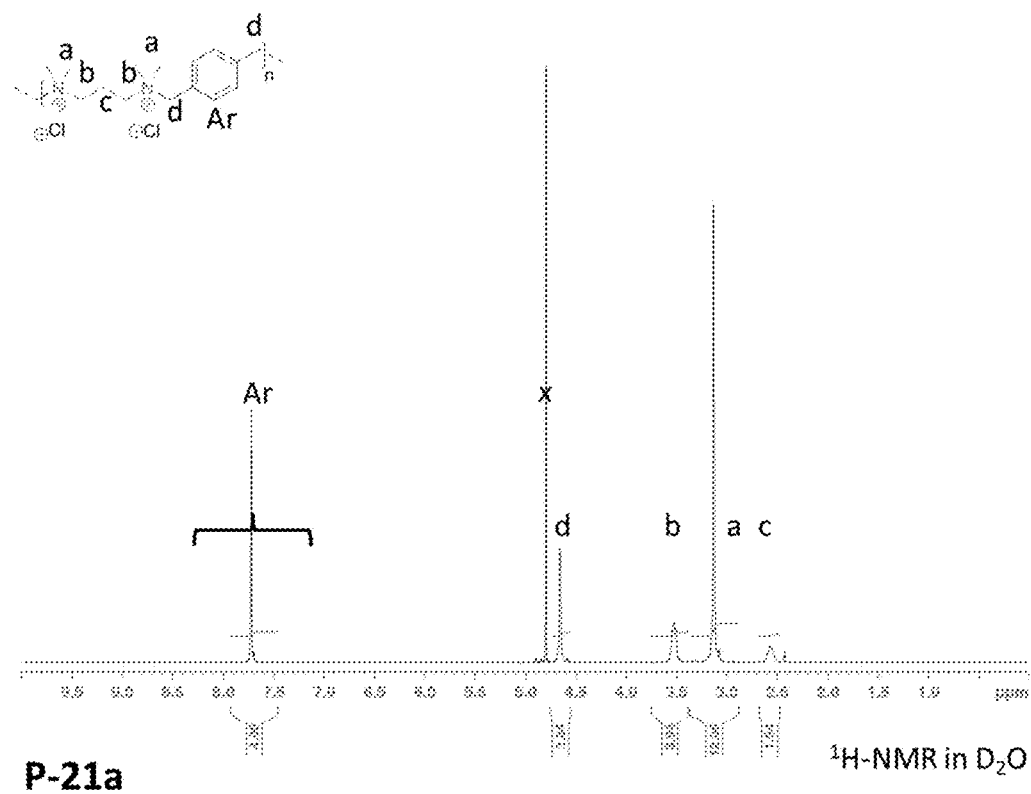
P-21a  $^1$H-NMR in D$_2$O
[Fig. 38]
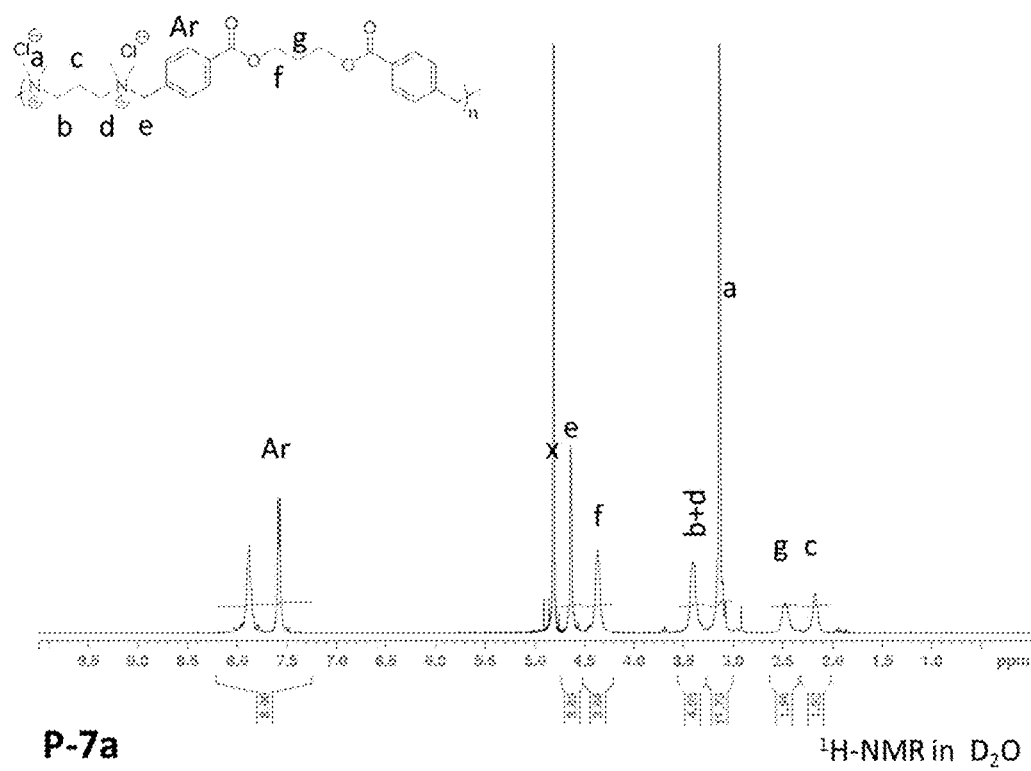
P-7a  $^1$H-NMR in D$_2$O

[Fig. 39]
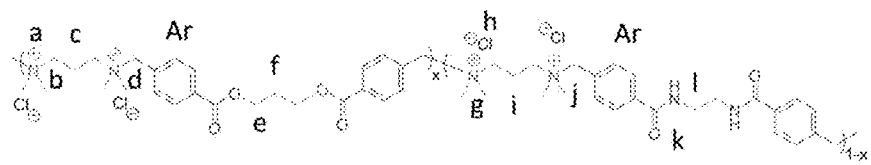
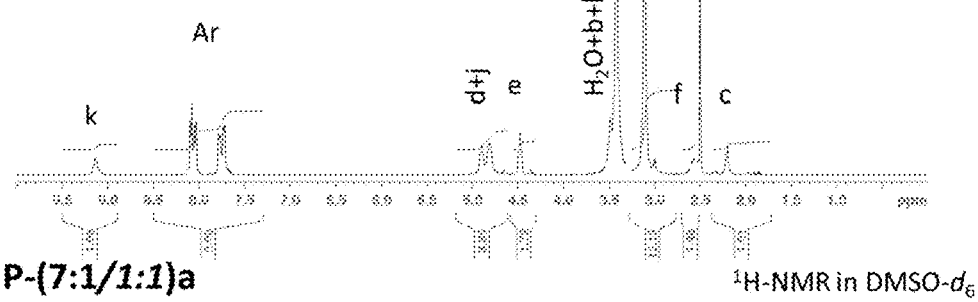
Estimation of ratio
(k) x = 1 − (1.42/2) ≈ 0.47;
1−x ≈ 0.53
P-(7:1/1:1)a  $^1$H-NMR in DMSO-$d_6$
7012A
Notes: Aromatic region integrated between 8.6 – 7.3 ppm and assigned as 8; -NH- protons corresponding to amides were integrated between 9.5 – 8.9 ppm and compared with the theoretical value of 2.00 for the polymer were to be of P-1a
[Fig. 40]
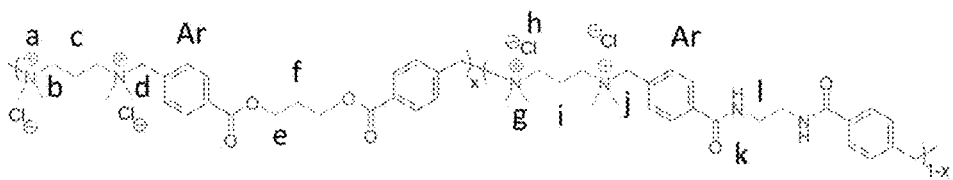
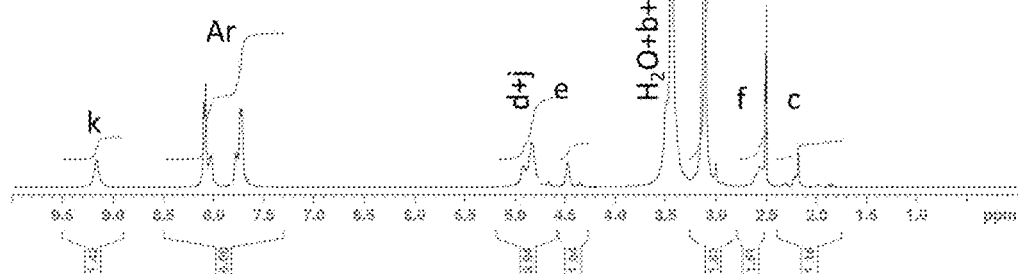
Estimation of ratio
(k) x = 1 − (1.42/2) ≈ 0.29;
1−x ≈ 0.71
P-(7:1/3:7)a  $^1$H-NMR in DMSO-$d_6$

[Fig. 41]
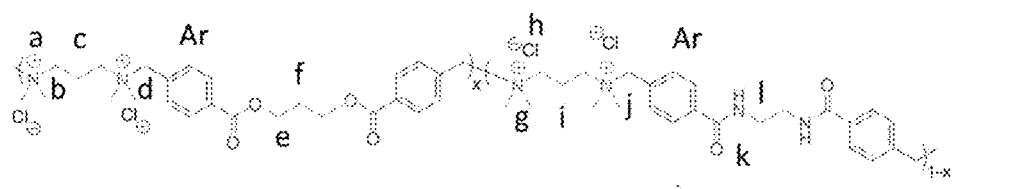
Estimation of ratio
(k) $x \approx 1 - (1.75/2) \approx 0.13$;
$1-x \approx 0.87$
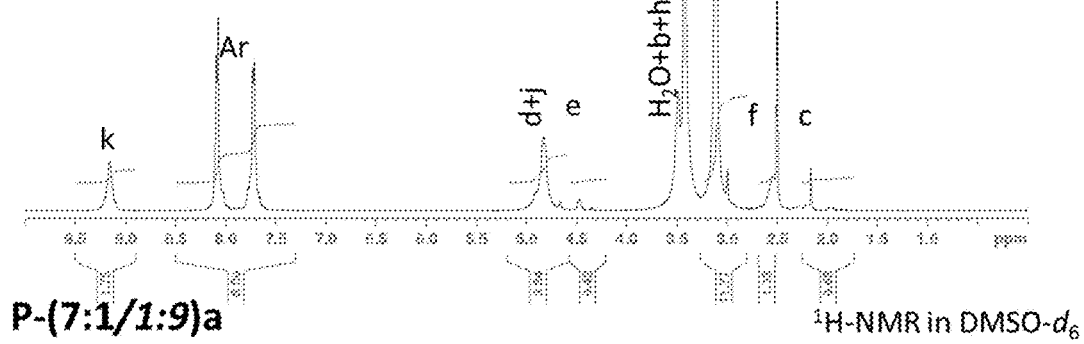
P-(7:1/1:9)a  $^1$H-NMR in DMSO-$d_6$
[Fig. 42]
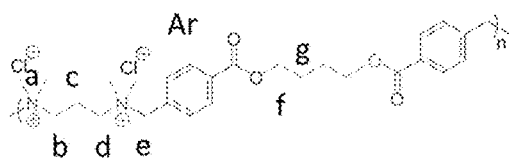
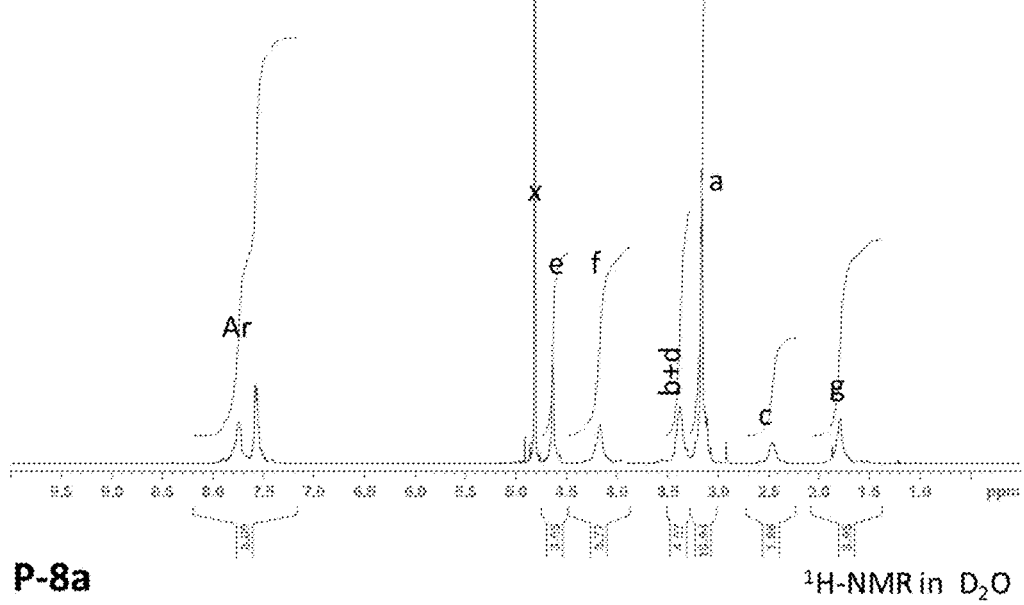
P-8a  $^1$H-NMR in D$_2$O

[Fig. 43]
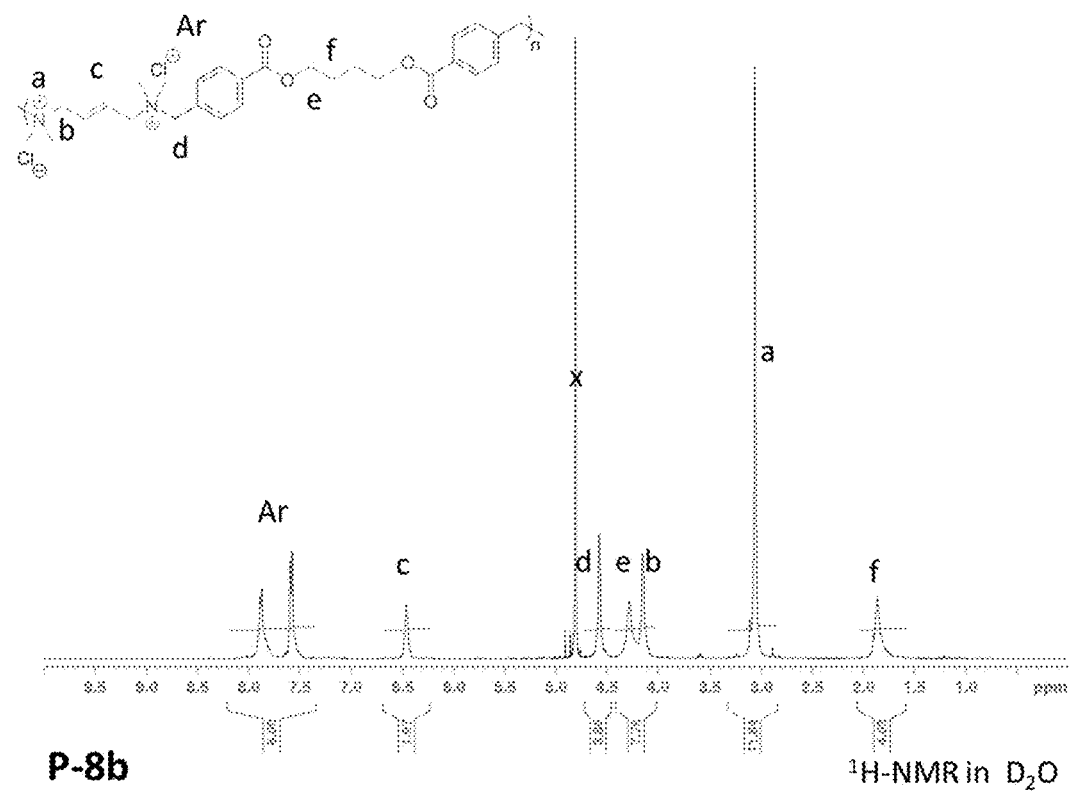
P-8b    ¹H-NMR in D₂O
[Fig. 44]
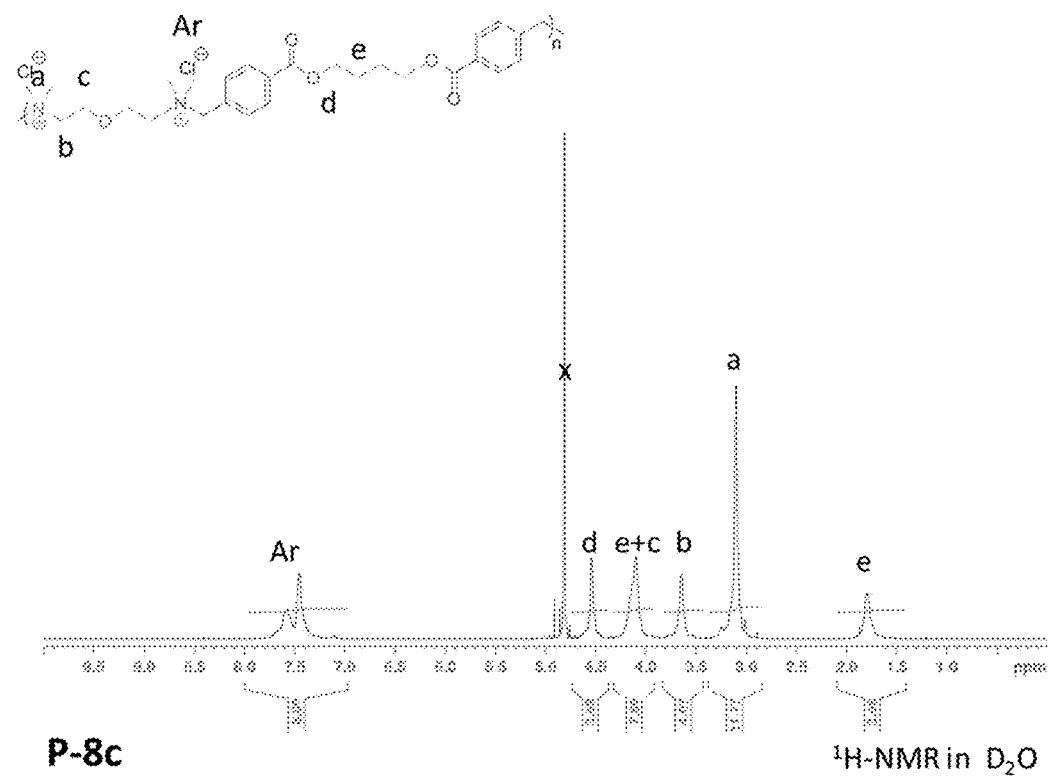
P-8c    ¹H-NMR in D₂O

[Fig. 45]
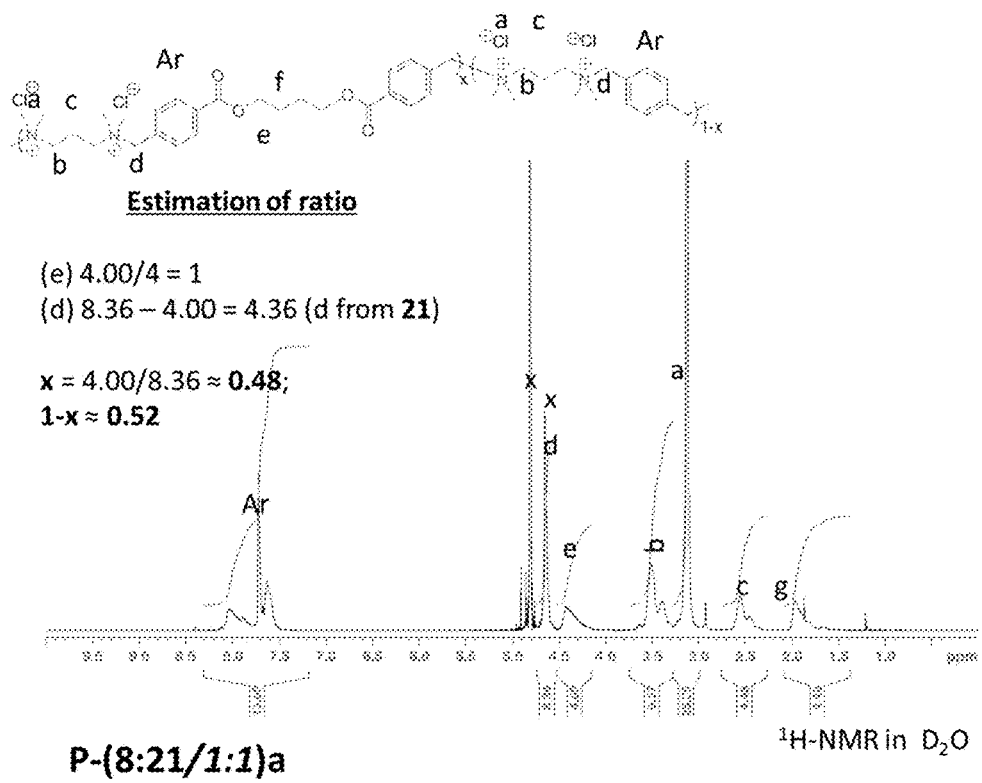
P-(8:21/1:1)a
[Fig. 46]
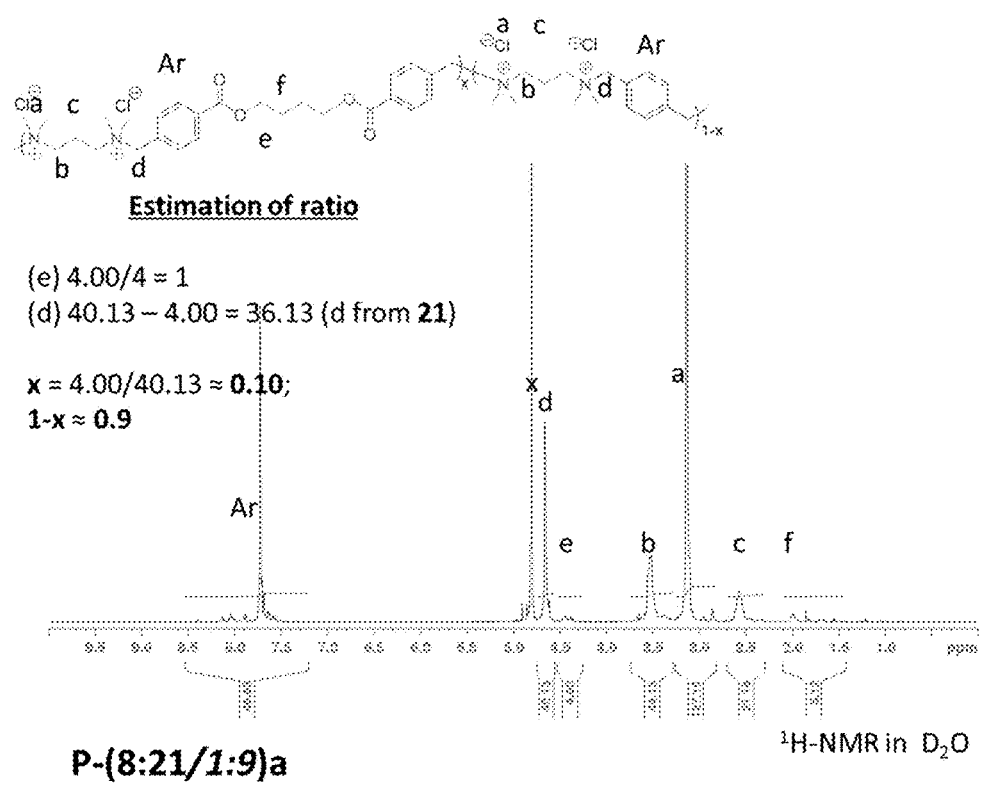
P-(8:21/1:9)a

[Fig. 47]
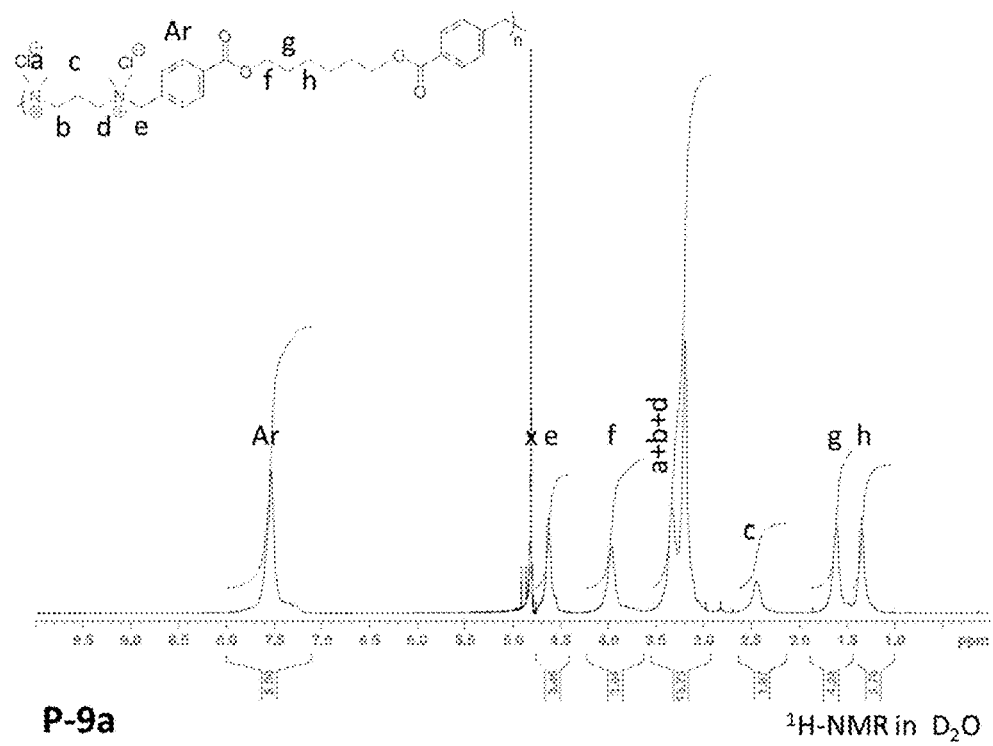
P-9a — $^1$H-NMR in $D_2O$
[Fig. 48]
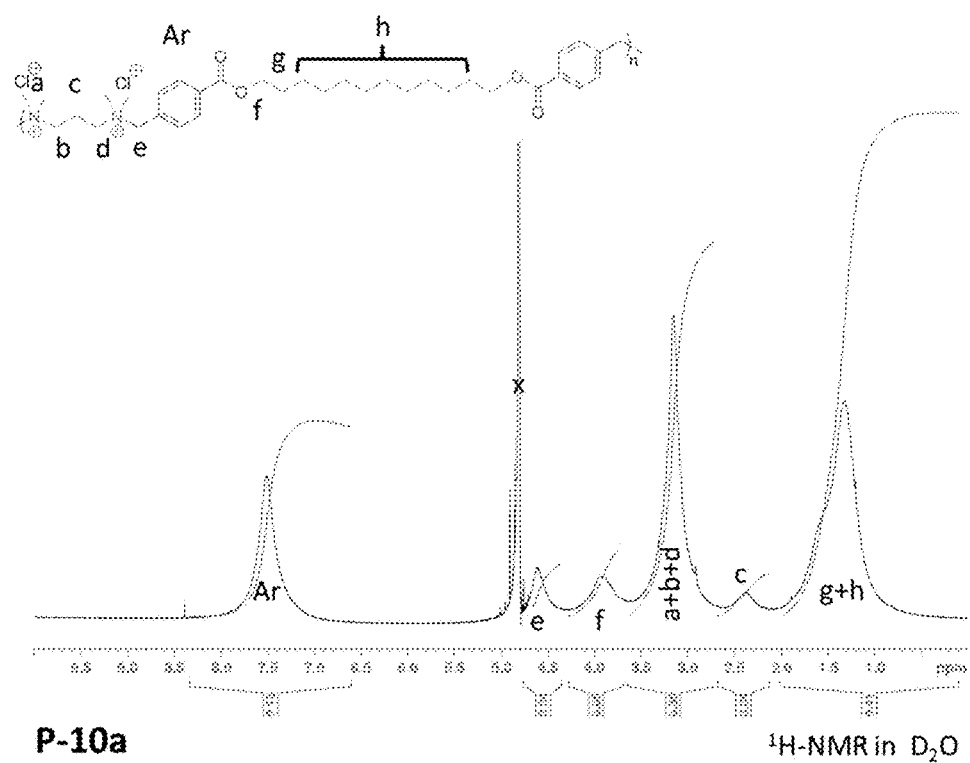
P-10a — $^1$H-NMR in $D_2O$
7007
Note: This sample has limited solubility in water (sample concentration ≈ 10 mg/600 uL $D_2O$), hence peaks are broad.

[Fig. 49]
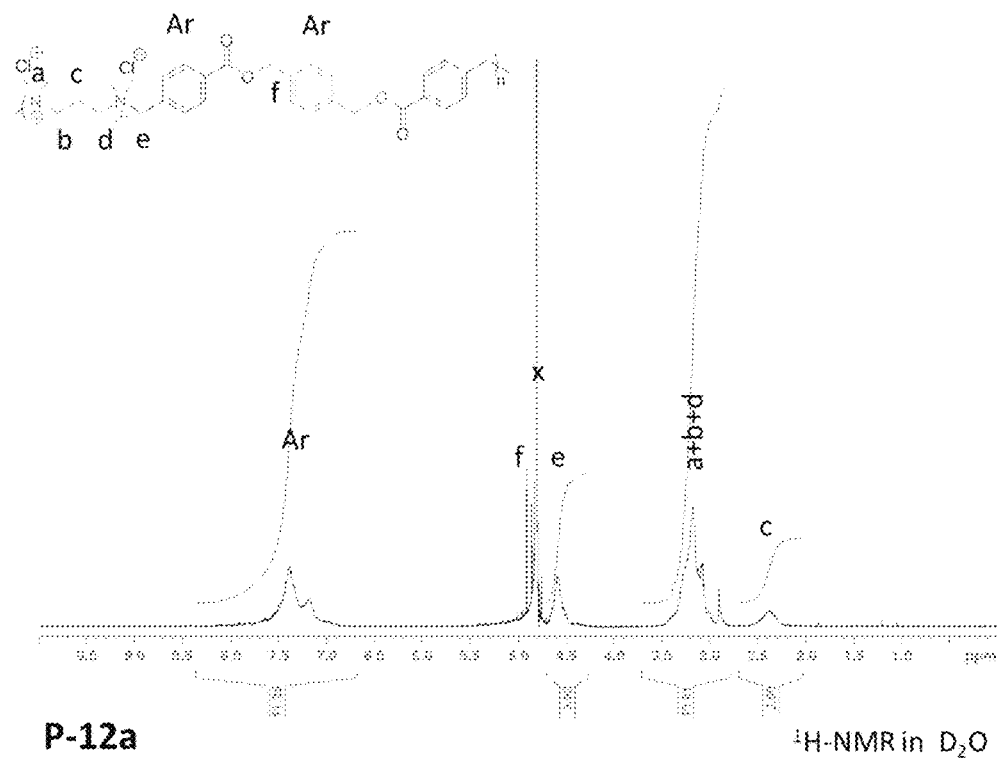
P-12a
7006
$^1$H-NMR in $D_2O$
Note: This sample has limited solubility in water (sample concentration ≈ 10 mg/600 uL D$_2$O), hence peaks are broad. Proton f, likely buried in the residual solvent peak near 4.8 ppm
[Fig. 50]
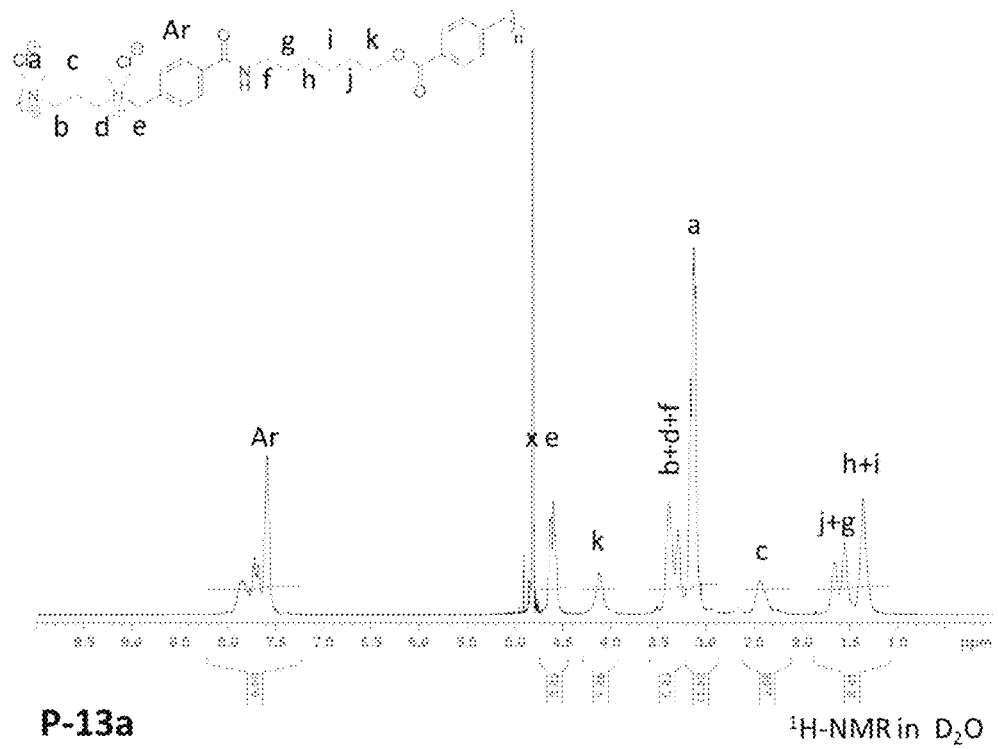
P-13a
$^1$H-NMR in $D_2O$

[Fig. 51]
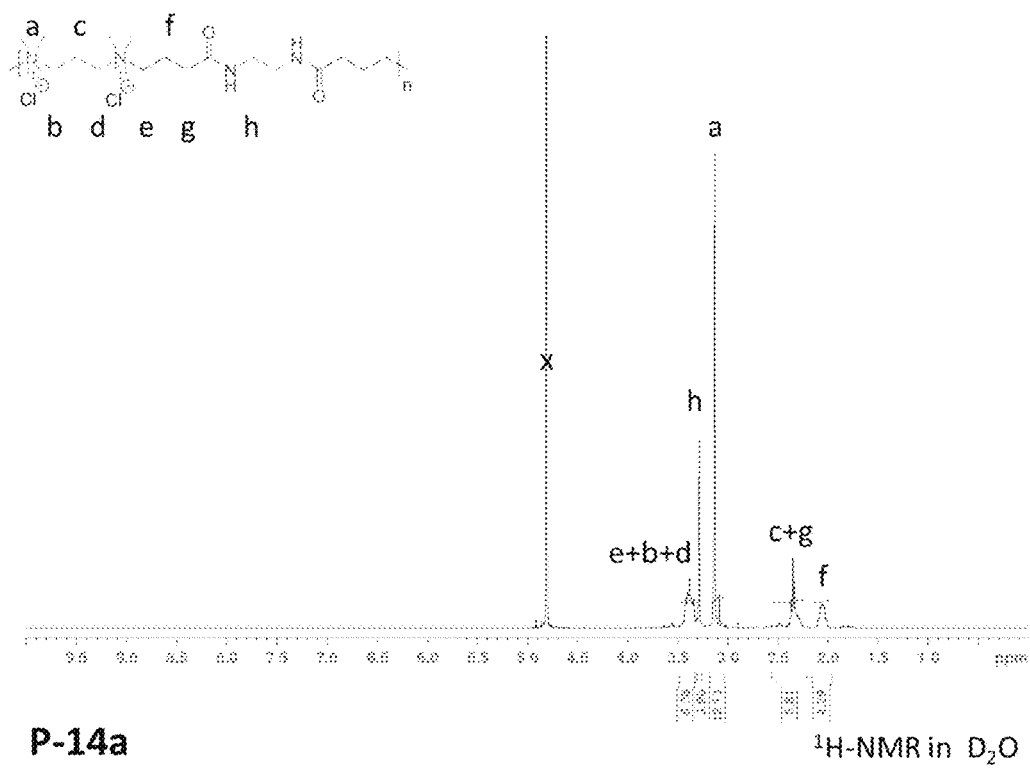
[Fig. 52]
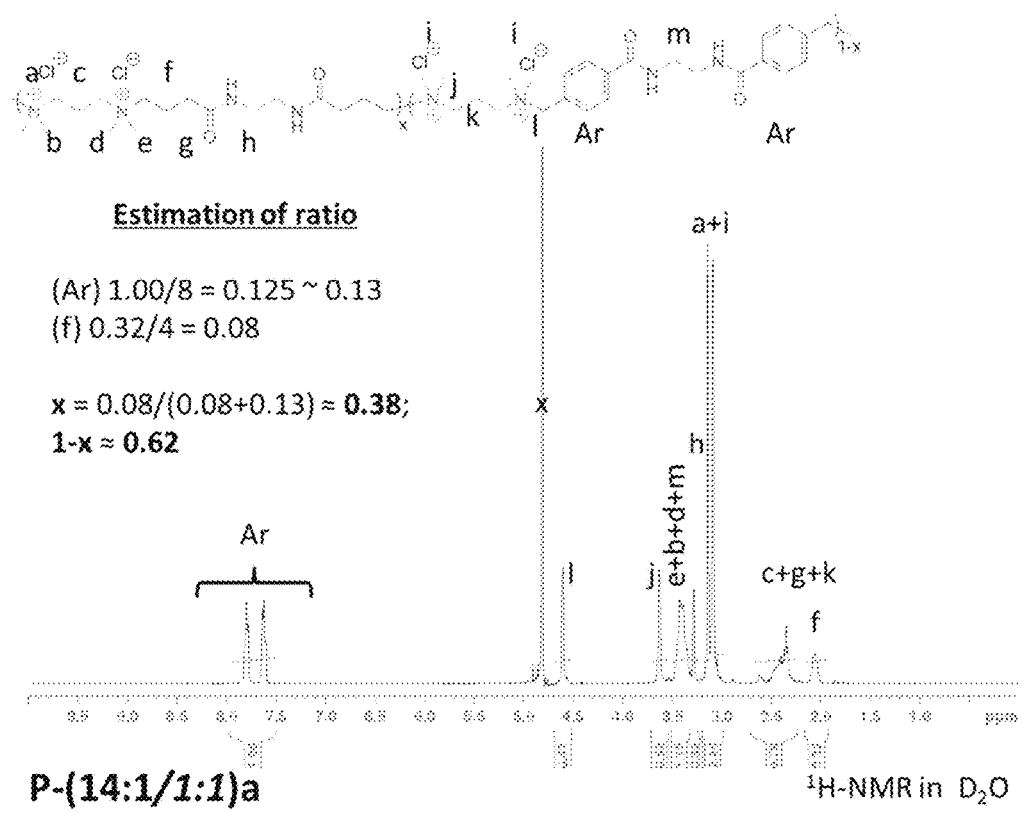

[Fig. 53]
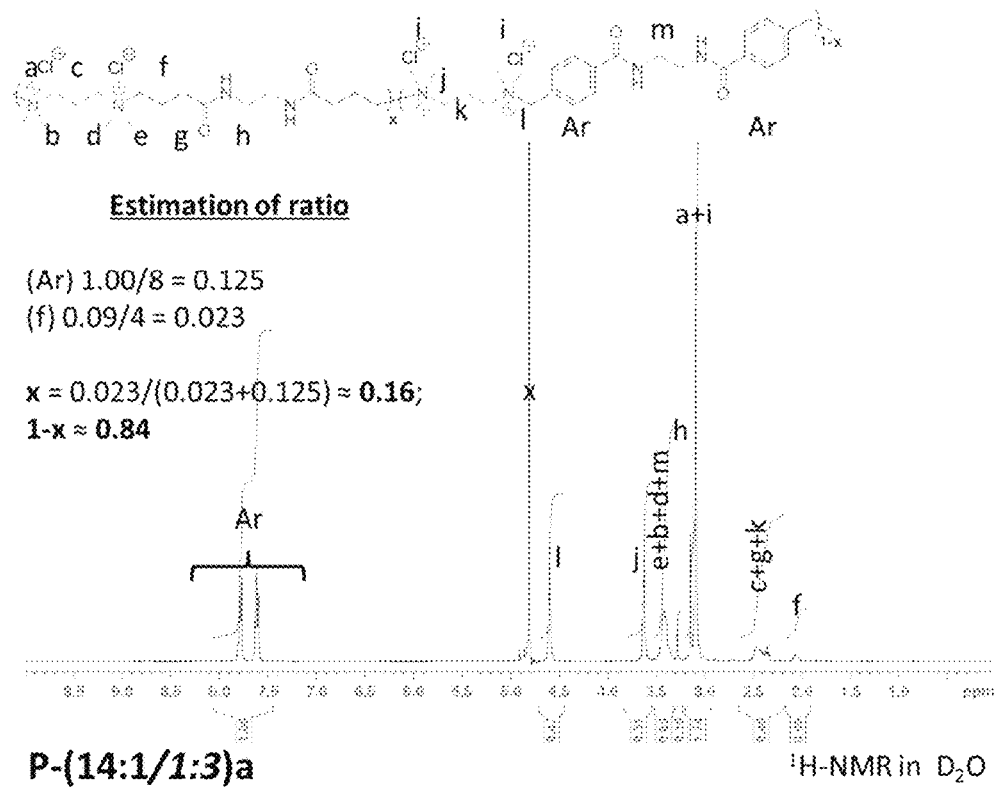
P-(14:1/1:3)a
[Fig. 54]
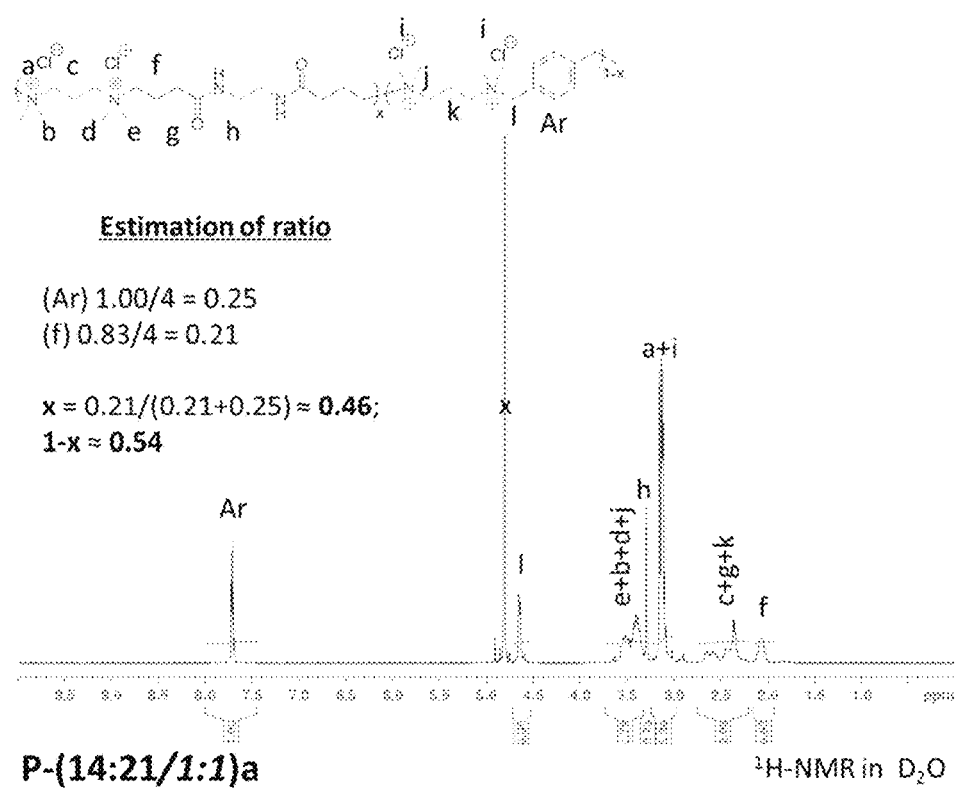
P-(14:21/1:1)a

[Fig. 55]
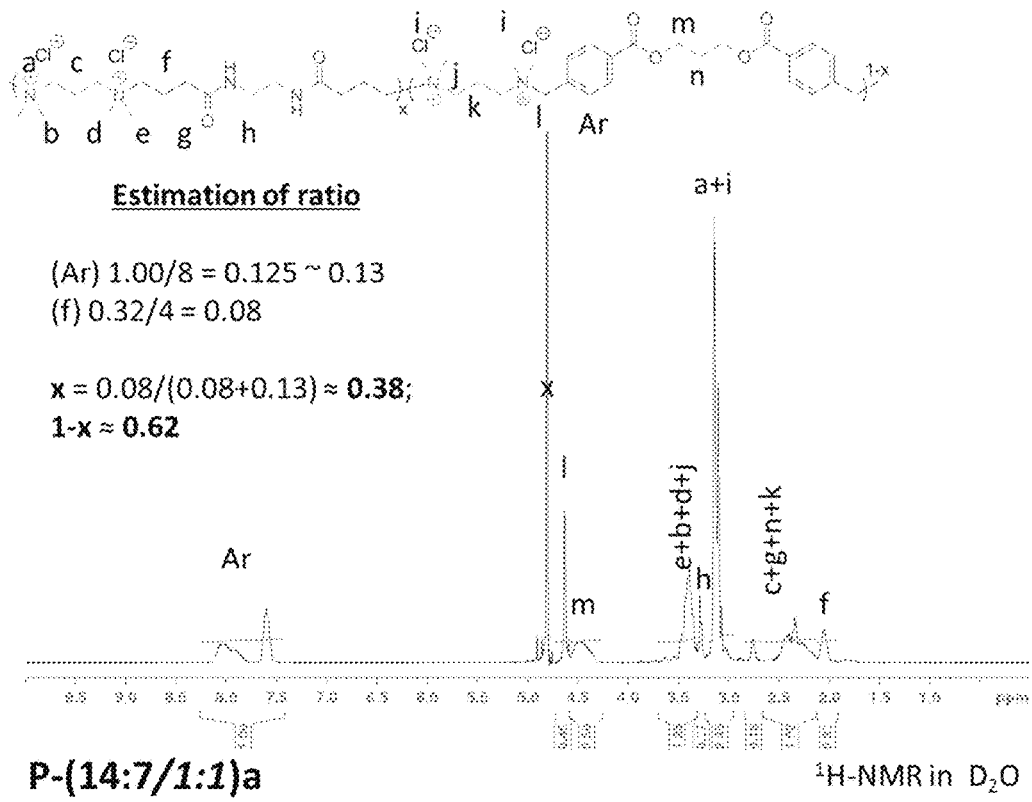
P-(14:7/1:1)a ¹H-NMR in D₂O
[Fig. 56]
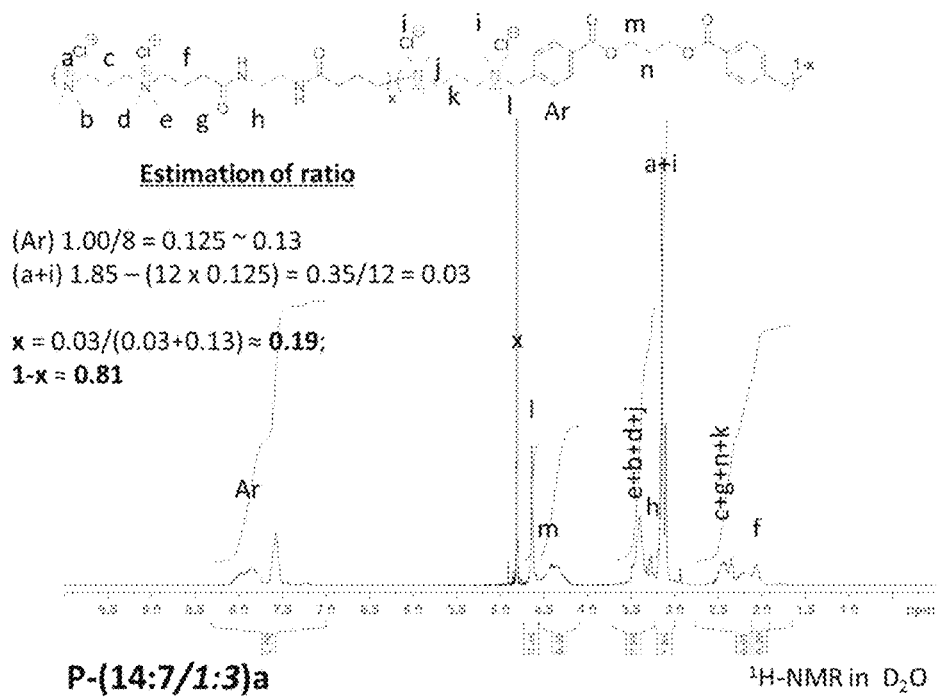
P-(14:7/1:3)a ¹H-NMR in D₂O
7070D
Note: As proton f significantly overlapped with the rest, estimation of ratio was conducted by back-calculation from a+i protons

[Fig. 57]
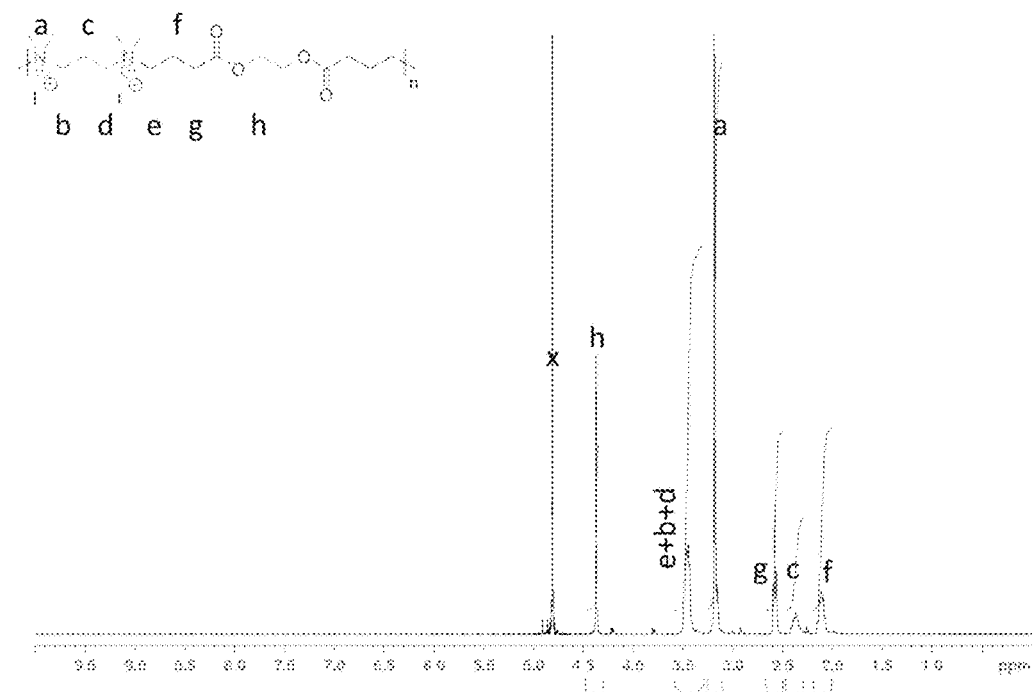
P-17a      ¹H-NMR in D₂O
[Fig. 58]
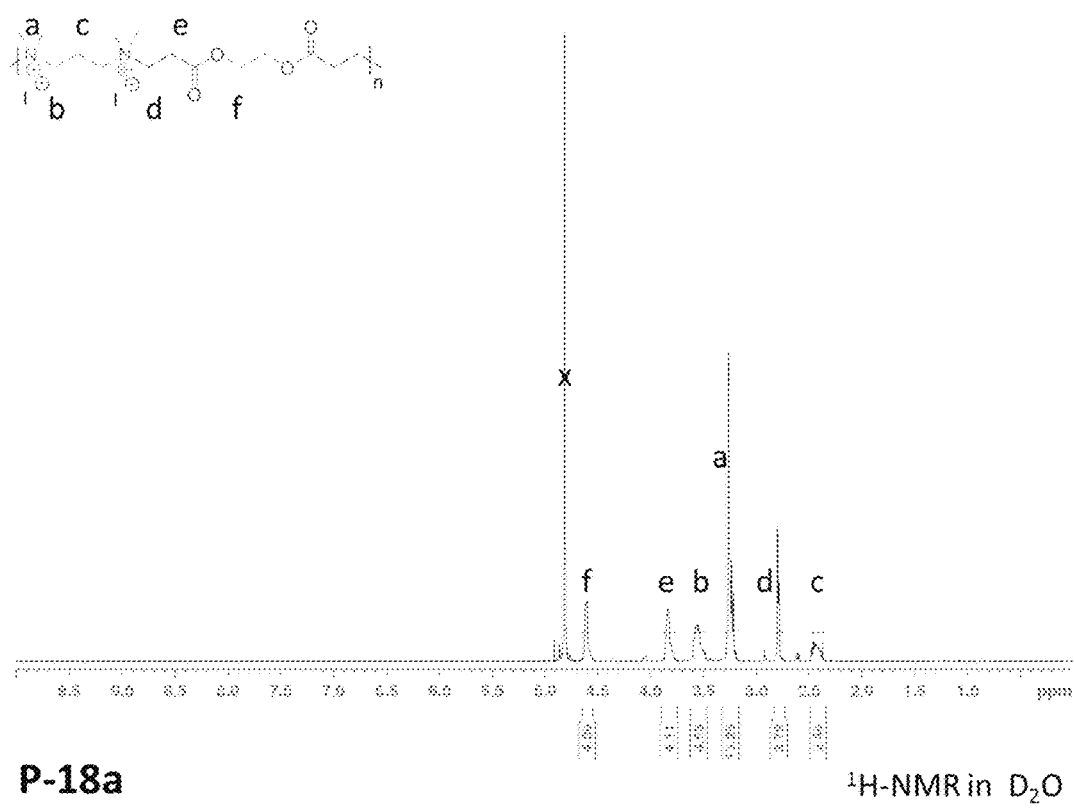
P-18a      ¹H-NMR in D₂O

[Fig. 59]
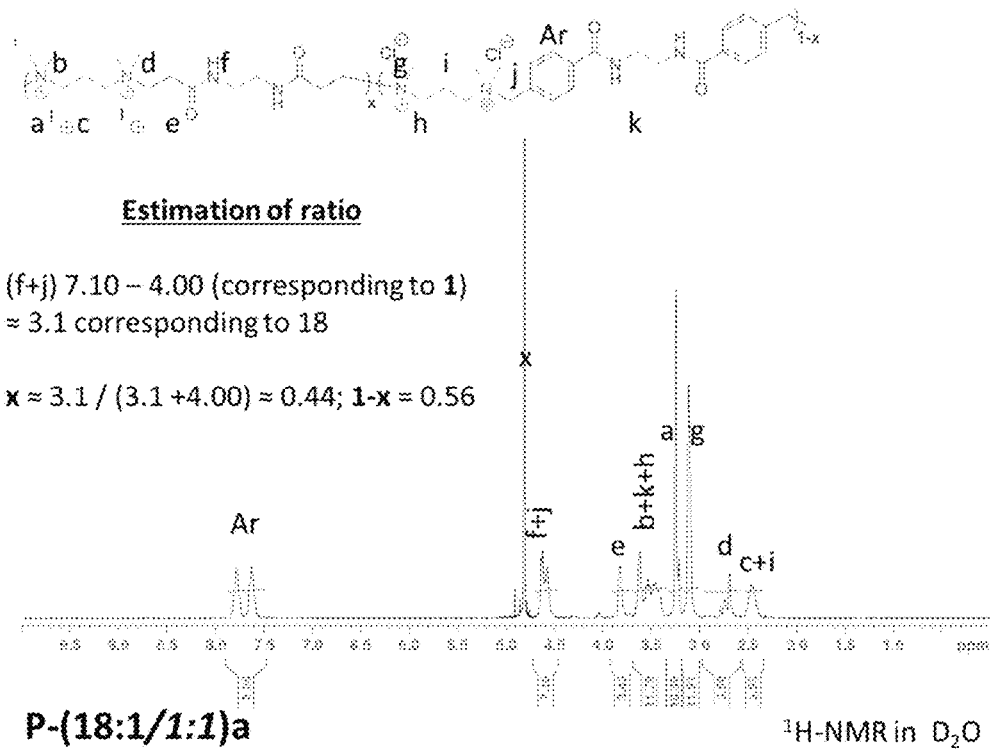
Estimation of ratio
(f+j) 7.10 – 4.00 (corresponding to 1)
≈ 3.1 corresponding to 18
x ≈ 3.1 / (3.1 + 4.00) ≈ 0.44; 1-x = 0.56
P-(18:1/1:1)a　　　　$^1$H-NMR in D$_2$O
[Fig. 60]
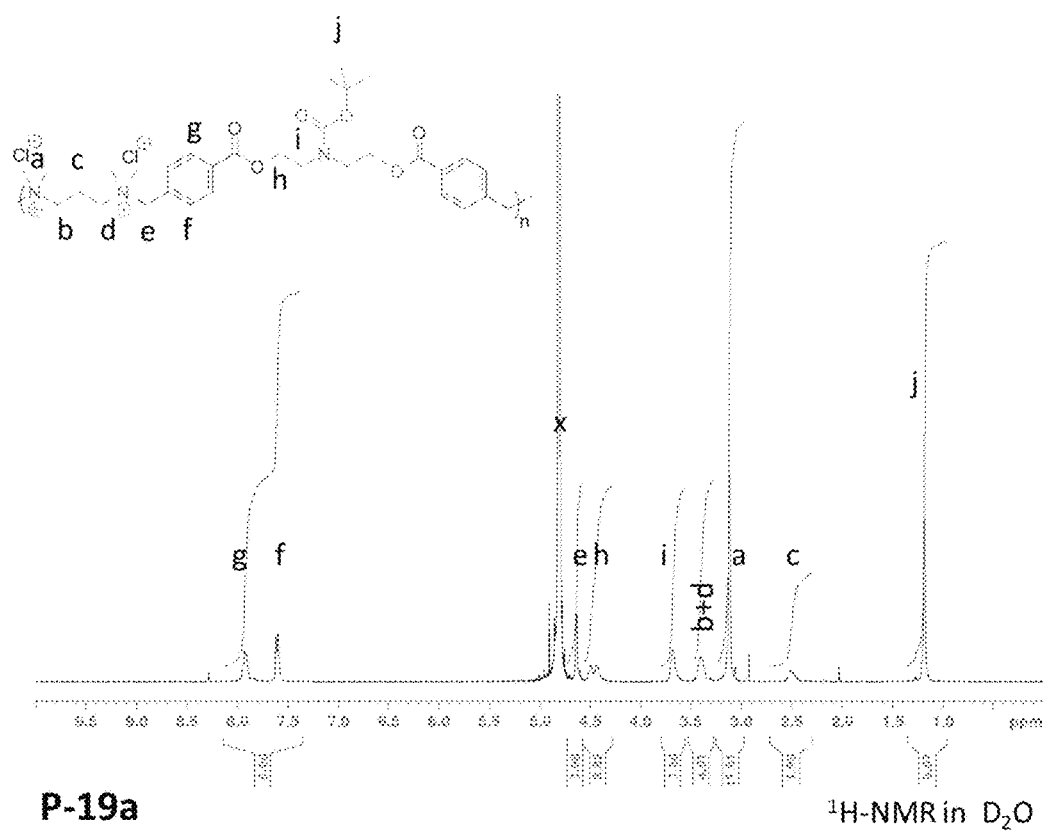
P-19a　　　　$^1$H-NMR in D$_2$O

[Fig. 61]
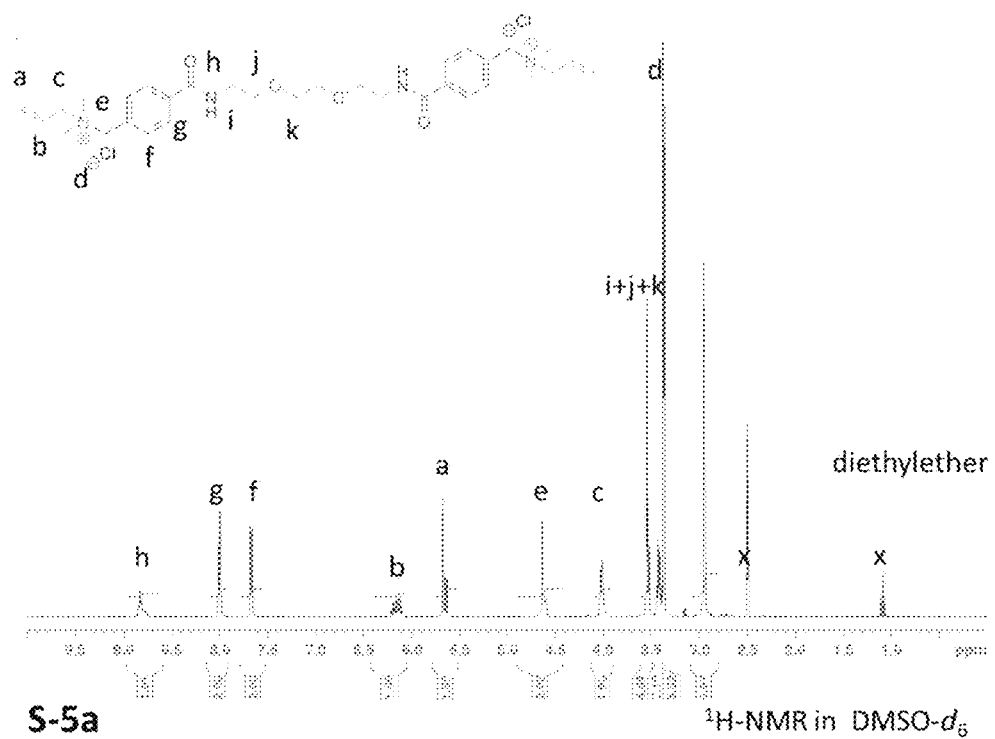
S-5a  $^1$H-NMR in DMSO-$d_6$
[Fig. 62]
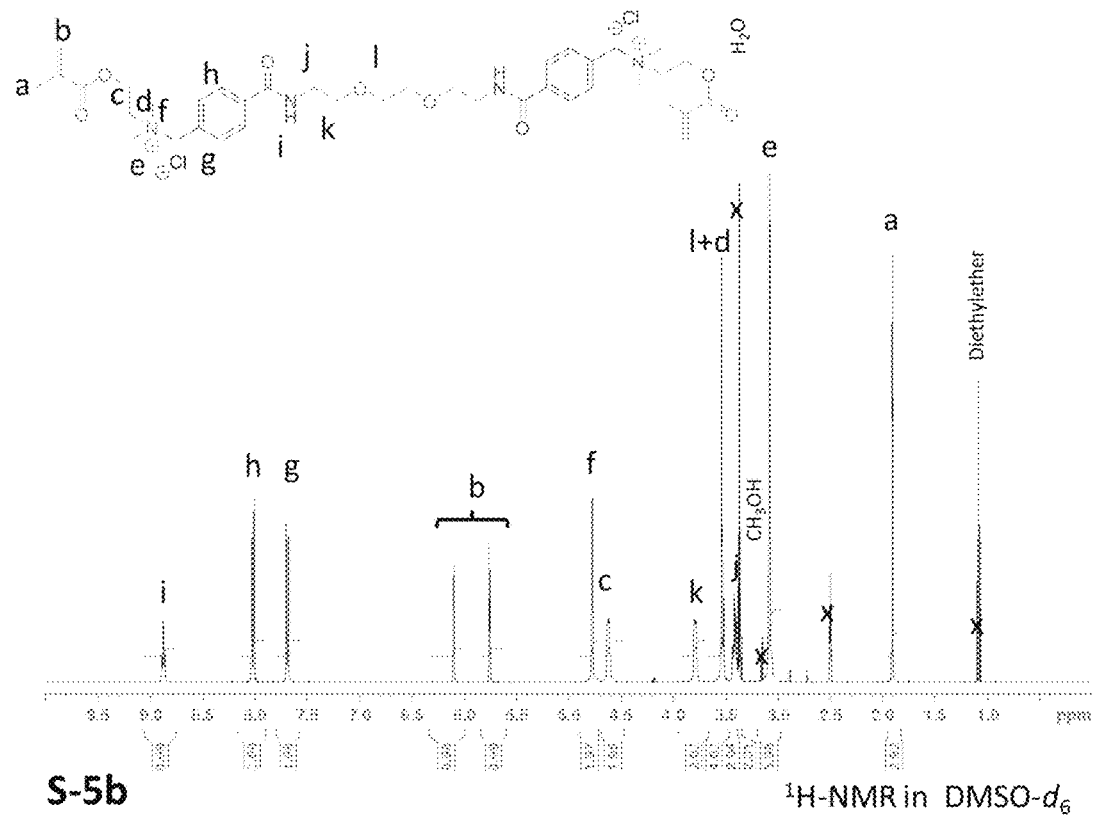
S-5b  $^1$H-NMR in DMSO-$d_6$

[Fig. 63]
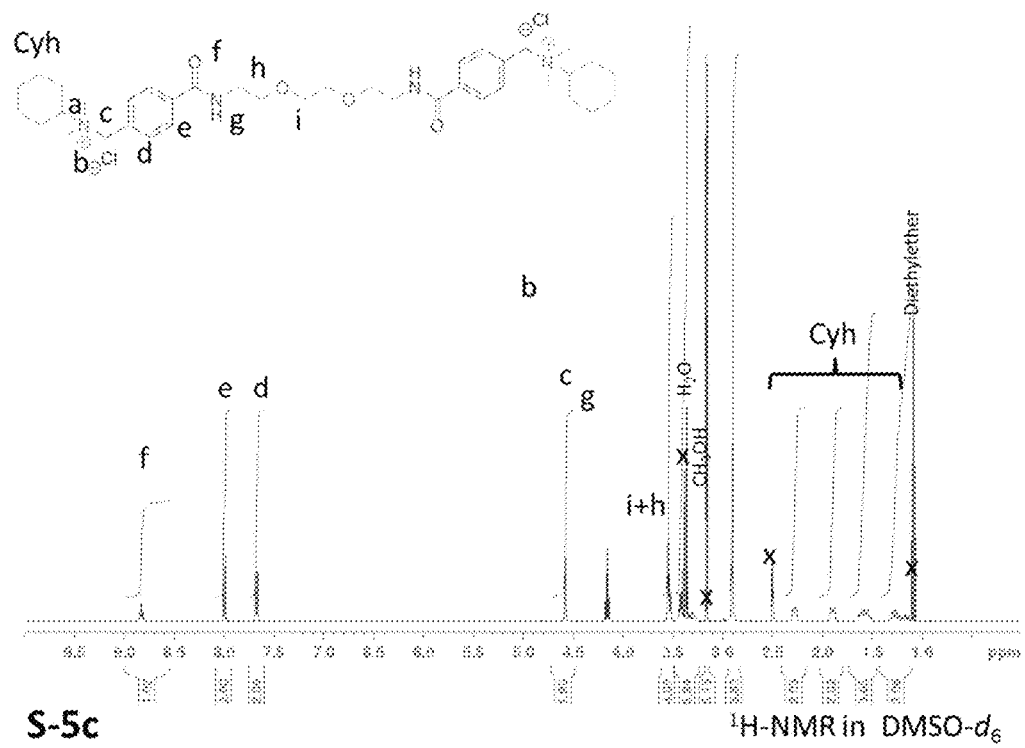
S-5c  $^1$H-NMR in DMSO-$d_6$
[Fig. 64]
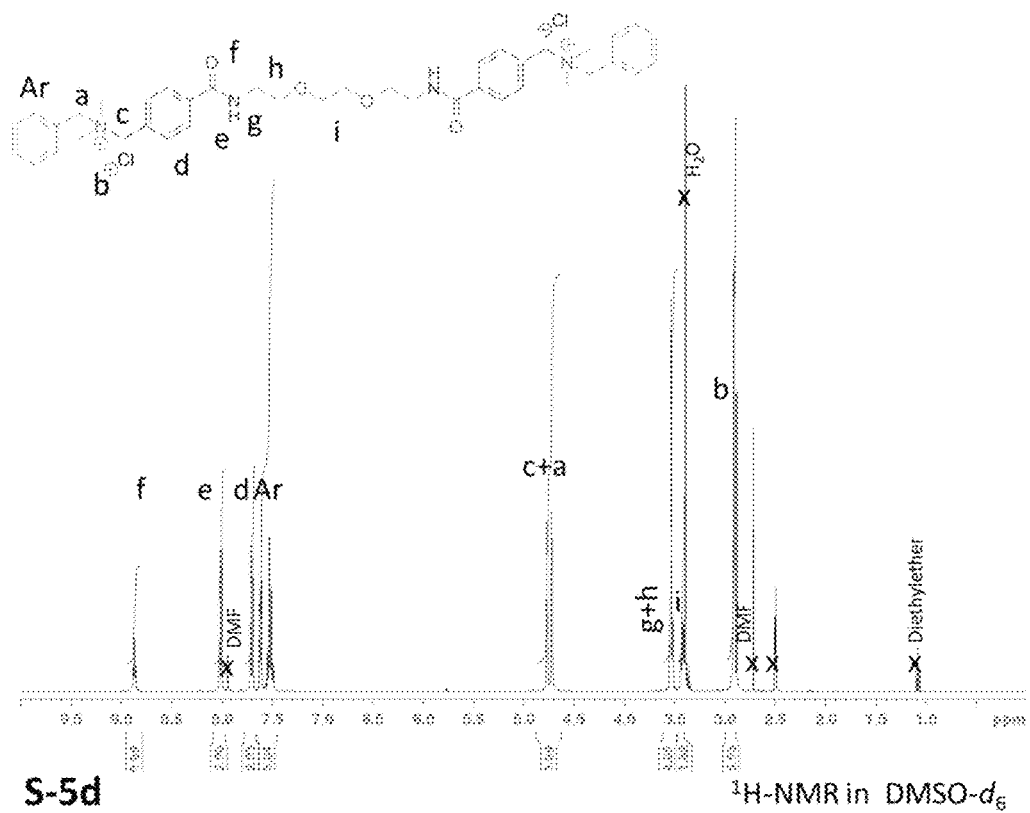
S-5d  $^1$H-NMR in DMSO-$d_6$

[Fig. 65]
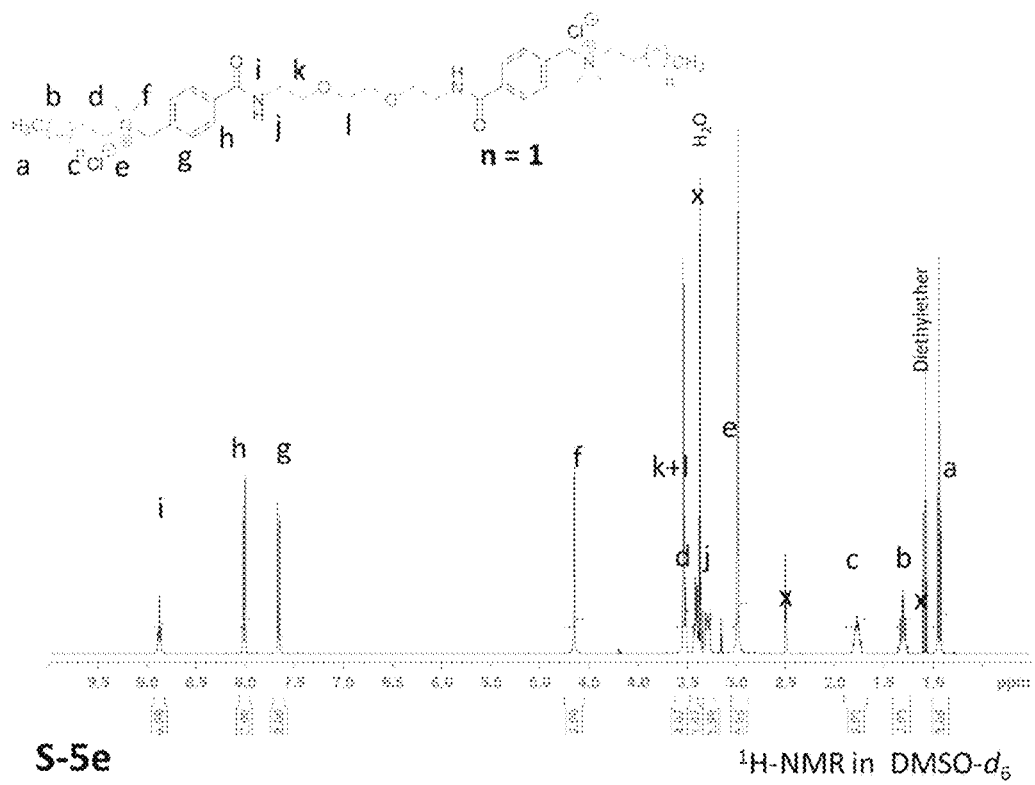
S-5e    $^1$H-NMR in DMSO-$d_6$
[Fig. 66]
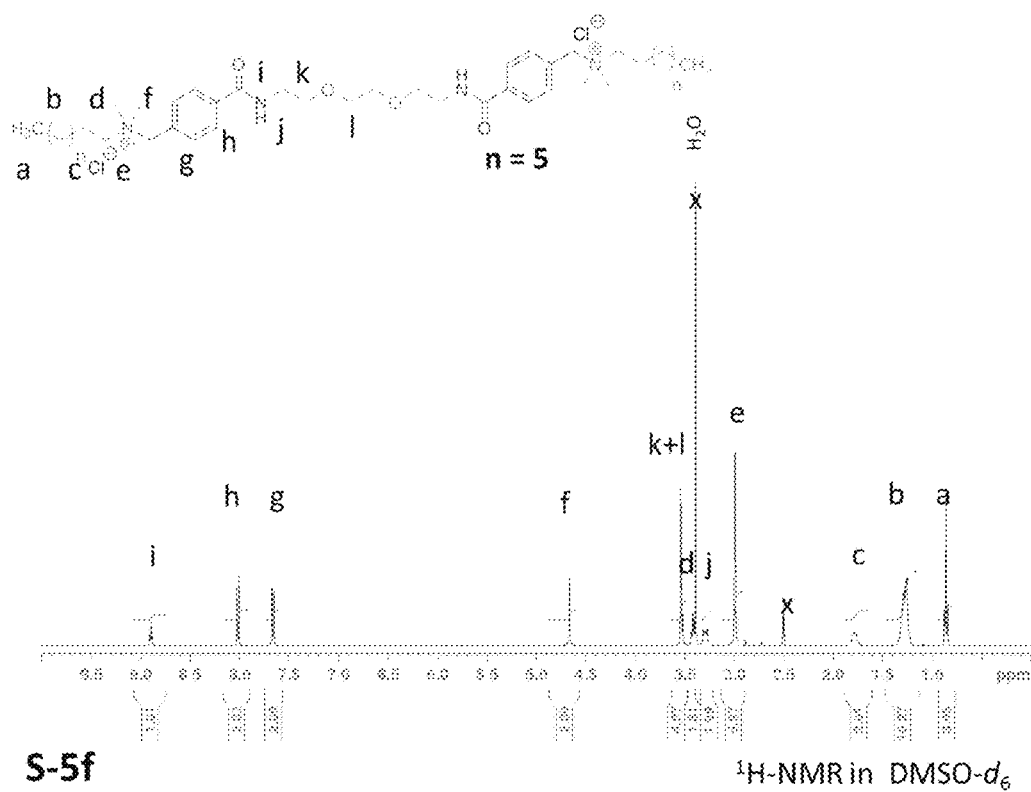
S-5f    $^1$H-NMR in DMSO-$d_6$

[Fig. 67]
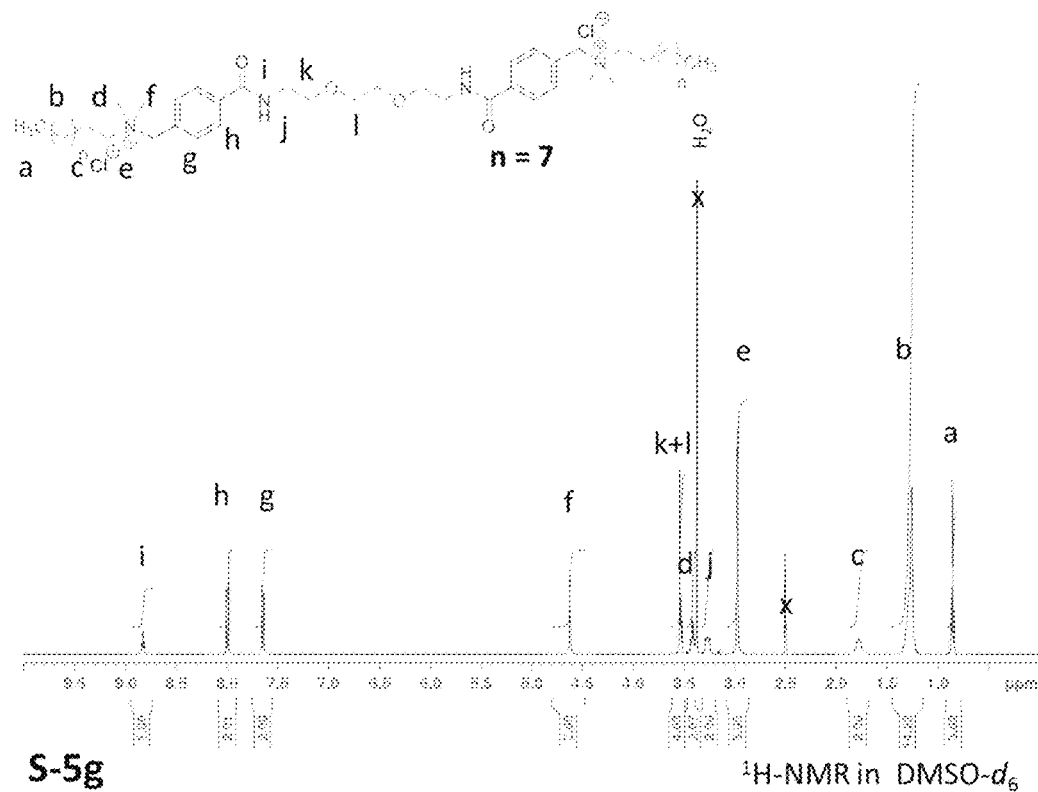
S-5g  $^1$H-NMR in DMSO-$d_6$
[Fig. 68]
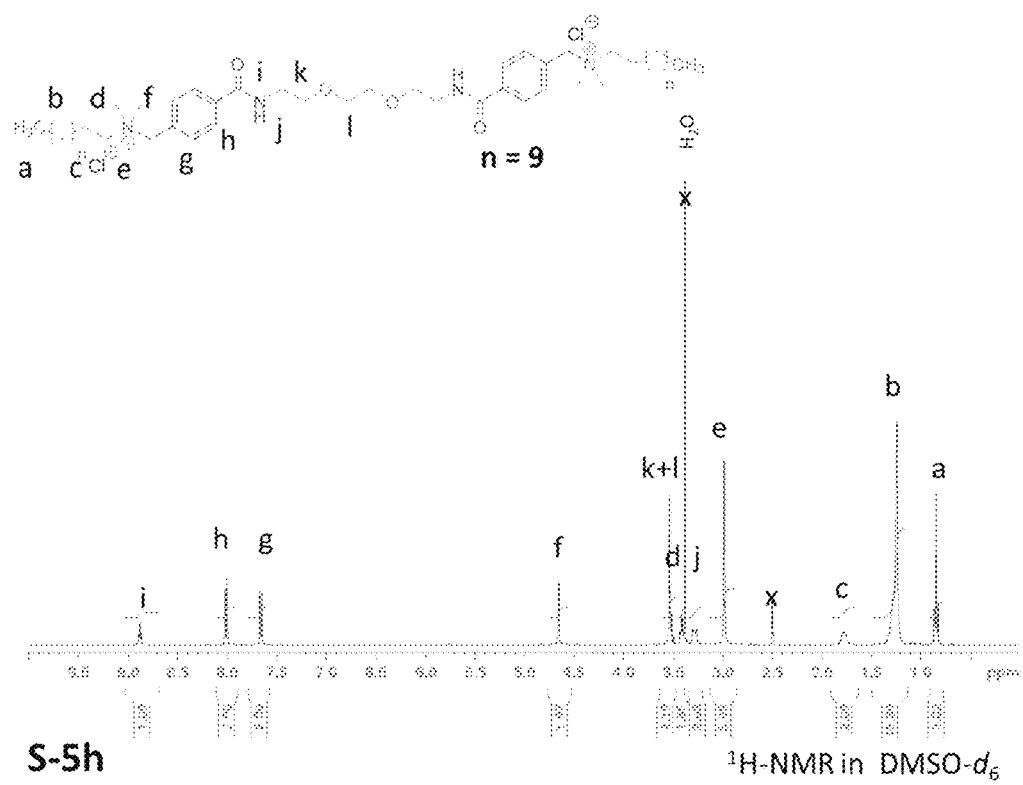
S-5h  $^1$H-NMR in DMSO-$d_6$

[Fig. 69]
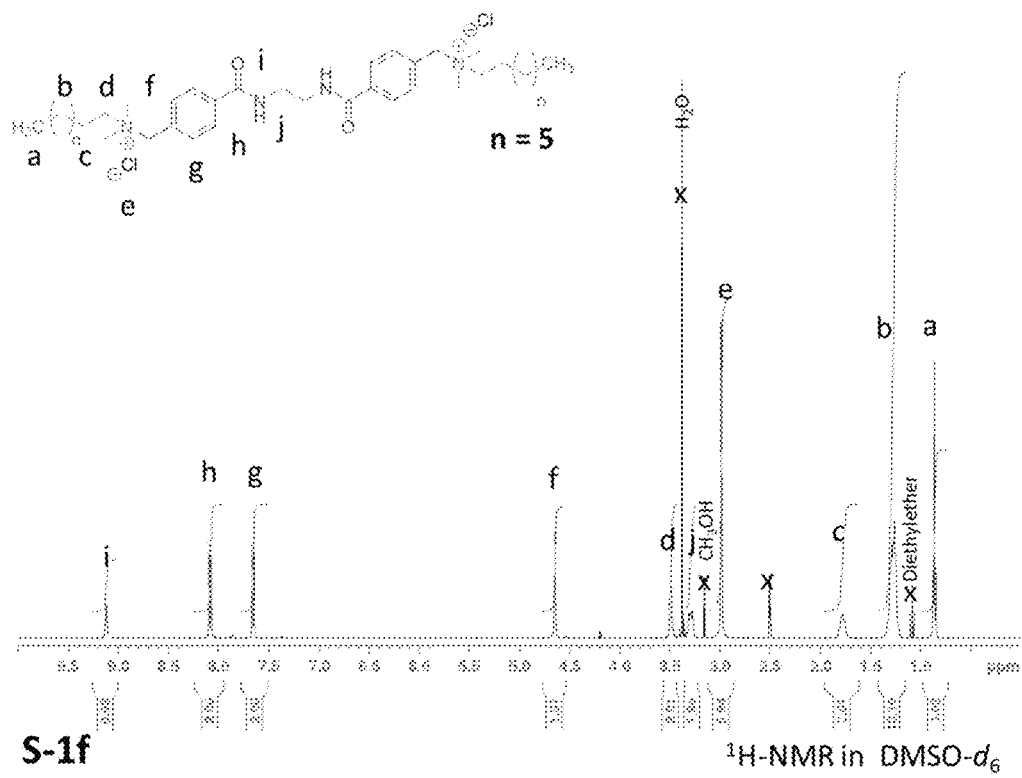
S-1f    $^1$H-NMR in DMSO-$d_6$
[Fig. 70]
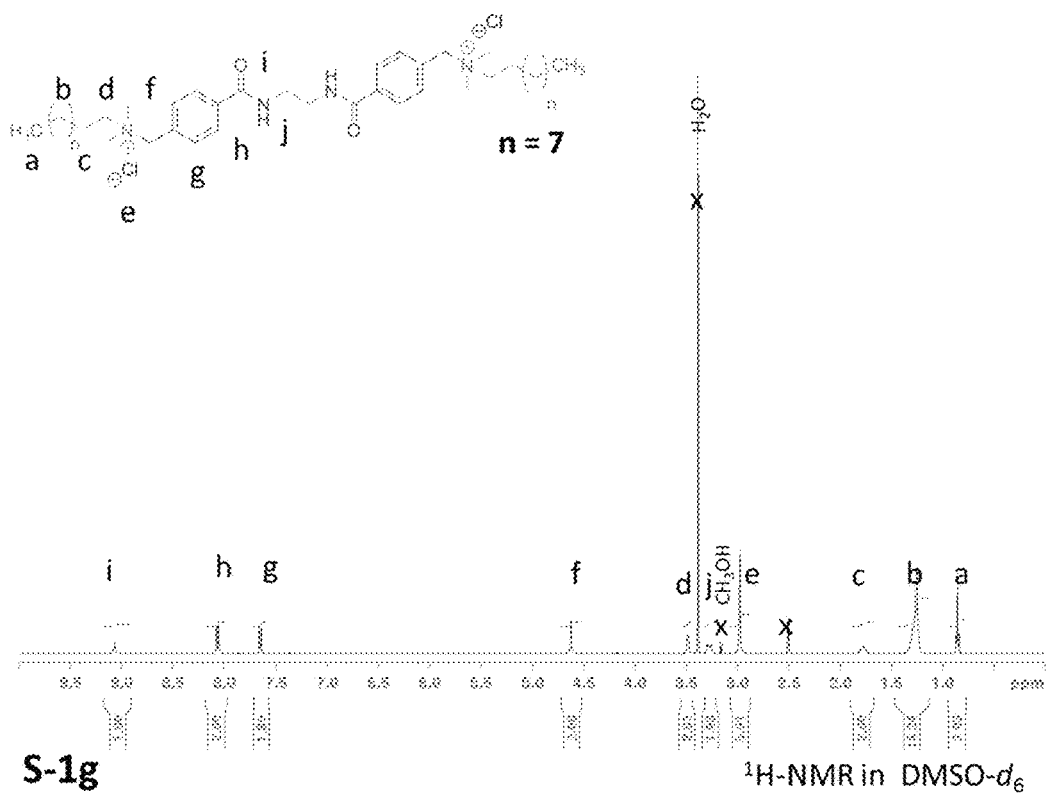
S-1g    $^1$H-NMR in DMSO-$d_6$

[Fig. 71]
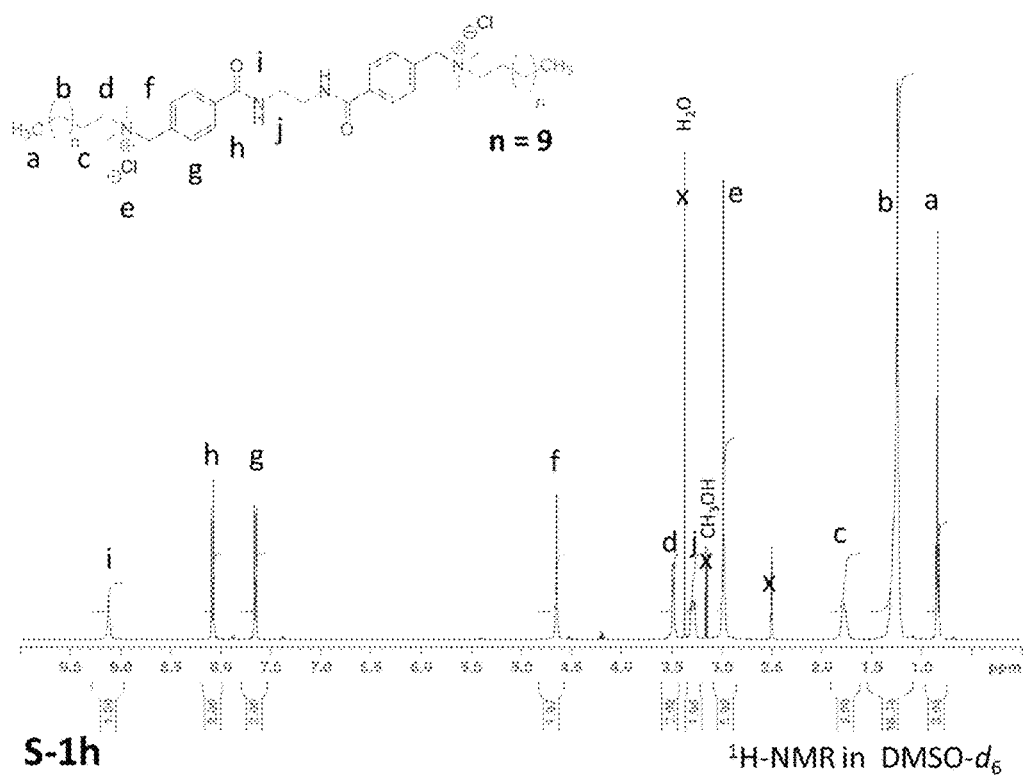
S-1h  $^1$H-NMR in DMSO-$d_6$
[Fig. 72]
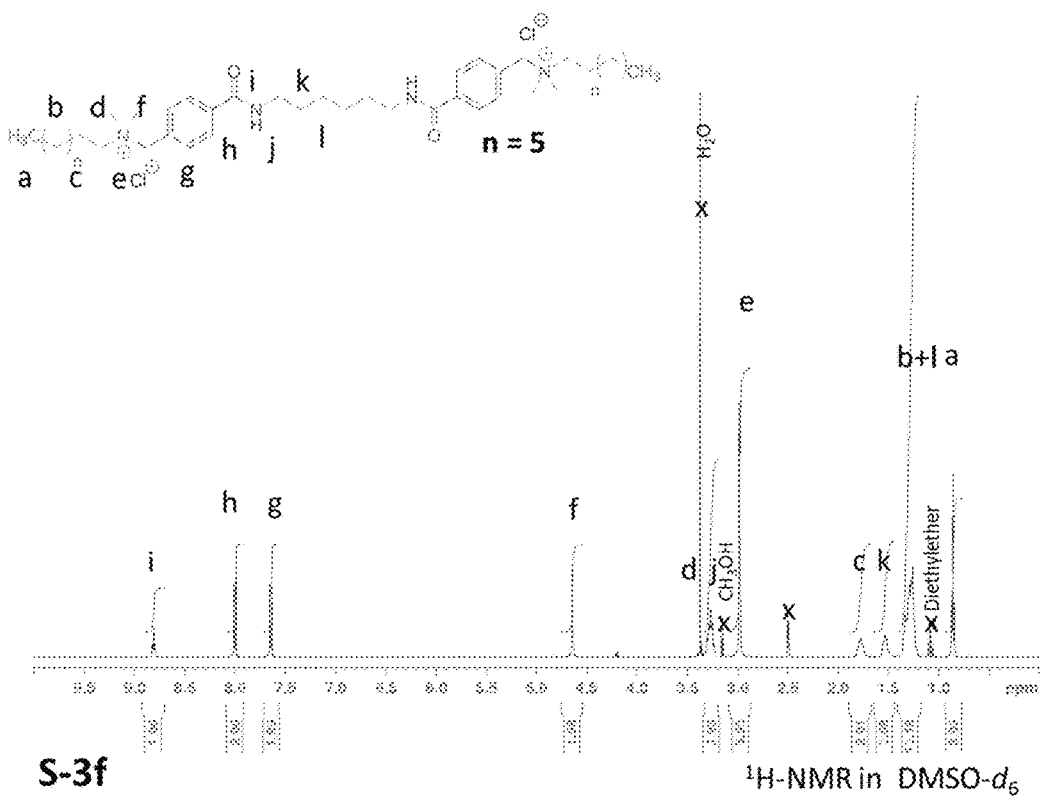
S-3f  $^1$H-NMR in DMSO-$d_6$

[Fig. 73]
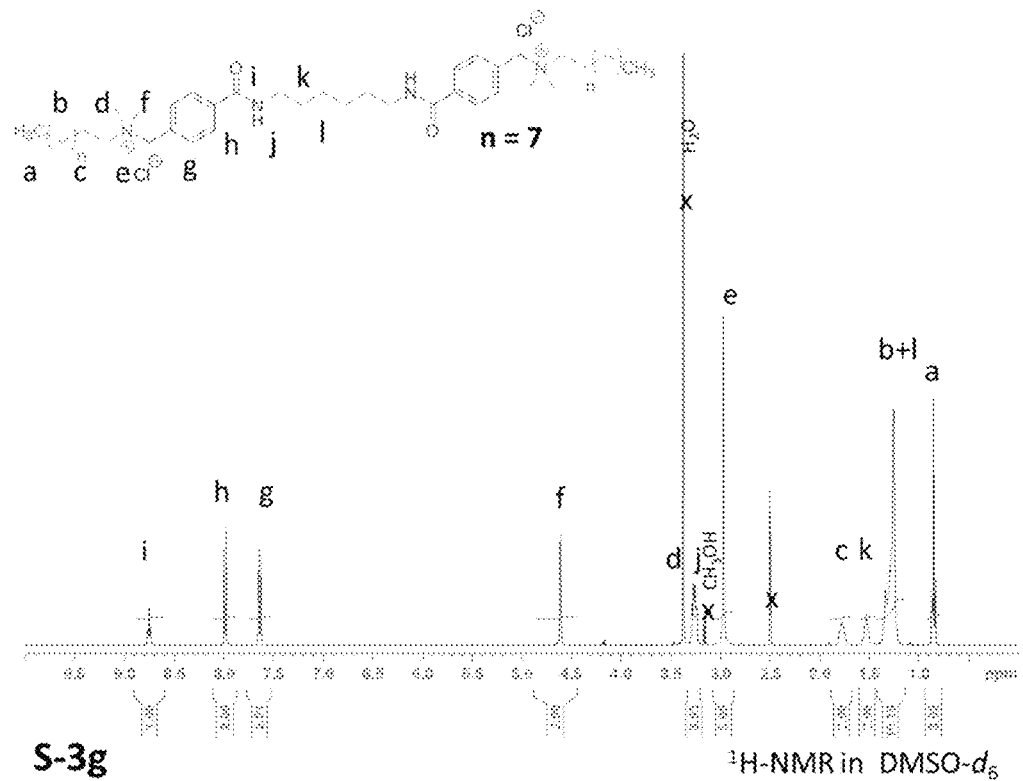
S-3g  ¹H-NMR in DMSO-$d_6$
[Fig. 74]
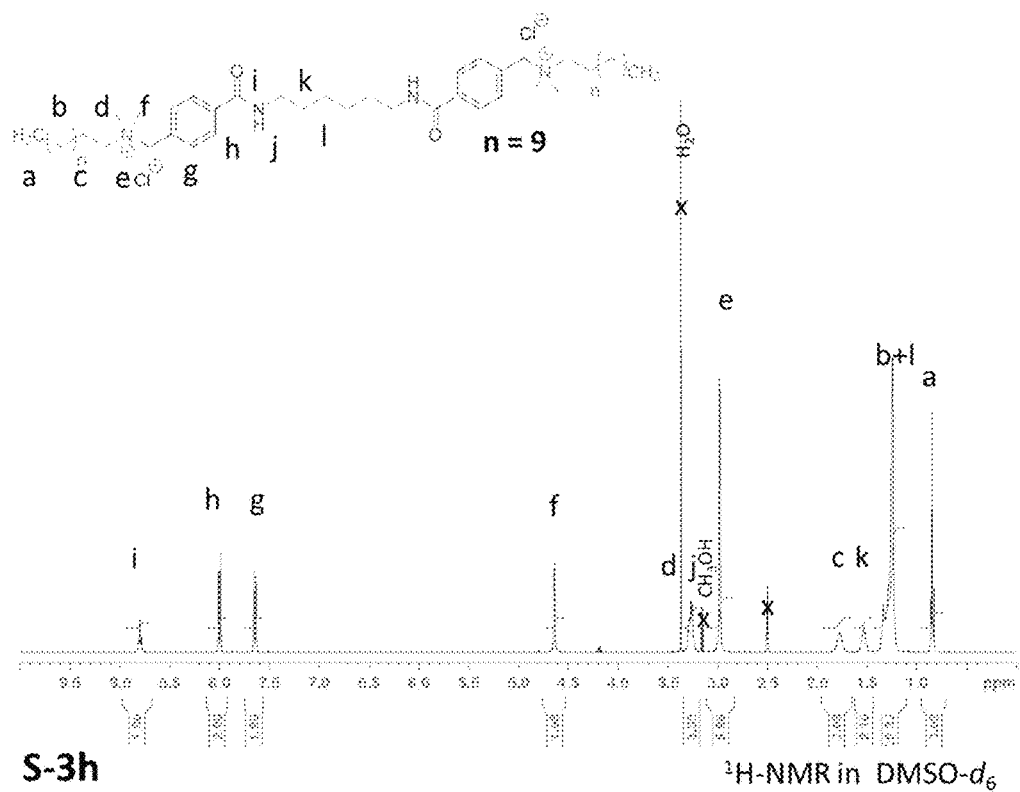
S-3h  ¹H-NMR in DMSO-$d_6$

[Fig. 75]
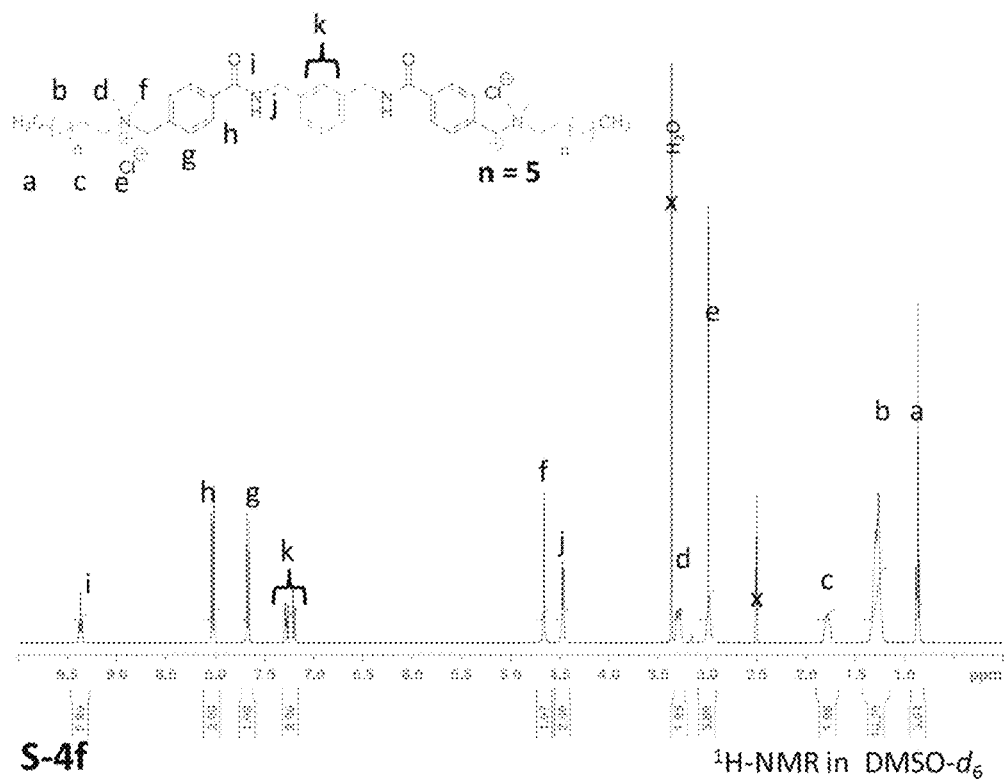
S-4f  $^1$H-NMR in DMSO-$d_6$
[Fig. 76]
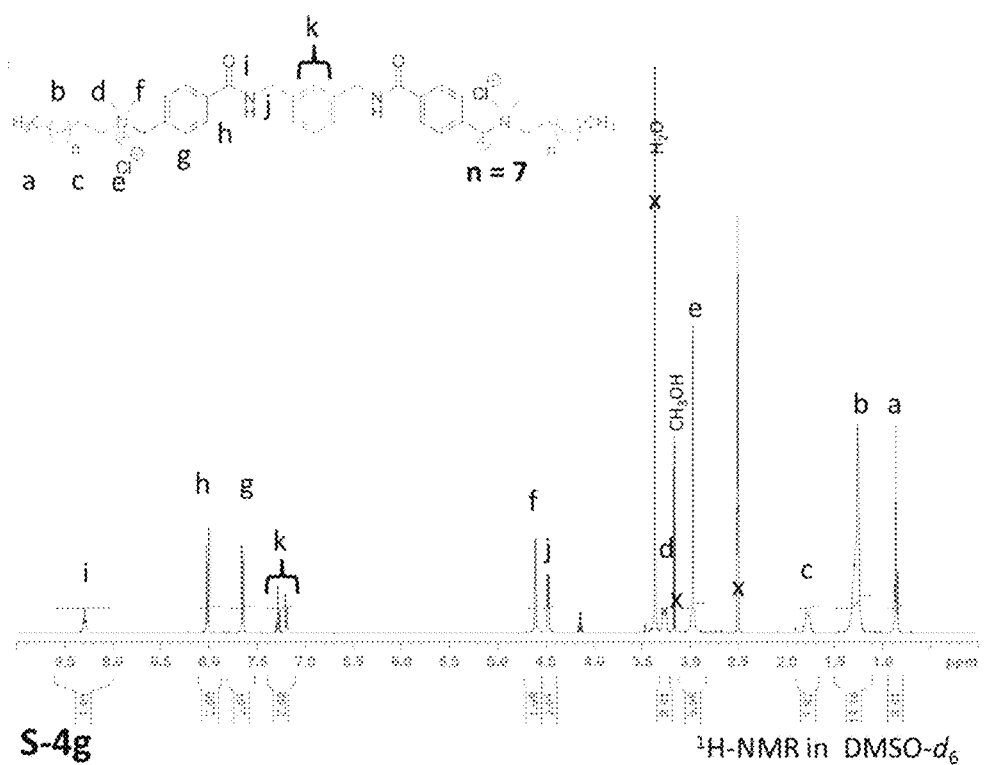
S-4g  $^1$H-NMR in DMSO-$d_6$

[Fig. 77]
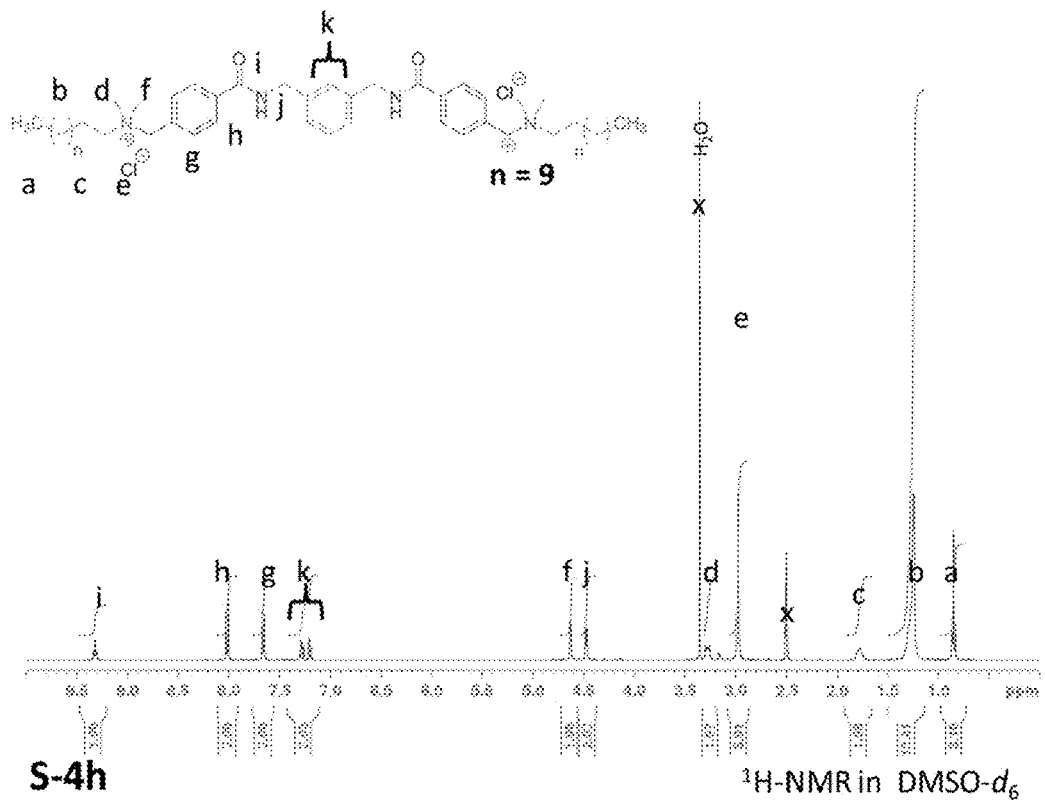
S-4h      $^1$H-NMR in DMSO-$d_6$
[Fig. 78]
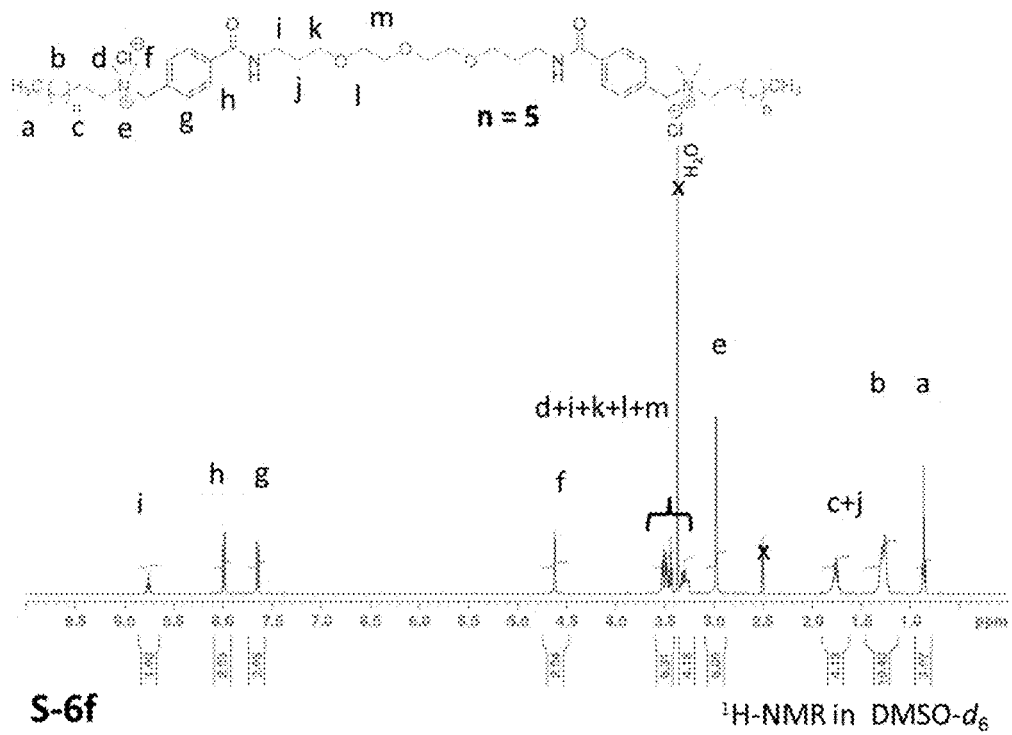
S-6f      $^1$H-NMR in DMSO-$d_6$

[Fig. 79]
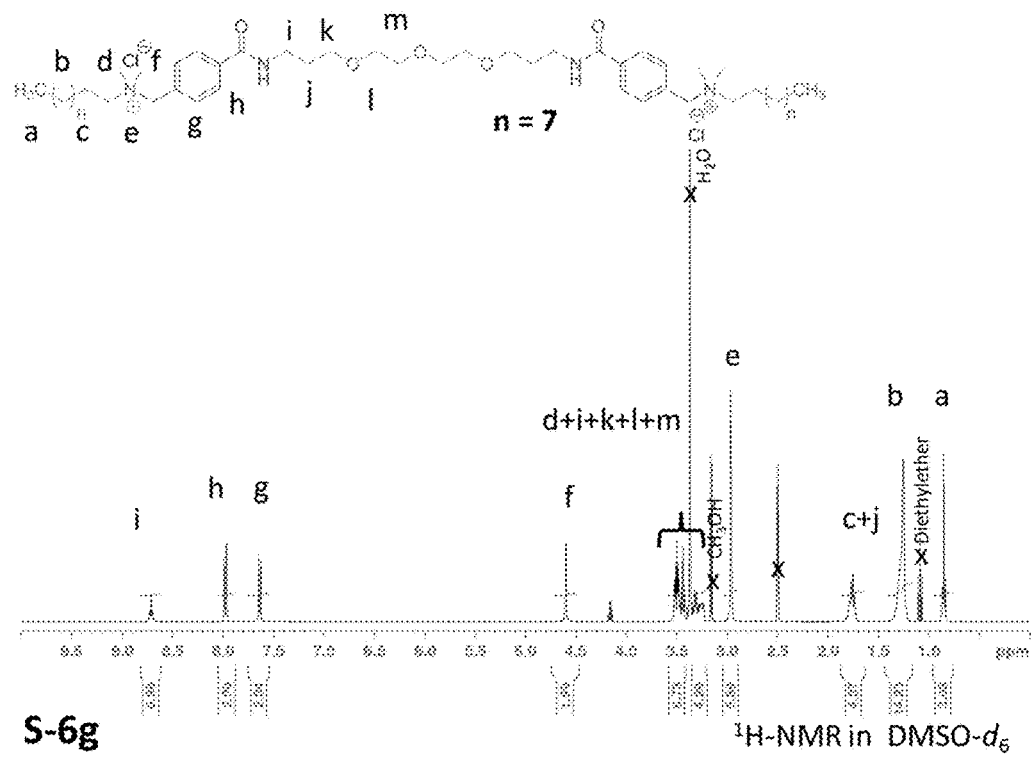
S-6g    ¹H-NMR in DMSO-$d_6$
[Fig. 80]
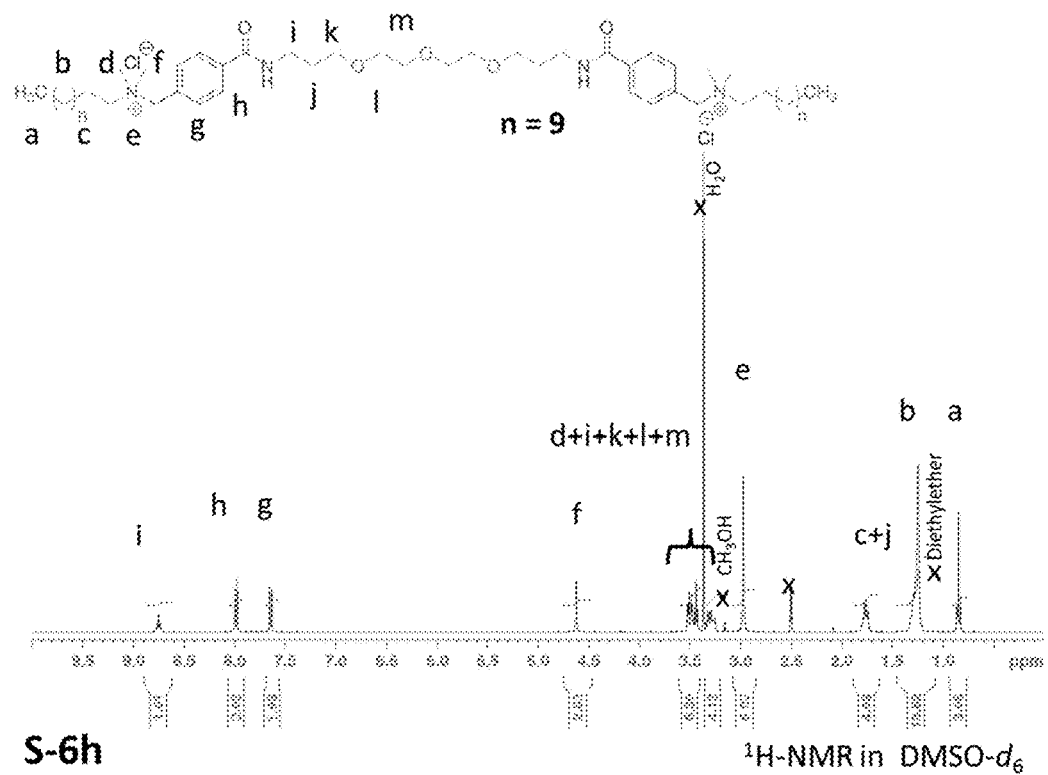
S-6h    ¹H-NMR in DMSO-$d_6$

[Fig. 81]
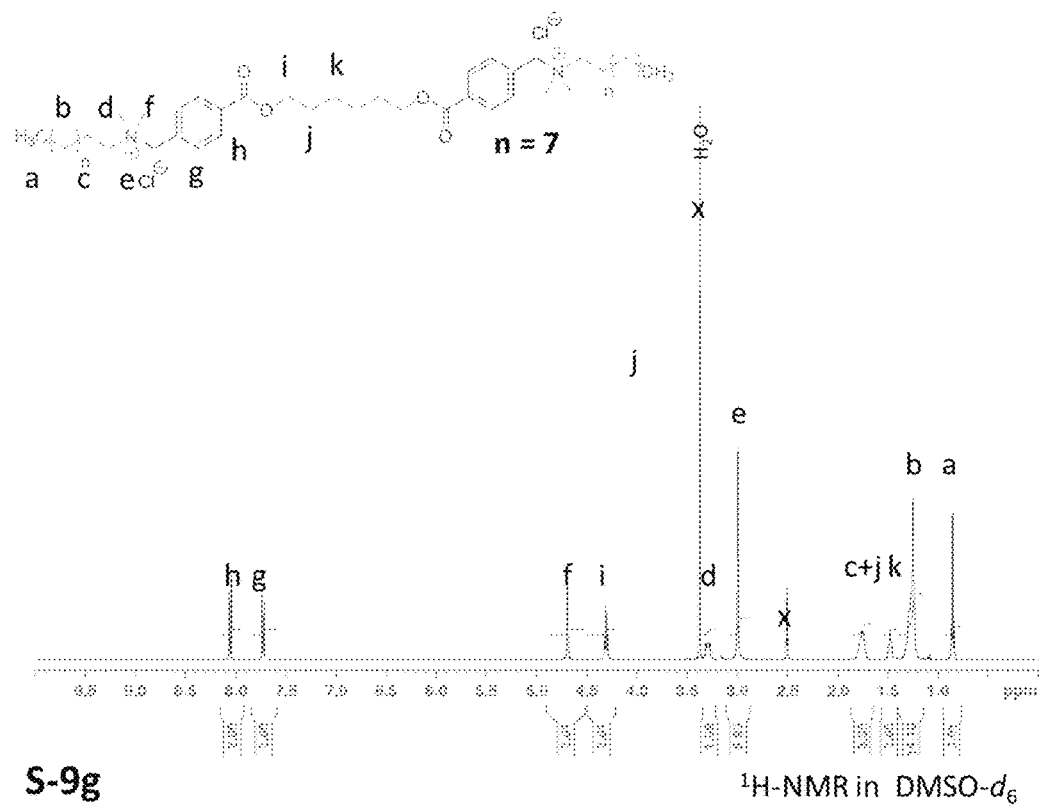
S-9g  $^1$H-NMR in DMSO-$d_6$
[Fig. 82]
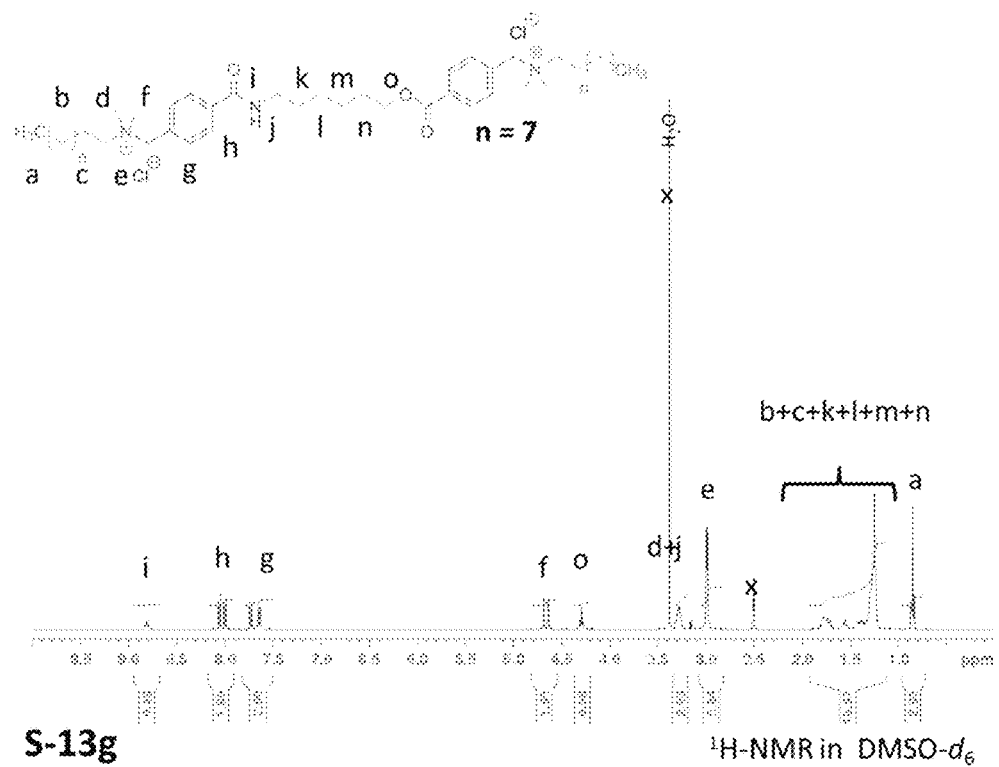
S-13g  $^1$H-NMR in DMSO-$d_6$

[Fig. 83]
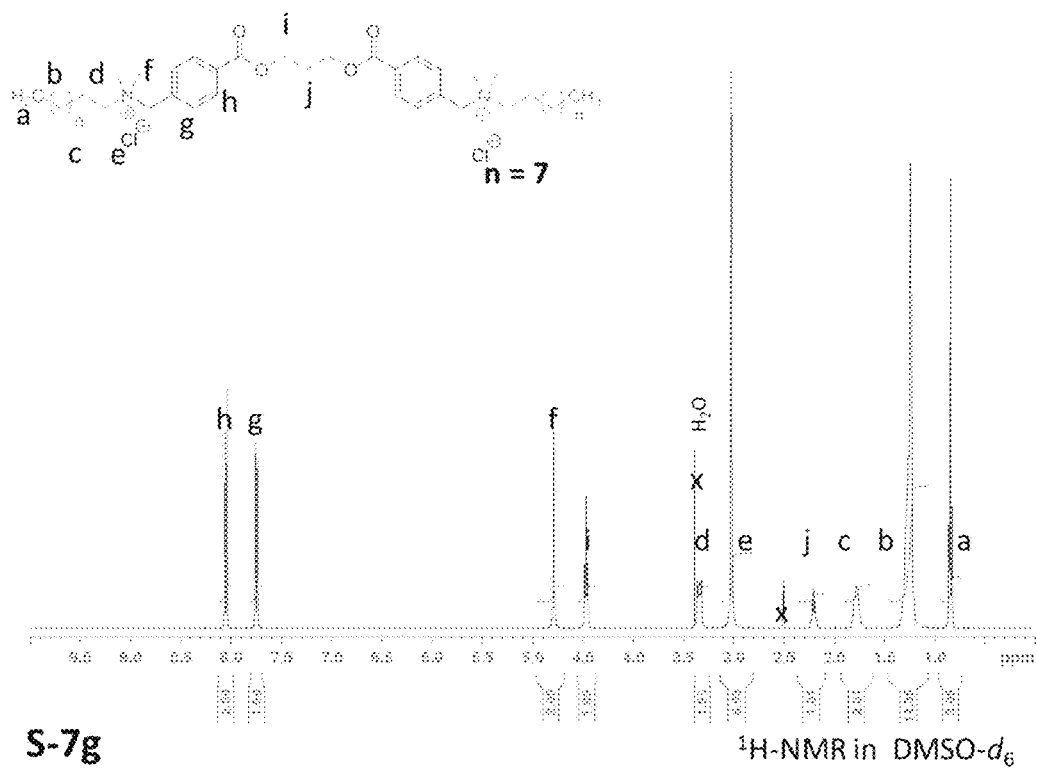
S-7g  ¹H-NMR in DMSO-$d_6$
[Fig. 84]
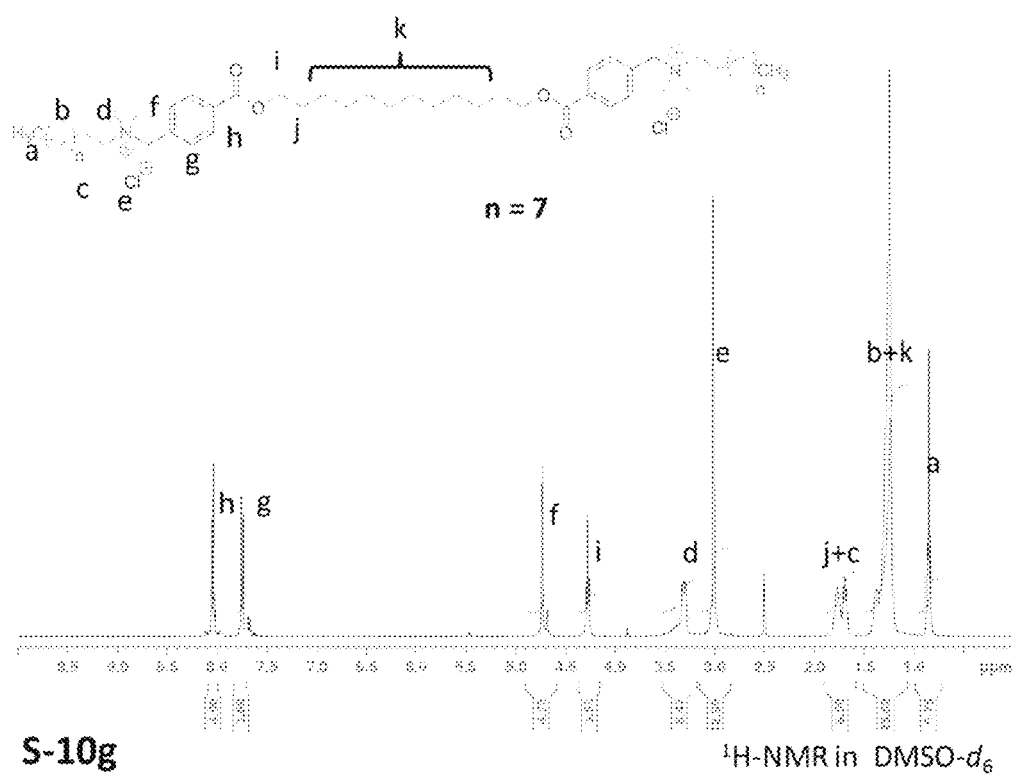
S-10g  ¹H-NMR in DMSO-$d_6$

[Fig. 85]
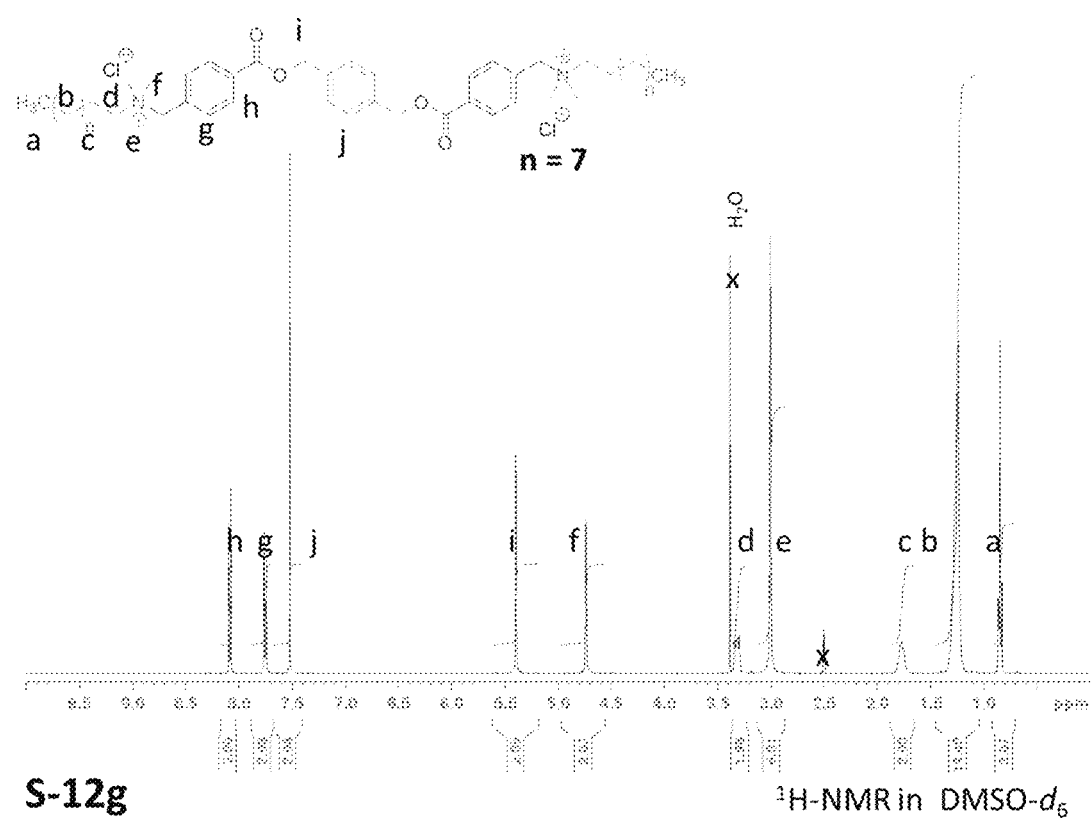

[Fig. 86]
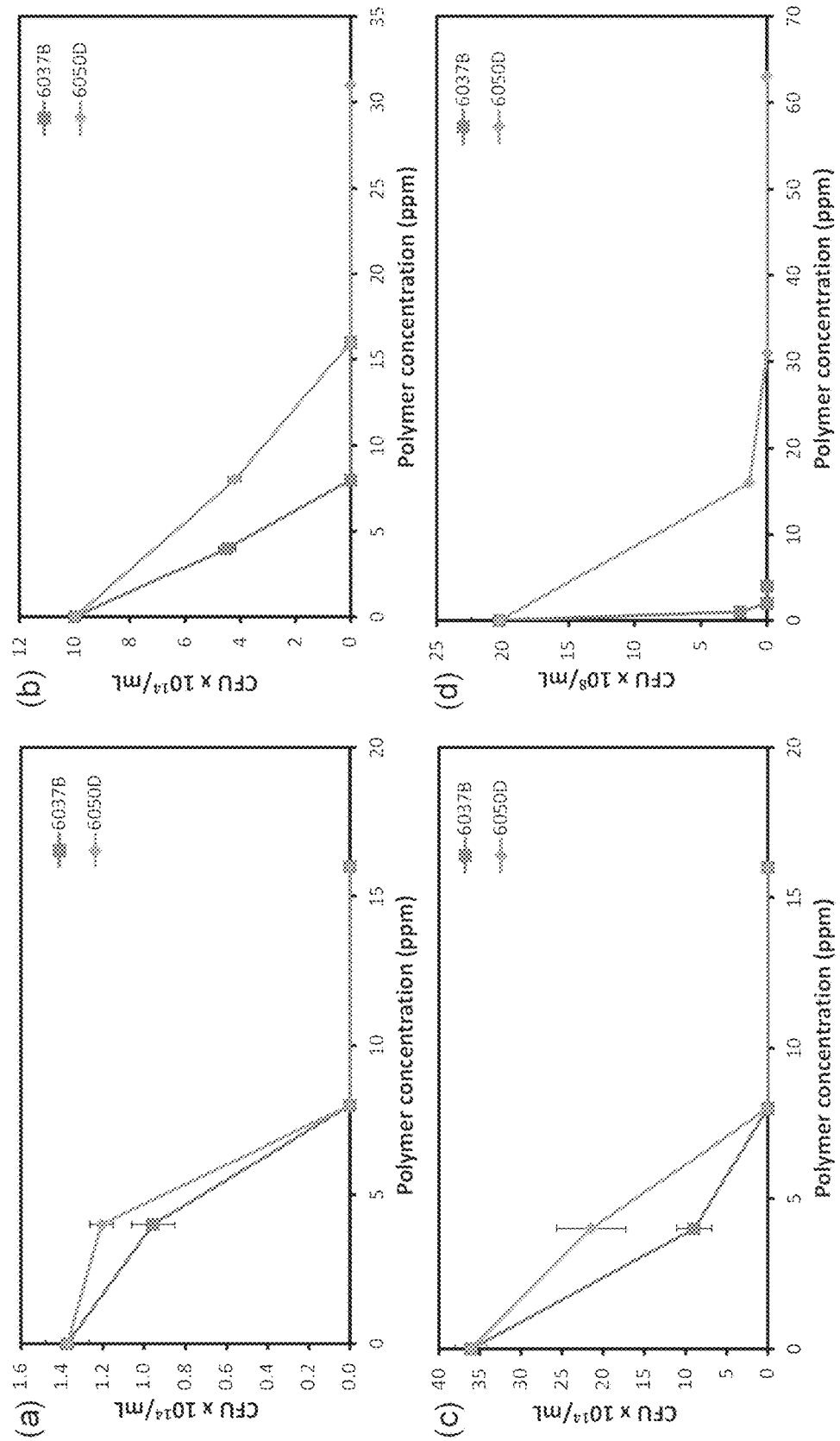

[Fig. 87]
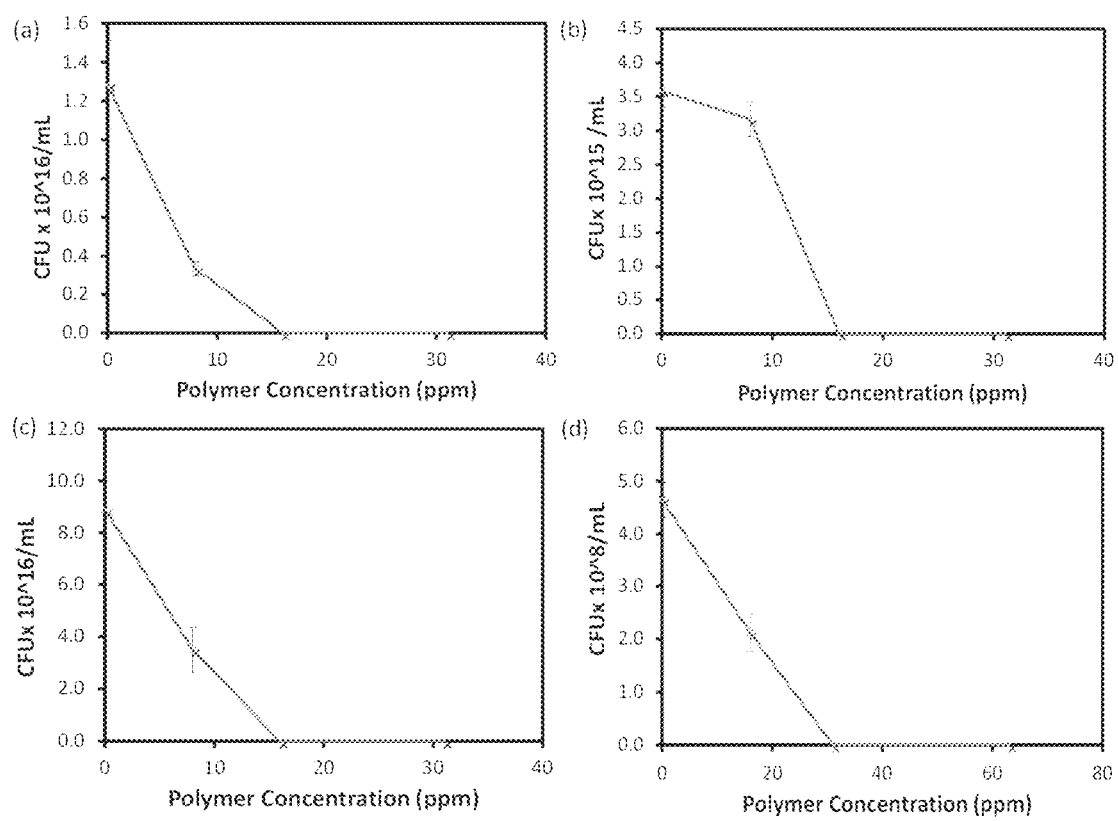

[Fig. 88]
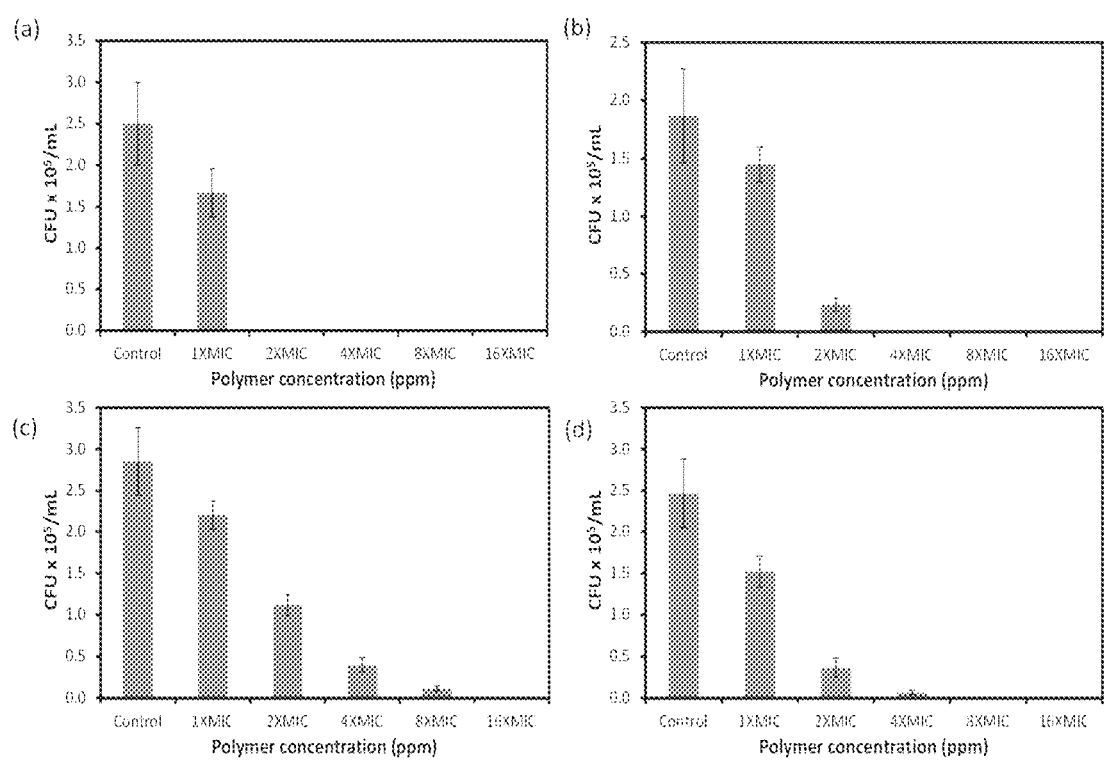

[Fig. 89]
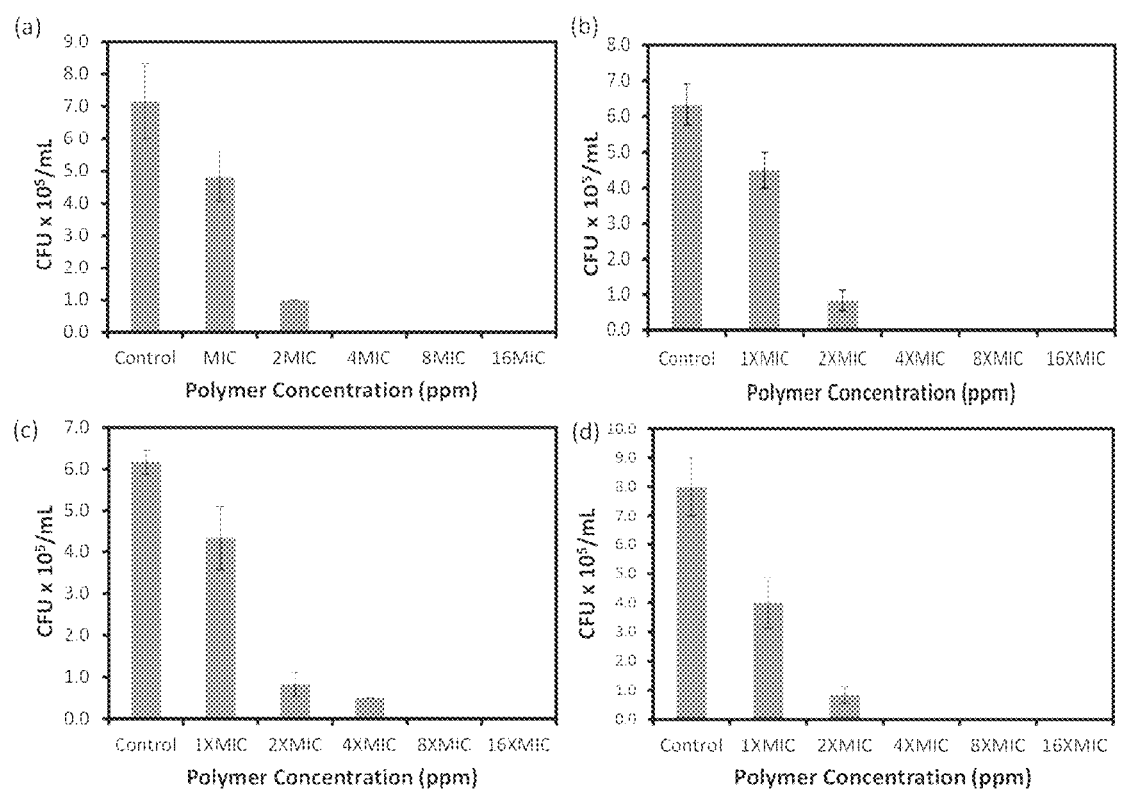

[Fig. 90]
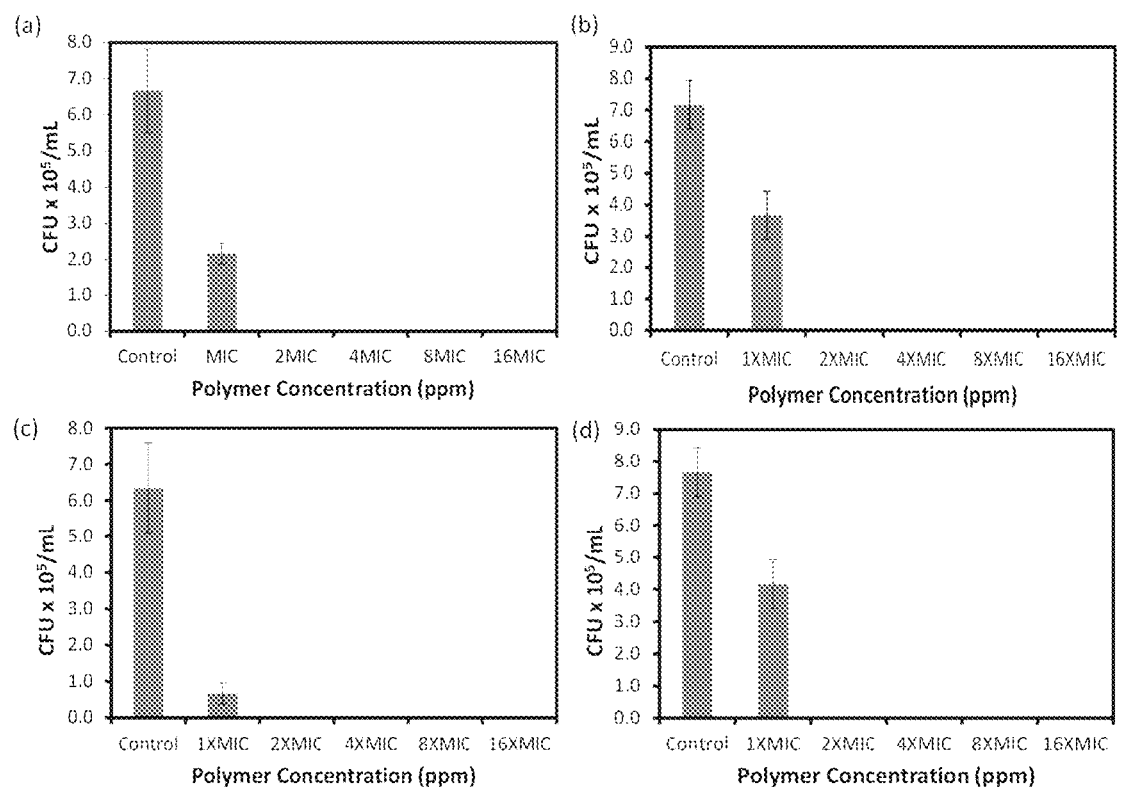

[Fig. 91]
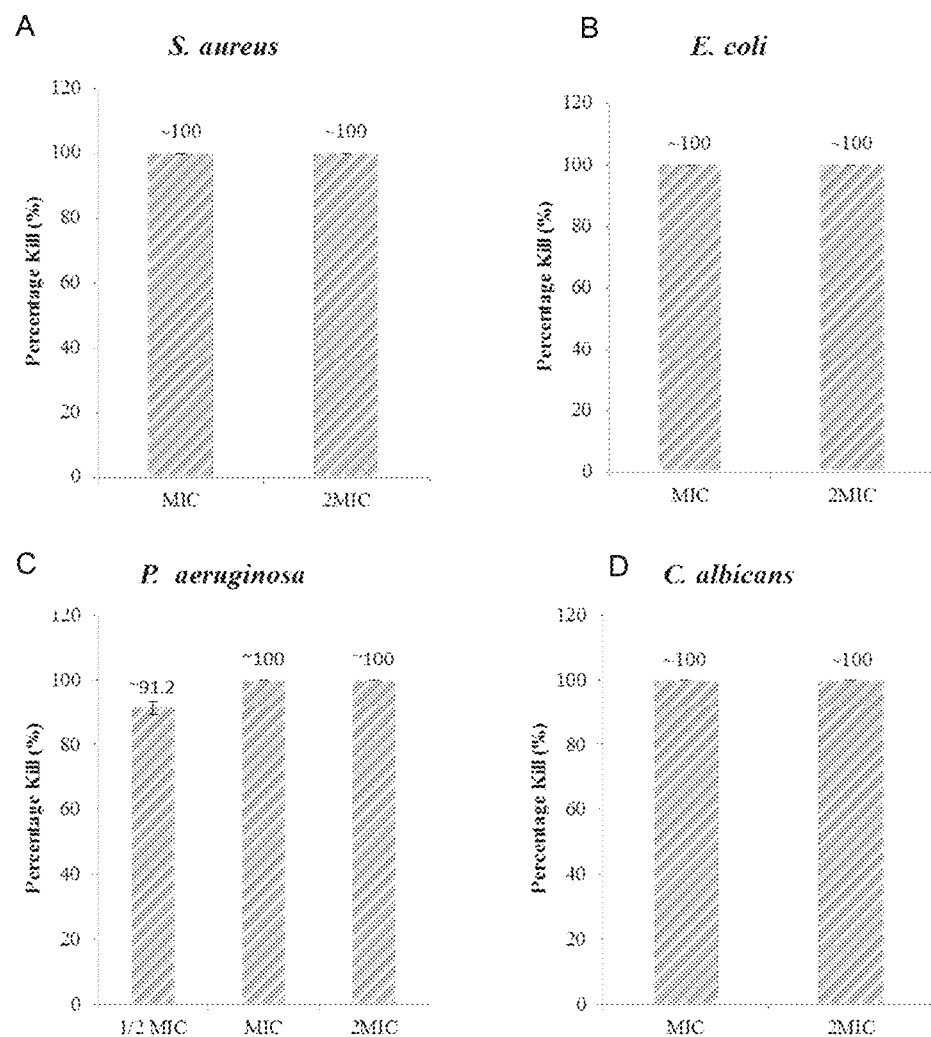

[Fig. 92]
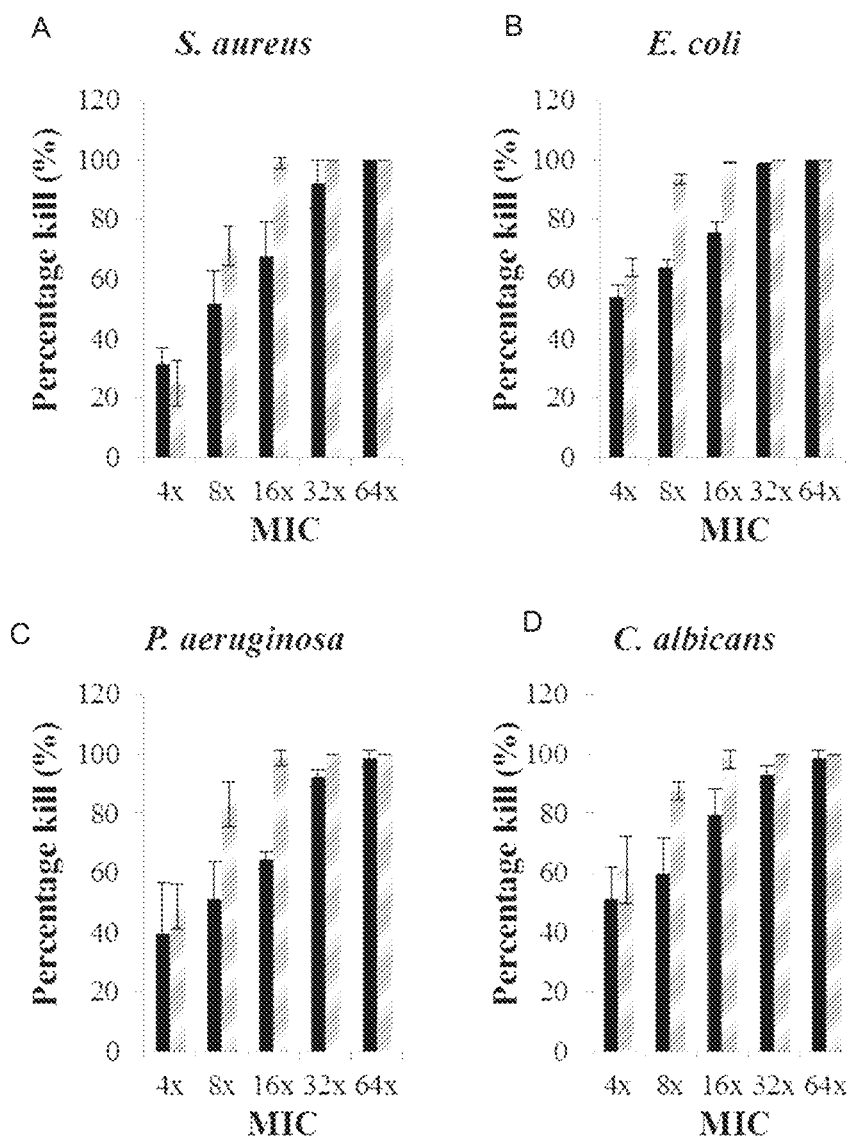

[Fig. 93]
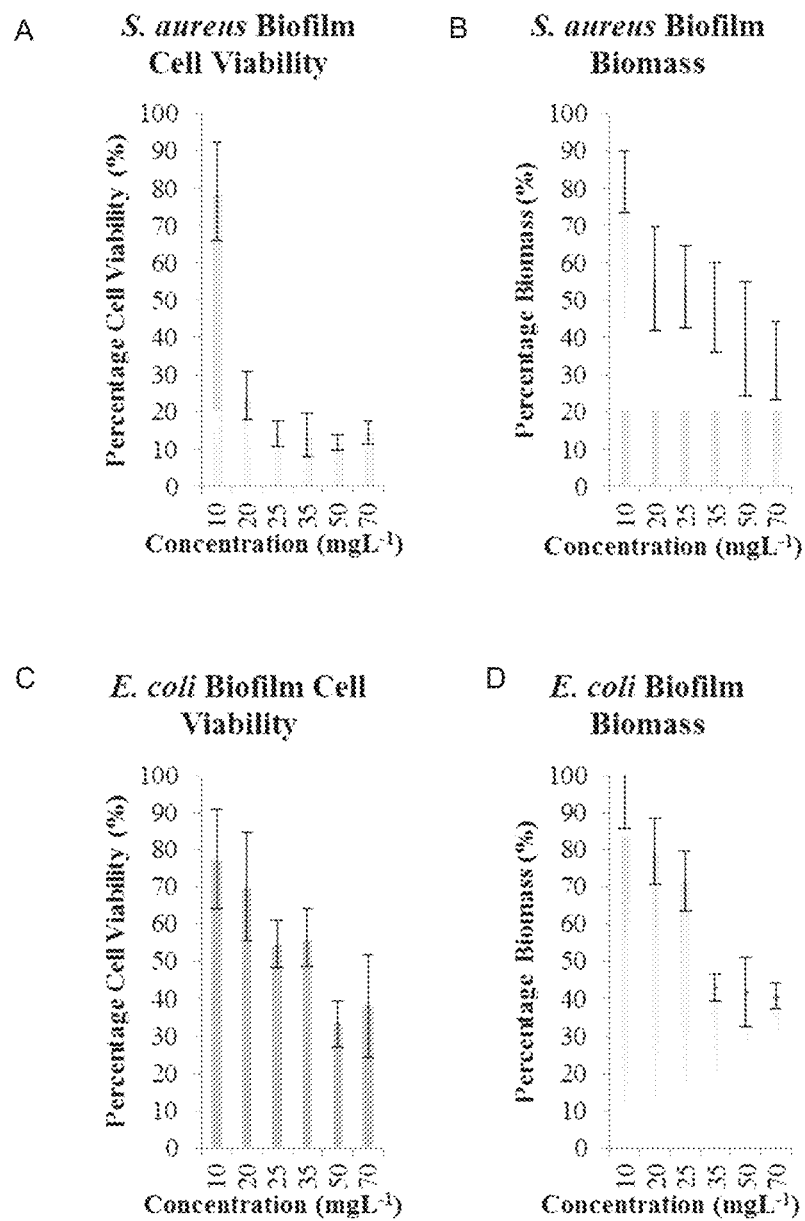

[Fig. 94]
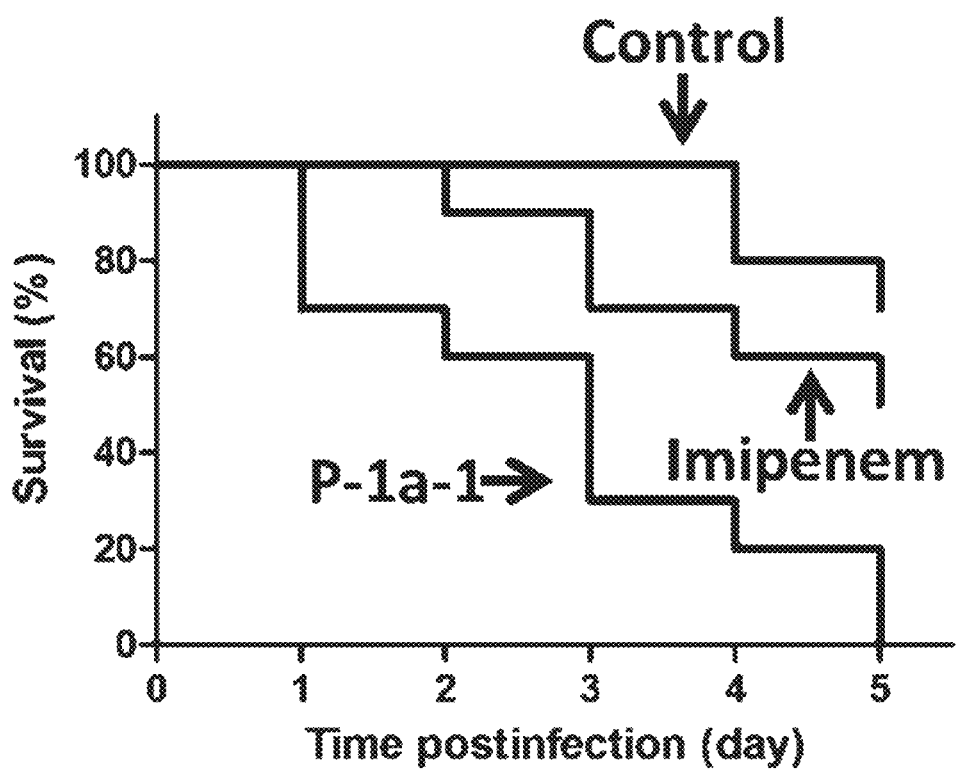

[Fig. 95]
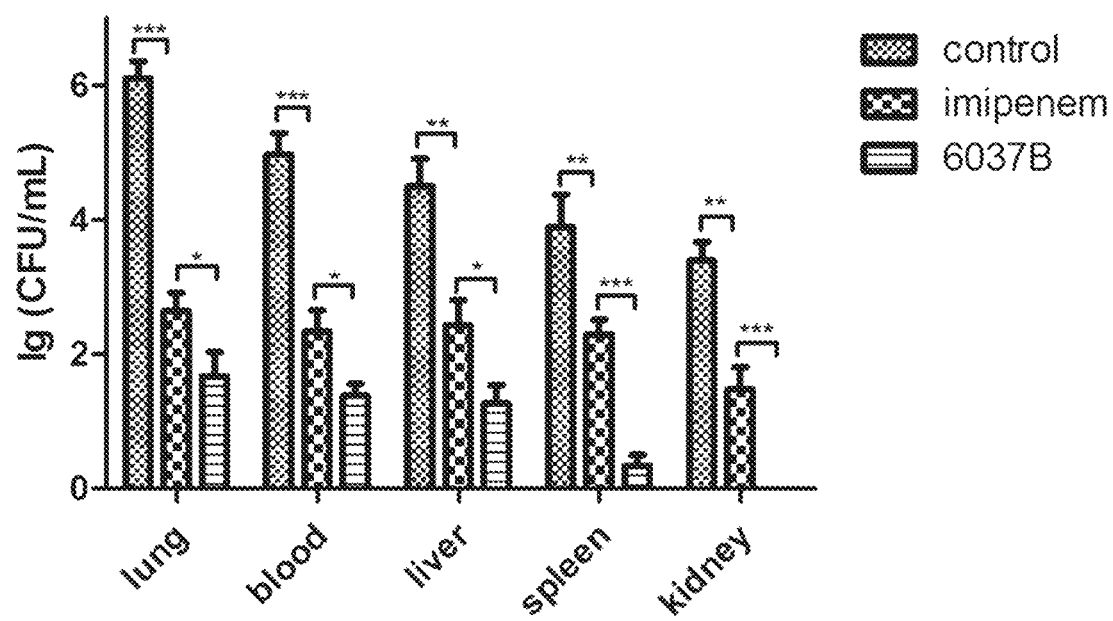

BIODEGRADABLE POLYIONENES

TECHNICAL FIELD

The present invention is related to novel $A_2$-type monomers containing degradable linkers, biodegradable cationic polyionene and Gemini surfactants containing biodegradable linkers synthesized using these monomers and commercially available tertiary amine-based reagents via addition chemistry, and their antimicrobial properties.

BACKGROUND ART

Triclosan is the most extensively used antimicrobial agent in personal care goods such as cosmetics, deodorant and soap. Although it is effective against Gram-positive bacteria, it has low activity against Gram-negative bacteria and mould in view that such Gram-negative bacteria have developed resistance against triclosan. In addition, like many antimicrobial agents used in the personal care products, triclosan has a persistent antimicrobial function in the environment after use, causing harm, for example to aquatic organisms. Because of these issues, FDA has banned the use of 19 antimicrobial agents in soap products including triclosan in September 2016.

Cationic polymers kill microbes via a membrane-lytic mechanism, hence preventing the development of drug resistance. Polyionenes are materials with charged species present along the polymer backbone and often, this term is used to describe cationic polymers. For the synthesis of cationic polyionenes, there are a wide variety of cationic residues that can be selected and often, nitrogen-based ammonium residues are commonly used. The main advantage of polyionenes is that charge distribution along the main chain can be configured with relative ease and these materials have found use in numerous applications such as gene-delivery vehicles, antimicrobials and solid-state ionics. A balance between cationic charge and hydrophobicity in cationic polyionenes is critical for achieving potency and selectivity towards microbes over mammalian cells. In previous studies, the length of alkyl groups in the monomers has been varied to modulate hydrophobicity. It has been found that although use of long alkyl chains in polymers enhanced antimicrobial activity, it also causes a correspondingly high toxicity. Nonetheless, toxicity has been able to be mitigated when an aryl group or a cyclic group is incorporated in the molecule. Monomers containing aryl groups have been used to synthesize polyionenes. The polymers having optimized compositions have been able to achieve high bactericidal effect and in vivo skin biocompatibility. However, from both the perspective of toxicity and effects on the environmental, it is highly desirable to have an in-built degradability of the polymer.

Emergence of antimicrobial resistance, coupled with toxicity issues associated with available antimicrobial agents for consumer care and biomedical applications, necessitates the development of novel degradable antimicrobial agents that can degrade in the body or environment after its use. There is therefore a need to provide a compound that overcomes or at least ameliorates, one or more of the disadvantages described above.

SUMMARY

In an aspect, there is provided a compound having the following formula (I), (Ia), or (Ib):

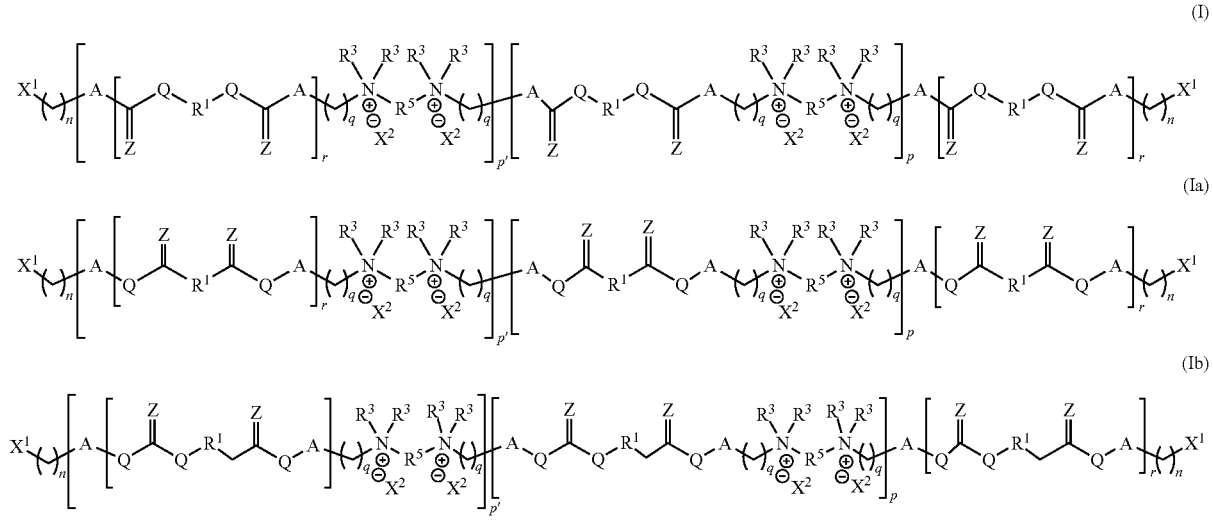

wherein

A is independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

$R^1$ is independently selected from the group consisting of —$R^2$—, —Ar—, —$R^2$—Ar—$R^2$—, —$R^2$—(O—$R^2$)$_m$—$R^2$—, —$R^2$—N($R^4$)—$R^2$— and —$R_2$—C($R^4$)$_2$—$R^2$—;

Ar is independently optionally substituted aryl or optionally substituted heteroaryl;

$R^2$ is independently optionally substituted alkyl, optionally substituted alkenyl or optionally substituted alkynyl;

$X^1$ is independently halogen, sulfate, tosylate, mesylate,

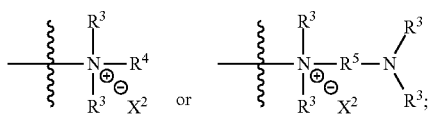

$X^2$ is independently absent or an anionic counterion;

$R^3$ is independently selected from the group consisting of hydrogen, optionally substituted alkyl, optionally substituted alkenyl and optionally substituted alkynyl;

$R^4$ is independently selected from the group consisting of hydrogen, $R^3$, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide, —$R^2$—OC(O)—$R^3$, —$R^2$—C(O)O—$R^3$, —$R^2$—Ar and —$R^2$—O—$R^2$—CH$_2$=CH$_2$;

$R^5$ is independently —$R^2$— or —$R^2$—O—$R^2$—;

Z is independently O or S;

Q is independently O or NH;

n, m and q are independently an integer from 1 to 10;

p and p' are independently 0 or is an integer of at least 1, and r is 0 or 1.

Advantageously, the disclosed compounds may have extremely low minimum inhibitory concentration (MIC) values of less than 40 μg/mL with a broad spectrum of activity against clinically relevant pathogens and microbes while having minimum toxicity against mammalian cells. For example, the hemolytic activity (HC$_{50}$) of the disclosed compounds against rat red blood cells may be greater than 1000 μg/mL. The disclosed compound may be effective for treating multidrug-resistant *K. pneumoniae* lung infection in a mouse model and for clearing bacteria from the blood and organs.

Further advantageously, the efficacy and selectivity of the disclosed compounds may be easily tuned. The disclosed compounds may make use of cationic polymers which has a charge distribution along the main chain that can be configured with relative ease. Without being bound to theory, the balance between the cationic charge and hydrophobicity of the cationic polymer may be important for achieving potency and selectivity towards microbes over mammalian cells. Further advantageously, the disclosed compounds may comprise long alkyl chains to enhance antimicrobial efficacy, while mitigating toxicity against mammalian cells by using aryl groups in the polymer main chain.

More advantageously, the disclosed compounds may comprise degradable linkers such as amide and ester linkers. Further advantageously, the linkers may be biodegradable. While the disclosed compounds may be highly effective against clinically relevant pathogens and microbes, the degradable linkers may facilitate fast degradation of the compounds, thereby avoiding the adverse effects of the compounds persisting in the environment after use. That is, incorporation of a degradable moiety into the compound may lead to biocompatible and environmentally-degradable antimicrobials.

Advantageously, the compound may be an A$_2$-type monomer containing degradable linkers. The compound may be a biodegradable cationic polyionene made from these monomers together with commercially available tertiary amine-based reagents via addition chemistry. Further advantageously, the compound may be a degradable Gemini surfactant made from A$_2$-type monomers containing degradable linkers and commercially available tertiary amine-based reagents via addition chemistry. Further advantageously, reactive unsaturated functionalities such as (meth)acrylic and allyl groups may be incorporated into the compounds to further extend the use of these compounds to prepare cross-linked coatings or gels. These biodegradable polymers and surfactants may exhibit extremely potent antimicrobial activity against a broad spectrum of microbes.

In another aspect, there is provided a method for making a compound as defined above, the method comprising the steps of:

contacting NH$_2$—$R^1$—NH$_2$ or HO—$R^1$—OH with a compound having the following formula (VI):

(VI)

wherein $R^1$ is selected from the group consisting of —$R^2$—, —Ar—, —$R^2$—Ar—$R^2$—, —$R^2$—(O—$R^2$)m-$R^2$—, —$R^2$—N($R^4$)—$R^2$— and —$R^2$—C($R^4$)$_2$—$R^2$—;

Ar is independently optionally substituted aryl or optionally substituted heteroaryl;

$R^2$ is independently optionally substituted alkyl, optionally substituted alkenyl or optionally substituted alkynyl;

Z is independently O or S;

A is independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

n and m are independently an integer from 1 to 10; and $X^3$ is halogen;

to form a halogen compound having the following formula (III):

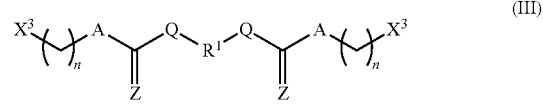

(III)

wherein Q is independently O or NH.

In another aspect, there is provided a method for making a compound as defined herein, wherein the method comprising the steps of:

Contacting

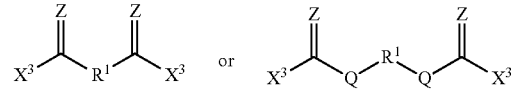

with a compound having the following formula (VIa):

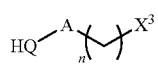
(VIa)

wherein $R^1$ is selected from the group consisting of —$R^2$—, —Ar—, —$R^2$—Ar—$R^2$—, —$R^2$—(O—$R^2$)$_m$—$R^2$—, —$R^2$—N($R^4$)—$R^2$— and —$R^2$—C($R^4$)$_2$—$R^2$—;

Ar is independently optionally substituted aryl or optionally substituted heteroaryl;

$R^2$ is independently optionally substituted alkyl, optionally substituted alkenyl or optionally substituted alkynyl;

Z is independently O or S;

A is independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

n and m are independently an integer from 1 to 10; and $X^3$ is halogen;

to form a halogen compound having the following formula (IIIa) or (IIIb):

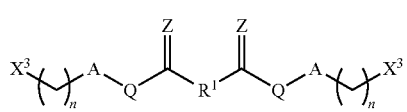
(IIIa)

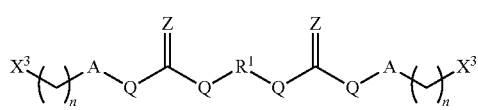
(IIIb)

wherein Q is independently O or NH.

The compound

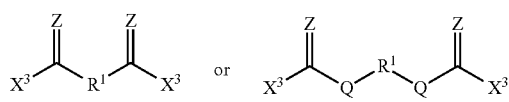

may be replaced by a diisocyanate or a diisothiocyanate.

The diisocyanate or diisothiocyanate may be selected from the group consisting of 1,3-bis(isocyanatomethyl)cyclohexane, cis-1,3-bis(isocyanatomethyl)cyclohexane, trans-1,3-bis(isocyanatomethyl)cyclohexane, 1,3-bis(1-isocyanato-1-methylethyl)benzene, 1-chloromethyl-2,4-diisocyanatobenzene, 4-chloro-6-methyl-1,3-phenylene diisocyanate, trans-1,4-cyclohexylene diisocyanate, 1,4-diisocyanatobutane, 1,12-diisocyanatododecane, 1,8-diisocyanatooctane, hexamethylene diisocyanate, isophorone diisocyanate, isophorone diisocyanate, 4,4'-methylenebis(phenyl isocyanate), 1,3-phenylene diisocyanate, tolylene-2,4-diisocyanate and tolylene-2,6-diisocyanate.

Advantageously, the disclosed compound may be synthesized by simple addition reactions and the properties of the disclosed compounds may be tuned by simply using different starting materials. The method of preparation of the disclosed compounds may therefore facilitate time- and cost-effective synthesis of a variety of related compounds where the properties may be tuned depending on the desired use.

In an embodiment, either bis-halide ($A_2$-type) monomer or bis-tert-amine ($B_2$) monomers may be synthesized and may be subsequently used to polymerize with commercially available bis-halide ($A_2$) monomer or bis-tert-amine ($B_2$) via an addition polymerization route to synthesize degradable (poly)ionenes. Advantageously, bis-halide (d-$A_2$) monomers having amide- and/or ester-linkers that may facilitate the degradation of the compounds have been synthesized. Further advantageously, the method of synthesis may be easily extended to other linkers such as acetal, carbonate, carbamate, urea and di-sulfide linkers so that the degradability of the polymer may be tuned. In addition, the synthesis may be further extended to the synthesis of cleavable bis-tert-amine (d-$A_2$) monomers.

Further advantageously, and recognizing the role of small molecule surfactants in numerous consumer-care product formulations, the synthesis may be extended to the preparation of Gemini surfactants from bis-halide (d-$A_2$) monomers. Compared to monomeric surfactants, dimeric Gemini-surfactants may have superior properties and hence these surfactants with the degradable linkers may be used as antimicrobial surfactants.

Further advantageously, reactive unsaturated functionalities such as (meth)acrylic and allyl groups may be introduced to further extend the use of these materials to prepare cross-linked coatings or gels.

In another aspect, there is provided a composition comprising the compound having the following formula (I), (Ia) or (Ib):

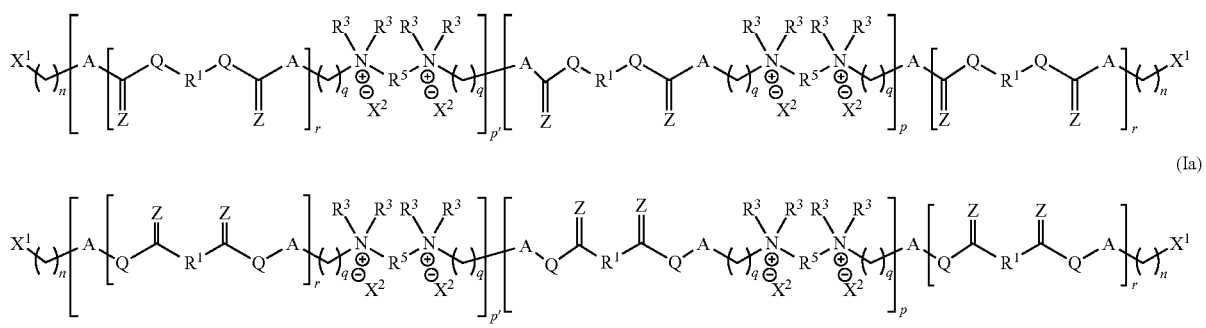

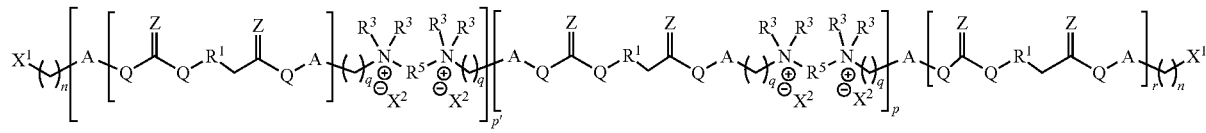

(Ib)

wherein

A is independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

$R^1$ is independently selected from the group consisting of —$R^2$—, —Ar—, —$R^2$—Ar—$R^2$—, —$R^2$—(O—$R^2$)$_m$—$R^2$—, —$R^2$—N($R^4$)—$R^2$— and —$R^2$—C($R^4$)$_2$—$R^2$—;

Ar is independently optionally substituted aryl or optionally substituted heteroaryl;

$R^2$ is independently optionally substituted alkyl, optionally substituted alkenyl or optionally substituted alkynyl;

$X^1$ is independently halogen, sulfate, tosylate and mesylate,

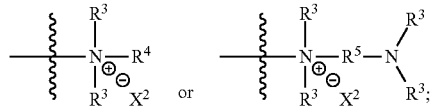

$X^2$ is independently absent or an anionic counterion;

$R^3$ is independently selected from the group consisting of hydrogen, optionally substituted alkyl, optionally substituted alkenyl and optionally substituted alkynyl;

$R^4$ is independently selected from the group consisting of hydrogen, $R^3$, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide, —$R^2$—OC(O)—$R^2$, —$R^2$—C(O)O—$R^2$, —$R^2$—Ar and $R^2$—O—$R^2$—CH$_2$=CH$_2$;

$R^5$ is independently —$R^2$— or —$R^2$—O—$R^2$—;

Z is independently O or S;

Q is independently O or NH;

n, m and q are independently an integer from 1 to 10;

p and p' are independently 0 or is an integer of at least 1; and r is 0 or 1.

In another aspect, there is provided the use of the compound as defined above as an additive, antimicrobial agent or preservative in personable care products.

In another aspect, there is provided a method for treating a bacterial infection or fungal infection comprising administering to a subject a compound as defined above or a composition as defined above.

In another aspect, there is provided a compound as defined above or a composition as defined above for use in treating bacterial infection or fungal infection in a subject.

In another aspect, there is provided the use of a compound as defined above or a composition as defined above in the manufacture of a medicament for treating a bacterial infection or fungal infection in a subject.

Definitions

In this specification a number of terms are used which are well known to a skilled addressee. Nevertheless for the purposes of clarity a number of terms will be defined. The following words and terms used herein shall have the meaning indicated:

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an R—C(=O)—NH— group in which the R group may be an alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-15 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are $C_1$-$C_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a $C_1$-$C_{15}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a Alkyl-NH— group, in which alkyl is as defined herein. "Dialkylamino" means a (alkyl)$_2$N— group, in which each alkyl may be the same or different and are each as defined herein for alkyl. The alkyl group is preferably a $C_1$-$C_6$ alkyl group. The group may be a terminal group or a bridging group. If the group is a terminal group it is bonded to the remainder of the molecule through the nitrogen atom.

"Alkylaminocarbonyl" refers to a group of the formula (Alkyl)$_x$(H)$_y$NC(=O)— in which alkyl is as defined herein, x is 1 or 2, and the sum of X+Y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkyloxyalkyl" refers to an alkyloxy-alkyl- group in which the alkyloxy and alkyl moieties are as defined herein. The group may be a terminal group or a bridging group. If the group is a terminal group it is bonded to the remainder of the molecule through the alkyl group.

"Alkyloxyary" refers to an alkyloxy-aryl- group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl- group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroaryl" refers to an alkyloxy-heteroaryl- group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl- group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$ alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-15 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$ alkynyloxy groups. The group may be a terminal group or a bridging group. If the group is a terminal group it is bonded to the remainder of the molecule through the oxygen atom.

"Aminoalkyl" means an NH$_2$-alkyl- group in which the alkyl group is as defined herein. The group may be a terminal group or a bridging group. If the group is a terminal group it is bonded to the remainder of the molecule through the alkyl group.

"Aminosulfonyl" means an NH$_2$—S(=O)$_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl- group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl- group in which the aryl and alkyl moieties are as defined herein. Preferred arylalkyl groups contain a $C_{1-5}$ alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono arylamino means a group of formula arylNH—, in which aryl is as defined herein. di arylamino means a group of formula (aryl)$_2$N— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl- group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl- group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl- group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl- group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

"Cycloalkynyl" means a non-aromatic monocyclic or multicyclic ring system containing at least one carbon-carbon triple bond and preferably having from 5-10 carbon atoms per ring. Exemplary monocyclic cycloalkynyl rings include cyclopentynyl, cyclohexynyl or cycloheptynyl. The cycloalkynyl group may be substituted by one or more substituent groups. A cycloalkynyl group typically is a $C_3$-$C_{12}$ alkynyl group. The group may be a terminal group or a bridging group.

"Cycloamino" refers to a saturated monocyclic, bicyclic, or polycyclic ring containing at least one nitrogen in at least one ring. Each ring is preferably from 3 to 10 membered, more preferably 4 to 7 membered. The group may be a terminal group or a bridging group. If the group is a terminal group it is bonded to the remainder of the molecule through the nitrogen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, one or more of which has been replaced by a heteroatom selected from S, O, P and N. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to an heteroalkyl-O— group in which heteroalkyl is as defined herein. Preferably the heteroalkyloxy is a $C_1$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3 thienyl. A heteroaryl group is typically a $C_1$-$C_{18}$ heteroaryl group. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl- group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl- group in which the heteroaryl and heteroalkyl moieties are as defined herein. The group may be a terminal group or a bridging group. If the group is a terminal group it is bonded to the remainder of the molecule through the heteroalkyl group.

"Heteroarylamino" refers to groups containing an aromatic ring (preferably 5 or 6 membered aromatic ring) having at least one nitrogen and at least another heteroatom as ring atoms in the aromatic ring, preferably from 1 to 3 heteroatoms in at least one ring. Suitable heteroatoms include nitrogen, oxygen and sulphur. Arylamino and aryl is as defined herein. The group may be a terminal group or a bridging group. If the group is a terminal group it is bonded to the remainder of the molecule through the nitrogen atom.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4 oxathiapane. A heterocycloalkyl group typically is a $C_2$-$C_{12}$ heterocycloalkyl group. The group may be a terminal group or a bridging group.

"Heterocycloalkylalkyl" refers to a heterocycloalkyl-alkyl- group in which the heterocycloalkyl and alkyl moieties are as defined herein. Exemplary heterocycloalkylalkyl groups include (2-tetrahydrofuryl)methyl, (2 tetrahydrothiofuranyl) methyl. The group may be a terminal group or a bridging group. If the group is a terminal group it is bonded to the remainder of the molecule through the alkyl group.

"Heterocycloalkylalkenyl" refers to a heterocycloalkyl-alkenyl- group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl- group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$ Heterocycloalkenyloxy. The group may be a terminal group or a bridging group. If the group is a terminal group it is bonded to the remainder of the molecule through the oxygen atom.

"Heterocycloalkynyl" refers to a heterocycloalkyl as defined herein but containing at least one triple bond. A heterocycloalkynyl group typically is a $C_2$-$C_{12}$ heterocycloalkynyl group. The group may be a terminal group or a bridging group.

"Heterocycloamino" refers to a saturated monocyclic, bicyclic, or polycyclic ring containing at least one nitrogen and at least another heteroatom selected from nitrogen, sulfur, oxygen, preferably from 1 to 3 heteroatoms in at least one ring. Each ring is preferably from 3 to 10 membered, more preferably 4 to 7 membered. The group may be a terminal group or a bridging group. If the group is a terminal group it is bonded to the remainder of the molecule through the nitrogen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n butyl, isobutyl or tertiary-butyl). The group may be a terminal group or a bridging group.

The term "optionally substituted" as used herein means the group to which this term refers may be unsubstituted, or may be substituted with one or more groups independently selected from alkyl, alkenyl, alkynyl, thioalkyl, cycloalkyl, cycloalkylalkyl, cycloalkenyl, cycloalkylalkenyl, heterocycloalkyl, cycloalkylheteroalkyl, cycloalkyloxy, cycloalkenyloxy, cycloamino, halo, carboxyl, carboxylic acid, haloalkyl, haloalkynyl, alkynyloxy, heteroalkyl, heteroalkyloxy, hydroxyl, hydroxyalkyl, alkoxy, thioalkoxy, alkenyloxy, haloalkoxy, haloalkenyl, haloalkynyl, haloalkenyloxy, nitro, amino, nitroalkyl, nitroalkenyl, nitroalkynyl, nitroheterocyclyl, alkylamino, dialkylamino, alkenylamine, aminoalkyl, alkynylamino, acyl, alkyloxy, alkyloxyalkyl, alkyloxyaryl, alkyloxycarbonyl, alkyloxycycloalkyl, alkyloxyheteroaryl, alkyloxyheterocycloalkyl, alkenoyl, alkynoyl, acylamino, diacylamino, acyloxy, alkylsulfonyloxy, heterocyclic, heterocycloalkenyl, heterocycloalkyl, heterocycloalkylalkyl, heterocycloalkylalkenyl, heterocycloalkylheteroalkyl, heterocycloalkyloxy, heterocycloalkenyloxy, heterocycloxy, heterocycloamino, haloheterocycloalkyl, alkylsulfinyl, alkylsulfonyl, alkylsulfenyl, alkylcarbonyloxy, alkylthio, acylthio, aminosulfonyl, phosphorus-containing groups such as phosphono and phosphinyl, sulfinyl, sulfinylamino, sulfonyl, sulfonylamino, aryl, heteroaryl, heteroarylalkyl, heteroarylalkenyl, heteroarylheteroalkyl, heteroarylamino, heteroaryloxy, arylalkenyl, arylalkyl, alkylaryl, alkylheteroaryl, aryloxy, aryloxyalkyl, aryloxyaryl, alkyloxyaryl, arylsulfonyl, cyano, cyanate, isocyanate, —C(O)NH(alkyl), and —C(O)N(alkyl)$_2$.

Preferably, the alkyl is an optionally substituted $C_1$-$C_6$ alkyl, the alkenyl is an optionally substituted $C_1$-$C_6$ alkenyl, the alkynyl is a $C_1$-$C_{12}$ alkynyl, the thioalkyl is an optionally substituted $C_1$-$C_6$ thioalkyl comprising 1 or 2 sulfur atoms, the alkyloxy is an optionally substituted $C_1$-$C_6$ alkyl-O— group, the cycloalkyl is an optionally substituted $C_3$-$C_9$ cycloalkyl, the cycloalkylalkyl is an optionally substituted $C_3$ to $C_9$ cycloalkylalkyl, the cycloalkenyl is an optionally substituted $C_3$-$C_9$ cycloalkenyl, the heterocycloalkyl is an optionally substituted heterocycloalkyl having a ring atom number of 3 to 8 and having 1 to 3 heteroatoms independently selected from the group consisting of N, O and S, the cycloalkoxy is an optionally substituted cycloalkoxy having a ring atom number of 3 to 8 and having 1 or 2 oxygen atoms, the cycloamino is an optionally substituted cycloamino having a ring atom number of 3 to 8 and having 1 or 2 nitrogen atoms, halo is selected from the group consisting of fluoro, chloro, bromo and iodo, haloalkyl is an optionally substituted $C_1$-$C_6$ haloalkyl having at least one halo group selected from the group consisting of fluoro, chloro, bromo and iodo, haloalkenyl is an optionally substituted $C_1$-$C_6$ haloalkenyl having at least one halo group selected from the group consisting of fluoro, chloro, bromo and iodo, haloalkynyl is an optionally substituted $C_1$-$C_6$ haloalkynyl having at least one halo group selected from the group consisting of fluoro, chloro, bromo and iodo, haloalkoxy is an optionally substituted $C_1$-$C_6$ haloalkoxy having at least one halo group selected from the group consisting of fluoro, chloro, bromo and iodo, haloalkenyloxy is an optionally substituted $C_1$-$C_6$ haloalkenyloxy having at least one halo group selected from the group consisting of fluoro, chloro, bromo and iodo, alkenyloxy is an optionally substituted $C_1$-$C_6$ alkenyloxy having at least one oxygen atom, heteroalkyl is an optionally substituted $C_2$-$C_6$ alkyl having a least one heteroatom selected from the group consisting of N, O, P and S, heteroalkyloxy is an optionally substituted $C_2$-$C_6$ alkyl having at least one oxygen atom and at least one other heteroatom selected from the group consisting of N, O, P and S, hydroxyalkyl is a substituted alkyl having the formula $C_nH_{(2n+1-x)}(OH)_x$ where n is 1 to 10, haloalkenyloxy is an optionally substituted $C_1$-$C_6$ alkenyloxy having at least one oxygen atom and at least one other substituent selected from the group consisting of fluoro, chloro, bromo and iodo, the nitroalkyl is an optionally substituted $C_1$-$C_6$ alkyl having at least one nitro group, the nitroalkenyl is an optionally substituted $C_1$-$C_6$ alkenyl having at least one nitro group, the nitroalkynyl is an optionally substituted $C_1$-$C_6$ alkynyl having at least one nitro group, the nitroheterocyclyl is an optionally substituted heterocycloalkyl having a ring atom number of 3 to 8 and having 1 to 3 heteroatoms independently selected from the group consisting of N, O and S and having at least one nitro group, the optionally substituted aryl is an optionally substituted $C_6$-$C_{18}$ aryl, the cycloalkylheteroaryl is an optionally substituted heteroaryl having a ring atom number of 3 to 8 and having 1 to 3 heteroatoms independently selected from the group consisting of N, O and S and with $C_1$-$C_6$ cycloalkyl group, the heteroaryl is an optionally substituted heteroaryl having a ring atom number of 3 to 8 and having 1 to 3 heteroatoms independently selected from the group consisting of N, O and S, alkylamino is an optionally substituted alkyl-NH— group having a $C_1$-$C_6$ alkyl group, dialkylamino is an optionally substituted (alkyl)$_2$N— group having a $C_1$-$C_6$ alkyl group, alkylaminoalkyl is an optionally substituted alkyl-NH-alkyl group having a $C_1$-$C_6$ alkyl group, alkenylamine is an optionally substituted alkenyl-NH— group having a $C_1$-$C_6$ alkenyl group, alkynyl amino is an optionally substituted alkynyl-NH— group having a $C_1$-$C_6$ alkynyl group, alkyloxycarbonyl is a an optionally substituted $C_1$-$C_{16}$ alkyloxy having a carbonyl group, alkanoyl is an optionally substituted $C_1$-$C_6$ alkyl having a carbonyl group, alkenoyl is an optionally substituted $C_1$-$C_6$ alkenyl having a carbonyl group, alkynoyl is an optionally substituted $C_1$-$C_6$ alkynyl having a carbonyl group, acyl is an optionally substituted R—C(=O)— group in which the R group may be a $C_1$-$C_6$ alkyl, $C_3$-$C_6$ cycloalkyl, $C_3$-$C_6$ heterocycloalkyl having 1 to 3 heteroatoms independently selected from the group consisting of N, O and S, acylamino is an optionally substituted R—C(=O)—NH— group in which the R group may be a $C_1$-$C_6$ alkyl, $C_3$-$C_6$ cycloalkyl, $C_3$-$C_6$ heterocycloalkyl having 1 to 3 heteroatoms independently selected from the group consisting of N, O and S, aryl having a ring atom number of 3 to 8 or heteroaryl group having a ring atom number of 3 to 8 and having 1 to 3 heteroatoms independently selected from the group consisting of N, O and S, the acyloxy is a $C_1$-$C_6$ acyloxy, the alkylsulfonyloxy is an optionally substituted $C_1$-$C_6$ alkyl-O— group having at least one sulfonyl group, the heterocycloalkylalkylaryl is a heterocycloalkylalkylaryl having a ring atom number of 3 to 8 and having 1 to 3 heteroatoms independently selected from the group consisting of N, O and S and $C_1$-$C_6$ alkyl group and $C_1$-$C_6$ aryl group, the heterocycloalkenyl is a heterocycloalkenyl having a ring atom number of 3 to 8 and having 1 to 3 heteroatoms independently selected from the group consisting of N, O and S, the heterocycloalkyl is a heterocycloalkyl having a ring atom number of 3 to 8 and having 1 to 3 heteroatoms independently selected from the group consisting of N, O and S, the heterocycloalkylalkyl is an optionally substituted $C_3$ to $C_9$ cycloalkylalkyl having 1 to 3 heteroatoms independently selected from the group consisting of N, O and S, the heterocycloalkylalkenyl is an optionally substituted $C_3$ to $C_9$ cycloalkylalkenyl having 1 to 3 heteroatoms independently selected from the group consisting of N, O and S, the heterocycloalkyloxy is an optionally substituted $C_3$ to $C_9$ cycloalkyl having 1 to 3 heteroatoms independently selected from the group consisting of N, O and S and an optionally substituted $C_1$-$C_6$ alkyl-O— group, the heterocycloamino is an optionally substituted heterocycloalkyl having a ring atom number of 3 to 8 and having 1 to 3 heteroatoms independently selected from the group consisting of N, O and S and an amino group, the haloheterocycloalkyl is an optionally substituted heterocycloalkyl having a ring atom number of 3 to 8 and having 1 to 3 heteroatoms independently selected from the group consisting of N, O and S and a halo group selected from the group consisting of fluoro, chloro, iodo and bromo, the alkylsufonyl is an optionally substituted $C_1$-$C_6$ alkyl group having at least one sulfonyl group, the alkylcarbonyloxy is an optionally substituted $C_1$-$C_6$ alkyl group having at least one carbonyl group and at least one hydroxy group, the alkylthio is an optionally substituted $C_1$-$C_6$ alkyl group having at least one thiol group, alkylthioalkyl is an optionally substituted $C_1$-$C_6$ alkyl group having at least one thiol group and another $C_1$-$C_6$ alkyl group, the acylthio is R—C(=O)—S in which R group may be a $C_1$-$C_6$ alkyl, $C_3$-$C_{12}$ cycloalkyl, $C_3$-$C_{12}$ heterocycloalkyl having 1 to 3 heteroatoms independently selected from the group consisting of N, O and S, aryl having a ring atom number of 3 to 8 or heteroaryl group having a ring atom number of 3 to 8 and having 1 to 3 heteroatoms independently selected from the group consisting of N, O and S, the heteroarylalkyl or alkylheteroaryl is an optionally substituted heteroaryl having a ring atom number of 3 to 8 and having 1 to 3 heteroatoms independently selected from the group consisting of N, O and S and a $C_1$-$C_{12}$ alkyl, the heteroarylalkenyl is an optionally substituted heteroaryl having a ring atom number of 3 to 8 and having 1 to 3 heteroatoms independently selected from the group consisting of N, O and S and a $C_1$-$C_{12}$ alkenyl, the heteroarylamino is an optionally substituted heteroaryl having a ring atom number of 3 to 8 and having 1 to 3 heteroatoms independently selected from the group consisting of N, O and S and an amino group, the heteroaryloxy is an optionally substituted heteroaryl having a ring atom number of 3 to 8 and having at least one oxygen group, the arylalkyl or alkylaryl is an optionally substituted heteroaryl having a ring atom number of 3 to 8 and having 1 to 3 heteroatoms independently selected from the group consisting of N, O and S and a $C_1$-$C_6$ alkyl or the aryloxy is an optionally substituted heteroaryl having a ring atom number of 3 to 8 and having at least one oxygen atom.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of disclosed compounds are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, the disclosed compounds are intended to cover, where applicable, solvated as well as unsolvated forms of the compounds. Thus, each formula includes compounds having the indicated structure, including the hydrated as well as the non-hydrated forms.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/–5% of the stated value, more typically +/–4% of the stated value, more typically +/–3% of the stated value, more typically, +/–2% of the stated value, even more typically +/–1% of the stated value, and even more typically +/–0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DESCRIPTION OF EMBODIMENTS

The present disclosure is related to novel $A_2$-type monomers containing degradable linkers, biodegradable cationic polyionene and Gemini surfactants containing biodegradable amine linkers synthesized using these monomers and commercially available tertiary amine-based reagents via addition chemistry, and their antimicrobial properties. These materials may have extremely low minimum inhibitory concentration (MIC) values with a broad spectrum of activity against clinically relevant pathogens, while having tunable selectivity.

These materials may have extremely low MIC values with broad spectrum of action against clinically relevant pathogens and tunable selectivity ($HC_{50}$). The compound, composition and method of synthesis may provide an inexpensive biodegradable antimicrobial material through a step-efficient synthetic route for use in personal care and biomedical applications.

There is provided a compound having the following formula (I), (Ia) or (Ib):

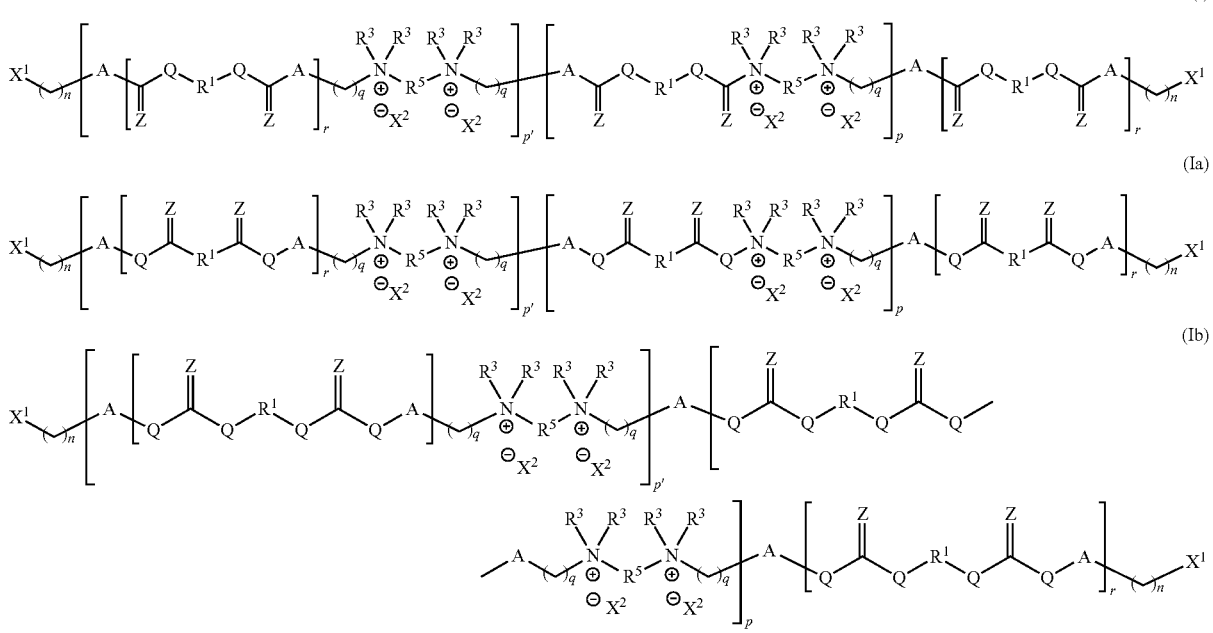

wherein

A may be independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl. A may be Ar.

The alkyl may be selected from the group consisting of methyl, ethyl, 1-propyl, 2-propyl, 1-butyl, 2-butyl, isobutyl, tert-butyl, 1-pentyl, tert-pentyl, neopentyl, isopentyl, sec-pentyl, 3-pentyl, 1-hexyl, 2-methylpentyl, 3-methylpentyl, 2,2-dimetlybutyl, 2,3-dimethylbutyl, 1-heptyl, 2-methylheptyl, 3-methylhexyl, 2,2-dimethylpentyl, 2,3-dimethylpentyl, 2,4-dimethylpentyl, 3,3-dimethylpentyl, 3-ethylpentyl, 2,2,3-trimethylbutyl, 1-octyl, 2-methylheptyl, 3-methylheptyl, 4-methylheptyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethylhexyl, 2,2,3-trimethylpentyl, 2,2,4-trimethylpentyl, 2,3,3-trimethylpentyl, 2,3,4-trimethylpentyl, 2-methyl-3-ethylpentyl, 3-methyl-3-ethylpentyl, tetramethylbutyl and 2-ethyl-1-hexyl. The alkylamino as used herein, may be the alkyl shown above having an amine group as the terminal group.

The alkenyl may be selected from the group consisting of ethenyl, 1-propenyl, 2-propenyl, 1-butenyl, trans-2-butenyl, cis-2-butenyl, 2-methylpropenyl, 1-pentenyl, trans-2-pentenyl, cis-2-pentenyl, 2-methyl-2-butenyl, 3-methyl-1butenyl, 2-methyl-2-butenyl, 1-hexenyl, cis-2-hexenyl, trans-2-hexenyl, cis-3-hexenyl, trans-3-hexenyl, 2-methyl-1-pentenyl, 2-ethyl-1-butenyl, cis-3-methyl-2-pentenyl, trans-3-methyl-2-pentenyl and 2,3-dimethyl-2-butenyl.

The alkynyl may be selected from the group consisting of ethynyl, 1-propynyl, 2-propynyl, 1-butenyl, 2-butenyl, 1-pentynyl, 2-pentynyl, 2-methyl-1butynyl, 1-hexynyl, 2-hexynyl, 3-hexynyl, 3,3-dimethyl-1-butynyl and 4-methyl-1-pentynyl.

The cycloalkyl may be selected from the group consisting of cyclopropanyl, cyclobutanyl, cyclopentanyl, cyclohexanyl, cycloheptanyl and cyclooctanyl.

The cycloalkenyl may be selected from the group consisting of cyclopropenyl, cyclobutenyl, cyclopentenyl, cyclohexenyl, cyclohepenyl and cyclooctenyl.

The cycloalkynyl may be selected from the group consisting of cyclopropynyl, cyclobutynyl, cyclohexynyl, cycloheptynyl and cyclooctynyl.

The heterocycloalkyl may be selected from the group consisting of aziridinyl, oxiranyl, thiiranyl, diaziridinyl, oxaziridinyl, dioxiranyl, azetidinyl, oxetanyl, thietanly, diazetidinyl, dioxetanyl, dithietanyl, pyrrolidinyl, tetrahydrofuranyl, tetrahydrothiophenyl, imidazolidinyl, pyrazolidinyl, oxazolidinyl, isoxazolidinyl, thiazolidinyl, isothiazolidinyl, dioxolanyl, dithiolanyl, piperidinyl, tetrahydropyranyl, thiazinyl, piperazinyl, morpholinyl, thiomorpholinyl, dioxanyl, dithianyl, hexahydro-1,3,5-trazinyl, trioxanyl, trithianyl, azepanyl, oxepanyl, thepanyl, diazepanyl, azocanyl, oxocanyl, thiocanly, azonanyl, oxonanly and thionanyl.

The heterocycloalkenyl may be selected from the group consisting of azirinyl, oxirenyl, thiirenyl, azetyl, oxetyl, thietyl, diazetyl, dioxetyl, dithietyl, dithiazolyl, tetrazolyl, oxatetrazolyl, thiatetrazolyl, pentazolyl, pyranyl, thiopyranyl, oxazinyl, thiazinyl, dioxinyl, dithiinyl, azepinyl, oxepinyl, thepinyl, diazepinyl, thiazepinyl, azocinyl, oxocinyl, thiocinyl, azoninyl, oxoninyl and thioninyl.

The aryl may be selected from the group consisting of phenyl, naphthyl, thracenyl, phenanthrecenyl, pyrenyl, tetrahydronaphthyl, indenyl and indanyl.

The heteroaryl may be selected from the group consisting of pyrrolyl, furanyl, thieophenyl, imidazolyl, pyrazolyl, oxazolyl, isoxazolyl, thiazolyl, isothiazolyl, triazolyl, furazanyl, oxadiazolyl, thiadazolyl, pyridinyl, pyridazinyl, pyrimidinyl, pyrazinyl, triazinyl, tetrazinyl, pentazinly, quinolyl, isoquinolyl, and indolyl.

$R^1$ may be independently selected from the group consisting of $-R^2-$, $-Ar-$, $-R^2-Ar-R^2-$, $-R^2-(O-R^2)_m-R^2)_m-$, $-R^2-N(R^6)-R^2-$ and $-R^2-C(R^6)_2-R^2$.

Ar may be independently optionally substituted aryl or optionally substituted heteroaryl. Ar may be optionally substituted aryl. Ar may be aryl. Ar may be selected from the group consisting of benzene, toluene, xylene, naphthalene, biphenyl and any mixture thereof. Ar may be benzene. Ar may be o-, p- or m-substituted.

$R^2$ may be independently optionally substituted alkyl, optionally substituted alkenyl or optionally substituted alkynyl. $R^2$ may be a $C_1$ to $C_{15}$ linear or branched alkyl. $R^2$ may be a $C_1$ to $C_{15}$ linear or branched alkenyl. $R^2$ may be a $C_1$ to $C_{15}$ linear or branched alkynyl. $R^2$ may be a $C_1$ to $C_{15}$ linear alkyl or $C_1$ to $C_{15}$ linear or branched alkenyl.

$R^2$ may be an optionally substituted alkyl. The optionally substituted alkyl may be an optionally substituted linear alkyl or an optionally substituted branched alkyl. The optionally substituted linear alkyl may be an optionally substituted $C_1$ to $C_{15}$ linear alkyl. The optionally substituted branched alkyl may be an optionally substituted $C_1$ to $C_{15}$ branched alkyl. The optionally substituted branched alkyl may have the following formula (VII).

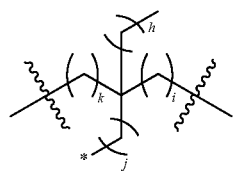

(VII)

j and k may be an integer selected from 0 to 13. h and i may independently be integers selected from 1 to 13.

j and k may be 0, i may be 1, and h may be 10.

j and k may be 0, i may be 1 and h may be 4.

The optionally substituted branched alkyl may be 2-ethylheptyl, 2-heptylhexadecyl, 2-heptylpentadecyl, 2-heptyltetradecyl, 2-heptyltridecyl, 2-heptyldodeclyl, 2-heptylundecyl, 2-heptyldecyl, 2-heptylnonyl, 2-heptyloctyl, 2-heptylheptyl, 2-octylhexadecyl, 2-octylpentadecyl, 2-octyltetradecyl, 2-octyltridecyl, 2-octyldodecyl, 2-octylundecyl, 2-octyldecyl, 2-octylnonyl, 2-octyloctyl, 2-nonyltetradecyl, 2-nonyltridecyl, 2-nonyldodecyl, 2-nonylundecyl, 2-nonyldecyl, 2-nonylnonyl, or 2-ethyldecyl.

$R^6$ may independently be selected from the group consisting of $-R^3-$, $-C(O)O-R^3$ and $-R^2-O-R^2-CH_2=CH_2$.

$X^1$ may be independently halogen, sulfate, tosylate, mesylate,

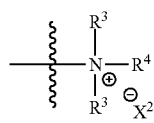 or 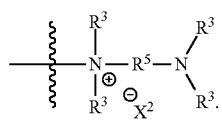

$X^1$ may be halogen. $X^1$ may be selected from fluorine, chlorine, iodine or bromine. $X^1$ may be chlorine.

$X^1$ may be

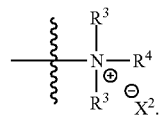

$X^1$ may be

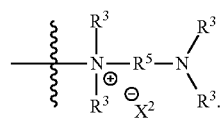

$X^2$ may be independently absent or an anionic counterion. $X^2$ may be selected from the group consisting of halogen, sulfate, tosylate and mesylate.

$R^3$ may be independently selected from the group consisting of hydrogen, optionally substituted alkyl, optionally substituted alkenyl and optionally substituted alkynyl. $R^3$ may be a linear or branched alkyl. $R^3$ may be selected from the group consisting of linear or branched methyl, ethyl, propyl, butyl, pentyl, hexyl, heptyl or octyl. $R^3$ may be methyl, ethyl, 1-propyl, 2-propyl, 1-butyl, 2-butyl, isobutyl, tert-butyl, 1-pentyl, tert-pentyl, neopentyl, isopentyl, sec-pentyl, 3-pentyl, 1-hexyl, 2-methylpentyl, 3-methylpentyl, 2,2-dimetlybutyl, 2,3-dimethylbutyl, 1-heptyl, 2-methylheptyl, 3-methylhexyl, 2,2-dimethylpentyl, 2,3-dimethylpentyl, 2,4-dimethylpentyl, 3,3-dimethylpentyl, 3-ethylpentyl, 2,2,3-trimethylbutyl, 1-octyl, 2-methylheptyl, 3-methylheptyl, 4-methylheptyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethylhexyl, 2,2,3-trimethylpentyl, 2,2,4-trimethylpentyl, 2,3,3-trimethylpentyl, 2,3,4-trimethylpentyl, 2-methyl-3-ethylpentyl, 3-methyl-3-ethylpentyl, tetramethylbutyl and 2-ethyl-1-hexyl. $R^3$ may be $CH_3$. $R^3$ may be ethyl. $R^3$ may be tert-butyl.

$R^4$ may be independently selected from the group consisting of hydrogen, $R^3$, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide, $-R^2-OC(O)-R^3$, $-R^2-C(O)O-R^3$, $-R^2-Ar$ and $R^2-O-R^2-CH_2=CH_2$.

Where $R^4$ is an optionally substituted alkyl, the alkyl may be substituted with at least one hydroxyl group(s). The alkyl substituted with the at least one hydroxyl group(s) may additionally be substituted with a carboxylic acid moiety.

$R^5$ may be independently $-R^2-$ or $-R^2-O-R^2-$.

Z may be independently O or S.

Q may be independently O or NH.

n, m and q may independently be an integer from 1 to 10. n, m and q may independently be an integer selected from 1, 2, 3, 4, 5, 6, 7, 8, 9 or 10. n may be 1. m may be 3. q may be 1.

p and p' may independently be 0 or may be an integer of at least 1. p and p' may independently be 0. p and p' may independently be an integer of at least 1.

r may be 0 or 1.

There is provided a compound having the following formulas (II), (IIa) or (IIb):

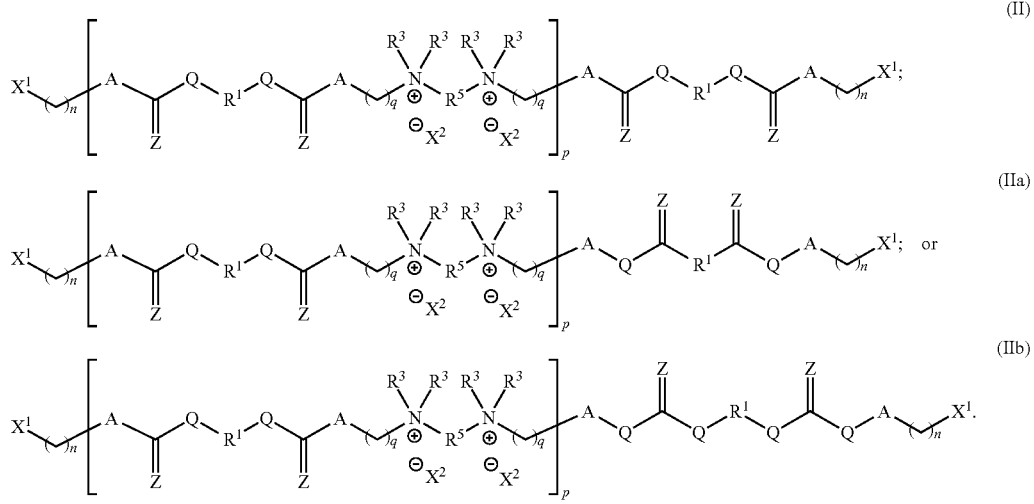

Z may be O and Q may be NH. Z may be O and Q may be O. Z may be O and Q may independently be a mixture of O and NH.

$R^1$ may be selected from the group consisting of: —$(CH_2)_2$—, —$(CH_2)_3$—, —$(CH_2)_4$—, —$(CH_2)_5$—, —$(CH_2)_6$—, —$(CH_2)_7$—,
—$(CH_2)_8$—, —$CH_2$—O—$CH_2CH_2$—O—$CH_2$—, —$(CH_2)_2$—O—$CH_2CH_2$—O—$(CH_2)_2$—,
—$CH_2$—{O—$CH_2CH_2$}$_2$—O—$CH_2$—, —$(CH_2)_2$—{O—$CH_2CH_2$}$_2$—O—$(CH_2)_2$—,
—$(CH_2)_3$—[O—$CH_2CH_2$]$_2$—O—$(CH_2)_3$—,

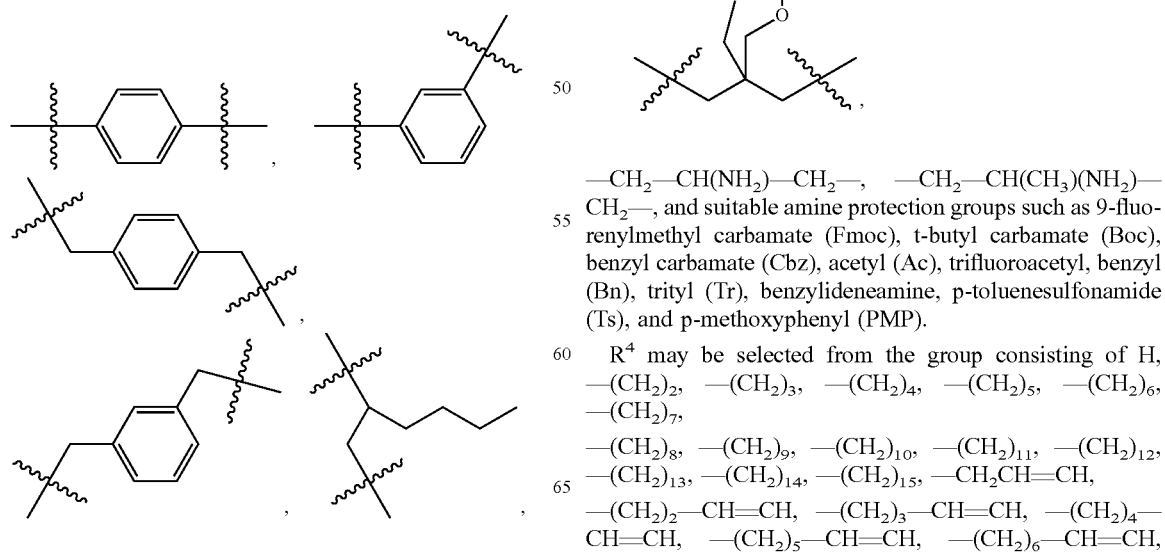

—$CH_2$—$CH(NH_2)$—$CH_2$—, —$CH_2$—$CH(CH_3)(NH_2)$—$CH_2$—, and suitable amine protection groups such as 9-fluorenylmethyl carbamate (Fmoc), t-butyl carbamate (Boc), benzyl carbamate (Cbz), acetyl (Ac), trifluoroacetyl, benzyl (Bn), trityl (Tr), benzylideneamine, p-toluenesulfonamide (Ts), and p-methoxyphenyl (PMP).

$R^4$ may be selected from the group consisting of H, —$(CH_2)_2$, —$(CH_2)_3$, —$(CH_2)_4$, —$(CH_2)_5$, —$(CH_2)_6$, —$(CH_2)_7$,
—$(CH_2)_8$, —$(CH_2)_9$, —$(CH_2)_{10}$, —$(CH_2)_{11}$, —$(CH_2)_{12}$, —$(CH_2)_{13}$, —$(CH_2)_{14}$, —$(CH_2)_{15}$, —$CH_2CH$=$CH$,
—$(CH_2)_2$—$CH$=$CH$, —$(CH_2)_3$—$CH$=$CH$, —$(CH_2)_4$—$CH$=$CH$, —$(CH_2)_5$—$CH$=$CH$, —$(CH_2)_6$—$CH$=$CH$, —(CH$_2$)$_7$—CH=CH, —(CH$_2$)$_8$—CH=CH, —(CH$_2$)$_9$—CH=CH, —(CH$_2$)$_{10}$—CH=CH, —(CH$_2$)$_{11}$—CH=CH, —(CH$_2$)$_{13}$—CH=CH, —CH$_2$—OC(O)—CH$_2$, —CH$_2$—OC(O)—(CH$_2$)$_2$, —CH$_2$—OC(O)—(CH$_2$)$_3$, —CH$_2$—OC(O)—(CH$_2$)$_4$, —(CH$_2$)$_2$—OC(O)—CH$_2$, —(CH$_2$)$_2$—OC(O)—(CH$_2$)$_2$, —(CH$_2$)$_2$—OC(O)—(CH$_2$)$_3$, —(CH$_2$)$_2$—OC(O)—(CH$_2$)$_4$, —(CH$_2$)$_2$—OC(O)—C(=CH$_2$)CH$_3$, —CH$_2$—C(O)O—CH$_2$, —CH$_2$—C(O)O—(CH$_2$)$_2$, —CH$_2$—C(O)O—(CH$_2$)$_3$, —CH$_2$—C(O)O—(CH$_2$)$_4$, —(CH$_2$)$_2$—C(O)O—CH$_2$, —(CH$_2$)$_2$—C(O)O—(CH$_2$)$_2$, —(CH$_2$)$_2$—C(O)O—(CH$_2$)$_3$, —(CH$_2$)$_2$—C(O)O—(CH$_2$)$_4$, —(CH$_2$)$_2$—C(O)O—C(=CH$_2$)CH$_3$, —NH$_2$, —SH,

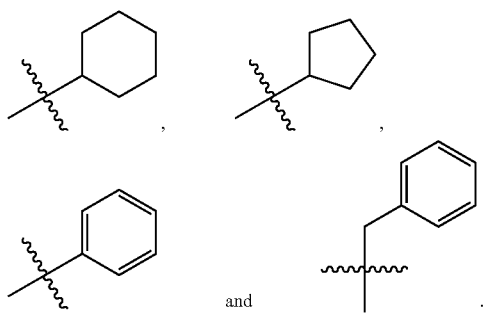

and

R$^5$ may be selected from the group consisting of —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —CH=CH—, —CH=CH—CH$_2$—, —CH$_2$—CH=CH—, —CH=CH—(CH$_2$)$_2$—, —CH$_2$—CH=CH—CH$_2$—, —(CH$_2$)$_2$—CH=CH—, —CH=CH=CH—, —CH=CH—(CH$_2$)$_3$—, —CH$_2$—CH=CH—(CH$_2$)$_2$—, —(CH$_2$)$_2$—CH=CH—CH$_2$—, —(CH$_2$)$_3$—CH=CH—, —CH=CH=CH—CH$_2$—, —CH$_2$—CH=CH=CH—, —CH$_2$—O—CH$_2$—, —CH$_2$—O—(CH$_2$)$_2$—, —(CH$_2$)$_2$—O—CH$_2$—, —(CH$_2$)—O—(CH$_2$)$_3$—, —(CH$_2$)$_2$—O—(CH$_2$)$_2$—, and —(CH$_2$)$_3$—O—CH$_2$—.

When p is 0, the compound may have the following formula (III), (IIIa) or (IIIb):

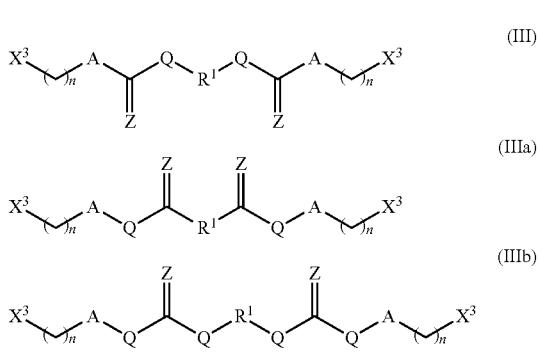

wherein X$^3$ may be halogen.

The compound of formula (III), (IIIa) or (IIIb) may be selected from the group consisting of:

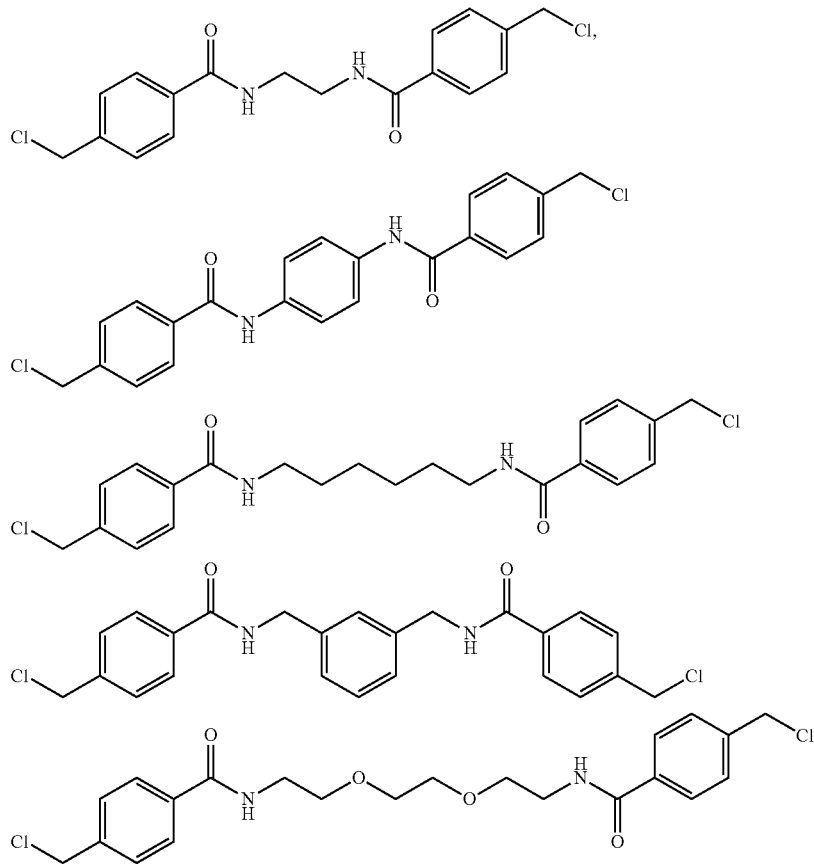

27 28
-continued
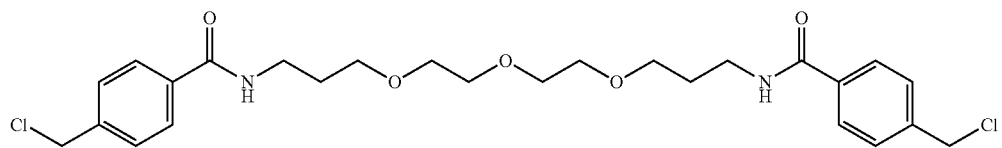
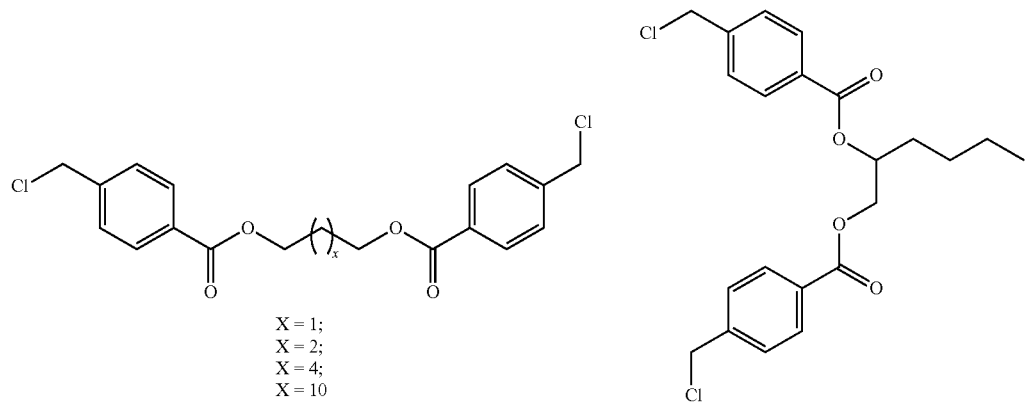
X = 1;
X = 2;
X = 4;
X = 10
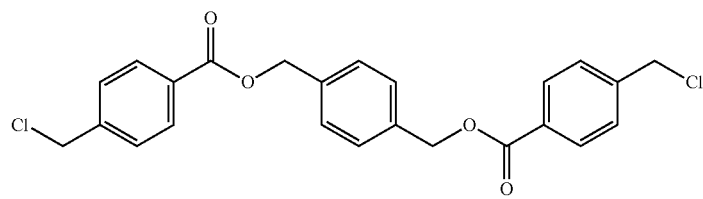
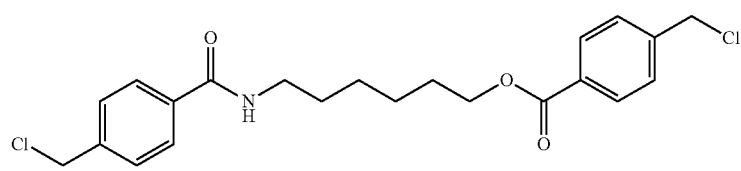
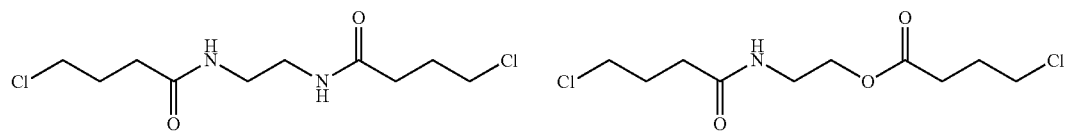
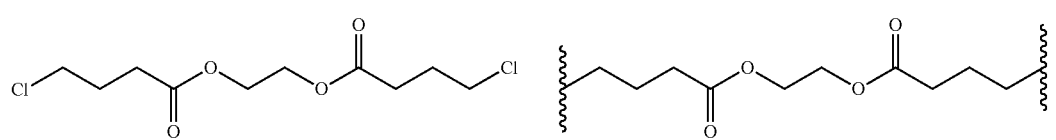

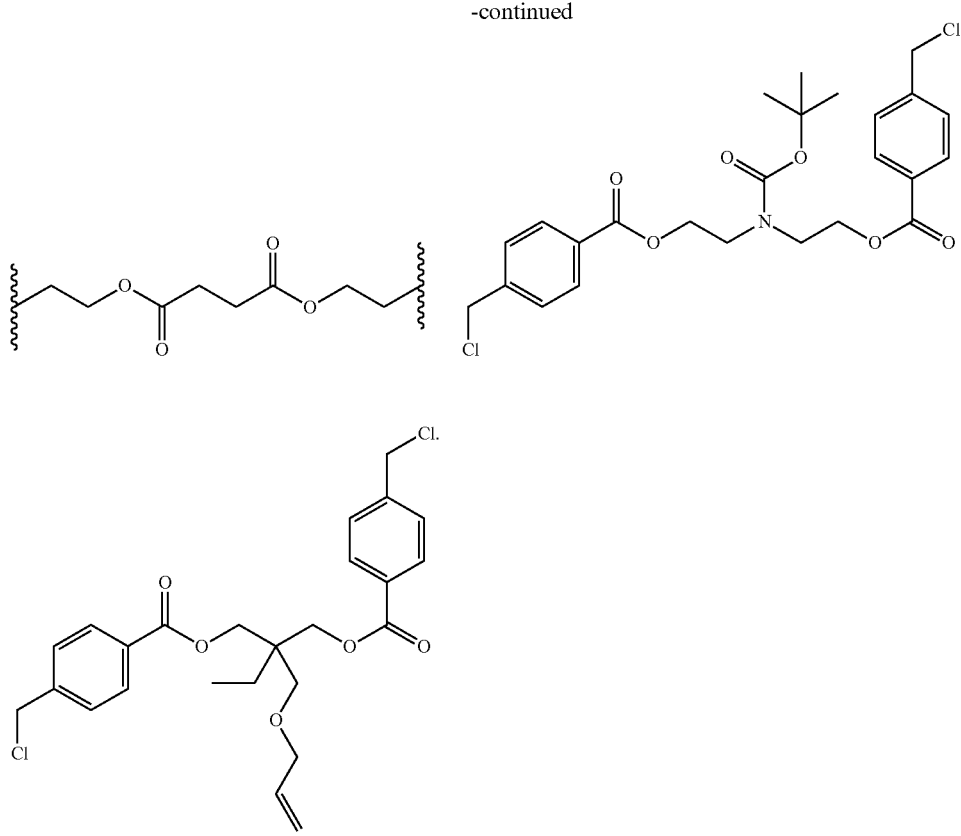
When p and p' are 0, the compound may have the following formula (IV), (IVb) or (IVc):
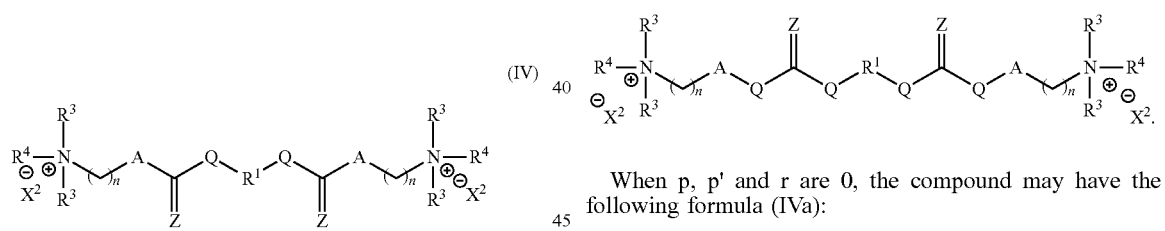
When p, p' and r are 0, the compound may have the following formula (IVa):
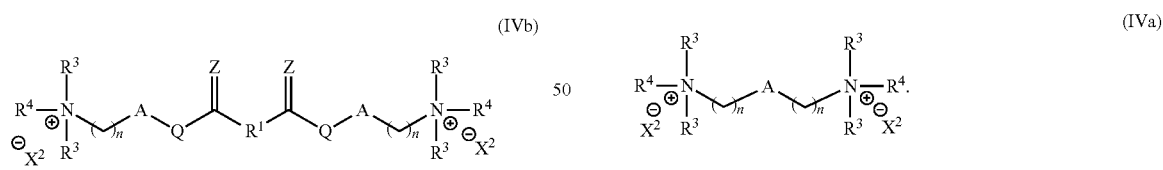
When p' is 0, r is 1 and p is an integer of at least 1, the compound may have the following formula (V):
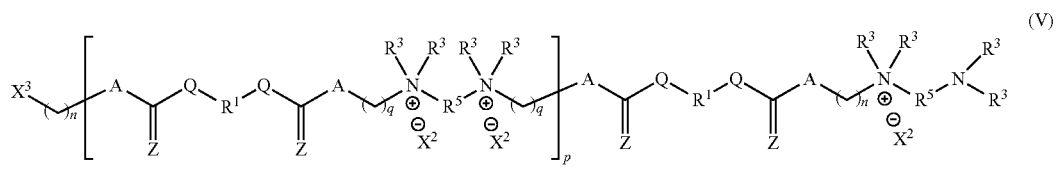

wherein $X^3$ may be halogen.

When p and p' are an integer of at least 1 and r is 1, the compound may have the following formula (Va), (Vb), (Vc), (Vd) or (Ve):

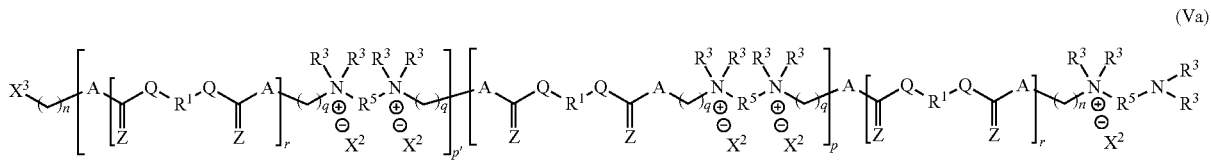

(Va)

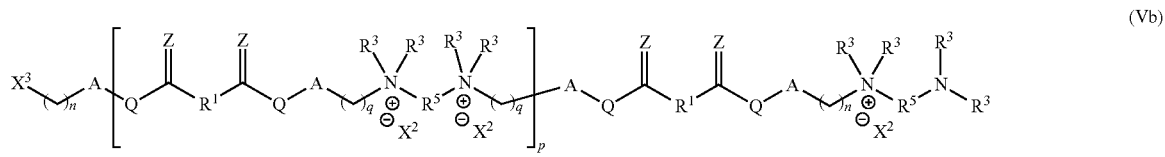

(Vb)

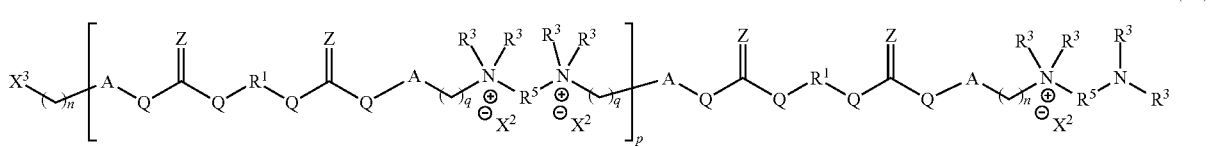

(Vc)

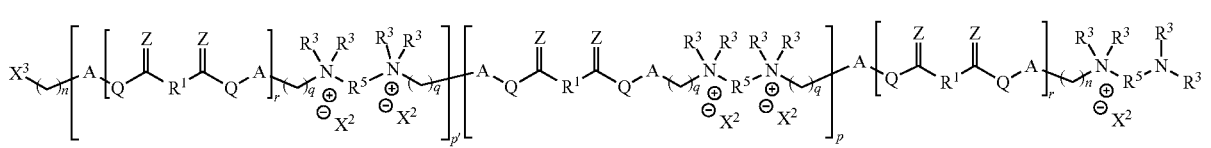

(Vd)

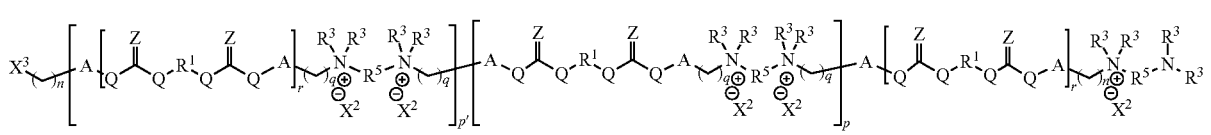

(Ve)

wherein $X^3$ may be halogen.

The p':p ratio in the compound may be in the range of about 1:10 to about 10:1, about 1:10 to about 1:9, about 1:10 to about 1:7, about 1:10 to about 1:5, about 1:10 to about 1:3, about 1:10 to about 1:1, about 1:10 to about 3:1, about 1:10 to about 5:1, about 1:10 to about 7:1, about 1:10 to about 9:1, about 1:9 to about 1:7, about 1:9 to about 1:5, about 1:9 to about 1:3, about 1:9 to about 1:1, about 1:9 to about 3:1, about 1:9 to about 5:1, about 1:9 to about 7:1, about 1:9 to about 9:1, about 1:9 to about 10:1, about 1:7 to about 1:5, about 1:7 to about 1:3, about 1:7 to about 1:1, about 1:7 to about 3:1, about 1:7 to about 5:1, about 1:7 to about 7:1, about 1:7 to about 9:1, about 1:7 to about 10:1, about 1:5 to about 1:3, about 1:5 to about 1:1, about 1:5 to about 3:1, about 1:5 to about 5:1, about 1:5 to about 7:1, about 1:5 to about 9:1, about 1:5 to about 10:1, about 1:3 to about 1:1, about 1:3 to about 3:1, about 1:3 to about 5:1, about 1:3 to about 7:1, about 1:3 to about 9:1, about 1:3 to about 10:1, about 1:1 to about 3:1, about 1:1 to about 5:1, about 1:1 to about 7:1, about 1:1 to about 9:1, about 1:1 to about 10:1, about 3:1 to about 5:1, about 3:1 to about 7:1, about 3:1 to about 9:1, about 3:1 to about 10:1, about 5:1 to about 7:1, about 5:1 to about 9:1, about 5:1 to about 10:1, about 7:1 to about 9:1, about 7:1 to about 10:1, or about 9:1 to about 10:1.

The p':p ratio in the compound may be about 1:1, about 3:7, about 7:3, about 1:9 or about 9:1.

The compound may have a molecular weight in the range of about 1 kDa to about 100 kDa, about 1 kDa to about 2 kDa, about 1 kDa to about 5 kDa, about 1 kDa to about 10 kDa, about 1 kDa to about 20 kDa, about 1 kDa to about 50 kDa, about 2 kDa to about 5 kDa, about 2 kDa to about 10 kDa, about 2 kDa to about 20 kDa, about 2 kDa to about 50 kDa, about 2 kDa to about 100 kDa, about 5 kDa to about 10 kDa, about 5 kDa to about 20 kDa, about 5 kDa to about 50 kDa, about 5 kDa to about 100 kDa, about 10 kDa to about 20 kDa, about 10 kDa to about 50 kDa, about 10 kDa to about 100 kDa, about 20 kDa to about 50 kDa, about 20 kDa to about 100 kDa or about 50 kDa to about 100 kDa.

The compound may have a molar mass dispersity in the range of about 1.1 to about 4.0, 1.1 to about 1.2, 1.1 to about 2.0, 1.1 to about 2.5, 1.1 to about 3.0, 1.1 to about 3.5, about 1.2 to about 2.9, about 1.2 to about 1.5, about 1.2 to about 2.0, about 1.2 to about 2.5, about 1.2 to about 3.5. about 1.2 to about 4.0, about 1.5 to about 2.0, about 1.5 to about 2.5 about 1.5 to about 2.9, about 1.5 to about 3.5, about 1.5 to about 4.0, about 2.0 to about 2.5, about 2.0 to about 2.9, about 2.0 to about 3.5, about 2.0 to about 4.0, about 2.5 to about 2.9, about 2.5 to about 3.5, about 2.5 to about 4.0, about 3.0 to about 3.5, about 3.0 to about 4.0 or about 3.5 to about 4.0.

There is also provided a method for making a compound as defined above, the method comprising the steps of:
contacting $NH_2-R^1-NH_2$ or $HO-R^1-OH$ with a compound having the following formula (VI):

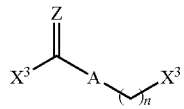
(VI)

wherein $R^1$ may be selected from the group consisting of $-R^2-$, $-Ar-$, $-R^2-Ar-R^2-$, $-R^2-(O-R^2)_m-R^2-$, $-R^2-N(R^4)-R^2-$ and $-R^2-C(R^4)_2-R^2-$;

Ar may be independently optionally substituted aryl or optionally substituted heteroaryl;

$R^2$ may be independently optionally substituted alkyl, optionally substituted alkenyl or optionally substituted alkynyl;

Z may be independently O or S;

A may be independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

n and m may be independently an integer from 1 to 10; and $X^3$ may be halogen;

to form a halogen compound having the following formula (III):

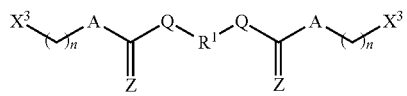
(III)

wherein Q may be independently O or NH.

Further, there is also provided a method for making a compound as defined above, the method comprising the steps of:
contacting

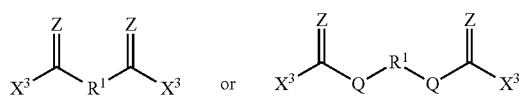

with a compound having the following formula (VIa):

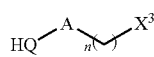
(VIa)

wherein $R^1$ is selected from the group consisting of $-R^2-$, $-Ar-$, $-R^2-Ar-R^2-$, $-R^2-(O-R^2)_m-R^2-$, $-R^2-N(R^4)-R^2-$ and $-R^2-C(R^4)_2-R^2-$;

Ar is independently optionally substituted aryl or optionally substituted heteroaryl;

$R^2$ is independently optionally substituted alkyl, optionally substituted alkenyl or optionally substituted alkynyl;

Z is independently O or S;

A is independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

n and m are independently an integer from 1 to 10; and $X^3$ is halogen;

to form a halogen compound having the following formula (IIIa) or (IIIb):

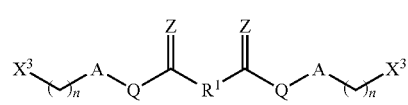
(IIIa)

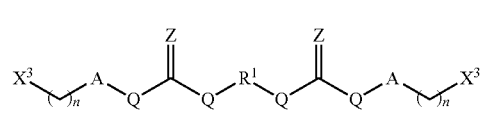
(IIIb)

wherein Q is independently O or NH.

The method may comprise the step of contacting the halogen compound having the formula (III), (IIIa) or (IIIb) or a compound having the formula $X^3$-A-$X^3$ with a tertiary amine $N(R^3)_2R^4$:

wherein $R^3$ may be independently selected from the group consisting of hydrogen, optionally substituted alkyl, optionally substituted alkenyl and optionally substituted alkynyl; and $R^4$ may be independently selected from the group consisting of hydrogen, $R^3$, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide, $-R^2-OC(O)-R^2$, $-R^2-C(O)O-R^2$, $-R^2-Ar$ and $-R^2-O-R^2-CH_2=CH_2$;

to form a tertiary amino compound having the following formula (IV), (IVa), (IVb) or (IVc):

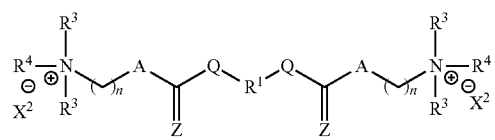
(IV)

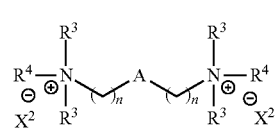
(IVa)

(IVb)

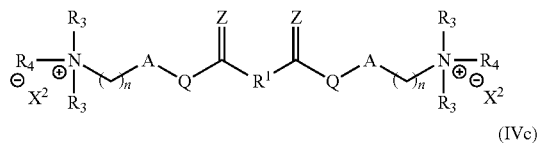

(IVc)

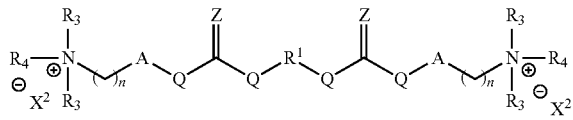

wherein

X² may be absent or an anionic counterion.

The method may comprise the step of contacting the halogen compound having the formula (III), (IIIa) or (IIIb) or a compound having the formula $X^3$-A-$X^3$ with a diamine $(R^3)_2N$—$R^2$—$N(R^3)_2$:

wherein $R^3$ may be independently selected from the group consisting of hydrogen, optionally substituted alkyl, optionally substituted alkenyl and optionally substituted alkynyl;

to form a polymer product having the following formula (V), (Va), (Vb), (Vc), (Vd) or (Ve):

(V)

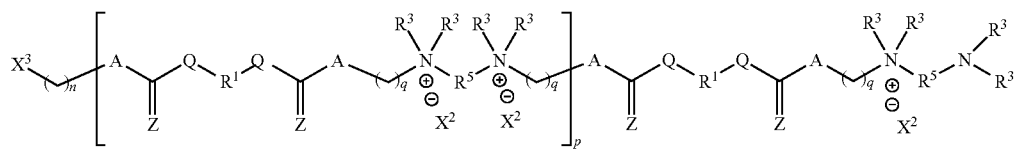

(Va)

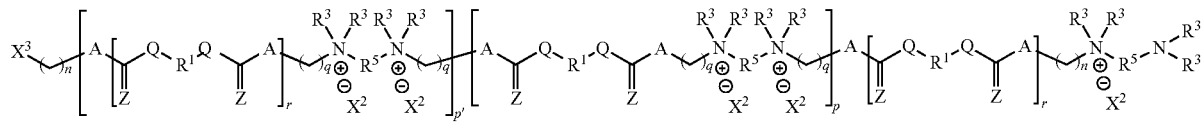

(Vb)

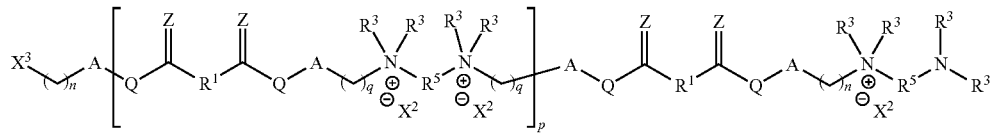

(Vc)

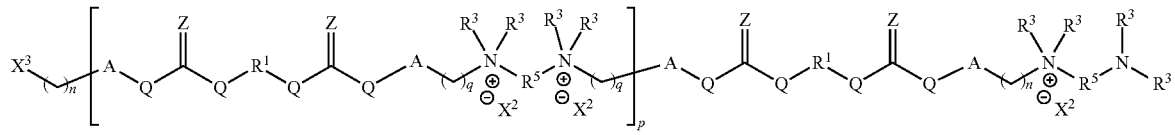

(Vd)

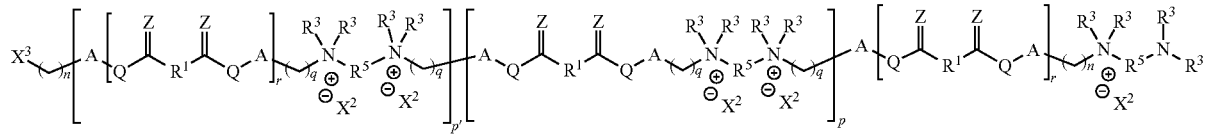

(Ve)

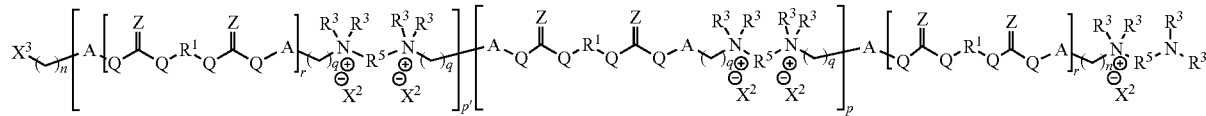

wherein
X² may be absent or an anionic counterion;
X³ may be halogen;
R⁵ is —R²— or —R²—O—R²—;
q is an integer from 1 to 10; and
p and p' are independently an integer of at least 1; and
r is 0 or 1.

The method may comprise the step of contacting the halogen compound having the formula (III), (IIIa) or (IIIb) or a compound having the formula X³-A-X³ with a diamine (R³)₂N—R²—N(R³)₂:

wherein R³ is independently selected from the group consisting of hydrogen, optionally substituted alkyl, optionally substituted alkenyl and optionally substituted alkynyl;

wherein the method further comprising the step of adding a second halogen compound having the formula (III), (IIIa) or (IIIb);

to form a polymer product having the following formula (V), (Va), (Vb), (Vc), (Vd) or (Ve)

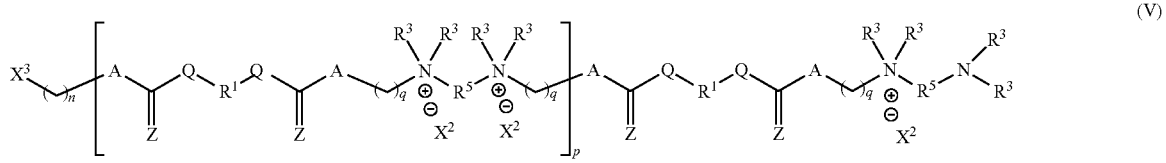
(V)

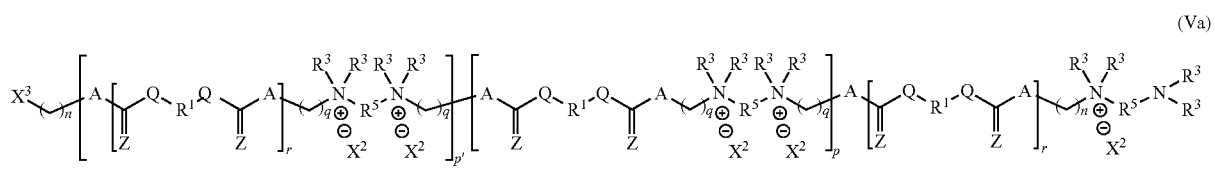
(Va)

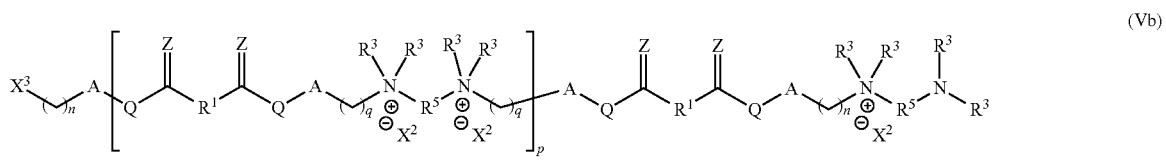
(Vb)

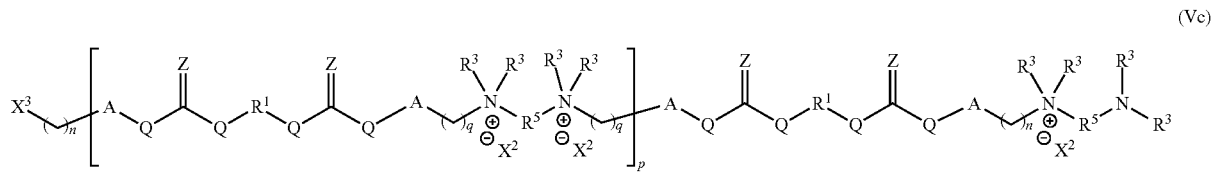
(Vc)

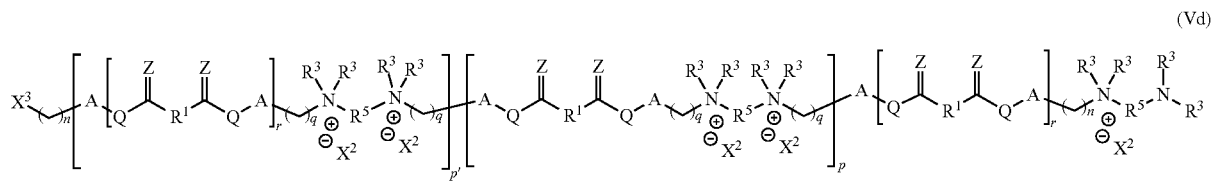
(Vd)

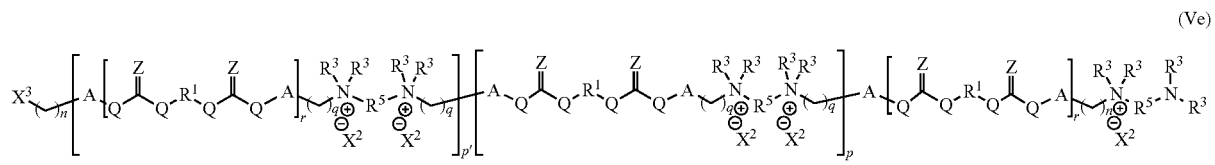
(Ve)

wherein
X² is absent or an anionic counterion;
X³ is halogen;
R⁵ is —R²— or —R²—O—R²
q is an integer from 1 to 10; and
p and p' are independently 0 or an integer of at least 1; and
r is 0 or 1.

group consisting of hydrogen, optionally substituted alkyl, optionally substituted alkenyl and optionally substituted alkynyl); and adding another halogen compound having the formula (III), (IIIa) or (IIIb);

to form a polymer product having the following formula (V), (Va), (Vb), (Vc), (Vd) or (Ve)

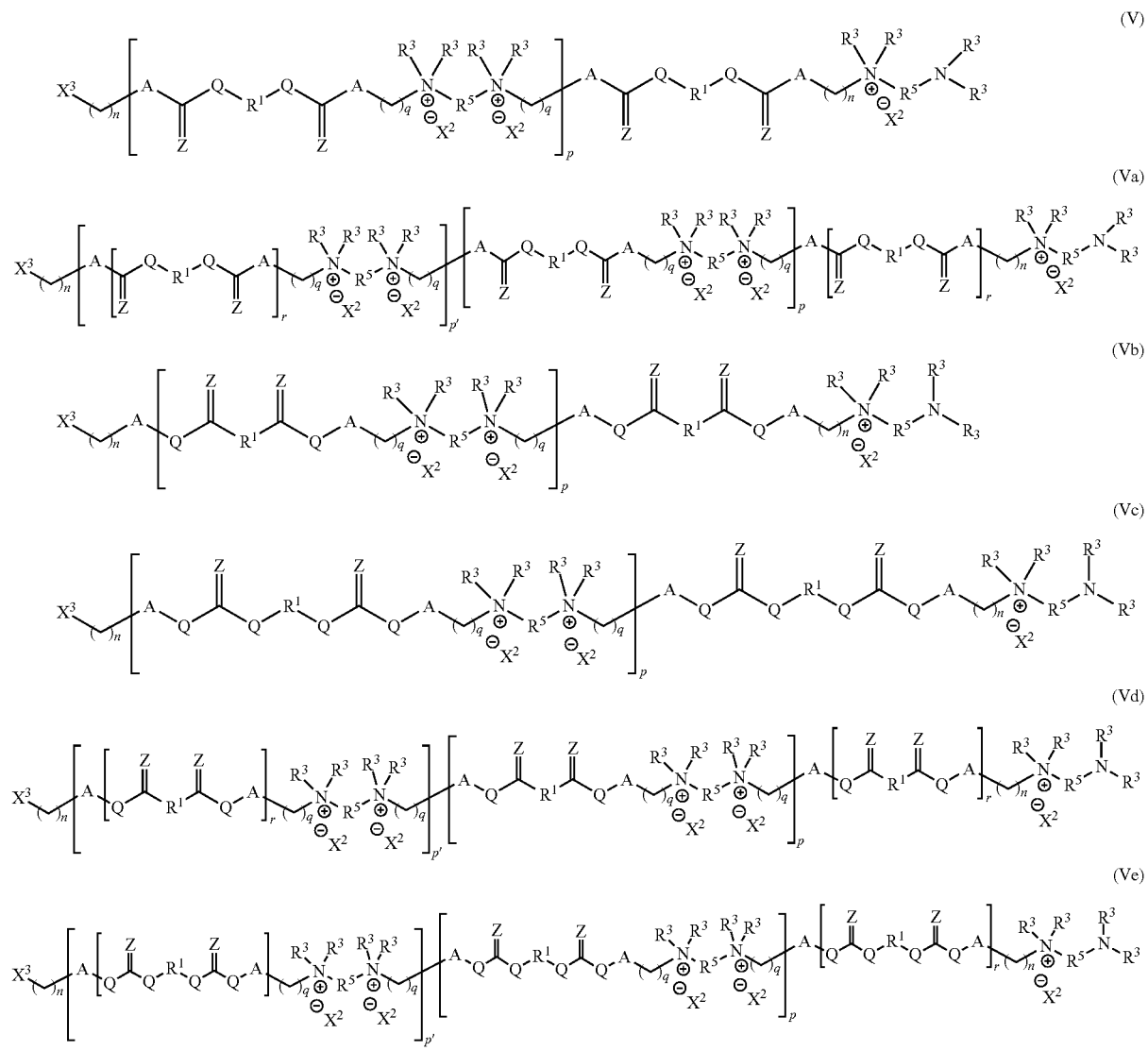

The method above may be undertaken in a reversal order. That is the second halogen compound having the formula (III), (IIIa) or (IIIb) may be contacted first with a diamine $(R^3)_2N—R^2—N(R^3)_2$ followed by adding the halogen compound having the formula (III), (IIIa) or (IIIb) into the mixture.

Therefore, there is also provided a method for making a compound as defined above, comprising the steps of:

contacting a halogen compound having the formula (III), (IIIa) or (IIIb) or a compound having the formula $X^3$-A-$X^3$ with a diamine $(R^3)_2N—R^2—N(R^3)_2$, wherein $R^3$ is as defined herein (that is, $R^3$ is independently selected from the wherein
X² is absent or an anionic counterion;
X³ is halogen;
R⁵ is —R²— or —R²—O—R²—;
q is an integer from 1 to 10; and
p and p' are independently 0 or an integer of at least 1; and
r is 0 or 1.

Depending on which step the halogen compound of formula (III), (IIIa) or (IIIb) is used, the halogen compound of formula (III), (IIIa) or (IIIb) may be termed as the "first halogen compound" or the "second halogen compound". For example, where the method encompasses two steps, each step requiring the halogen compound of formula (III), (IIIa)

or (IIIb), the halogen compound used in the first step is thus termed as the "first halogen compound" and the halogen compound used in the second step is thus termed the "second halogen compound". For avoidance of doubt, where the steps of the method can be reversed, whereby the second step is performed first and is thus treated as the first step, the halogen compound of formula (III), (IIIa) or (IIIb) used in this "first step" will then be regarded as the "first halogen compound". The same terminology is used for the halogen compound of formula (III), (IIIa) or (IIIb) used in the "second step", being termed as the "second halogen compound".

It should also be noted that one or more of the compounds of formula (III), (IIIa) or (IIIb) or a compound having the formula $X^3$-A-$X^3$ may be polymerized to form a homopolymer or a co-polymer. The copolymer may comprise different combinations of the compounds of formula (III), (IIIa) or (IIIb) or a compound having the formula $X^3$-A-$X^3$ in various orders. For example, the copolymer may comprise a compound of formula (III) with a compound of formula (III), a compound of formula (III) with a compound of formula (IIIa), a compound of formula (III) with a compound of formula (IIIb), a compound of formula (III) with a compound having the formula $X^3$-A-$X^3$, a compound of formula (IIIa) with a compound of formula (III), a compound of formula (IIIa) with a compound of formula (IIIa), a compound of formula (IIIa) with a compound of formula (IIIb), a compound of formula (IIIa) with a compound having the formula $X^3$-A-$X^3$, a compound of formula (IIIb) with a compound of formula (III), a compound of formula (IIIb) with a compound of formula (IIIa), a compound of formula (IIIb) with a compound of formula (IIIb), a compound of formula (IIIb) with a compound having the formula $X^3$-A-$X^3$, a compound having the formula $X^3$-A-$X^3$ with a compound of formula (III), a compound having the formula $X^3$-A-$X^3$ with a compound of formula (IIIa), or a compound having the formula $X^3$-A-$X^3$ with a compound of formula (IIIb).

Any combination and permutation of the compounds of formula (III), (IIIa) or (IIIb) or a compound having the formula $X^3$-A-$X^3$ known in the art may be possible. The compound having the formula $X^3$-A-$X^3$ may be

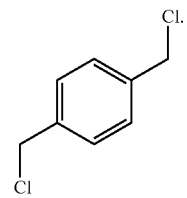

The duration of the reaction in the method above may be in the range from about 1 hour to about 24 hours, such as about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

When a two-steps reaction or method is carried out, the duration above may apply to the duration of each or individual step, hence, if the method has a "first step" and a "second step", the duration for each of the "first step" and a "second step" is independently selected from the duration in the preceding paragraph. As an example, the duration of the first step may be 18 hours and the duration of the second step may be 18 hours. In another example, the duration of the first step may be 18 hours and the duration of the second step may be 2 hours.

There is also provided a composition comprising the compound having the following formula (I), (Ia) or (Ib):

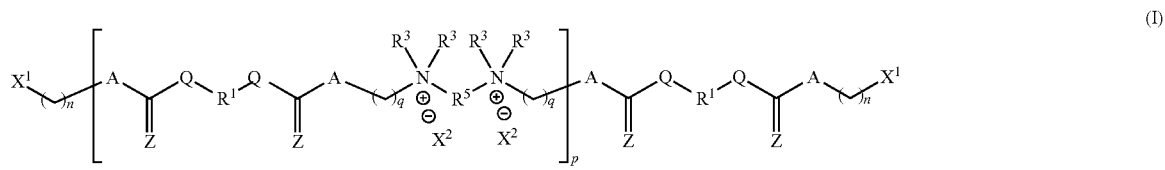

(I)

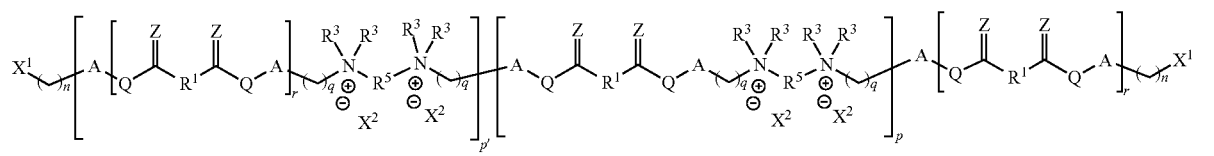

(Ia)

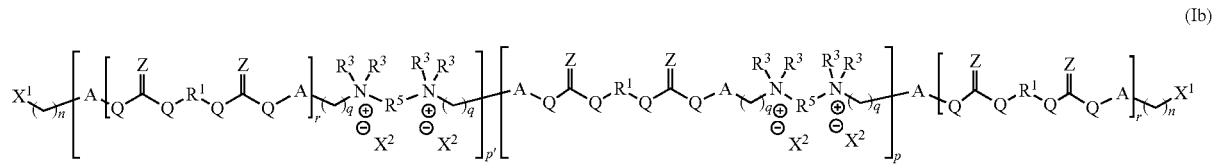

(Ib)

as defined above,
wherein

A may be independently selected from the group consisting of optionally substituted alkyl, optionally substituted alkylamino, optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl.

$R^1$ may be independently selected from the group consisting of —$R^2$—, —Ar—, —$R^2$—Ar—$R^2$—, —$R^2$—(O—$R^2$)$_m$—$R^2$—, —$R^2$—N($R^4$)—$R^2$— and —$R^2$—C($R^4$)$_2$—$R^2$—.

Ar may be independently optionally substituted aryl or optionally substituted heteroaryl.

$R^2$ may be independently optionally substituted alkyl, optionally substituted alkenyl or optionally substituted alkynyl.

$X^1$ may be independently halogen, sulfate, tosylate and mesylate,

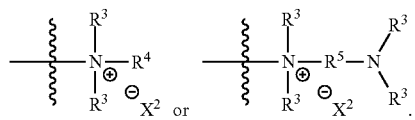

$X^2$ may be independently absent or an anionic counterion.

$R^3$ may be independently selected from the group consisting of hydrogen, optionally substituted alkyl, optionally substituted alkenyl and optionally substituted alkynyl.

$R^4$ may be independently selected from the group consisting of hydrogen, $R^3$, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide, —$R^2$—OC(O)—$R^2$, —$R^2$—C(O)O—$R^2$, $R^2$—Ar and $R^2$—O—$R^2$—CH$_2$=CH$_2$.

$R^5$ may be independently —$R^2$— or —$R^2$—O—$R^2$—.

Z may be independently O or S.

Q may be independently O or NH.

n, m and q may independently be an integer from 1 to 10.

p and p' may independently be 0 or may be an integer of at least 1.

r may independently be 0 or 1.

The composition may comprise a compound have the following formula (IV), (IVa), (IVb) or (IVc):

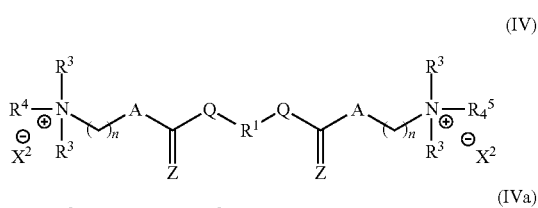

(IV)

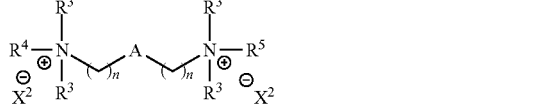

(IVa)

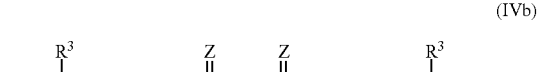

(IVb)

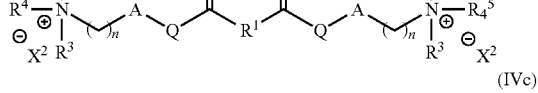

(IVc)

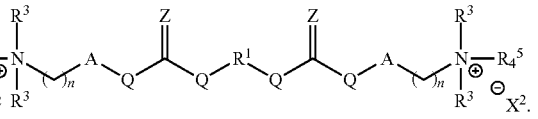

$R^4$ may be $R^2$. $R^2$ may be a $C_5$ to $C_{15}$ linear alkyl.

The composition may comprise a compound have the following formula (V), (Va), (Vb), (Vc), (Vd) or (Ve):

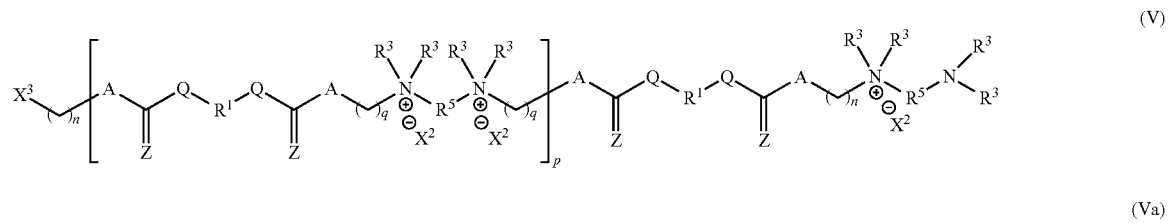

(V)

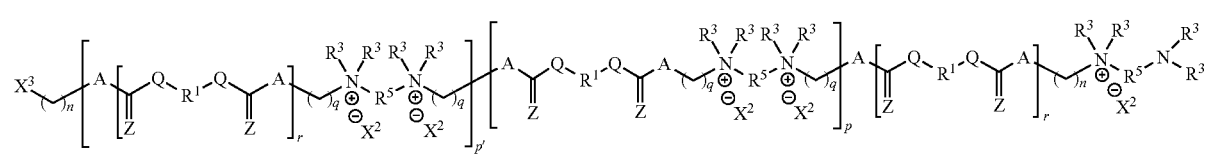

(Va)

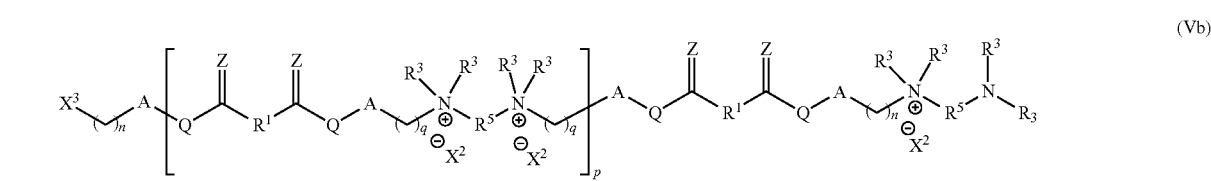

(Vb)

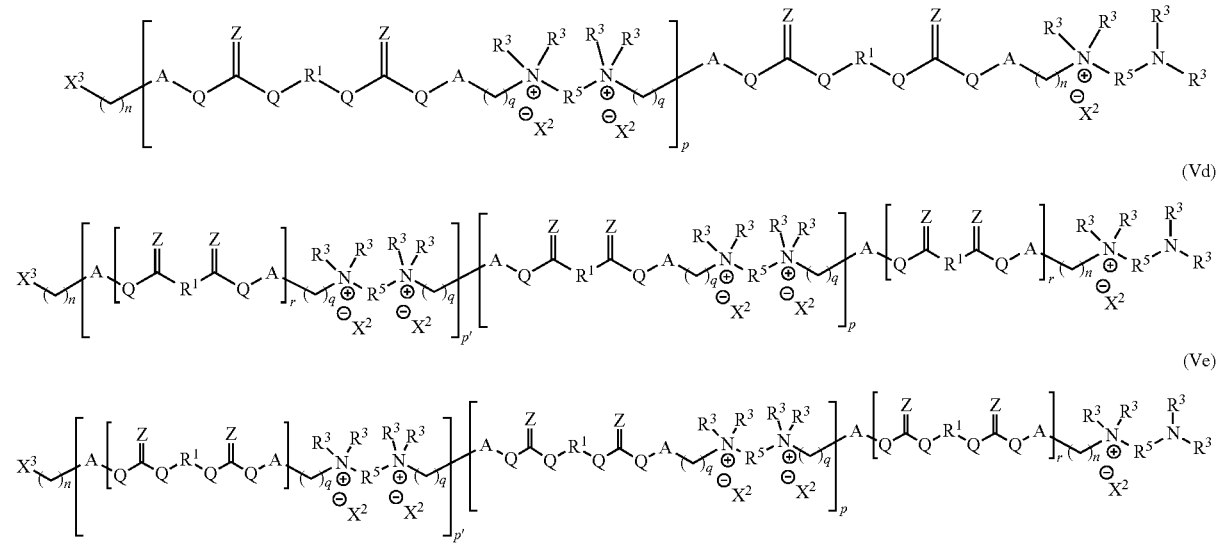

wherein X³ may be halogen.

The composition may be a pharmaceutical composition or an antimicrobial composition.

The composition may comprise a compound as defined above or pharmaceutically acceptable salts, hydrates and solvates thereof and a pharmaceutically acceptable excipient.

The pharmaceutically acceptable excipient may be a non-toxic carrier, adjuvant, or vehicle that does not destroy the pharmacological activity of the compound with which it is formulated. Pharmaceutically acceptable carriers, adjuvants or vehicles that may be used in the compositions of this disclosure may include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol or wool fat.

These compositions may also contain adjuvants such as preservative, wetting agents, emulsifying agents, and dispersing agents. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

The composition may further comprise a thickening agent. The thickening agent may be methylcellulose or hydroxymethylcellulose. The thickening agent may be hydroxymethylcellulose.

The composition may further comprise a detergent. The detergent may be branched octylphenoxy poly(ethyleneoxy) ethanol, IGEPAL®, N,N-Bis(2-hydroxyethyl)dodecanamide (HDA), N-Decyl-b-D-glucopyranoside (DGP) and any combination thereof.

The amount of compound in the compositions may be such that it is effective to measurably treat the disease, disorder or condition associated with glycine metabolism. The amount of compound in the compositions may be such that it is effective to measurably treat the disease, disorder or condition associated with glycine and serine metabolism. The amount of compound in the compositions may be such that it is effective to measurably treat the disease, disorder or condition associated with serine metabolism. The composition may be formulated for administration to a patient in need of such composition.

The composition may comprise the compound as defined above in the range of about 0.2 wt % to about 1 wt %, a thickening agent in the range of about 0.5 wt % to about 1.5 wt %, and a detergent in the range of about 3 wt % to about 15 wt %, with the remainder being water so that the total is 100 wt %

The composition may comprise the compound as defined above in the range of about 0.2 wt % to about 1 wt %, 0.2 wt % to about 0.4 wt %, about 0.2 wt % to about 0.6 wt %, about 0.2 wt % to about 0.8 wt %, about 0.4 wt % to about 0.6 wt %, about 0.4 wt % to about 0.8 wt %, about 0.4 wt % to about 1 wt %, about 0.6 wt % to about 0.8 wt %, about 0.6 wt % to about 1.0 wt %, or about 0.8 wt % to about 1.0 wt %.

The composition may comprise a thickening agent in the range of about 0.5 wt % to about 1.5 wt %, about 0.5 wt % to about 0.75 wt %, about 0.5 wt % to about 1.0 wt %, about 0.5 wt % to about 1.25 wt %, about 0.75 wt % to about 1.0 wt %, about 0.75 wt % to about 1.25 wt %, about 0.75 wt % to about 1.5 wt %, about 1.0 wt % to about 1.25 wt %, about 1.0 wt % to about 1.5 wt %, or about 1.25 wt % to about 1.5 wt %.

The composition may comprise a detergent in the range of about 3 wt % to about 15 wt %, about 3 wt % to about 5 wt %, about 3 wt % to about 7 wt %, about 3 wt % to about 10 wt %, about 3 wt % to about 13 wt %, about 5 wt % to about 7 wt %, about 5 wt % to about 10 wt %, about 5 wt % to about 13 wt %, about 5 wt % to about 15 wt %, about 7 wt % to about 10 wt %, about 7 wt % to about 13 wt %, about 7 wt % to about 15 wt %, about 10 wt % to about 13 wt %, about 10 wt % to about 15 wt %, or about 13 wt % to about 15 wt %.

The composition may comprise multiple detergents, which in combination, may be present in the range of about 3 wt % to about 15 wt %, about 3 wt % to about 5 wt %, about 3 wt % to about 7 wt %, about 3 wt % to about 10 wt %, about 3 wt % to about 13 wt %, about 5 wt % to about 7 wt %, about 5 wt % to about 10 wt %, about 5 wt % to about 13 wt %, about 5 wt % to about 15 wt %, about 7 wt % to about 10 wt %, about 7 wt % to about 13 wt %, about 7 wt % to about 15 wt %, about 10 wt % to about 13 wt %, about 10 wt % to about 15 wt %, or about 13 wt % to about 15 wt %.

The composition may comprise about 0.5 wt % of the compound as defined above, about 1 wt % of a hydromethoxyclelulose, about 5 wt % of a branched octylphenoxy poly(ethyleneoxy)ethanol, and about 5 wt % of N,N-Bis(2-hydroxyethyl)dodecanamide (HDA).

The composition may comprise about 0.5 wt % of the compound as defined above, about 1 wt % of a hydromethoxyclelulose, about 5 wt % of a branched octylphenoxy poly(ethyleneoxy)ethanol, and about 5 wt % of N-Decyl-b-D-glucopyranoside (DGP).

If desired, and for more effective distribution, the compounds may be incorporated into slow release or targeted delivery systems such as polymer matrices, liposomes, and microspheres.

There is also provided the use of the compound as defined above as an additive, antimicrobial agent or preservative in personable care products.

The minimum inhibitory concentration (MIC) of the compound may be in the range of about 1 ppm to about 500 ppm. The MIC of the compound may be in the range of about 1 ppm to about 2 ppm, about 1 ppm to about 5 ppm, about 1 ppm to about 10 ppm, about 1 ppm to about 20 ppm, about 1 ppm to about 50 ppm, about 1 ppm to about 100 ppm, about 1 ppm to about 200 ppm, about 2 ppm to about 5 ppm, about 2 ppm to about 10 ppm, about 2 ppm to about 20 ppm, about 2 ppm to about 50 ppm, about 2 ppm to about 100 ppm, about 2 ppm to about 200 ppm, about 2 ppm to about 500 ppm, about 5 ppm to about 10 ppm, about 5 ppm to about 20 ppm, about 5 ppm to about 50 ppm, about 5 ppm to about 100 ppm, about 5 ppm to about 200 ppm, about 5 ppm to about 500 ppm, about 10 ppm to about 20 ppm, about 10 ppm to about 50 ppm, about 10 ppm to about 100 ppm, about 10 ppm to about 200 ppm, about 10 ppm to about 500 ppm, about 20 ppm to about 50 ppm, about 20 ppm to about 100 ppm, about 20 ppm to about 200 ppm, about 20 ppm to about 500 ppm, about 50 ppm to about 100 ppm, about 50 ppm to about 200 ppm, about 50 ppm to about 500 ppm, about 100 ppm to about 200 ppm, about 100 ppm to about 500 ppm, or about 200 ppm to about 500 ppm.

There is also provided a method for treating a bacterial infection or fungal infection comprising administering to a subject a compound as defined above or a composition as defined above.

There is also provided a compound as defined above or a composition as defined above for use in treating a bacterial infection or fungal infection in a subject.

There is also provided the use of a compound as defined above or a composition as defined above in the manufacture of a medicament for treating a bacterial infection or fungal infection in a subject.

The subject may be an animal. The animal may be a mouse. The animal may be a human.

The compound may be administered orally, intravenously, topically or intraperitoneally. The compound may be administered topically or intraperitoneally.

Pharmaceutically acceptable compositions as defined above may also be administered topically, especially when the target of treatment includes areas or organs readily accessible by topical application, including diseases of the eye, the skin, or the lower intestinal tract. Suitable topical formulations may be readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of compounds or compositions as defined above may include, but are not limited to, mineral oil, liquid petrolatum, white petrolatum, propylene glycol, polyoxyethylene, polyoxypropylene compound, emulsifying wax and water. Alternatively, the pharmaceutically acceptable compositions may be formulated in a suitable lotion or cream containing the active components suspended or dissolved in one or more pharmaceutically acceptable carriers. Suitable carriers may include, but are not limited to, mineral oil, sorbitan monostearate, polysorbate 60, cetyl esters wax, cetearyl alcohol, 2 octyldodecanol, benzyl alcohol and water.

The compound may be administered at a dose in the range of about 0.01 mg/kg to about 35 mg/kg, about 0.01 mg/kg to about 0.1 mg/kg, about 0.1 mg/kg to about 0.2 mg/kg, about 0.2 mg/kg to about 0.5 mg/kg, about 0.2 mg/kg to about 0.7 mg/kg, about 0.2 mg/kg to about 1 mg/kg, about 0.2 mg/kg to about 1.2 mg/kg, about 0.2 mg/kg to about 1.5 mg/kg, about 0.2 mg/kg to about 1.7 mg/kg, about 0.5 mg/kg to about 0.7 mg/kg, about 0.5 mg/kg to about 1 mg/kg, about 0.5 mg/kg to about 1.2 mg/kg, about 0.5 mg/kg to about 1.5 mg/kg, about 0.5 mg/kg to about 1.7 mg/kg, about 0.5 mg/kg to about 2 mg/kg, about 0.7 mg/kg to about 1 mg/kg, about 0.7 mg/kg to about 1.2 mg/kg, about 0.7 mg/kg to about 1.5 mg/kg, about 0.7 mg/kg to about 1.7 mg/kg, about 0.7 mg/kg to about 2 mg/kg, about 1 mg/kg to about 1.2 mg/kg, about 1 mg/kg to about 1.5 mg/kg, about 1 mg/kg to about 1.7 mg/kg, about 1 mg/kg to about 2 mg/kg, about 1.2 mg/kg to about 1.5 mg/kg, about 1.2 mg/kg to about 1.7 mg/kg, about 1.2 mg/kg to about 2 mg/kg, about 1.5 mg/kg to about 1.7 mg/kg, about 1.5 mg/kg to about 2 mg/kg, about 1.7 mg/kg to about 2 mg/kg, about 2 mg/kg to about 5 mg/kg, about 5 mg/kg to about 10 mg/kg, about 10 mg/kg to about 15 mg/kg, about 15 mg/kg to about 20 mg/kg, about 20 mg/kg to about 25 mg/kg, 25 mg/kg to 30 mg/kg, or about 30 mg/kg to about 35 mg/kg.

The median lethal does (LD50) of the compound may be in a range of about 60 mg/kg to about 75 mg/kg, about 60 mg/kg to about 62.5 mg/kg, about 60 mg/kg to about 65 mg/kg, about 60 mg/kg to about 67.5 mg/kg, about 60 mg/kg to about 70 mg/kg, about 60 mg/kg to about 72.5 mg/kg, about 62.5 mg/kg to about 65 mg/kg, about 62.5 mg/kg to about 67.5 mg/kg, about 62.5 mg/kg to about 70 mg/kg, about 62.5 mg/kg to about 72.5 mg/kg, about 62.5 mg/kg to about 75 mg/kg, about 65 mg/kg to about 67.5 mg/kg, about 65 mg/kg to about 70 mg/kg, about 65 mg/kg to about 72.5 mg/kg, about 65 mg/kg to about 75 mg/kg, about 67.5 mg/kg to about 70 mg/kg, about 67.5 mg/kg to about 72.5 mg/kg, about 67.5 mg/kg to about 75 mg/kg, about 70 mg/kg to about 72.5 mg/kg, about 70 mg/kg to about 75 mg/kg, or about 72.5 mg/kg to about 75 mg/kg. The LD50 may be about 67.5 mg/kg.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 refers to a schematic diagram showing the synthesis of degradable polyionenes, P and Gemini-surfactants S synthesized through novel $A_2$-type bis-halide monomers d-$A_2$ and other readily commercially available reagents such as di-tertiary amines $B_2$ and functional tertiary amines B, respectively.

FIG. 2 refers to a schematic guide and chemical structures of the different types of d-$A_2$ monomers synthesized, the chemical structures of other difunctional monomers and monofunctional reagents used for the synthesis of the polyionenes (P) and surfactants (S).

FIG. 3 is a $^1$H NMR spectrum of monomer d-$A_2$-1.
FIG. 4 is a $^1$H NMR spectrum of monomer d-$A_2$-2.
FIG. 5 is a $^1$H NMR spectrum of monomer d-$A_2$-3.
FIG. 6 is a $^1$H NMR spectrum of monomer d-$A_2$-4.
FIG. 7 is a $^1$H NMR spectrum of monomer d-$A_2$-5.
FIG. 8 is a $^1$H NMR spectrum of monomer d-$A_2$-6.
FIG. 9 is a $^1$H NMR spectrum of monomer d-$A_2$-7.
FIG. 10 is a $^1$H NMR spectrum of monomer d-$A_2$-8.
FIG. 11 is a $^1$H NMR spectrum of monomer d-$A_2$-9.
FIG. 12 is a $^1$H NMR spectrum of monomer d-$A_2$-10.
FIG. 13 is a $^1$H NMR spectrum of monomer d-$A_2$-11.
FIG. 14 is a $^1$H NMR spectrum of monomer d-$A_2$-12.
FIG. 15 is a $^1$H NMR spectrum of monomer d-$A_2$-13.
FIG. 16 is a $^1$H NMR spectrum of monomer d-$A_2$-14.
FIG. 17 is a $^1$H NMR spectrum of monomer d-$A_2$-15.
FIG. 18 is a $^1$H NMR spectrum of monomer d-$A_2$-16.
FIG. 19 is a $^1$H NMR spectrum of monomer d-$A_2$-17.
FIG. 20 is a $^1$H NMR spectrum of monomer d-$A_2$-18.
FIG. 21 is a $^1$H NMR spectrum of monomer d-$A_2$-19.
FIG. 22 is a $^1$H NMR spectrum of monomer d-$A_2$-20.
FIG. 23 is a $^1$H NMR spectrum of P-1a-1.
FIG. 24 is a $^1$H NMR spectrum of P-1c-1.
FIG. 25 is a $^1$H NMR spectrum of P-3a.
FIG. 26 is a $^1$H NMR spectrum of P-3c.
FIG. 27 is a $^1$H NMR spectrum of P-5c-1.
FIG. 28 is a $^1$H NMR spectrum of P-6a.
FIG. 29 is a $^1$H NMR spectrum of P-6b.
FIG. 30 is a $^1$H NMR spectrum of P-6c.
FIG. 31 is a $^1$H NMR spectrum of P-4a.
FIG. 32 is a $^1$H NMR spectrum of P-4b.
FIG. 33 is a $^1$H NMR spectrum of P-4c.
FIG. 34 is a $^1$H NMR spectrum of P-1b.
FIG. 35 is a $^1$H NMR spectrum of P-5a.
FIG. 36 is a $^1$H NMR spectrum of P-5b.
FIG. 37 is a $^1$H NMR spectrum of P-21a.
FIG. 38 is a $^1$H NMR spectrum of P-7a.
FIG. 39 is a $^1$H NMR spectrum of P-(7:1/1:1)a.
FIG. 40 is a $^1$H NMR spectrum of P-(7:1/3:7)a.
FIG. 41 is a $^1$H NMR spectrum of P-(7:1/1:9)a.
FIG. 42 is a $^1$H NMR spectrum of P-8a.
FIG. 43 is a $^1$H NMR spectrum of P-8b.
FIG. 44 is a $^1$H NMR spectrum of P-8c.
FIG. 45 is a $^1$H NMR spectrum of P-(8:21/1:1)a.
FIG. 46 is a $^1$H NMR spectrum of P-(8:21/1:9)a.
FIG. 47 is a $^1$H NMR spectrum of P-9a.
FIG. 48 is a $^1$H NMR spectrum of P-10a.
FIG. 49 is a $^1$H NMR spectrum of P-12a.
FIG. 50 is a $^1$H NMR spectrum of P-13a.
FIG. 51 is a $^1$H NMR spectrum of P-14a.
FIG. 52 is a $^1$H NMR spectrum of P-(14:1/1:1)a.
FIG. 53 is a $^1$H NMR spectrum of P-(14:1/1:3)a.
FIG. 54 is a $^1$H NMR spectrum of P-(14:21/1:1)a.
FIG. 55 is a $^1$H NMR spectrum of P-(14:7/1:1)a.
FIG. 56 is a $^1$H NMR spectrum of P-(14:7/1:3)a.
FIG. 57 is a $^1$H NMR spectrum of P-17a.
FIG. 58 is a $^1$H NMR spectrum of P-18a.
FIG. 59 is a $^1$H NMR spectrum of P-(18:1/1:1)a.
FIG. 60 is a $^1$H NMR spectrum of P-19a.
FIG. 61 is a $^1$H NMR spectrum of S-5a.
FIG. 62 is a $^1$H NMR spectrum of S-5b.
FIG. 63 is a $^1$H NMR spectrum of S-5c.
FIG. 64 is a $^1$H NMR spectrum of S-5d.
FIG. 65 is a $^1$H NMR spectrum of S-5e.
FIG. 66 is a $^1$H NMR spectrum of S-5f.
FIG. 67 is a $^1$H NMR spectrum of S-5g.
FIG. 68 is a $^1$H NMR spectrum of S-5h.
FIG. 69 is a $^1$H NMR spectrum of S-1f.
FIG. 70 is a $^1$H NMR spectrum of S-1g.
FIG. 71 is a $^1$H NMR spectrum of S-1h.
FIG. 72 is a $^1$H NMR spectrum of S-3f.
FIG. 73 is a $^1$H NMR spectrum of S-3g.
FIG. 74 is a $^1$H NMR spectrum of S-3h.
FIG. 75 is a $^1$H NMR spectrum of S-4f.
FIG. 76 is a $^1$H NMR spectrum of S-4g.
FIG. 77 is a $^1$H NMR spectrum of S-4h.
FIG. 78 is a $^1$H NMR spectrum of S-6f.
FIG. 79 is a $^1$H NMR spectrum of S-6g.
FIG. 80 is a $^1$H NMR spectrum of S-6h.
FIG. 81 is a $^1$H NMR spectrum of S-9g.
FIG. 82 is a $^1$H NMR spectrum of S-13g.
FIG. 83 is a $^1$H NMR spectrum of S-7g.
FIG. 84 is a $^1$H NMR spectrum of S-10g.
FIG. 85 is a $^1$H NMR spectrum of S-12g.
FIG. 86 refers to a plot of viable microbe CFU after 18 hours (bacteria) or 42 hours (fungi) treatment at various polymer concentrations of P-1a-1 (6037B) and P-5c-1 (6050 D) (0, ½ MIC, MIC and 2×MIC). (a) *S. aureus*, (b) *E. coli*, (c) *P. aeruginosa* and (d) *C. albicans*.

FIG. 87 is a graph showing viable microbes CFU after incubation with P-9a for 18 hours (bacteria) or 42 hours (fungi) at various concentrations (0, ½×MIC, 1×MIC and 2×MIC) (a) *S. aureus*, (b) *E. coli*, (c) *P. aeruginosa* and (d) *C. albicans*.

FIG. 88 is a graph showing viable microbes CFU after incubation with P-7a for 30 seconds at various concentrations (0, 1×MIC, 2×MIC, 4×MIC, 8×MIC and 16×MIC) (a) *S. aureus*, (b) *E. coli*, (c) *P. aeruginosa* and (d) *C. albicans*.

FIG. 89 is a graph showing viable microbes CFU after incubation with P-(1:7/1:1)a for 30 seconds at various concentrations (0, 1×MIC, 2×MIC, 4×MIC, 8×MIC and 16×MIC) (a) *S. aureus*, (b) *E. coli*, (c) *P. aeruginosa* and (d) *C. albicans*.

FIG. 90 is a graph showing viable microbes CFU after incubation with P-1a-1 for 30 seconds at various concentrations (0, 1×MIC, 2×MIC, 4×MIC, 8×MIC and 16×MIC) (a) S. aureus, (b) E. coli, (c) P. aeruginosa and (d) C. albicans.

FIG. 91 is a graph showing the percentage kill (%) of respective microbial strains (A: S. aureus, B: E. coli, C: P. aeruginosa and D: C. albicans) after incubation with surfactant S-3g for 18 hours (bacteria) or 42 hours (fungi).

FIG. 92 is a graph showing the percentage kill (%) of respective microbial strains (A: S. aureus, B: E. coli, C: P. aeruginosa and D: C. albicans) after 30 seconds (solid) and 2 minutes (striped) of mixing with S-3g for concentrations of 4×, 8×, 16×, 32× and 64×MIC.

FIG. 93 is a graph showing the percentage biofilm cell viability (A) and biomass (B) of A: S. aureus and biofilm cell viability (C) and biomass (D) of E. coli after treatment with surfactant S-3g for 18 hours.

FIG. 95 is a graph showing the survival of K. pneumoniae 8637-infected mice without treatment (control) or treated with the polymer P-1a-1 (6037B) and imipenem. n=10.

FIG. 95 is a graph showing bacterial counts in the blood and major organs of K. pneumoniae 8637-infected mice without treatment (control) or treated with the polymer P-1a-1 (6037B) and imipenem. n=3. (*, $p<0.05$; , $p<0.01$; *, $p<0.001$).

EXAMPLES

Non-limiting examples of the disclosure will be further described in greater detail by reference to specific Examples, which should not be construed as in any way limiting the scope of the invention.

Example 1: Materials and Methods

Materials

All chemical reagents were purchased from Sigma-Aldrich (USA) or Tokyo Chemical Industry (Japan) and used as received unless specified. Mueller Hinton Broth (MHB) powder was purchased from BD Diagnostics (France) and used to prepare the microbial broths according to the manufacturer's instruction. Hydroxypropyl methyl cellulose (HPMC) H3785 and H7509, Igepal CO-520 and sodium dodecyl sulfate (SDS) were bought from Sigma-Aldrich. Igepal CA-630 was bought from MP Biochemicals Inc. (USA). N,N-bis(2-hydroxyethyl)dodecanamide (HDA) and N-decyl-b-D-glucopyranoside (DGP) were obtained from Flurochem. (UK). Cell lines of S. aureus (ATCC No. 6538), E. coli (ATCC No. 25922), P. aeruginosa (ATCC No. 9027), and C. albicans (ATCC No 10231) were obtained from ATCC, U.S.A., and reconstituted according to the suggested protocols. Rat red blood cells (rRBCs) were obtained from the Animal Handling Unit of Biomedical Research Centre, Singapore.

Methods $^1$H NMR Spectroscopy $^1$H-NMR spectra using a Bruker Avance 400 spectrometer: operated at 400 MHz with the solvent proton signal as the internal reference standard.

Size Exclusion Chromatography (SEC)

Aqueous size exclusion chromatography (SEC) was conducted in the following solvent mixture: HPLC H2O:methanol:acetic acid=54:23:23 with 0.5 M sodium acetate (salt concentration with respect to entire solvent mixture) as the eluent at 0.5 mL/min flowrate. SEC was recorded on a Waters 2695 separation module equipped with a Waters 2414 differential refractometer and Waters Ultrahydrogel 120 and 500 columns (7.8×300 mm). Polymer solutions were prepared at 5 mg/mL and injection volume was 100 µL. Empower 3 software (Waters Corporation, U.S.A.) was used for data collection and analysis. The columns were calibrated with a combination of poly(ethylene glycol) and poly(ethylene oxide) standards (PSS Polymer Standard Service, GmbH, Germany).

MIC Measurement

Bacterial and fungal samples were inoculated according to ATCC's requirement. Briefly, bacteria and fungi were grown in Mueller Hinton Broth (MHB) at 37° C. and room temperature, respectively overnight to allow the microbes to enter the log growth phase with constant 100 rpm shaking. Minimum inhibitory concentration (MIC) of the polymers was determined using the broth microdilution method. 100 µL of 20% v/v water-containing broth with various polymer or Gemini-surfactant concentrations was first added into each well of a 96-well tissue culture plate. The inoculated overnight microbe solution was first diluted to an optical density (O.D.) reading of 0.07 using a microplate reader (TECAN, Switzerland). This will correspond to $3\times10^8$ CFU/mL based on the McFarland 1 standard solution (CFU=colony forming units). The microbe solution was further diluted 1000 times to achieve a final $3\times10^5$ CFU/mL. To each well, an equal volume of diluted microbes solution was added and incubated at 37° C. for 18 hours for bacteria samples and at room temperature for 42 hours for fungi samples. There were 6 replicates for each concentration tested, with negative control being microbes added into broth containing 20% v/v deionized water. MIC was taken as the lowest concentration at which there was no observable microbe growth when measured by the microplate reader.

Killing Efficiency Test

After MIC testing, all solutions from the control, ½MIC, MIC and 2MIC wells were collected and subjected to a series of ten-fold dilution. 20 µL of the diluted microbe solution was streaked onto pre-casted agar plates using LB+1.5% agar from the first Base. Agar plates with bacteria samples were incubated at 37° C. for 18 hours while those with fungi samples were incubated for 42 hours at room temperature before the CFUs were counted.

Killing Kinetics

Each polymer was diluted to 2, 4, 8 and 16×MIC with Mueller Hinton Broth (MHB) and distilled water. 600 µL of $3\times10^5$ CFU/mL microbial suspension was added to each concentration of the polymer. After 30 seconds, the solution of polymer and microbes are serial diluted by folds of ten. 20 µL of the diluted microbial suspension was then plated onto agar plates and incubated for 24 hours and 42 hours at 37° C. and room temperature for bacteria and fungi respectively, then manually counted for CFU.

Biofilm Culturing

The bacteria stock was diluted in Mueller Hinton Broth (MHB) to get an optical density (OD) reading of 0.07 at 600 nm. 48 wells of a 96 flat-well plate were plated with 100 µL of bacteria suspension each. The plate was then incubated at 37° C. Every day over the next 7 days, MHB was carefully removed from the plate so as not to disturb the biofilm at the bottom of the well, and replaced with 100 µL of fresh MHB to each well.

XTT Assay for Cell Viability of Biofilms

After the biofilm was cultured, at the end of 7 days, MHB was removed from the wells. The biofilms were washed carefully with PBS 3 times to remove planktonic cells. The surfactant was weighed in a micro-centrifuge tube, and the weighed sample was diluted to 10,000 mg $L^{-1}$ using distilled water. Serial dilution was conducted to obtain surfactant solutions having concentrations of 100 mg $L^{-1}$, 70 mg $L^{-1}$, 50 mg $L^{-1}$, 35 mg $L^{-1}$, 25 mg $L^{-1}$, 20 mg $L^{-1}$, and 10 mg $L^{-1}$. The solvent was 20% distilled water and 80% MHB for each solution. The control was 20% distilled water and 80% MHB without surfactant. The surfactant solutions of different concentrations were added to the wells, 100 µL into each, with 6 replicates for each concentration. The plate was then incubated at 37° C. for 18 hours. Diluted XTT solution of 200 µL of PBS, 20 µL of XTT solution (1 mg mL) and 4 µL of menadione solution (1 mM) was added into each well. At the end of the incubation period, the surfactant solution was removed and 100 µL of XTT solution was added to each well. The plate was incubated at 37° C. in the dark for 3 hours. At the end of the incubation period, the optical density (OD) reading of the plate was taken at 490 nm.

Biomass Assay

After the biofilm was cultured, at the end of 7 days, MHB was removed from the wells. The biofilms were washed carefully with PBS 3 times to remove planktonic cells. The surfactant was weighed in a micro-centrifuge tube, and the weighed sample was diluted to 10000 mg $L^{-1}$ using distilled water. Serial dilution was conducted to obtain surfactant solutions of concentrations 100 mg $L^{-1}$, 70 mg $L^{-1}$, 50 mg $L^{-1}$, 35 mg $L^{-1}$, 25 mg $L^{-1}$, 20 mg $L^{-1}$, and 10 mg $L^{-1}$. The solvent was 20% distilled water and 80% MHB for each solution. The control was 20% distilled water and 80% MHB without surfactant. The surfactant solutions of different concentrations were added to the wells, 100 µL into each, with 6 replicates for each concentration. The plate was incubated at 37° C. for 18 hours. At the end of the incubation period, the surfactant solution was removed and 100 µL of 0.1% safranin O solution was added to each well. The plate was incubated at 37° C. in the dark for 15 minutes. At the end of the incubation period, the excess stain was removed by washing at least three times with PBS. Ethanol (200 µL of 70% solution) was then added to each well. The plate was incubated at 37° C. in the dark for 15 minutes. At the end of the incubation period, the optical density (OD) reading of the plate was taken at 550 nm.

Hemolysis Assay

Freshly obtained rat red blood cells (rRBC) from the Animal Handling Unit of Biomedical Research Center (Singapore) was used to test the hemolytic activity of the polymers and Gemini-surfactants. The rRBC was diluted to 4% v/v with phosphate-buffered saline (PBS) and added to an equal volume of 0.2% v/v Triton-X solution. A microplate reader was used to measure the optical density (O.D.) reading to make sure the value is between 0.5 and 0.6. An equal volume of different polymer or Gemini-surfactant concentrations was added to the diluted blood and incubated for 1 hour at 37° C. The samples were centrifuged at 1000 g at 4° C. for 5 minutes and 100 µL of the supernatant was collected and transferred to a 96-well tissue culture plate. There were 4 replicates for each concentration. Haemoglobin release was measured using the microplate reader at 576 nm. rRBCs treated with PBS were used as the positive control, while those treated with 0.2% v/v Triton-X was used as the negative control.

Percentage of hemolysis was calculated as follows:

Hemolysis (%)=[(O.D.$_{576\ nm}$ of the treated sample−O.D.$_{576\ nm}$ of negative control)/(O.D.$_{576}$ nm of positive control−O.D.$_{576\ nm}$ of negative control)]×100%

$HC_{50}$ was taken as the polymer concentration at which the polymer causes 50% hemolysis.

Bacterial Strain and Culture Conditions for In Vivoassay

Clinically isolated multidrug-resistant *K. pneumoniae* strain was extracted from a patient's phlegm and provided by The First Affiliated Hospital of Medical College, Zhejiang University (Hangzhou, China). The isolate was identified by routine laboratory methods and stored in 20% (v/v) glycerol at −80° C. Bacteria were grown in Mueller-Hinton (MH) agar plate at 37° C. prior to use. Animals ICR mice (female, 7 weeks old, 24-26 mg) were used for the in vivo studies. Immunosuppression was induced by intraperitoneal injection of 200 mg/Kg cyclophosphamide (Hengrui Corp, Jiangsu Province, P. R. China) 4 days prior to infection. Mice were anesthetized by intra-peritoneal injection of 1% pentobarbital (40 mg/kg, Sigma).

In Vivo Toxicity Study

To assess the acute systemic toxicity of P-1a-1 (6037B) to the mice, the median lethal dose ($LD_{50}$) was determined. Specifically, the mice were randomly assigned into six treatment groups (six mice per group). After dissolution in phosphate buffered serum (PBS), P-1a-1 (6037B) was administered intraperitoneally at designated doses (i.e. 20.0, 30.0, 45.0, 67.5, 101.3, and 151.9 mg/kg, 0.2 mL/20 g). The number of surviving mice in each group was monitored for five days after treatment, and the values of $LD_{50}$ were calculated by a regression technique such as the BLISS method. Such method may involve the use of software BLISS LD50, which allows one to obtain the $LD_{50}$ upon input of the relevant data to the software. Other suitable regression techniques may also be used as appropriate.

Pulmonary Infection

To investigate the in vivo antibacterial efficacy of P-1a-1 (6037B), a pneumonia mouse model was established. The immunosuppression of mice was induced as described above. Overnight cultures of *K. pneumoniae* 8637 were harvested and suspended in PBS. Before instillation with *K. pneumoniae* 8637, the mice were anesthetized using an intraperitoneal injection with 1% pentobarbital (40 mg/kg). Each of the immunosuppressed mice was infected intranasally with 0.03 mL of the bacterial suspension at designated doses (i.e. $1 \times 10^9$, $1.5 \times 10^9$, $2.3 \times 10^9$, $3.5 \times 10^9$, $5.3 \times 10^9$, $8.0 \times 10^9$ CFU/ml, four mice per group). The minimum lethal dose was defined as the lowest dose, which was sufficient to cause 100% mortality. It was determined from the survival rate of mice at 5 days post-infection by the BLISS method.

Efficacy of P-1a-1 (6037B) in Treating *K. pneumoniae* 8637-Induced Pneumonia

The bacterial suspension having the minimum lethal dose (0.03 mL/mice) was introduced to mice intranasally, after which P-1a-1 (6037B) and imipenem (a clinically used antibiotic for treatment of Gram-negative bacterial infections) were administered intraperitoneally once daily for 3 days starting at 4 hours after infection at designated doses (i.e. 0.1, 0.5, 1.0, 2.0, 4.0, 8.0 mg/kg for P-1a-1 (6037B), 0.1, 1.0, 5.0, 10.0, 20.0, 40.0 mg/kg for imipenem, 0.2 mL/20 g, four mice per group). The number of surviving mice in each group was recorded for 5 days to assess $ED_{50}$ by the BLISS method.

To further determine the in vivo therapeutic efficacy of P-1a-1 (6037B), survival of the *K. pneumoniae* 8637-infected mice was monitored with and without treatment. Briefly, the mice were randomly divided into a control group, a P-1a-1 (6037B)-treated group and an imipenem-treated group (ten mice per group). After being anesthetized, each of the immunosuppressed mice was inoculated intranasally with 0.03 mL of bacterial suspension at the minimum lethal dose determined above. Then, P-1a-1 (6037B)

and imipenem (i.e. 2.0 mg/kg for imipenem, 1.0 mg/kg for P-1a-1 (6037B)) were administered intraperitoneally once daily for 3 consecutive days starting at 4 hours after infection. The mice were monitored for a period of five days, and the number of surviving mice in each group was recorded. Survival was expressed using the Kaplan-Meier curve.

Lung, blood, liver, spleen and kidney samples were obtained to assess bacterial counts. Briefly, after anesthesia with 40 mg/kg pentobarbital, immunosuppressed mice were instilled intra-nasally with $2 \times 10^7$ (three mice/group) colony-forming units (CFUs) of *K. pneumoniae* 8637. The polymer sample P-1a-1 (6037B) and imipenem at ED95 doses (0.2 mL/20g) were administered intraperitoneally once daily for 3 consecutive days starting at 4 hours after infection. At five days post-infection, the count of bacteria in the lung, blood, liver, spleen and kidney were determined by Mueller-Hinton (MH) agar plating. The results were shown as mean±SD.

Example 2: Synthesis

General Procedure for the Degradable d-$A_2$ Monomer

Method A: Monomers Containing Aromatic Esters and Amides

Representative Example—Synthesis of N, N'-((ethane-1,2-diylbis(oxy)bis(ethane-2,1-diyl))bis(4-(chloromethyl) benzamide) (d-$A_2$-4)

In a round two-necked bottom flask (500 mL) equipped with a magnetic stir bar and nitrogen inlet adaptor, 4-(chloromethyl)benzoyl chloride (10.55 g, 55.81 mmol, 2.0 equiv.) and tetrahydrofuran (THF, 20 mL) were allowed to equilibrate under ice-cold conditions for about 30 minutes. To this solution, a mixture of 2,2'-(ethane-1,2-diylbis(oxy))bis (ethan-1-amine) (4.14 g, 27.94 mmol, 1.0 equiv.) and triethylamine (12.0 mL, 8.7 g, 86.1 mmol, 3.1 equiv.), dissolved in THF (40 mL) were added dropwise via a dropping funnel over approximately 30 minutes. A white precipitate formed immediately. The reaction was allowed to proceed at room temperature for an additional 90 minutes. Deionized water (about 200 mL) was added to the reaction mixture to dissolve the triethylamine salts and also precipitate the product. This suspension was further chilled in an ice bath for about an hour, followed by the isolation of the products as a solid by vacuum filtration. The product was washed with deionized water and was dried under high vacuum to yield a white powdery solid (11.3 g, 89.3%).

Monomers d-$A_2$-1 to 5 and 12 were prepared by this method. Typical yields~70-94%.
N, N'-(ethane-1,2-diyl)bis(4-(chloromethyl)benzamide) (d-$A_2$-1)
N, N'-(1,4-phenylene)bis(4-(chloromethyl)benzamide) (d-$A_2$-2)
N, N'-(hexane-1,6-diyl)bis(4-(chloromethyl)benzamide) (d-$A_2$-3)
N,N'-(1,3-phenylenebis(methylene))bis(4-(chloromethyl) benzamide) (d-$A_2$-4)
N, N'-((ethane-1,2-diylbis(oxy))bis(ethane-2,1-diyl))bis(4-(chloromethyl) benzamide) (d-$A_2$-5)

Method B

Representative Example—Synthesis of N,N'-(((oxybis(ethane-2,1-diyl))bis(oxy))bis (propane-3,1-diyl)) bis(4-(chloromethyl) benzamide (d-$A_2$-6)

A protocol similar to Method A was used. However, d-$A_2$-6 did not precipitate upon addition of water (about 100 mL). Instead, an oily layer separated. The product was first extracted from the reaction mixture with ethyl acetate (3×200 mL). The combined organic layers were dried with sodium sulphate and the volatiles were removed to result in pale yellow crude product, which was further purified by recrystallizing from a minimal amount of ethyl acetate. Isolated yield: 10.16 g (65.2% crop 1—recrystallized from ethyl acetate).

Monomers d-$A_2$-6—11, 13, 19 and 20 were prepared by Method B. Typical yields~55-85%. If the crude product by thin layer chromatography was not a single spot, the monomer was further purified by recrystallization or flash column chromatography using hexane/ethyl acetate or chloroform/ethylacetate combination. In general, for the di-ester series, a protocol, similar to that of d-$A_2$-6 synthesis was followed (Method B). Typically reaction was conducted overnight.

Method C: Monomers Containing Aliphatic Esters and Amides

Representative Example—Synthesis of N,N'-(ethane-(1,2-diyl)bis(4-chlorobutanamide) (d-$A_2$-4)

In a two-necked round bottom flask (250 mL) equipped with magnetic stir bar and nitrogen inlet adaptor, 4-Chlorobutyryl chloride (11.4 mL, 14.2 g, 100.7 mmol, 2.02 equiv.) and tetrahydrofuran (THF, 25 mL) were allowed to equilibrate under ice-cold conditions for about 30 minutes. To this solution, a mixture of ethylene diamine (3.00 g, 49.8 mmol, 1.0 equiv.) and triethylamine (15.0 mL, 10.9 g, 107.7 mmol, 2.16 equiv.), dissolved in THF (75 mL) were added drop-wise via dropping funnel over ~30 minutes. White precipitates were formed immediately. The reaction mixture was allowed to proceed at room temperature for additional 90 minutes. DI water (~100 mL) was added to the reaction mixture to dissolve the triethylamine salts and the product was extracted into ethylacetate (150 mL). Organic layer was washed with 2×1N HCl (100 mL), 2×Satd. NaHCO$_3$ aqueous solution and 1×Satd. NaCl aqueous solution and dried over Na$_2$SO$_4$ and concentrated in vacuuo to yield a pale yellow solid as the crude product. Crude product was recrystallized from hot acetonitrile and the crystalline solid was washed with ethylacetate:hexane (1:1 v/v) mixture. The product was dried under high vacuum to yield white crystalline solid (4.42 g, ~33%).

Monomers d-$A_2$-15 and 16 were prepared by this method. However the crude product was purified by flash column chromatography using hexane/ethyl acetate solvent mixtures. Monomers d-$A_2$-18 was also prepared by this method. However succinyl chloride and iodoethanol were used instead. Typical yields~50-70%.

Method D: Monomers Containing Aliphatic Esters with Alkyl Iodides, Obtained Via Standard Finkelstein Reaction Representative Example—Synthesis of ethane-1,2-diyl bis(4-iodobutanoate) (d-$A_2$-17)

In a round bottom flask (50 mL) equipped with magnetic stir bar, condenser (with circulating cooling water) and nitrogen inlet adaptor, ethane-1,2-diyl bis(4-chlorobutanoate) (d-$A_2$-16 2.71 g, 10 mmol, 1.0 equiv.), sodium iodide (5.12 g, 34.2 mmol, 3.4 equiv.) and acetone (30 mL) were added and the reaction mixture was allowed to proceed for 48 hours at refluxing conditions by maintaining the oil bath at 60° C. Then, insolubles were removed by filtration and solvent removed under vaccuo to result in crude product, which was further purified by flash column chromatography to result in target compound as an oil (3.46 g 76.2%).

General Procedure for the Synthesis of Degradable Polyionenes Via Addition Route Method A Unless otherwise noted, Method A was the standard method used for the synthesis of polyionenes from monomers containing benzylchloride derivatives Representative Example—Synthesis of poly(d-$A_2$-1-co-tetramethyl-1,3-diaminopropane), P-1a In a scintillation vial (20 mL) equipped with a magnetic stir bar, monomer d-$A_2$-1 ($A_2$-type, 360.0 mg, 985.6 µmol) and tetramethyl-1,3-diaminopropane ($B_2$-type, 131.0 mg, 1006 µmol) were suspended in dimethylformamide (DMF) (3.0 mL). The reaction mixture was gently heated with a heat gun to render a clear solution. The clear solution was allowed to stir at room temperature. The reaction mixture tuned cloudy and at about 1.5 hours, a polymer was found to deposit on the walls of the vial. The reaction mixture was allowed to stir further overnight, and was precipitated into diethyl ether (50 mL) to result in a solid white powder. The white power was dissolved/suspended in about 5 mL methanol, then about 45 mL diethylether was slowly added to precipitate the polymer and this process was repeated once more. The solids were isolated and dried in vacuuo to result in a white solid at near quantitative yields. The product was further purified by first dissolving in deionized water, followed by extensive dialysis against deionized water using a dialysis membrane (MWCO=1 kDa), and lyophilization to result in the target polymer.

For the synthesis of copolymers, the combined molar ratio of different d-$A_2$ and/or $A_2$ to $B_2$ monomers were kept at 1:1.

Method B: Copolymerization of Monomers Containing Aliphatic Chlorides

Representative Example—Synthesis of poly(d-$A_2$-14-co-tetramethyl-1,3-diaminopropane), P-14a In a scintillation vial (20 mL) equipped with magnetic stir bar, monomer d-$A_2$-14 ($A_2$-type, 539.2 mg, 2003 µmol) and tetramethyl-1,3-diaminopropane ($B_2$-type, 260.8 mg, 2003 µmol) were suspended in DMF (3.0 mL). The reaction mixture was allowed to stir at 60° C. overnight (~18h), and was then precipitated into diethyl ether (50 mL) to result in a viscous semi-solid. The solid was dissolved/suspended in 5 mL methanol, and 45 mL diethylether was slowly added to precipitate the polymer and this process was repeated once more. The solids were isolated and dried in vacuuo to result in white solid. Polymer was further purified by first dissolving in DI water, followed by extensive dialysis against DI water using dialysis membrane (MWCO=1 kDa), and lyophilization to result in target polymer.

Method C: Copolymerization of Monomers Containing Benzylchloride Derivatives and Aliphatic Chlorides Representative Example—Synthesis of poly(d-$A_2$-14-co-tetramethyl-1,3-diaminopropane/d-A2-1-co-tetramethyl-1,3-diaminopropane), P-(14:1/1:1)a In a scintillation vial (20 mL) equipped with magnetic stir bar, monomer d-$A_2$-14 ($A_2$-type, 270.2 mg, 1004 µmol) and tetramethyl-1,3-diaminopropane ($B_2$-type, 260.9 mg, 2003 µmol) were suspended in DMF (3.0 mL). The reaction mixture was allowed to stir at 60° C. overnight (~18h). To this reaction mixture comonomer d-$A_2$-1 ($A_2$-type, 365.2 mg, 1000 µmol) along with additional DMF (3.0 mL) was added. The reaction was allowed to proceed for another 2 hours at 60° C. and was then precipitated into diethyl ether (2×50 mL). Precipitates were dissolved/suspended in ~5 mL methanol, and ~45 mL diethylether was slowly added to precipitate the polymer and this process was repeated once more. The solids were isolated and dried in vacuuo to result in solid. Polymer was further purified by first dissolving in DI water, followed by extensive dialysis against DI water using dialysis membrane (MWCO=1 kDa), and lyophilization to result in target polymer.

Method D: Copolymerization of Monomers Containing Aliphatic Iodide

Representative Example—Synthesis of poly($A_2$-18-co-tetramethyl-1,3-diaminopropane), P-18a In a scintillation vial (20 mL) equipped with magnetic stir bar, monomer d-$A_2$-18 ($A_2$-type, 428.5 mg, 1006 µmol) and tetramethyl-1,3-diaminopropane ($B_2$-type, 130.6 mg, 1003 µmol) were suspended in DMF (1.5 mL). The reaction mixture was allowed to stir at room temperature overnight (~18h), and was then precipitated into diethyl ether (50 mL) to result in a viscous semi-solid. The solid was dissolved/suspended in ~2-3 mL methanol, and ~45 mL diethylether was slowly added to precipitate the polymer and this process was repeated once more. The solids were isolated and dried in vacuuo to result in white solid. Polymer was further purified by first dissolving in DI water, followed by extensive dialysis against DI water using dialysis membrane (MWCO=1 kDa), and lyophilization to result in target polymer.

Method E: Copolymerization of Monomers Containing Benzylchloride Derivatives and Aliphatic Iodides Representative Example; Synthesis of poly(d-$A_2$-18-co-tetramethyl-1,3-diaminopropane/d-$A_2$-1-co-tetramethyl-1,3-diaminopropane), P-(18:1/1:1)a In a scintillation vial (20 mL) equipped with magnetic stir bar, monomer d-$A_2$-18 ($A_2$-type, 211.4 mg, 496 µmol) and tetramethyl-1,3-diaminopropane ($B_2$-type, 130.6 mg, 1003 µmol) were suspended in DMF (1.5 mL). The reaction mixture was allowed to stir at room temperature overnight (~18h). To this reaction mixture comonomer d-$A_2$-1 ($A_2$-type, 185.4 mg, 508 µmol) along with additional DMF (1.5 mL) was added and the reaction mixture was allowed to stir at room temperature additional 18h, followed by precipitation into diethyl ether (50 mL) to result in a viscous semi-solid. The solid was dissolved/suspended in ~2-3 mL methanol, and ~45 mL diethylether was slowly added to precipitate the polymer and this process was repeated once more. The solids were isolated and dried in vacuuo to result in white solid. Polymer was further purified by first dissolving in DI water, followed by extensive dialysis against DI water using dialysis membrane (MWCO=1 kDa), and lyophilization to result in target polymer.

General Procedure for the Synthesis of Degradable Gemini-Surfactants

Representative Example—Synthesis of S-1g

In a scintillation vial (20 mL) equipped with a magnetic stir bar, monomer d-$A_2$-1 ($A_2$-type, 369.3 mg, 1010.9 µmol) and N,N-dimethyldodecylamine (g, B-type, 1200 µL, 944 mg, 4424 µmol) were suspended in dimethylformamide (DMF) (2.0 mL). The reaction mixture was gently heated with a heat gun to render a clear solution. The clear solution was allowed to stir at room temperature overnight. The reaction mixture was then precipitated into diethyl ether (50 mL) to result in a solid. The solid was dissolved/suspended in about 5 mL methanol, then about 45 mL diethylether was slowly added to precipitate the surfactant. This process was repeated once more. The solids were isolated and dried in vacuuo to result in a white solid.

Preparation of Surgical Scrub Formulation

Polymer P-1a-1 (6037B) was diluted with de-ionized (DI) water to obtain a 5 wt % stock. Igepal 630, hydroxpropyl methylcellulose (HPMC) 3785 and either N,N-bis(2-hydroxyethyl)dodecanamide (HDA) or N-decyl-b-D-glucopyranoside (DGP) was prepared at a ratio of 5:1:5 wt %. 100 µL of P-1a-1 (6037B) and 900 µL of DI water were added to the rest of the mixture. The mixture was sonicated at room temperature for 5 minutes before mixing by vortexing. This was repeated for another 2 more times. The tubes were placed in 4° C. overnight to ensure that all the HPMC was totally dissolved. 0.1 mL of each formulation (3 replicates) was added into each well in a 96-well plate before 100 µL of bacteria suspension was added. *Staphylococcus aureus, Escherichia coli* and *Pseudomonas aeruginosa* obtained from ATCC were reconstituted from its lyophilized form according to the manufacturer's protocol. Microbial samples were cultured in MHB at 37° C. under constant shaking of 300 rpm. Prior to mixing, the microbial sample was first inoculated overnight to enter its log growth phase. The concentration of microbial solution was adjusted to give an initial optical density (O.D.) reading of approximately 0.07 at 600 nm wavelength on microplate reader (TECAN, Switzerland), which corresponds to the concentration of McFarland Standard No. 1 ($3 \times 10^8$ CFU $ml^{-1}$), the microbial solution was further diluted by 1000 to achieve an initial loading of $3 \times 10^1$ CFU $ml^{-1}$. Three different incubation times (10 sec, 30 sec and 10 minutes) were tested for each formulation. The microbial samples were taken out from each well for a series of 10-fold dilutions. 20 µL of the diluted microbial solution was streaked onto an agar plate (LB Agar from first Base). The plates were incubated for 24 hours at 37° C. and counted for colony-forming units (CFU).

Example 3: 1H NMR Characterization of the Synthesized Compounds

The synthesized compounds were characterized by $^1H$ NMR spectroscopy. The $^1H$ NMR spectra for the respective compounds are in the Figures as outlined in Table 1 below:

TABLE 1

| $^1$H NMR spectra of the synthesized compounds | |
|---|---|
| Compound | FIG. |
| d-A2-1 | FIG. 3 |
| d-A2-2 | FIG. 4 |

TABLE 1-continued

| $^1$H NMR spectra of the synthesized compounds | |
|---|---|
| Compound | FIG. |
| d-A2-3 | FIG. 5 |
| d-A2-4 | FIG. 6 |
| d-A2-5 | FIG. 7 |
| d-A2-6 | FIG. 8 |
| d-A2-7 | FIG. 9 |
| d-A2-8 | FIG. 10 |
| d-A2-9 | FIG. 11 |
| d-A2-10 | FIG. 12 |
| d-A2-11 | FIG. 13 |
| d-A2-12 | FIG. 14 |
| d-A2-13 | FIG. 15 |
| d-A2-14 | FIG. 16 |
| d-A2-15 | FIG. 17 |
| d-A2-16 | FIG. 18 |
| d-A2-17 | FIG. 19 |
| d-A2-18 | FIG. 20 |
| d-A2-19 | FIG. 21 |
| d-A2-20 | FIG. 22 |
| P-1a-1 | FIG. 23 |
| P-1c-1 | FIG. 24 |
| P-3a | FIG. 25 |
| P-3b | FIG. 26 |
| P-3c | FIG. 27 |
| P-5c-1 | FIG. 27 |
| P-6a | FIG. 28 |
| P-6b | FIG. 29 |
| P-6c | FIG. 30 |
| P-4a | FIG. 31 |
| P-4b | FIG. 32 |
| P-4c | FIG. 33 |
| P-1b | FIG. 34 |
| P-5a | FIG. 35 |
| P-5b | FIG. 36 |
| P-21a | FIG. 37 |
| P-7a | FIG. 38 |
| P-(7:1/1:1)a | FIG. 39 |
| P-(7:1/3:7)a | FIG. 40 |
| P-(7:1/1:9)a | FIG. 41 |
| P-8a | FIG. 42 |
| P-8b | FIG. 43 |
| P-8c | FIG. 44 |
| P-(8:21/1:1)a | FIG. 45 |
| P-(8:21/1:9)a | FIG. 46 |
| P-9a | FIG. 47 |
| P-10a | FIG. 48 |
| P-12a | FIG. 49 |
| P-13a | FIG. 50 |
| P-14a | FIG. 51 |
| P-(14:1/1:1)a | FIG. 52 |
| P-(14:1/1:3)a | FIG. 53 |
| P-(14:21/1:1)a | FIG. 54 |
| P-(14:7/1:1)a | FIG. 55 |
| P-(14:7/1:3)a | FIG. 56 |
| P-17a | FIG. 57 |
| P-18a | FIG. 58 |
| P-(18:1/1:1)a | FIG. 59 |
| P-19a | FIG. 60 |
| S-5a | FIG. 61 |
| S-5b | FIG. 62 |
| S-5c | FIG. 63 |
| S-5d | FIG. 64 |
| S-5e | FIG. 65 |
| S-5f | FIG. 66 |
| S-5g | FIG. 67 |
| S-5h | FIG. 68 |
| S-1f | FIG. 69 |
| S-1g | FIG. 70 |
| S-1h | FIG. 71 |
| S-3f | FIG. 72 |
| S-3g | FIG. 73 |
| S-3h | FIG. 74 |
| S-4f | FIG. 75 |
| S-4g | FIG. 76 |
| S-4h | FIG. 77 |
| S-6f | FIG. 78 |
| S-6g | FIG. 79 |
| S-6h | FIG. 80 |

TABLE 1-continued

¹H NMR spectra of the synthesized compounds

| Compound | FIG. |
|---|---|
| S-9g | FIG. 81 |
| S-13g | FIG. 82 |
| S-7g | FIG. 83 |
| S-10g | FIG. 84 |
| S-12g | FIG. 85 |

Example 3: Discussion of the Synthesis of (Poly)Ionenes

Synthesis of d-A2 Monomers

It was found that (poly)ionenes with tunable degradability can be developed from functional monomers with built-in cleavable bonds. To achieve this, first a robust and facile method to produce a functional bis(halide), comprising a cleavable bond, was developed. Incorporation of an amide bond as the cleavable linker would result in the requisite stability for the compounds that would translate to meaningful shelf-life while at the same time, introducing potential biodegradability to the resultant (poly)ionenes.

A library of degradable bis(halide) $A_2$-type monomers were synthesized by reacting two equivalence of chloromethyl benzoyl chloride with a diamine in the presence of a base, to result in d-$A_2$ monomers 1 to 6, with good yields (FIG. 1 and FIG. 2). The selection of diamine would enable the tailoring of the hydrophobicity/hydrophilicity and/or the flexibility/rigidity, which are also determined by the spacer between the benzyl chloride functionalities. This degradable bis(halide) d-$A_2$ monomer could be polymerized with commercially available $B_2$-type bis(dimethylamino)-monomers to result in polyionenes P using dimethylformamide (DMF) as the solvent at room temperature.

By replacing diamine with a diol or aminoalcohol, d-$A_2$ monomers 7 to 13 could be synthesized. Readily available precursors enable systematic variation of the spacer lengths in these monomers. For example, monomers containing diesters were synthesized by increasing the spacer lengths from propyl to dodecyl (d-$A_2$ monomers 7 to 11). Similarly with a fixed hexyl spacer, the specific linker chemistry has been varied from di-amides, to di-esters to amide-ester combination (d-$A_2$ monomers 3, 9 and 13 respectively). By replacing chloromethyl benzoyl chloride with 4-chlorobutyryl chloride, monomers with aliphatic di-amides, diesters and amide-ester combinations were synthesized (d-$A_2$ monomers 14 to 16).

To modulate the reactivity of aliphatic halides, Finkelstein reaction can be conducted to exchange the chloride to bromide or iodide. To this end, d-$A_2$ monomer 16 was subjected to halogen exchange reaction in the presence of sodium iodide to result in d-$A_2$ monomer 17. With an aliphatic iodide, this monomer would enable higher reactivity so that subsequent polymerization and reactions can be conducted at a significantly lower temperature than the aliphatic chlorides. Alternatively, similar reactive monomers with aliphatic esters can also be directly synthesized from a corresponding iodoalcohol such as iodoethanol with a bis-acidchloride such as succinyl chloride to result in target d-$A_2$ monomer 18. Functionalities can also be introduced along with the linker. As a proof-of-concept, a protected secondary amine was introduced via commercially available diethanol amine-based precursor or allyl side-chain functionality introduced via commercially available precursors to result in d-$A_2$ monomer 19 and 20, respectively. The choice of difunctional spacer (diamine or diol or amino alcohols) can be used to tailor the hydrophobic/hydrophilic, flexibility/rigidity and degradability of the polymers.

Synthesis of Polyionenes

This degradable bis(halide) d-$A_2$ monomers can be polymerized with commercially available $B_2$-type bis(dimethylamino)-monomers to result in polyionenes P using DMF as the solvent. This reaction can proceed well at room temperature for monomers containing benzyl chloride-derivatives and alkyliodides. For monomers with alkylchlorides, polymerization was conducted at 60° C. The resulting polyionenes had degradable amides, esters or a combination of both amide and ester bonds along the backbone. Post polymerization, the reaction mixture was precipitated thrice into diethylether and the resultant solids were further purified by extensive dialysis against de-ionized (DI) water, followed by lyophilization to result in solids.

These polymers are in general coded by three characters. For, example P-1a, denotes the polymer synthesized using d-$A_2$ monomer 1 and $B_2$ monomer a (FIG. 1, FIG. 2 and Table 2). Additionally monomers such as P-1a-n, indicate that this entry is from $n^{th}$ independently repeated synthesis. If a combination of two different monomers were used for the polymerization, then these polymers are coded as follows: P-(1:21/1:1)a; this polymer has been prepared by using a combination of two-different A2 monomers 1 and 21 (with an initial feed ratio of 1:1, respectively) together with $B_2$ monomer a (FIG. 1, FIG. 2 and Table 2). It is important to note that the overall molar ratio of $A_2$ to $B_2$ was kept 1:1.

Apart from having the ability to tailor the polymer composition from the choice of a single d-$A_2$ monomer, these monomers can be successfully combined with other monomers comprising of different classes (such as di-amides and di-esters) in different ratios to modulate polymer properties. Moreover, commercially readily available $A_2$ monomer 21, can also be well integrated onto these platforms. Addition polymerization of d-$A_2$ monomers, irrespective of the nature of their linkers (di-amides or di-esters or a combination of ester and amide), benzyl chloride-derivatives and alkyliodides proceeded well with the $B_2$ monomer at room temperature.

In order to copolymerize the less-activated alkyl chloride-functionalized monomers with that of activated benzyl chloride monomers, a two-step approach has been used. For example, in entry 41 of Table 2, 0.5 equivalents of d-$A_2$ monomer 14 is first reacted with 1.0 equiv. of $B_2$ monomer at 60° C. for 18 hours. To this reaction mixture, the remaining equivalents of d-$A_2$ monomer, (for this example, an additional 0.5 equivalents of d-$A_2$ monomer 7) is added and the reaction is allowed to proceed for another 2 hours at 60° C. to result in a polymer that has not only the combination of both amide and ester linkers but also successful integration of monomers with different reactivities.

In general, polyionenes were obtained with a molecular weight in the range of about 2 to 20 kDa and molar mass dispersity in the range of about 1.2 to 2.9. It is important to note that, the approach described here can be readily extended to degradable $B_2$-type bis(dimethylamino)-containing monomers as well. Also by changing from a diamino linker to a diol linker, one could potentially change the nature of the degradable bond from amide to ester, impacting the rate of degradation. Installation of degradable moieties into polyionenes could lead to biocompatible and environmentally-degradable antimicrobials.

The resulting polyionenes have degradable amide bonds along the backbone. Post polymerization, the reaction mixture was precipitated thrice into diethylether and the resultant solids were further purified by extensive dialysis against deionized (DI) water, followed by lyophilization to result in a fluffy solid.

For the purposes of this disclosure, these polymers are coded by three characters. For, example P-1a, denotes the polymer synthesized using d-$A_2$ monomer 1 and $B_2$ monomer a (FIG. 2). Likewise, by using excess of the functional tertiary amines, under similar conditions to that of polymerization, a library of Gemini-surfactants S were readily accessed.

After reaction, the surfactant was purified by precipitating thrice into diethylether, to remove DMF and excess tertiary amines, to result in a solid product. For the purposes of this disclosure, these surfactants are coded by three characters. For, example S-5a, denotes the surfactant synthesized using d-$A_2$ monomer 5 and B tertiary amine a (FIG. 2). It is important to note that, the approach described here can be readily extended to degradable $B_2$-type bis(dimethylamino)-containing monomers as well. In addition, by changing from a diamino linker to a diol linker, one could change the nature of the degradable bond from amide to ester, altering the rate of degradation.

Example 4: Antimicrobial and Hemolytic Activities of Polyionenes (P)

Minimum inhibitory concentrations (MIC) of the (poly)ionenes were evaluated by a broth microdilution method against clinically relevant microorganisms such as *S. aureus* (Gram-positive bacteria), *E. coli* and *P. aeruginosa* (Gram-negative bacteria), and *C. albicans* (fungi). Also as an indication of toxicity of these (poly)ionenes, hemolytic assays were conducted to evaluate their hemolytic activity ($HC_{50}$ values) against rat red blood cells (rRBCs).

Remarkably, most of the polymers tested were shown to have relatively low MIC values of 2 to 31 ppm across different microbes and relatively high $HC_{50}$ values of >1000 ppm (Table 2). Performance of polymer P-1a (Table 2, entry 1) was found to be optimal with extremely low MICs of 2 to 8 ppm and at the same time demonstrated very high $HC_{50}$ values of >2000 ppm. These results were consistent across multiple batches, highlighting the reproducibility of these materials (Table 2, entries 1, 12, 18 and 22).

By comparing different types of commercially available $B_2$ monomer (a, b and c, FIG. 2), used as a comonomer with the addition polymerization of d-$A_2$ monomers (FIG. 2, 1 to 6 and 8), in general there was no major change in the MIC values that could be attributed due to the change in $B_2$ monomer (Table 2, entries 1-17 and 22-29).

Among d-$A_2$ monomers from di-ester series (FIG. 2, 7 to 12), it is evident that, in general, the shorter the spacer, the better the potency and selectivity (Table 2, entries 23, 27, 32-34). In this di-ester series, polymer P-8a was found to have the highest potency and selectivity. For a fixed spacer length of hexyl, by probing the role of the linker chemistry, in terms of di-amide versus di-ester versus amide-ester combination, it was found that although the potency was not affected, selectivity was (Table 2, entries 3, 32 and 35). $HC_{50}$ values were highly dependent on the nature of linker chemistry and followed the following trend: P-3a>P-13a>>P-9a. This finding underscores the importance of the combination of amide and ester bonds in tailoring selectivity.

The amide-ester combinations can be introduced not just from a well-defined monomer (d-$A_2$ monomer 13 and 15), but also by copolymerizing different classes of monomers. Unlike monomers where the ratio of amide to ester is fixed at 1:1, copolymerization of di-ester and di-amide monomers offers the ability to better tailor the ratio of ester to amide. Apart from having an effect on selectivity, this approach can also improve the potency (Table 2, entries 23-26). By increasing the content of d-$A_2$ monomer 1 in the polymerization of d-$A_2$ monomer 7, it was found that the potency of these polymers was improved, across multiple strains. These findings are also supported by killing kinetics and MBC data (discussed further below).

Ability to incorporate aliphatic amides and esters along with aromatic amides and/or esters can offer unprecedented opportunity to tailor biodegradation, owing to high selectivities of the enzymes that cleave these bonds. To this end, d-$A_2$ monomers 14 to 18 were synthesized and selected examples were polymerized with other classes of monomers and their biological properties were evaluated (Table 2, entries 36-44). Collectively these results demonstrate that these monomers containing aliphatic amides or esters can be well integrated into other classes of monomers containing aromatic benzyl chloride-type derivatives. More importantly, these polymers have a broad spectrum of action and high selectivity.

The polymers from d-$A_2$ monomers 14 and 17 were found to be active against bacteria but not very potent against fungi (Table 2, entries 36 and 42). This can be advantageous for selective eradication of bacteria and for selectively growing commercially relevant fungi and hence may have implications in biotechnology, food and a multitude of other disciplines where such selective killing of microbes is necessary.

Ability to copolymerize different sub-classes of d-$A_2$ monomers and also with other commercially readily available, inexpensive $A_2$ monomer (for example compound 21 of FIG. 2) to result in polymers that are potent and selective illustrates the versatility and practical relevance of this approach. This approach also offers unprecedented opportunity to tailor physical, chemical and biological properties of materials (Table 2, entries 19, 20, 24-26, 30, 31, 37-41 and 44). Moreover, the extent and speed of degradation of these polymers in the biological and environmental contexts can also be controlled.

Additional functionalities can be introduced in this d-$A_2$ monomer via the linkers as illustrated by monomer 19 and 20. Resultant polymers from some of these polymers were also found to be potent and their selectivity modulated through additional chemical manipulation (Table 2, entries 45 and 46). Compared to pristine polymer P-19a, the partially hydrolyzed polymer P-19a-DP obtained from P-19a through the acidolysis (by subjecting the polymer P-19a to 20×TFA per ′Boc-; TFA as 33% v/v in dichloromethane for 1 hour at room temperature), resulted in improvement of selectivity. Moreover the secondary amines, exposed after acidolysis can be used for additional reactions including, but not limited to dye-labelling, cross-linking and surface coating. Similarly, allyl-functionalities can also be used for post-polymerization transformation that can offer opportunities to incorporate radical and photo-mediated reactions for coatings, crosslinking, and hydrogel formation.

Collectively, these findings demonstrate that these polyionenes have high selectivity and broad spectrum of antimicrobial activity against several microbes over mammalian cells.

TABLE 2

Minimum inhibitory concentrations (MICs) and hemolytic activity (HC$_{50}$) of polymer series, P

| S. No. | d-A2 monomer or A2 monomer type-1 | d-A2 monomer or A2 monomer type-2 | Initial feed ratio of type-1: type-2 monomers | B2 monomer | Code | Ref. | SA (ppm) | EC (ppm) | PA (ppm) | CA (ppm) | Hemolysis, HC$_{50}$ (ppm) |
|---|---|---|---|---|---|---|---|---|---|---|---|
| 1 | 1 | — | — | a | P-1a-1 | 6037B | 8 | 8 | 8 | 2 | >2000 |
| 2 | 1 | — | — | c | P-1c-1 | 6050A | 8 | 8 | 4 | 16 | >2000 |
| 3 | 3 | — | — | a | P-3a | 7016 | 8 | 16 | 8 | 8 | >2000 |
| 4 | 3 | — | — | c | P-3c | 6050C | 8 | 16 | 16 | 16 | 1000 |
| 5 | 5 | — | — | c | P-5c-1 | 6050D | 8 | 16 | 8 | 31 | >2000 |
| 6 | 6 | — | — | a | P-6a | 6080A | 16 | 8 | 8 | >500 | >2000 |
| 7 | 6 | — | — | b | P-6b | 6080B | 16 | 8 | 8 | >500 | >2000 |
| 8 | 6 | — | — | c | P-6c | 6080C | 16 | 8 | 8 | >500 | >2000 |
| 9 | 4 | — | — | a | P-4a | 6081A | 63 | 63 | 63 | 63 | >2000 |
| 10 | 4 | — | — | b | P-4b | 6081B | 31 | 31 | 31 | 16 | >2000 |
| 11 | 4 | — | — | c | P-4c | 6081C | 31 | 31 | 31 | 16 | >2000 |
| 12 | 1 | — | — | a | P-1a-2 | 6083A | 8 | 8 | 8 | 2 | >2000 |
| 13 | 1 | — | — | b | P-1b | 6083B | 8 | 8 | 8 | 16 | >2000 |
| 14 | 1 | — | — | c | P-1c-2 | 6083C | 8 | 4 | 4 | 4 | >2000 |
| 15 | 5 | — | — | a | P-5a | 6084A | 8 | 8 | 8 | 63 | >2000 |
| 16 | 5 | — | — | b | P-5b | 6084B | 8 | 8 | 8 | >500 | >2000 |
| 17 | 5 | — | — | c | P-5c-2 | 6084C | 8 | 8 | 8 | >500 | >2000 |
| 18 | 1 | — | — | a | P-1a-3 | 6104A | 8 | 8 | 8 | 2 | >2000 |
| 19 | 1 | 21 | 1:1 | a | P-(1:21/1:1)a | 6104B | 8 | 8 | 8 | 4 | >2000 |
| 20 | 1 | 21 | 1:9 | a | P-(1:21/1:9)a | 6104C | 4 | 8 | 8 | 4 | >2000 |
| 21 | 21 | — | — | a | P-21a | 6029A | 4 | 4 | 4 | 8 | >2000 |
| 22 | 1 | — | — | a | P-1a-4 | 7004 | 8 | 8 | 8 | 2 | >2000 |
| 23 | 7 | — | — | a | P-7a | 7011A | 16 | 8 | 31 | 8 | >2000 |
| 24 | 7 | 1 | 1:1 | a | P-(7:1/1:1)a | 7012A | 8 | 8 | 16 | 4 | >2000 |
| 25 | 7 | 1 | 3:7 | a | P-(7:1/3:7)a | 7020 | 8 | 8 | 8 | 4 | >2000 |
| 26 | 7 | 1 | 1:9 | a | P-(7:1/1:9)a | 7012B | 8 | 8 | 8 | 4 | >2000 |
| 27 | 8 | — | — | a | P-8a | 6110A | 8 | 8 | 8 | 4 | >2000 |
| 28 | 8 | — | — | b | P-8b | 6110B | 8 | 16 | 8 | 4 | 1000-2000 |
| 29 | 8 | — | — | c | P-8c | 6110C | 8 | 8 | 8 | 4 | >2000 |
| 30 | 8 | 21 | 1:1 | a | P-(8:21/1:1)a | 6110D | 2 | 8 | 8 | 4 | >2000 |
| 31 | 8 | 21 | 1:9 | a | P-(8:21/1:9)a | 6110E | 2 | 8 | 8 | 4 | >2000 |
| 32 | 9 | — | — | a | P-9a | 7008 | 16 | 16 | 16 | 31 | 63-125 |
| 33 | 10 | — | — | a | P-10a | 7007 | >500 | 250 | 250 | 125 | >8 |
| 34 | 12 | — | — | a | P-12a | 7006 | >500 | 31 | 125 | 16 | >2000 |
| 35 | 13 | — | — | a | P-13a | 7014A | 8 | 8 | 16 | 8 | 500-1000 |
| 36 | 14 | — | — | a | P-14a | 7050A | 4 | 8 | 8 | 250 | >1000 |
| 37 | 14 | 1 | 1:1 | a | P-(14:1/1:1)a | 7050B | 4 | 4 | 2 | 4 | >1000 |
| 38 | 14 | 1 | 1:3 | a | P-(14:1/1:3)a | 7050C | 8 | 8 | 8 | 4 | >1000 |
| 39 | 14 | 21 | 1:1 | a | P-(14:21/1:1)a | 7070A | 2 | 8 | 4 | 8 | >1000 |
| 40 | 14 | 7 | 1:1 | a | P-(14:7/1:1)a | 7070C | 8 | 8 | 16 | 4 | >1000 |
| 41 | 14 | 7 | 1:3 | a | P-(14:7/1:3)a | 7070D | 8 | 8 | 16 | 8 | >1000 |
| 42 | 17 | — | — | a | P-17a | 7082B | 16 | 16 | 8 | >500 | >1000 |
| 43 | 18 | — | — | a | P-18a | 7085A | 31 | 16 | 31 | 125 | >1000 |
| 44 | 18 | 1 | 1:1 | a | P-(18:1//1:1)a | 7085B | 16 | 8 | 8 | 16 | >1000 |
| 45 | 19 | — | — | a | P-19a | 7014-B | 8 | 16 | 63 | 63 | 500-1000 |
| 46 | 19 | — | — | a | P-19a-DP | 7014-B-DP | 8 | 8 | 31 | 500 | >2000 | ppm—parts per million;
*Staphylococcus aureus* (SA);
*Escherichia coli* (EC);
*Pseudomonas aeruginosa* (PA);
Candida albicans (CA);
HC$_{50}$: Lowest concentration that produces 50% hemolysis.—means not applicable.

Example 5: Bacterial Mechanism

Based on the MIC and hemolysis data, the polymers with the best activity and selectivity were tested again for bactericidal activity against all microbes. At MIC and 2×MIC, at least a 99.99% reduction in the colony forming units (CFU) was achieved for all the microbes (FIG. 86). There was a 8-14 log reduction in the CFU counts after 18 hours of incubation for all microbes tested at MIC and 2×MIC. This suggested a bactericidal mechanism at a concentration higher than the MIC.

The polymers (P-7a and P-9a) that have shown good antimicrobial properties were chosen to treat microbes using the agar gel assay. At MIC and 2×MIC concentrations, both polymers displayed more than 99.99% killing efficiency against all the microbes tested, suggesting a bactericidal mechanism. As seen from the colony forming units (CFU) counts after 18 hours incubation (FIG. 87), at MIC and 2×MIC, there was an 8 to 16 log reduction in colony counts for all 4 strains of microbes.

Example 6: Killing Kinetics

P-7a, P-(1:7/1:1)a and P-1a-1 were incubated with different strains of microbes at various concentration for 30 seconds before the viability of the microbes was checked using the agar gel assay. For P-7a (FIG. 88), the killing efficiency against PA is >90% at 8×MIC and for 16×MIC, 100% killing efficiency was achieved. A greater than 3 log reduction of SA colonies is seen at 16×MIC after 30 sec incubation. Against EC, the killing efficiency reached 100% at 8×MIC. For CA, only 4×MIC is needed to achieve more than 3 log reduction. With the incorporation of a small amount of amides (P-(1:7/1:1)a), a 30 sec kill (FIG. 89) could be achieved at a lower concentration (8×MIC for all bacteria and 4×MIC for fungi). A 100% kill is observed at 2×MIC against all 4 microbes (FIG. 90) for P-1a-1 showing that more amide groups present lead to better killing efficacy.

Example 7: Synthesis of Gemini-Surfactants (S)

By using excess of functional tertiary amines, under similar conditions to that of polymerization, a library of Gemini-surfactants S were readily accessed. After reaction the surfactant was purified by precipitating thrice into diethylether, to remove DMF and excess tertiary amines, to result in solids. These surfactants are coded by three characters. For, example S-5a, denotes the surfactant synthesized using d-$A_2$ monomer 5 and B tertiary amine a (FIG. 1 and FIG. 2).

Example 8: Antimicrobial and Hemolytic Activities of Gemini-Surfactants (S)

Similar to polymers, MIC and $HC_{50}$ values of the surfactants were evaluated.

The MIC values were highly dependent on both d-$A_2$ precursor and functional tertiary amine used to synthesize the target surfactant. Comparing different compositions by varying the amine (B; a to h) with a fixed d-$A_2$ precursor (d-$A_2$-5), only the derivatives with longer linear alkyl chains (S-5f, S-5g and S-5h with octyl, decyl and dodecyl, respectively), were found to be potent against the pathogens tested (Table 3, entries 1 to 8). Likewise for other d-$A_2$ precursors (d-$A_2$-1, d-$A_2$-3, d-$A_2$-4 and d-$A_2$-6), in general, derivatives with decyl and dodecyl derivatives were found to be potent against the pathogens tested (Table 3, entries 9 to 20, S-Xg and S-Xh, where is X is an integer from 1 to 12).

By taking hemolysis into consideration, decyl chains were found to be optimal, offering high potency and relatively good selectivity. Additionally surfactants with decyl chains were evaluated to further probe the role of d-$A_2$ precursors (Table 3, entries 7, 10, 13, 16, 19 and 21 to 25) and it was found that d-$A_2$ precursors with hexyl spacers, d-$A_2$-3 and d-$A_2$-13, resulting in S-3g and S-13g were optimal.

Collectively these findings demonstrate that these surfactants can be tailored to have broad spectrum of antimicrobial activity against several microbes and tunable selectivity over mammalian cells.

Based on the MIC and hemolysis data, the bactericidal activity of the best candidate (S-3g) was tested against all the microbes. At MIC and 2×MIC, at least a 99.9% reduction in the colony forming units (CFU) was achieved for all the microbes, suggesting a bactericidal mechanism at MIC or higher concentrations (FIG. 91). Rapid killing of pathogens are important for a variety of applications including disinfectants. For this purpose, killing kinetics data was evaluated across multiple strains of microbes. It was found that at 16 and 32×MIC, all four strains of microbes tested were completely killed for 2 minutes (FIG. 92). A higher concentration of 64×MIC was needed to completely eradicate the microbes in 30 seconds.

The ability of an antimicrobial to eradicate microbes in the form of biofilms is important in infection control. S-3g was evaluated against *S. aureus* and *E. coli* biofilms. Cell viability and biomass of biofilm for both types of bacteria were found to be reduced in a dose dependent manner (FIG. 93). These findings demonstrate that these small molecule Gemini-surfactants are promising for use in consumer-care applications as potent disinfectant and/or preservatives.

TABLE 3

Minimum inhibitory concentrations (MICs) and hemolytic activity ($HC_{50}$) of Gemini-surfactant series, S

| S. No. | Code | Ref. | SA (ppm) | EC (ppm) | PA (ppm) | CA (ppm) | Hemolysis, $HC_{50}$(ppm) |
|---|---|---|---|---|---|---|---|
| 1 | S-5a | 6044A | >500 | >500 | >500 | >500 | >2000 |
| 2 | S-5b | 6044D | >500 | >500 | >500 | >500 | >2000 |
| 3 | S-5c | 6044C | >500 | >500 | >500 | >500 | >2000 |
| 4 | S-5d | 6039A | >500 | >500 | >500 | >500 | >2000 |
| 5 | S-5e | 6044B | >500 | >500 | >500 | >500 | >2000 |
| 6 | S-5f | 6039B | 31 | 250 | >500 | 125 | >2000 |
| 7 | S-5g | 6092D | 2 | 4 | 63 | 2 | 125-250 |
| 8 | S-5h | 6039C | 2 | 4 | 16 | 1 | 16-31 |
| 9 | S-1f | 6045E | 31 | 250 | >500 | 125 | >2000 |
| 10 | S-1g | 6092A | 1 | 2 | 16 | 2 | 125-250 |
| 11 | S-1h | 6045F | 16 | 8 | 31 | 2 | 125-250 |
| 12 | S-3f | 6048E | 4 | 16 | 500 | 8 | 500-1000 |
| 13 | S-3g | 6092B | 1 | 1 | 8 | 2 | 125-250 |
| 14 | S-3h | 6048F | 4 | 16 | 16 | 2 | 125-250 |
| 15 | S-4f | 6071E | 2 | 8 | 250 | 125 | 250-500 |
| 16 | S-4g | 6092C | 1 | 1 | 8 | 1 | 63-125 |
| 17 | S-4h | 6071F | 8 | 8 | 31 | 2 | 63-125 |
| 18 | S-6f | 6073E | 16 | 125 | >500 | 16 | >2000 |
| 19 | S-6g | 6092E | 2 | 4 | 63 | 4 | 250-500 |
| 20 | S-6h | 6073F | 1 | 2 | 8 | 4 | 31-63 |
| 21 | S-9g | 7015B | 1 | 2 | 8 | 1 | 125-250 |
| 22 | S-13g | 7015C | 1 | 1 | 4 | 1 | 63-125 |
| 23 | S-7g | 7019D | 1 | 1 | 8 | 1 | 63-125 |
| 24 | S-10g | 7019B | 16 | 500 | 500 | 16 | 63-125 |
| 25 | S-12g | 7019A | 1 | 2 | 8 | 2 | 125-250 |

Example 9: Surgical Scrub Formulation

Several formulations were prepared and tested for their antimicrobial efficacy for use as a surgical scrub. Two different hydroxypropyl methyl cellulose (HPMC) (H3785 and H7509) and Igepal (520 and 630) were used and the outcome of the different combinations was tabulated in Table 4. The compositions were made to 100% with deionized water. 1 wt % of HPMC was chosen in the preferred composition as the mixture is homogeneous. The most preferred formulation is shown in Table 5 and was chosen due to homogeneity, transparency and fluidity among all the different combinations from Table 4.

TABLE 4

Outcome of different compositions of HPMC and Igepal.

| HPMC (wt %) | | Igepal (wt %) | | Remarks |
|---|---|---|---|---|
| H3785 | H7509 | 520 | 630 | |
| — | 1 | — | 5 | Single phase, slightly opaque, slightly viscous |
| — | 2 | — | 5 | 2 phase, slightly opaque, viscous |
| — | 1 | 5 | — | Single phase, clear, slightly viscous |
| — | 2 | 5 | — | 2 phase, slightly opaque, viscous |

TABLE 4-continued

Outcome of different compositions of HPMC and Igepal.

| HPMC (wt %) | | Igepal (wt %) | | Remarks |
|---|---|---|---|---|
| H3785 | H7509 | 520 | 630 | |
| 1 | — | — | 5 | Single phase, clear, fluid |
| 2 | — | — | 5 | 2 phase, slightly opaque, slightly viscous |
| 1 | — | 5 | — | 2 phase, slightly opaque, slightly viscous |
| 2 | — | 5 | — | 2 phase, slightly opaque, slightly viscous |

TABLE 5

Optimized composition.

| | |
|---|---|
| P-1a-1 (6037B) | 0.5 wt % |
| HPMC 3785 | 1 wt % |
| Igepal 630 | 5 wt % |
| N,N-Bis(2-hydroxyethyl)dodecanamide (HDA) or N-Decyl-b-D-glucopyranoside (DGP) | 5 wt % |

After incubating the bacteria with the formulation at different time points (10 seconds, 30 seconds and 2 minutes), the mixture was plated onto agar plates. It was found that regardless of the initial colony forming units (CFU) of bacteria ($3 \times 10^5$ or $3 \times 10^8$ CFU/mL) used, no CFU was found on the agar plate (Table 6). This finding demonstrated that the formulation can be used as a hand wash or surgical scrub.

TABLE 6

Killing effectiveness of different formulations with different initial bacteria loading and various incubation time periods.

| Bacteria Count | Incubation Time | SA | | EC | | PA | |
|---|---|---|---|---|---|---|---|
| | | HDA | DGP | HDA | DGP | HDA | DGP |
| $3 \times 10^5$ CFU/mL | 2 minutes | 100% | 100% | 100% | 100% | 100% | 100% |
| | 30 seconds | 100% | 100% | 100% | 100% | 100% | 100% |
| $3 \times 10^8$ CFU/mL | 2 minutes | 100% | 100% | 100% | 100% | 100% | 100% |
| | 30 seconds | 100% | 100% | 100% | 100% | 100% | 100% |
| | 10 seconds | 100% | 100% | 100% | 100% | 100% | 100% |

Example 10: In Vivo Toxicity

The $LD_{50}$ and $LD_5$ values of P-1a-1 (6037B) were determined to be 67.5 and 37.3 mg/kg (mouse weight) by intraperitoneal injection, respectively. The $ED_{50}/ED_{95}$ values of P-1a-1 (6037B) and imipenem were determined to be 0.62/3.08 mg/kg and 2.75/20.0 mg/kg, respectively, indicating that the polymer was more effective than the antibiotic imipenem. At doses of 1.0 mg/kg and 2.0 mg/kg for P-1a-1 (6037B) and imipenem respectively, P-1a-1 (6037B) saved more infected mice than imipenem (survival: 80% and 60% for 6037B and imipenem, respectively) (FIG. 94). In addition, the treatment with P-1a-1 (6037B) and imipenem cleared the bacteria from blood and the major organs, with P-1a-1 (6037B) being significantly more effective, as shown in FIG. 95. In particular, more than 99.9% bacteria were removed after P-1a-1 (6037B) treatment.

INDUSTRIAL APPLICABILITY

The compounds and compositions as defined above may have useful applications as an antimicrobial agent in personal care goods such as cosmetics, deodorant and soap, as well as in the medical field, such as in hand washes and surgical scrubs. The compounds as defined above may also have useful applications in treating antimicrobial infections. The compounds and compositions as defined above may be ideal for use in personal care and biomedical applications.

The compounds and compositions as defined above may also have useful applications as food additives or preservatives, coatings, precursors for cross-linked resins, ingredients for additive manufacturing, surfactants, and agents to selectively promote a certain microbial strain by killing other agents, for instance, by promoting fungi, while killing bacterial strains.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A compound having the following formula (I), (Ia) or (Ib):

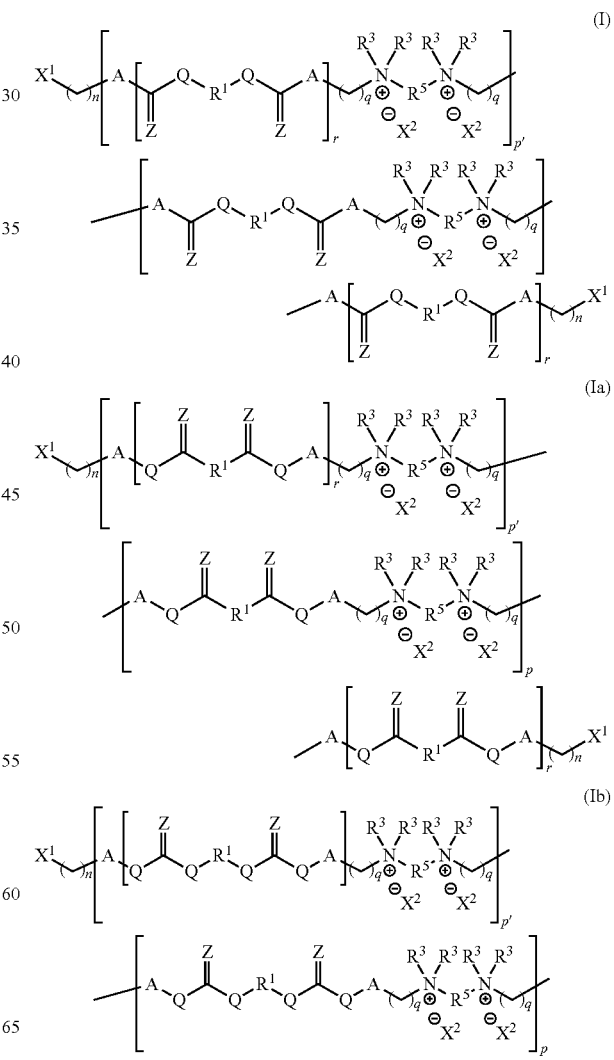

-continued

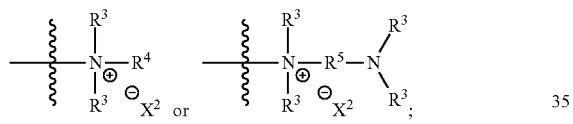

wherein
A is independently selected from the group consisting of optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

$R^1$ is independently selected from the group consisting of optionally substituted $C_2$-$C_{15}$ alkyl, optionally substituted $C_2$-$C_{15}$ alkenyl, optionally substituted $C_2$-$C_{15}$ alkynyl, —Ar—, —$R^2$—Ar—$R^2$—, —$R^2$—(O—$R^2$)$_m$—$R^2$—, —$R^2$—N($R^4$)—$R^2$— and —$R^2$—C($R^4$)$_2$—$R^2$—;

Ar is independently optionally substituted aryl or optionally substituted heteroaryl;

$R^2$ is independently optionally substituted alkyl, optionally substituted alkenyl or optionally substituted alkynyl;

$X^1$ is independently halogen, sulfate, tosylate, mesylate, $X^2$ is independently absent or an anionic counterion;

$R^3$ is independently selected from the group consisting of hydrogen, optionally substituted alkyl, optionally substituted alkenyl and optionally substituted alkynyl;

$R^4$ is independently selected from the group consisting of hydrogen, $R^3$, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide, —$R^2$—OC(O)—$R^3$, —$R^2$—C(O)O—$R^3$, —$R^2$—Ar and —$R^2$—O—$R^2$—CH$_2$=CH$_2$;

$R^5$ is independently —$R^2$— or —$R^2$—O—$R^2$—;

Z is independently O or S;

Q is independently O or NH;

n is an integer from 1 to 3;

m and q are independently an integer from 1 to 10;

p' is 0 or is an integer of at least 1;

p is 0 or in an integer of at least 1; and r is 0 or 1, wherein when p is 0, then r is 1; or when p is an integer of at least 1, then r is 0 or 1.

2. The compound according to claim 1, wherein Z is O and Q is NH, or Z is O and Q is O, or A is Ar, or n is 1 or m is 3.

3. The compound according to claim 1, wherein $R^2$ is a $C_1$ to $C_{15}$ linear alkyl or $C_1$ to $C_{15}$ linear or branched alkenyl or wherein $R^1$ is selected from the group consisting of:
—(CH$_2$)$_2$—, —(CH$_2$)$_3$—, —(CH$_2$)$_4$—, —(CH$_2$)$_5$—, —(CH$_2$)$_6$—, —(CH$_2$)$_7$—,
—(CH$_2$)$_8$—, —CH$_2$—O—CH$_2$CH$_2$—O—CH$_2$—, —(CH$_2$)$_2$—O—CH$_2$CH$_2$—O—(CH$_2$)$_2$—,
—CH$_2$—{O—CH$_2$CH$_2$}2-O—CH$_2$—, —(CH$_2$)$_2$—{O—CH$_2$CH$_2$}2-O—(CH$_2$)$_2$—,
—(CH$_2$)$_3$—{O—CH$_2$CH$_2$}2—O—(CH$_2$)$_3$—,

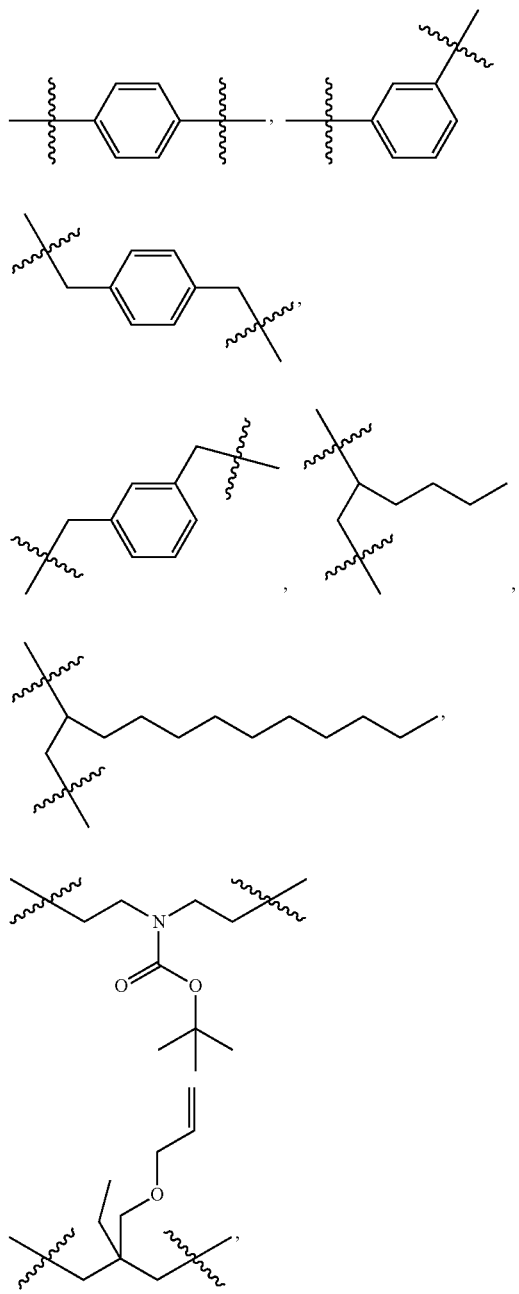

CH$_2$—C(NH$_2$)—CH$_2$—, —CH$_2$—CH(CH$_3$)(NH$_2$)—CH$_2$—, 9-fluorenylmethyl carbamate (Fmoc), t-butyl carbamate(Boc), benzyl carbamate (Cbz), acetyl (Ac), trifluoroacetyl, benzyl (Bn), trityl (Tr), benzylideneamine, p-toluenesulfonamide (Ts), and p-methoxyphenyl (PMP).

4. The compound according to claim 1, wherein $X^1$ is halogen or $X^1$ is

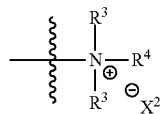

or $X^1$ is

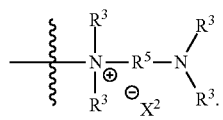

5. The compound according to claim 1, wherein $R^3$ is alkyl or wherein $R^4$ is selected from the group consisting of H, —(CH$_2$)$_2$, —(CH$_2$)$_3$, —(CH$_2$)$_4$, —(CH$_2$)$_5$, —(CH$_2$)$_6$, —(CH$_2$)$_7$,
—(CH$_2$)$_8$, —(CH$_2$)$_9$, —(CH$_2$)$_{10}$, —(CH$_2$)$_{11}$, —(CH$_2$)$_{12}$, —(CH$_2$)$_{13}$, —(CH$_2$)$_{14}$, —(CH$_2$)$_{15}$, —CH$_2$CH=CH, —(CH$_2$)$_2$—CH=CH, —(CH$_2$)$_3$—CH=CH, —(CH$_2$)$_4$—CH=CH, —(CH$_2$)$_5$—CH=CH, —(CH$_2$)$_6$—CH=CH,
—(CH$_2$)$_7$—CH=CH, —(CH$_2$)$_8$—CH=CH, —(CH$_2$)$_9$—CH=CH, —(CH$_2$)$_{10}$—CH=CH, —(CH$_2$)$_{11}$—CH=CH,
—(CH$_2$)$_{13}$—CH=CH, —CH$_2$—OC(O)—CH$_2$, —CH$_2$—OC(O)—(CH$_2$)$_2$, —CH$_2$—OC(O)—(CH$_2$)$_3$, —CH$_2$—OC(O)—(CH$_2$)$_4$, —(CH$_2$)$_2$—OC(O)—CH$_2$, —(CH$_2$)$_2$—OC(O)—(CH$_2$)$_2$, —(CH$_2$)$_2$—OC(O)—(CH$_2$)$_3$,
—(CH$_2$)$_2$—OC(O)—(CH$_2$)$_4$, —(CH$_2$)$_2$—OC(O)—C(=CH$_2$)CH$_3$, —CH$_2$—C(O)O—CH$_2$,
—CH$_2$—C(O)O—(CH$_2$)$_2$, —CH$_2$—C(O)O—(CH$_2$)$_3$, —CH$_2$—C(O)O—(CH$_2$)$_4$, —(CH$_2$)$_2$—C(O)O—CH$_2$, —(CH$_2$)$_2$—C(O)O—(CH$_2$)$_2$, —(CH$_2$)$_2$—C(O)O—(CH$_2$)$_3$, —(CH$_2$)$_2$—C(O)O—(CH$_2$)$_4$,
—(CH$_2$)$_2$—C(O)O—C(=CH$_2$)CH$_3$, —NH$_2$, —SH,

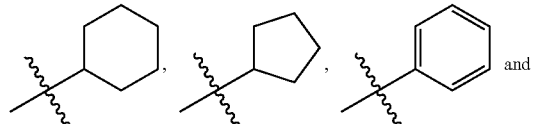 and

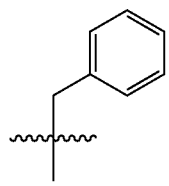

or wherein $R^5$ is selected from the group consisting of —(CH$_2$)$_2$—, —(CH$_2$)$_3$—, —(CH$_2$)$_4$—, —(CH$_2$)$_5$—, —(CH$_2$)$_6$—, —(CH$_2$)$_7$—,
—CH=CH—, —CH=CH—CH$_2$—, —CH$_2$—CH=CH—, —CH=CH—(CH$_2$)$_2$—, —CH$_2$—CH=CH—CH$_2$—,
—(CH$_2$)$_2$—CH=CH—, —CH=CH—CH—, —CH=CH—(CH$_2$)$_3$—, —CH$_2$—CH=CH—(CH$_2$)$_2$—,
—(CH$_2$)$_2$—CH=CH—CH$_2$—, —(CH$_2$)$_3$—CH=CH—, —CH=CH—CH$_2$—, —CH$_2$—CH=CH—CH—,
—CH$_2$—O—CH$_2$—, —CH$_2$—O—(CH$_2$)$_2$—, —(CH$_2$)$_2$—O—CH$_2$—, —(CH$_2$)—O—(CH$_2$)$_3$—, —(CH$_2$)$_2$—O—(CH$_2$)$_2$—, and
—(CH$_2$)$_3$—O—CH$_2$—.

6. The compound according to claim 1, wherein $X^2$ is selected from the group consisting of halogen, sulfate, tosylate, and mesylate.

7. The compound according to claim 1, wherein p is 0, having the following formula (III), (IIIa) or (IIIb):

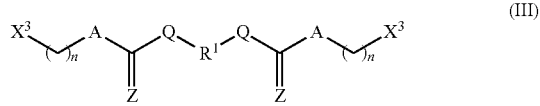

(III)

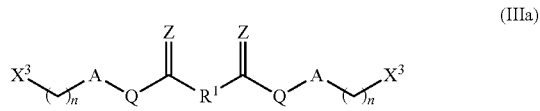

(IIIa)

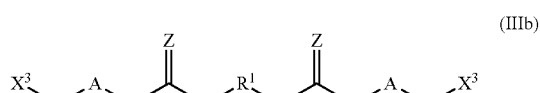

(IIIb)

wherein $X^3$ is halogen, or having the following formula (IV), (IVb), or (IVc):

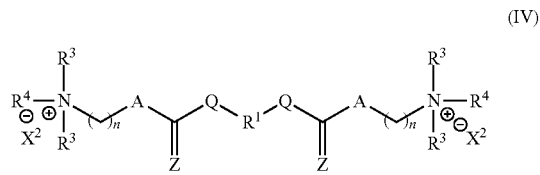

(IV)

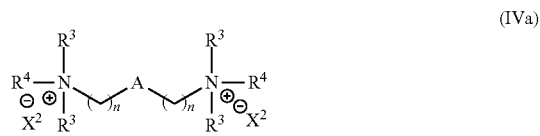

(IVa)

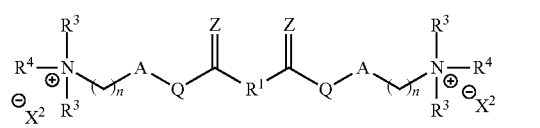

(IVb)

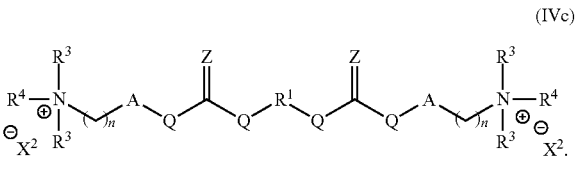

(IVc)

8. The compound according to claim 1 wherein p is an integer of at least 1, having the following formula (V), (Va), (Vb), (Vc), (Vd) or (Ve):

(V)
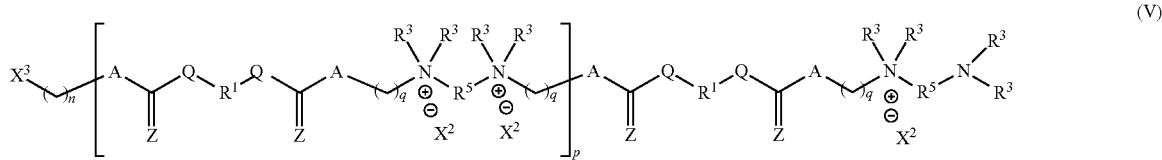

(Va)
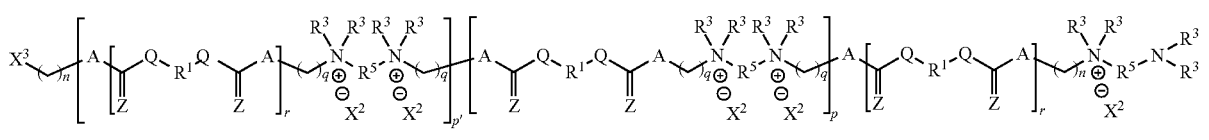

(Vb)
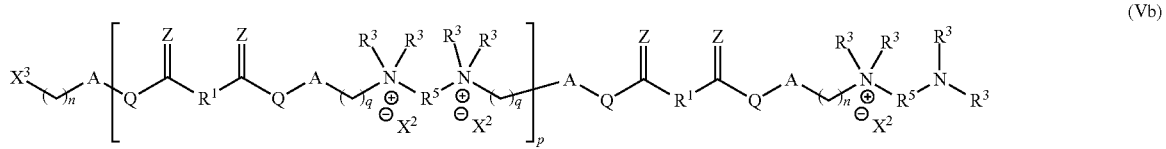

(Vc)
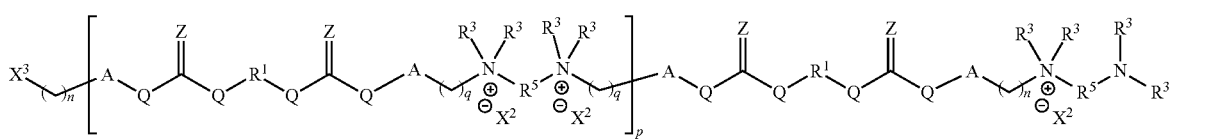

(Vd)
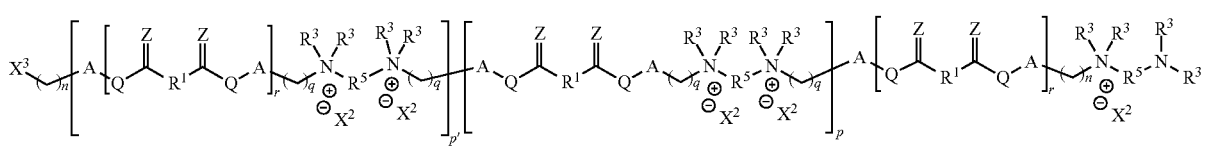

(Ve)
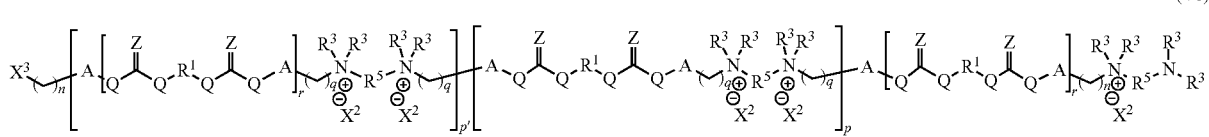

wherein $X^3$ is halogen.

9. The compound according to claim 1, wherein when p and p' are both an integer of at least 1, the p':p ratio is in the range of about 1:10 to about 10:1, having a molecular weight in the range of about 1 kDa to about 100 kDa or having a molar mass dispersity in the range of about 1.1 to about 4.0.

10. A method for making a compound according to claim 1, the method comprising the steps of:
 (A) contacting $NH_2—R^1—NH_2$ or $HO—R^1—OH$ with a compound having the following formula (VI):

(VI)
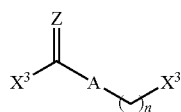

wherein $R^1$ is selected from the group consisting of optionally substituted $C_2$-$C_{15}$ alkyl, optionally substituted $C_2$-$C_{15}$ alkenyl, optionally substituted $C_2$-$C_{15}$ alkynyl, —Ar—, —$R^2$—Ar—$R^2$—, —$R^2$—(O—$R^2$)$_m$—$R^2$—, —$R^2$—N($R^4$)—$R^2$— and —$R^2$—C($R^4$)$_2$—$R^2$—;

Ar is independently optionally substituted aryl or optionally substituted heteroaryl;

$R^2$ is independently optionally substituted alkyl, optionally substituted alkenyl or optionally substituted alkynyl;

Z is independently O or S;

A is independently selected from the group consisting of optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

n is an integer from 1 to 3;

m is an integer from 1 to 10; and $X^3$ is halogen;

to form a halogen compound having the following formula (III):

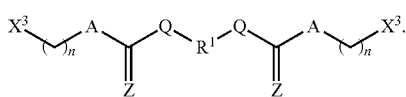
(III)

or (B) contacting

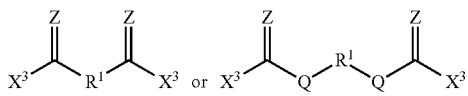

with a compound having the following formula (VIa):

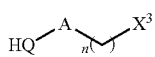
(IVa)

wherein R¹ is selected from the group consisting of optionally substituted $C_2$-$C_{15}$ alkyl, optionally substituted $C_2$-$C_{15}$ alkenyl, optionally substituted $C_2$-$C_{15}$ alkynyl, —Ar—, —R²—Ar—R²—, —R²—(O—R²)$_m$—R²—, —R²—N(R⁴)—R²— and —R²—C(R⁴)$_2$—R²—;

Ar is independently optionally substituted aryl or optionally substituted heteroaryl;

R² is independently optionally substituted alkyl, optionally substituted alkenyl or optionally substituted alkynyl;

Z is independently O or S;

A is independently selected from the group consisting of optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

n is an integer from 1 to 3;

m is an integer from 1 to 10; and

X³ is halogen;

to form a halogen compound having the following formula (IIIa) or (IIIb):

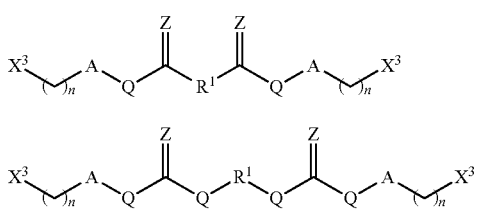
(IIIa)

(IIIb)

wherein Q is independently O or NH.

11. The method according to claim 10, comprising the step of contacting the halogen compound having the formula (III), (IIIa), or (IIIb) with an amine N(R³)₂R⁴:

wherein

R³ is independently selected from the group consisting of hydrogen, optionally substituted alkyl, optionally substituted alkenyl and optionally substituted alkynyl; and R⁴ is independently selected from the group consisting of hydrogen, R³, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide-R²—OC(O)—R³, —R²—C(O)O—R³, —R²—Ar and —R²—O—R²—CH₂═CH₂;

to form a tertiary amino compound having the following formula (IV), (IVb) or (IVc):

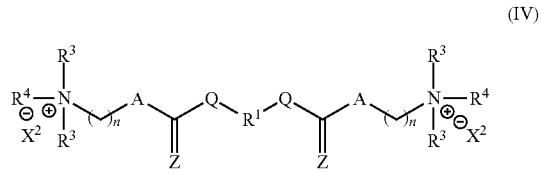
(IV)

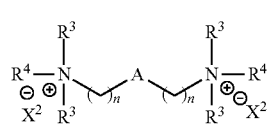
(IVa)

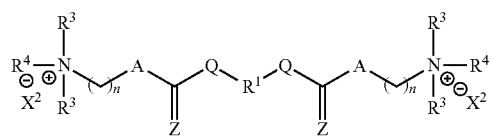
(IVb)

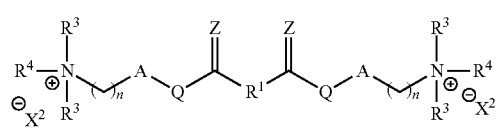
(IVc)

wherein

X² is absent or an anionic counterion.

12. The method according to claim 10, comprising the step of contacting the halogen compound having the formula (III), (IIIa) or (IIIb) with a diamine $(R^3)_2 N—R^2—N(R^3)_2$:

wherein $R^3$ is independently selected from the group consisting of hydrogen, optionally substituted alkyl, optionally substituted alkenyl and optionally substituted alkynyl;

to form a polymer product having the following formula (V), (Va), (Vb), (Vc), (Vd) or (Ve)

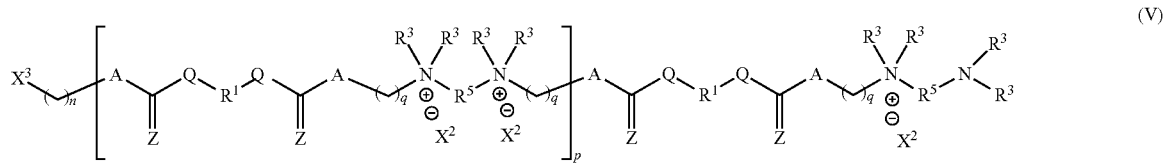
(V)

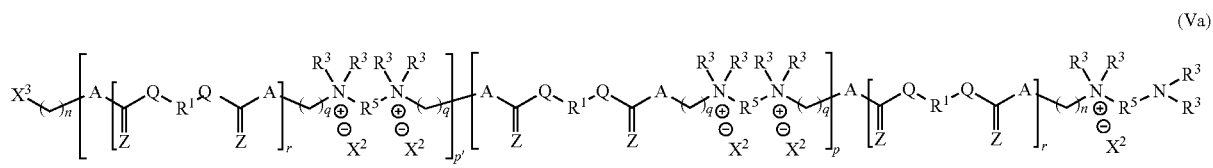
(Va)

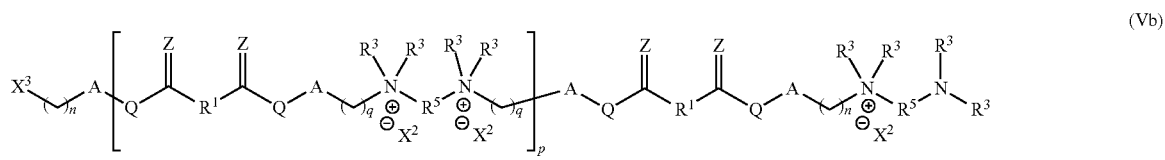
(Vb)

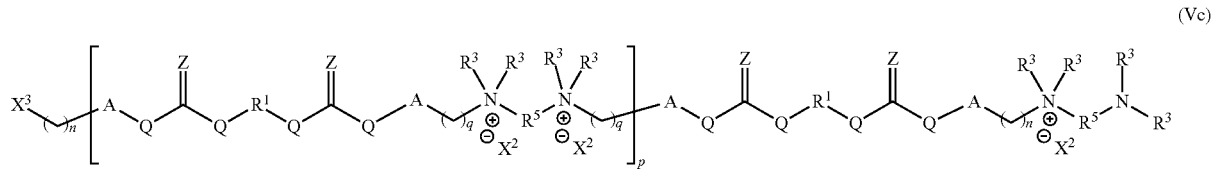
(Vc)

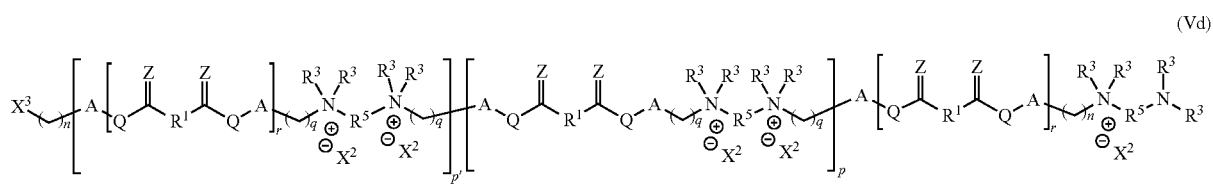
(Vd)

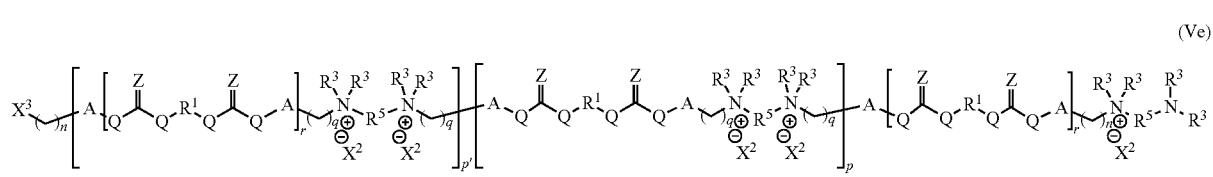
(Ve)

wherein
X² is absent or an anionic counterion;
X³ is halogen;
R⁵ is —R²— or —R²—O—R²—;
q is an integer from 1 to 10;
p' is 0 or an integer of at least 1; and
r is 0 or 1,
wherein when p is an integer of at least 1, then r is 0 or 1.

13. The method according to claim 12, comprising the steps of:
contacting the halogen compound having the formula (III), (IIIa) or (IIIb) with the diamine $(R^3)_2$ N—$R^2$—$N(R^3)_2$, wherein $R^3$ is as defined in claim 12; and
adding another halogen compound having the formula (III), (IIIa) or (IIIb);
to form the polymer product having the following formula (V), (Va), (Vb), (Vc), (Vd) or (Ve)

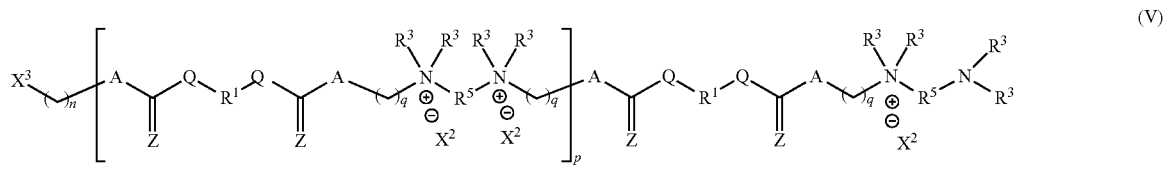

(V)

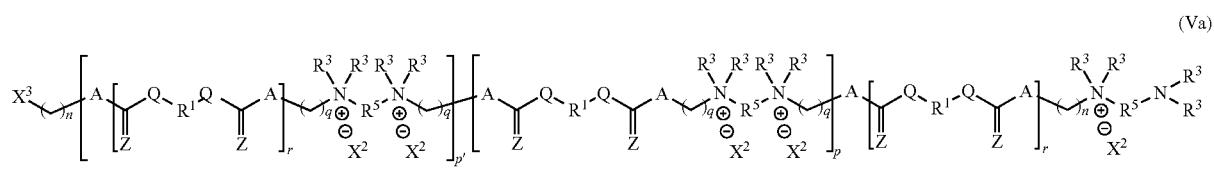

(Va)

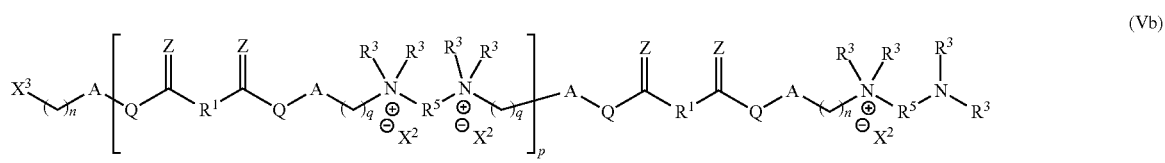

(Vb)

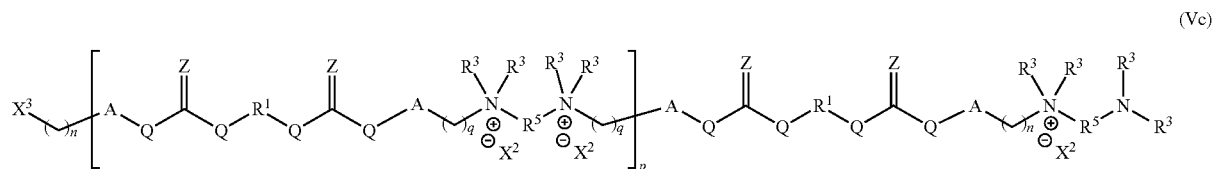

(Vc)

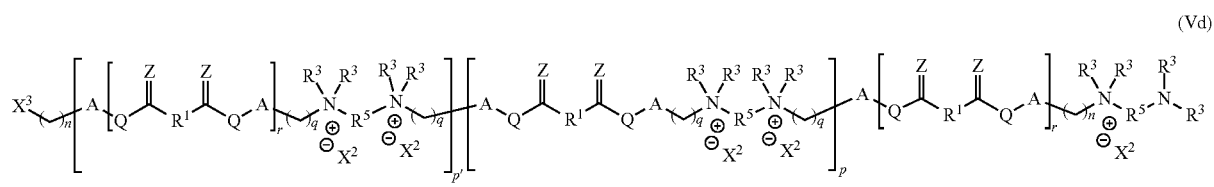

(Vd)

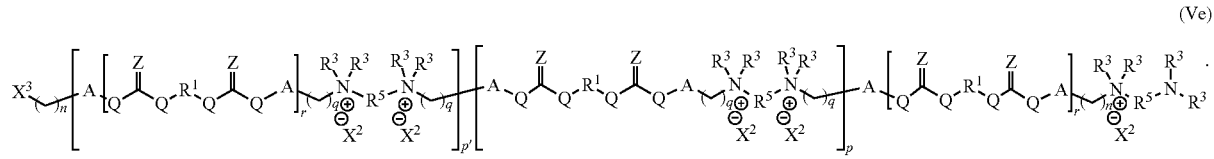

(Ve)

14. A composition comprising the compound having the following formula (I), (Ia) or (Ib):

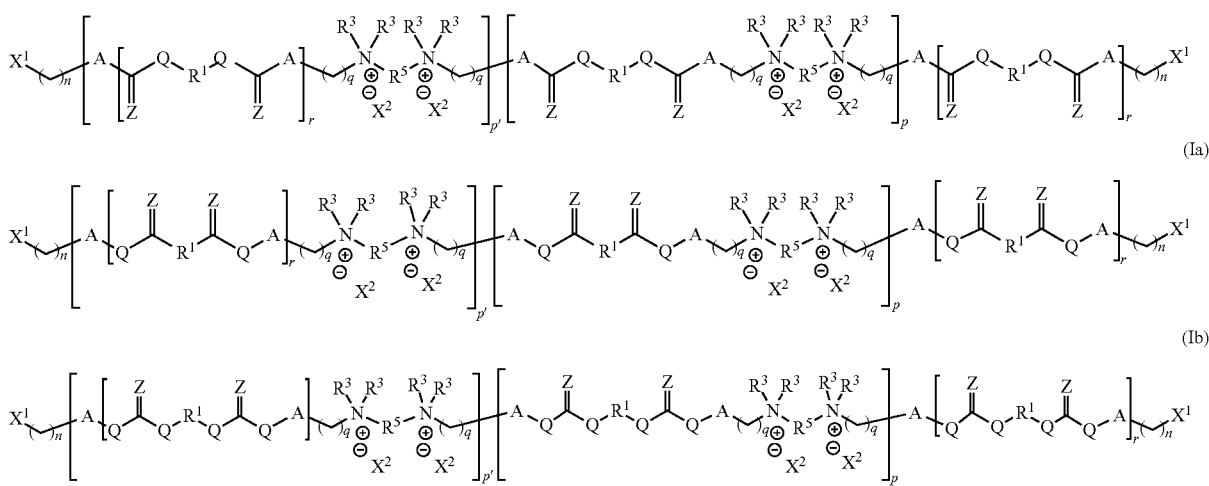

wherein
A is independently selected from the group consisting of optionally substituted alkoxy, optionally substituted aminoalkoxy, optionally substituted alkenyl, optionally substituted alkynyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted aryl and optionally substituted heteroaryl;

$R^1$ is independently selected from the group consisting of optionally substituted $C_2$-$C_{15}$ alkyl, optionally substituted $C_2$-$C_{15}$ alkenyl, optionally substituted $C_2$-$C_{15}$ alkynyl, —Ar—, —$R^2$—Ar—$R^2$—, —$R^2$—(O—$R^2$)$_m$—$R^2$—, —$R^2$—N($R^4$)—$R^2$— and —$R^2$—C($R^4$)$_2$—$R^2$—;

Ar is independently optionally substituted aryl or optionally substituted heteroaryl;

$R^2$ is independently optionally substituted alkyl, optionally substituted alkenyl or optionally substituted alkynyl;

$X^1$ is independently halogen, sulfate, tosylate and mesylate,

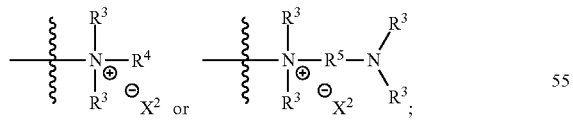

$X^2$ is independently absent or an anionic counterion;

$R^3$ is independently selected from the group consisting of hydrogen, optionally substituted alkyl, optionally substituted alkenyl and optionally substituted alkynyl;

$R^4$ is independently selected from the group consisting of hydrogen, $R^3$, optionally substituted alkyl, optionally substituted cycloalkyl, optionally substituted cycloalkenyl, optionally substituted cycloalkynyl, optionally substituted heterocycloalkyl, optionally substituted heterocycloalkenyl, optionally substituted heterocycloalkynyl, optionally substituted amino, optionally substituted alkylsulfide, —$R^2$—OC(O)—$R^3$, —$R^2$—C(O)O—$R^3$, —$R^2$—Ar and —$R^2$—O—$R^2$—CH$_2$=CH$_2$;

$R^5$ is independently —$R^2$— or —$R^2$—O—$R^2$—;
Z is independently O or S;
Q is independently O or NH;
n is an integer from 1 to 3;
m and q are independently an integer from 1 to 10;
p' is 0 or is an integer of at least 1;
p is 0 or an integer of at least 1; and
r is 0 or 1,
wherein when p is 0, then r is 1; or
when p is an integer of at least 1, then r is 0 or 1.

15. The composition according to claim 14, wherein the compound has the following formula (IV), (IVb) or (IVc):

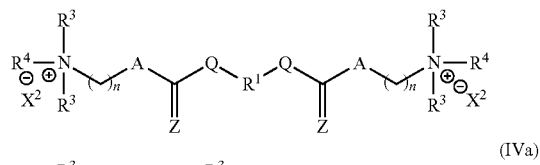

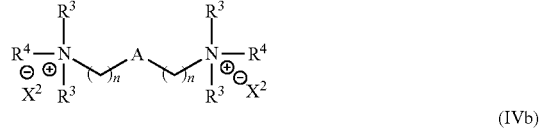

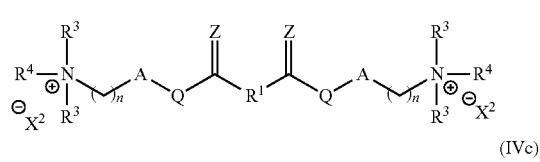

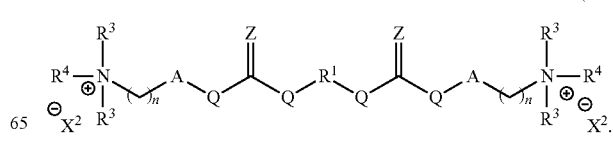

16. The composition according to claim 14, wherein the compound has the following formula (V), (Va), (Vb), (Vc), (Vd) or (Ve):

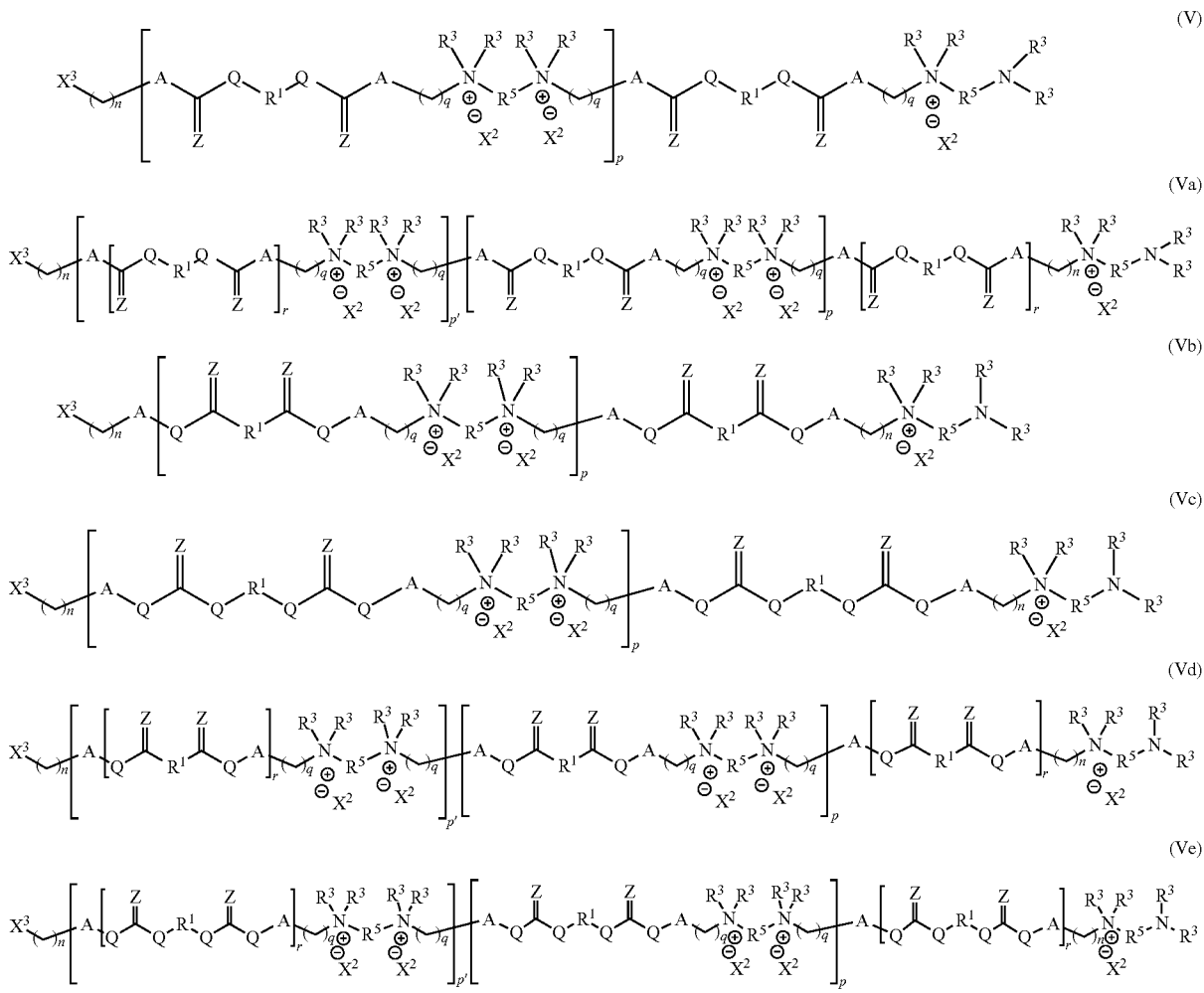

wherein $X^3$ is halogen.

17. The composition according to claim 14 further comprising a thickening agent and/or a detergent.

18. The composition according to claim 17, wherein the composition comprises the compound in the range of about 0.2 wt % to about 1 wt %, a thickening agent in the range of about 0.5 wt % to about 1.5 wt %, and a detergent in the range of about 3 wt % to about 15 wt %, with the remaining wt % being water so that the total is 100 wt %.

19. A method for treating a bacterial infection or fungal infection comprising administering to a subject a compound according to claim 1.

* * * * *